United States Patent
Lapotko et al.

(10) Patent No.: US 12,207,901 B1
(45) Date of Patent: Jan. 28, 2025

(54) OPTICAL DETECTION OF TRANSIENT VAPOR NANOBUBBLES IN A MICROFLUIDIC DEVICE

(71) Applicant: Masimo Corporation, Irvine, CA (US)

(72) Inventors: Dmitri O. Lapotko, Dana Point, CA (US); Katsiaryna Hleb, Irvine, CA (US); Mohamed K. Diab, Ladera Ranch, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 18/545,276

(22) Filed: Dec. 19, 2023

Related U.S. Application Data

(63) Continuation of application No. 16/992,596, filed on Aug. 13, 2020, now abandoned.

(60) Provisional application No. 62/888,060, filed on Aug. 16, 2019.

(51) Int. Cl.
    *A61B 5/00* (2006.01)

(52) U.S. Cl.
    CPC .......... *A61B 5/0077* (2013.01); *A61B 5/0064* (2013.01); *A61B 5/0082* (2013.01); *A61B 2562/0238* (2013.01); *A61B 2562/0285* (2013.01)

(58) Field of Classification Search
    CPC . A61B 5/0077; A61B 5/0064; A61B 5/00082; A61B 2562/0238; A61B 2562/0285
    See application file for complete search history.

(56) References Cited

U.S. PATENT DOCUMENTS

| | | | |
|---|---|---|---|
| 174,504 A | 11/1979 | Chenausky | |
| 4,818,710 A * | 4/1989 | Sutherland | G01N 21/648 436/805 |
| 4,960,128 A | 10/1990 | Gordon et al. | |
| 4,964,408 A | 10/1990 | Hink et al. | |
| 5,319,355 A | 6/1994 | Russek | |
| 5,337,744 A | 8/1994 | Branigan | |

(Continued)

FOREIGN PATENT DOCUMENTS

| | | |
|---|---|---|
| WO | WO 2007/104098 | 9/2007 |
| WO | WO 2013/109722 | 7/2013 |
| WO | WO 2019/224822 | 11/2019 |

OTHER PUBLICATIONS

US 2022/0192529 A1, 06/2022, Al-Ali et al. (withdrawn)

(Continued)

*Primary Examiner* — Sean A Frith
(74) *Attorney, Agent, or Firm* — Knobbe, Martens, Olson & Bear, LLP

(57) ABSTRACT

A system for generating and detecting transient vapor nanobubbles in a fluid from a patient can include a micro-fluidic device to receive a flow of the fluid from the patient, a laser pulse source to provide a laser pulse to the flow of the fluid from a first side of the micro-fluidic device, a probe light source to provide a probe light to the flow from the first side of the micro-fluidic device, and a photodetector located at a second side of the micro-fluidic device opposite the first side. The photodetector can detect scattered, reflected, and/ or deflected probe light and output a nanobubble signal including characteristics of optical scattering, reflecting, and/or deflecting by the transient vapor nanobubble.

18 Claims, 101 Drawing Sheets

(56) References Cited

U.S. PATENT DOCUMENTS

| | | | |
|---|---|---|---|
| 5,341,805 A | 8/1994 | Stavridi et al. |
| 5,377,676 A | 1/1995 | Vari et al. |
| 5,431,170 A | 7/1995 | Mathews |
| 5,436,499 A | 7/1995 | Namavar et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Ai-Ai |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,230,708 B2 | 6/2007 | Lapotko et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |

(56) References Cited

U.S. PATENT DOCUMENTS

| | | |
|---|---|---|
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 7,999,161 B2 | 8/2011 | Oraevsky et al. |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,243,272 B2 | 8/2012 | Adams |
| 8,255,026 B1 | 8/2012 | Ai-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Ai-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,155,497 B1 | 10/2015 | Plumley et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Ai-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |

(56) References Cited

U.S. PATENT DOCUMENTS

| | | |
|---|---|---|
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Ai-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Ai-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |

(56) References Cited

U.S. PATENT DOCUMENTS

| | | |
|---|---|---|
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 12,004,869 B2 | 6/2024 | Kiani et al. |
| 12,014,328 B2 | 6/2024 | Wachman et al. |
| D1,036,293 S | 7/2024 | Al-Ali et al. |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| 12,106,752 B2 | 10/2024 | Campbell et al. |
| 12,114,974 B2 | 10/2024 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2006/0241459 A1 | 10/2006 | Tai |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2008/0247425 A1 | 10/2008 | Welford |
| 2009/0000614 A1 | 1/2009 | Carrano |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0141997 A1 | 6/2009 | Lee et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0304033 A1 | 12/2009 | Ogilvy et al. |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0121163 A1 | 5/2010 | Vestel et al. |
| 2010/0222774 A1* | 9/2010 | Hegg .................. G02B 21/10 |
| | | 606/34 |
| 2010/0234718 A1 | 9/2010 | Sampath et al. |
| 2010/0268042 A1* | 10/2010 | Wang ................ A61B 5/14546 |
| | | 73/587 |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0172508 A1 | 7/2011 | Chickering, III et al. |
| 2011/0176127 A1 | 7/2011 | Kanda et al. |
| 2011/0189701 A1* | 8/2011 | Kim .................... B01L 3/50273 |
| | | 422/69 |
| 2011/0230733 A1 | 9/2011 | Al-Ali |
| 2012/0046593 A1 | 2/2012 | Oraevsky et al. |
| 2012/0069860 A1 | 3/2012 | Inbar |
| 2012/0123231 A1 | 5/2012 | O'Reilly |
| 2012/0165629 A1 | 6/2012 | Merritt et al. |
| 2012/0165801 A1 | 6/2012 | Bragagna et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0012224 A1 | 1/2014 | Zhang |
| 2014/0049190 A1 | 2/2014 | Oh |
| 2014/0120167 A1 | 5/2014 | Lapotko et al. |
| 2014/0163353 A1 | 6/2014 | Razansky et al. |
| 2014/0166076 A1 | 6/2014 | Kiani et al. |
| 2014/0180160 A1 | 6/2014 | Brown et al. |
| 2014/0182385 A1 | 7/2014 | Oh et al. |
| 2014/0187973 A1 | 7/2014 | Brown et al. |
| 2014/0273188 A1* | 9/2014 | Mohan ................ G02B 21/125 |
| | | 422/82.05 |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0072337 A1* | 3/2015 | Lapotko ............... G01N 21/636 |
| | | 435/283.1 |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106121 A1 | 4/2015 | Muhsin et al. |
| 2015/0351841 A1 | 12/2015 | Whiteside et al. |
| 2016/0166185 A1 | 6/2016 | Liepmann et al. |
| 2016/0196388 A1 | 7/2016 | Lamego |
| 2016/0287141 A1 | 10/2016 | Sidlesky |
| 2016/0341747 A1 | 11/2016 | Ewert |
| 2016/0341945 A1 | 11/2016 | Ou et al. |
| 2016/0367173 A1 | 12/2016 | Dalvi et al. |
| 2017/0016827 A1 | 1/2017 | Gervais et al. |
| 2017/0024748 A1 | 1/2017 | Haider |
| 2017/0042488 A1 | 2/2017 | Muhsin |
| 2017/0055896 A1 | 3/2017 | Al-Ali |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0000351 A1 | 1/2018 | Zharov |
| 2018/0103874 A1 | 4/2018 | Lee et al. |
| 2018/0136193 A1* | 5/2018 | Messerschmidt ......... G01J 3/42 |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0326208 A1 | 11/2018 | Ingman et al. |
| 2018/0344228 A1 | 12/2018 | Yelin |
| 2018/0356418 A1* | 12/2018 | Capocasale .......... G01N 33/505 |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |

(56) References Cited

U.S. PATENT DOCUMENTS

| | | |
|---|---|---|
| 2019/0320906 A1 | 10/2019 | Olsen |
| 2019/0345478 A1 | 11/2019 | Lapotko et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0388069 A1 | 12/2019 | Weber et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Ai-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Ai-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |

OTHER PUBLICATIONS

US 2024/0016391 A1, 01/2024, Lapotko et al. (withdrawn)

Anderson et al., "Optically Guided Controlled Release from Liposomes with Tubable Plasmonic Nanobubbles," Journal of Controlled Release, vol. 144, Issue 2, Jun. 1, 2010, in 22 pages.

Brusnichkin et al., "Determination of Various *Hemoglobin* Species with Thermal-Lens Spectrometry," Moscow University Chemistry Bulletin, vol. 64, Issue 1, Feb. 2009, pp. 45-54.

Conjusteau et al., "Metallic Nanoparticles as Optoacoustic Contrast Agents for Medical Imaging," SPIE Proceedings, vol. 6086, Photons Plus Ultrasound: Imaging and Sensing 2006: The Seventh Conference on Biomedical Thermoacoustics, Optoacoustics, and Acousto-optics, Mar. 6, 2006, in 9 pages.

Danysh et al., "The MUCI Ectodomain: A Novel and Efficient Target for Gold Nanoparticle Clustering and Vapor Nanobubble Generation," Theranostics, 2, No. 8, Ivyspring International Publisher, 2012, pp. 777-787.

Lapotko et al., "Clusterization of Nanoparticles During their Interaction with Living Cells," Nanomedicine, vol. 2, No. 2, Apr. 2007, pp. 241-253.

Lapotko et al., "Elimination of Leukemic Cells from Human Transplants by Laser Nano-Thermolysis," SPIE Proceedings, vol. 6086, Photons Plus Ultrasound: Imaging and Sensing 2006: The Seventh Conference on Biomedical Thermoacoustics, Optoacoustics, and Acousto-optics, Mar. 6, 2006, in 8 pages.

Lapotko et al., "Lantcet: Novel Laser Nanotechnology for Graft Purging," Biology of Blood and Marrow Transplantation, Feb. 2006, in 2 pages.

Lapotko et al., "Laser Activated Nanothermolysis of Leukemia Cells Monitored by Photothermal Microscopy,"SPIE Proceedings, vol. 5697, Photons Plus Ultrasound: Imaging and Sensing 2006: The Seventh Conference on Biomedical Thermoacoustics, Optoacoustics, and Acousto-optics, May 5, 2005, pp. 82-89.

Lapotko et al., "Laser Heating Diagnoses and Treats Cancerous Cells," SPIE Newsroom, The International Society for Optical Engineering, 2006, in 3 pages.

Lapotko et al., "Method of Laser Activated Nano-Thermolysis for Elimination of Tumor Cells," Cancer Letters, vol. 239, Issue 1, Jul. 28, 2006, pp. 36-45.

Lapotko, "Monitoring of Apoptosis in Intact Single Cells with Photothermal Microscope," Journal of the International Society for Advancement of Cytometry, vol. 58A, Issue 2, Apr. 2004, pp. 111-119.

(56) References Cited

OTHER PUBLICATIONS

Lapotko, "Optical Excitation and Detection of Vapor Bubbles Around Plasmonic Nanoparticles," Optics Express, vol. 17, Issue 4, Feb. 16, 2009, pp. 2538-2556.

Lapotko et al., "Photothermal and Photoacoustic Processes in Laser Activated Nano-Thermolysis of Cells," SPIE Proceedings, vol. 6437, Photons Plus Ultrasound: Imaging and Sensing 2007: The Eighth Conference on Biomedical Thermoacoustics, Optoacoustics, and Acousto-optics, Mar. 2007, in 13 pages.

Lapotko et al., "Photothermal Detection of Laser-Induced Damage in Single Intact Cells," Lasers in Surgery and Medicine, vol. 33, Issue 5, Dec. 2003, pp. 320-329.

Lapotko et al., "Photothermal Image Cytometry of Human Neutrophils," Journal of the International Society for Advancement of Cytometry, vol. 24, Issue 3, Jul. 1, 1996, pp. 198-203.

Lapotko et al., "Photothermal Response of Live Cells Depends Upon Cell Metabolic State," SPIE Proceedings, vol. 4618, Biomedical Optoacoustics III, Jun. 10, 2002, in 8 pages.

Lapotko et al., "Photothermal Time-Resolved Imaging of Living Cells," Lasers in Surgery and Medicine, vol. 31, Issue 1, Jul. 2002, pp. 53-63.

Lapotko et al., "Photothermolysis by Laser-Induced Microbubbles Generated Around Gold Nanorod Clusters Selectively Formed in Leukemia Cells," SPIE Proceedings, vol. 6856, Photons Plus Ultrasound: Imaging and Sensing 2008: The Ninth Conference on Biomedical Thermoacoustics, Optoacoustics, and Acousto-optics, Feb. 28, 2008, in 10 pages.

Lapotko, "Plasmonic Nanobubbles as Tunable Cellular Probes for Cancer Theranostics," Cancers, vol. 3, No. 1, 2011 pp. 802-840.

Lapotko, "Plasmonic Nanoparticle-Generated Photothermal Bubbles and their Biomedical Applications," Nanomedicine, vol. 4, No. 7, Oct. 2009, pp. 813-845.

Lapotko, "Nanophotonics and Theranostics: Will Light do the Magic?" Theranostics 2013, vol. 3, Issue 3, pp. 138-140.

Lapotko et al., "Nonstationary Heating and Phase Transitions in a Live Cell in Absorption of Laser Radiation," Heat Transfer Research, vol. 38, Issue 8, Jan. 2007, pp. 695-708.

Lapotko et al., "Selective Laser Nano-Thermolysis of Human Leukemia Cells with Microbubbles Generated Around Clusters of Gold Nanoparticles," Lasers in Surgery and Medicine, vol. 38, Issue 6, Jul. 2006, pp. 631-642.

Lapotko, "Therapy with Gold Nanoparticles and Lasers: What Really Kills the Cells?" Nanomedicine, vol. 4, No. 3, Apr. 2009, pp. 253-256.

Lukianova-Hleb et al., "All-in-one Processing of Heterogeneous Human Cell Grafts for Gene and Cell Therapy," Molecular Therapy—Methods & Clinical Development, vol. 3, Article 16012, 2016, in 8 pages.

Lukianova-Hleb et al., "Cell-Specific Multifunctional Processing of Heterogeneous Cell Systems in a Single Laser Pulse Treatment," ACS Nano, vol. 6, Issue 12, Dec. 21, 2012, pp. 10973-10981.

Lukianova-Hleb et al., "Cell-Specific Transmembrane Injection of Molecular Cargo with Gold Nanoparticle-Generated Transient Plasmonic Nanobubbles," Biomaterials, vol. 33, Issue 21, Jul. 2012, pp. 5441-5450.

Lukianova-Hleb et al., "Experimental Techniques for Imaging and Measuring Transient Vapor Nanobubbles," Applied Physics Letters, vol. 101, Dec. 2012, pp. 264102-1-264102-5.

Lukianova-Hleb et al., "Generation and Detection of Plasmonic Nanobubbles in Zebrafish," Nanotechnology, vol. 21, No. 22, Jun. 4, 2010, in 22 pages.

Lukianova-Hleb et al., "Hemozoin-Generated Vapor Nanobubbles for Transdermal Reagent and Needle-Free Detection of Malaria," Proceedings of the National Academy of Sciences of the United States of America, vol. 111, No. 3, Jan. 21, 2014, pp. 900-905.

Lukianova-Hleb et al., "Improved Cellular Specificity of Plasmonic Nanobubbles versus Nanoparticles in Heterogeneous Cell Systems," PLoS One, vol. 7, Issue 4, Apr. 2012, in 10 pages.

Lukianova-Hleb et al., "Intraoperative Diagnostics and Elimination of Residual Micro-Tumours with Plasmonic Nanobubbles," Nature Nanotechnology, 2015, in 31 pages.

Lukianova-Hleb et al., "Influence of Transient Environmental Photothermal Effects on Optical Scattering by Gold Nanoparticles," Nano Letters, vol. 9, Issue 5, May 2009, pp. 2160-2166.

Lukianova-Hleb et al., "Laser Pulse Duration is Critical for the Generation of Plasmonic Nanobubbles," Langmuir, vol. 30, Issue 25, 2014, pp. 7425-7434.

Lukianova-Hleb et al., "Malaria Theranostics Using Hemozoin-Generated Vapor Nanobubbles," Theranostics, vol. 4, Issue 7, 2014, pp. 761-769.

Lukianova-Hleb et al., "Multifunctional Cell Processing with Plasmonic Nanobubbles," International Journal of Medical, Health, Biomedical, Bioengineering and Pharmaceutical Engineering, vol. 7, No. 11, 2013, pp. 677-681.

Lukianova-Hleb et al., "Plasmonic Nanobubbles Enhance Efficacy and Selectivity of Chemotherapy Against Drug-Resistant Cancer Cells," Advanced Materials, vol. 24, Issue 28, Jul. 24, 2012, pp. 3831-3837.

Lukianova-Hleb et al., "Plasmonic Nanobubbles for Intracellular Targeting and Gene Therapy," NTSI-Nanotech 2011, vol. 3, pp. 291-294.

Lukianova-Hleb et al., "Plasmonic Nanobubbles as Transient Vapor Nanobubbles Generated Around Plasmonic Nanoparticles," ACS Nano, vol. 4, Issue 4, Apr. 27, 2010, pp. 2109-2123.

Lukianova-Hleb et al., "Plasmonic Nanobubble-Enhanced Endosomal Escape Processes for Selective and Guided Intracellular Delivery of Chemotherapy to Drug-Resistant Cancer Cells," Biomaterials, vol. 33, Issue 6, Feb. 2012, pp. 1821-1826.

Lukianova-Hleb et al., "Plasmonic Nanobubbles Rapidly Detect and Destroy Drug-Resistant Tumors," Theranostics, vol. 2, No. 10, 2012, pp. 976-787.

Lukianova-Hleb et al., "Plasmonic Nanobubbles for Cell Theranostic," Proceedings of SPIE, 2012, vol. 8234, pp. 82341F-1-82341F-10.

Lukianova-Hleb et al., "Plasmonic Nanobubbles as Tunable Theranostic Agents," NSTI-Nanotech 2011, vol. 3, pp. 367-370.

Lukianova-Hleb et al., "Plasmonic Nanobubbles: Tunable and Transient Probes for Cancer Diagnosis, Therapy and Theranostics," NSTI-Nanotech 2010, vol. 3, 2010 in 5 pages.

Lukianova-Hleb et al., "Rainbow Plasmonic Nanobubbles: Synergistic Activation of Gold Nanoparticle Clusters," Journal of Nanomedicine & Nanotechnology, vol. 2, Issue 104, Jan. 1, 2011, in 21 pages.

Lukianova-Hleb et al., "Safety and Efficacy of Quadrapeutics Versus Chemoradiation in Head and Neck Carcinoma Xenograft Model," American Journal of Cancer Research, vol. 5, Issue 12, 2015, pp. 3534-3547.

Lukianova-Hleb et al., "Selective Gene Transfection of Individual Cells In Vitro with Plasmonic Nanobubbles," Journal of Controlled Release, vol. 152, Issue 2, Jun. 10, 2011, pp. 286-293.

Lukianova-Hleb et al., "Selective and Self-Guided Micro-Ablation of Tissue with Plasmonic Nanobubbles," Journal of Surgical Research, vol. 166, Issue 1, Mar. 2011, pp. e3-e13.

Lukianova-Hleb et al., "Short Laser Pulse-Induced Irreversible Photothermal Effects in Red Blood Cells," Lasers in Surgery and Medicine, vol. 43, Issue 3, Mar. 2011, pp. 249-260.

Lukianova-Hleb et al., "Transdermal Diagnosis of Malaria Using Vapor Nanobubbles," Emerging Infectious Diseases, vol. 21, No. 7, Jul. 2015, pp. 1122-1127.

Lukianova-Hleb et al., "Transient Enhancement and Spectral Narrowing of the Photothermal Effect of Plasmonic Nanoparticles Under Pulsed Excitation," Advanced Materials, vol. 25, Issue 5, Feb. 6, 2013, pp. 772-776.

Lukianova-Hleb et al., "Transient Photothermal Spectra of Plasmonic Nanobubbles," Langmuir, vol. 28, Issue 10, Feb. 2012, pp. 4858-4866.

Lukianova-Hleb et al., "Tunable Plasmonic Nanobubbles for Cell Theranostics," Nanotechnology, vol. 21, No. 8, Feb. 26, 2010, in 19 pages.

Lukianova-Hleb et al., "Tunable Plasmonic Nanoprobes for Theranostics of Prostate Cancer," Theranostics, vol. 1, 2011, pp. 3-17.

(56) References Cited

OTHER PUBLICATIONS

Potkin et al., "The Influence of Heterocyclic Compound-Pamam Dendrimer Complexes on Evoked Electrical Responses in Slices of Hypoxic Brain Tissue," Cellular & Molecular Biology Letters, vol. 19, 2014, pp. 243-248.

Vasiliev et al., "Bubble Generation in Micro-Volumes of 'nonofluids'," International Journal of Heat and Mass Transfer, vol. 52, Issues 5-6, Feb. 2009, pp. 1534-1539.

Choi et al., A High Throughput Microelectroporation Device to Introduce a Chimeric Antigen Receptor to Redirect the Specificity of Human T Cells, Biomed Microdevice, 2010, 12, pp. 855-863.

* cited by examiner

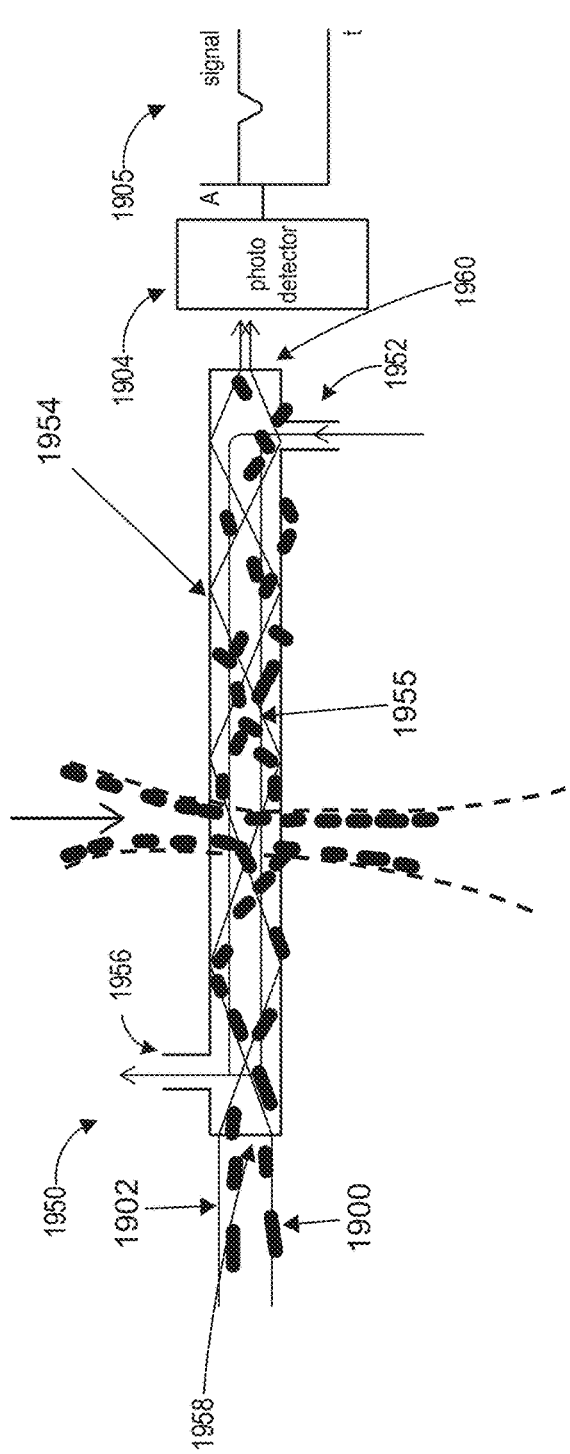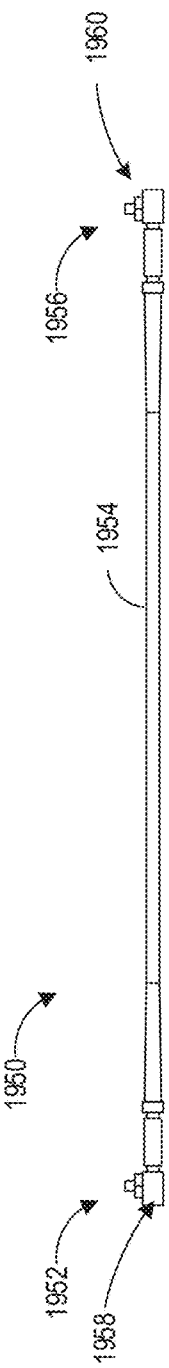
FIG. 19A
FIG. 19B

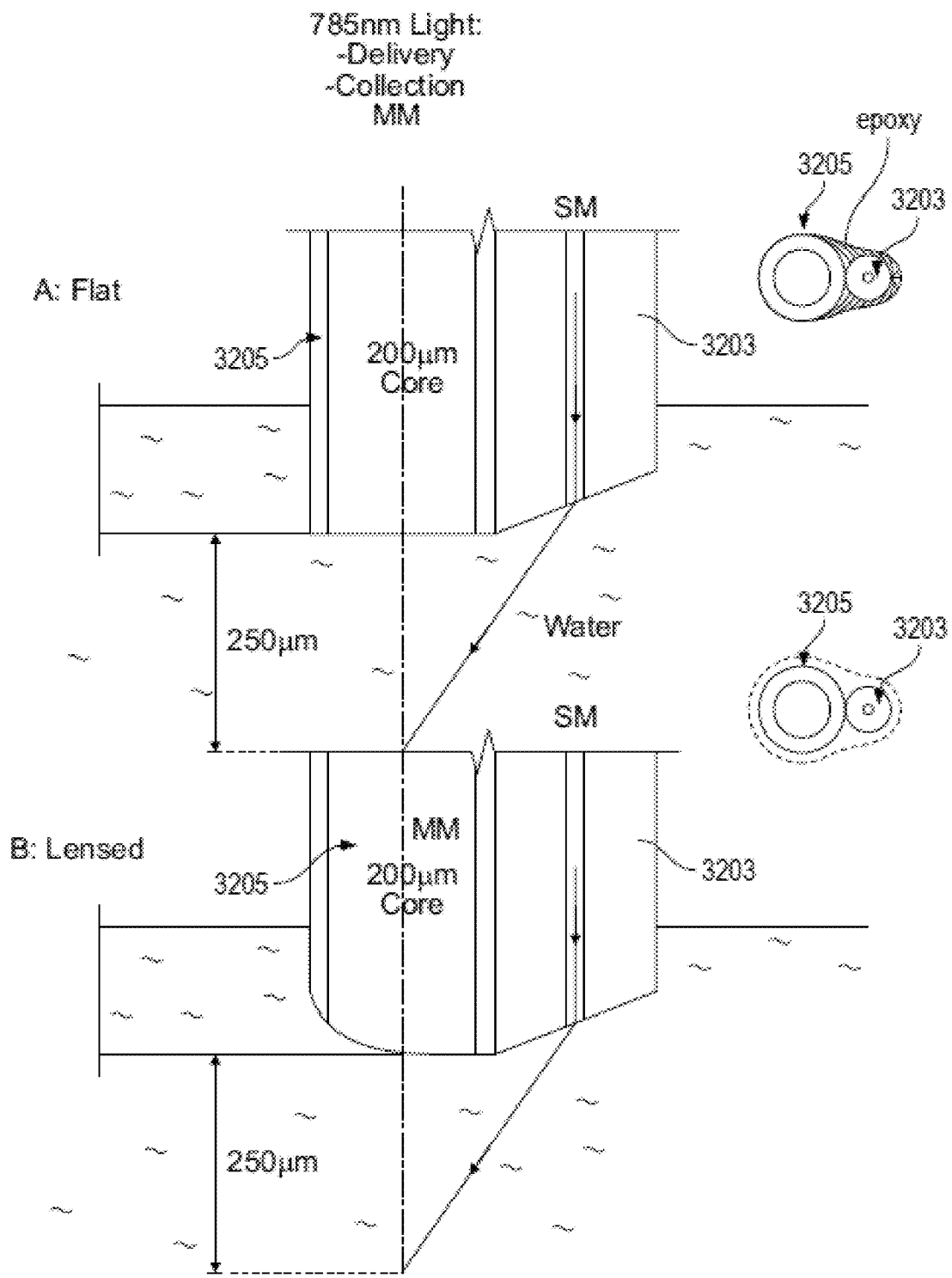
FIGS. 32A-B

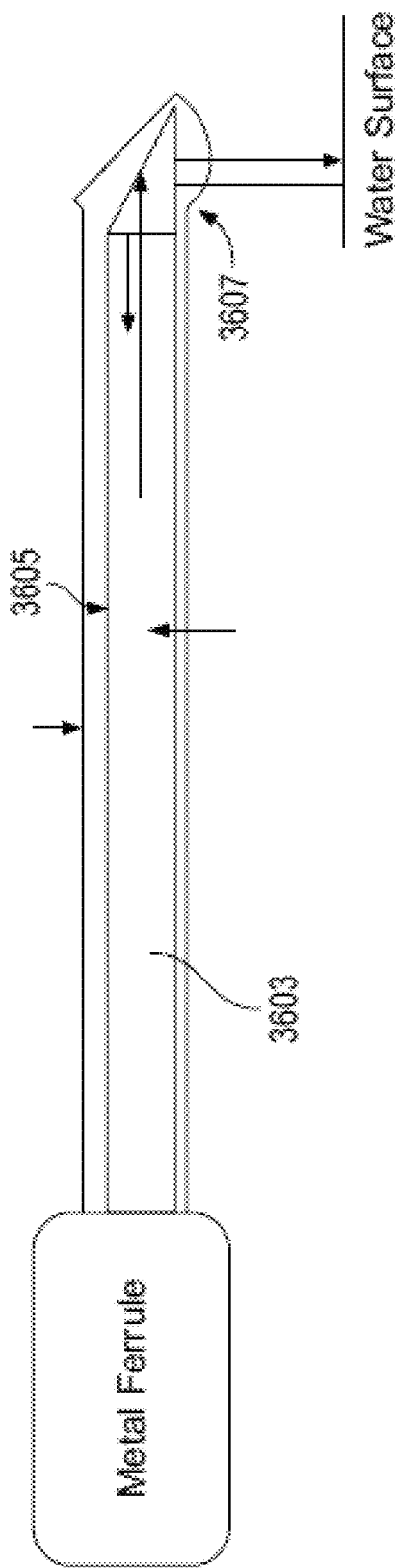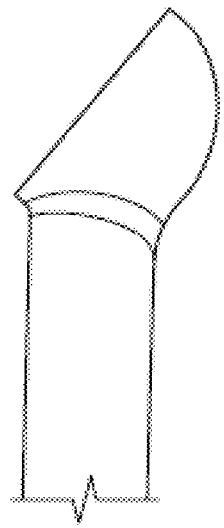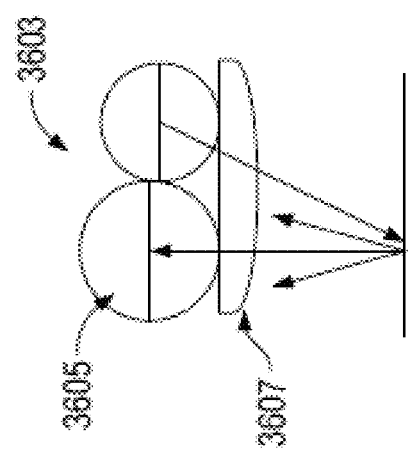
FIG. 36A
FIG. 36C
FIG. 36B

NB optical detection $S_1$
(tight focus)

NB pressure pulse optical $S_2$

NB pressure pulse accoustic $S_3$ $S_1 > S_2 > S_3$

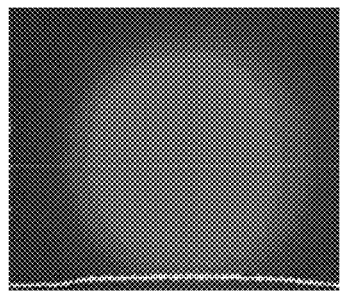
FIG. 43A
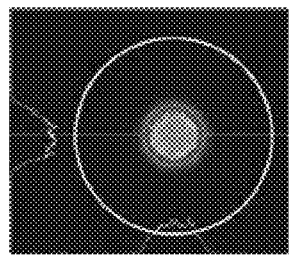 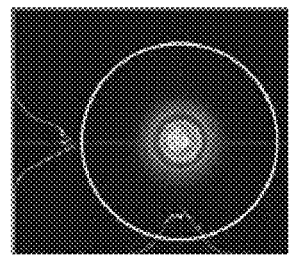
FIG. 43B     FIG. 43C
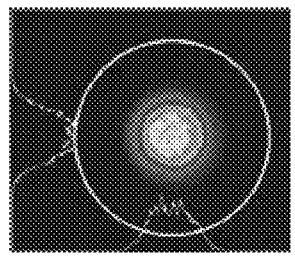 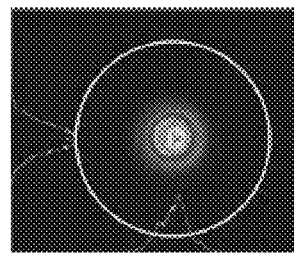
FIG. 43D     FIG. 43E

OPTICAL DETECTION OF TRANSIENT VAPOR NANOBUBBLES IN A MICROFLUIDIC DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The present application is a continuation of U.S. application Ser. No. 16/992,596, filed Aug. 13, 2020, which claims priority benefit under 35 U.S.C. § 119 (e) to U.S. Provisional Application No. 62/888,060, filed Aug. 16, 2019, which is hereby incorporated by reference in its entirety herein.

This application is also related to U.S. application Ser. No. 16/213,923, filed Dec. 7, 2018 and titled "APPARATUS FOR DIAGNOSING AND/OR TREATING MALARIA," and U.S. application Ser. No. 16/829,609, filed Mar. 25, 2020 and title "MINIMALLY INVASIVE MALARIA SENSOR WITH MICRONEEDLE OR OPTICAL CAP," the entirety of each of which are incorporated by reference herein and are part of this disclosure. Many of the embodiments described below are compatible with and can be part of the embodiments described in these related applications. Moreover, some or all of the features described herein can be used or otherwise combined together or with any of the features described in the related applications listed above.

FIELD

The present application relates generally to the fields of detection of malaria parasites in a patient's body, in particular, with the use of laser-induced transient vapor nanobubbles.

BACKGROUND

Malaria is a widespread and infectious disease that can cause serious illness and death in humans. A patient can be infected when a malaria parasite infects cells of the patient, also known as a host. The parasite can produce Hemozoin, which are nanocrystals formed when the parasite digests the hemoglobin in the host's red blood cells. Malaria-infected red blood cells or other body tissue infected by malaria parasites contain Hemozoin nanocrystals.

Current malaria diagnosis techniques include, for example, rapid diagnostic tests (RDTs), microscopy, and polymerase chain reaction (PCR). These diagnosis techniques analyze a patient's blood samples. RDT analyzes the proteins in the blood to look for presence of malaria parasites and is approved by the World Health Organization (WHO). Microscopy uses stain of a thick blood slide, such as with a 200 to 500 white blood cell count, to determine malaria parasite density and gametocyte counts. Microscopy is also WHO-approved for malaria diagnosis. PCR analyzes DNAs in the blood to determine presence of malaria parasites.

Malaria can be treated and/or prevented by administration of antimalarial drugs, such as quinine, chloroquine, atovaquone/proguanil, and others.

SUMMARY

Laser-induced transient vapor nanobubbles can be used to diagnose malaria. The diagnosis can be in a noninvasive, efficient, and/or reproducible manner. The transient vapor nanobubbles can be generated around one or more malaria-specific nanoparticles, that is, one or more Hemozoin nanocrystals (with or without an active malaria parasite) when laser pulses are applied to the nanoparticles. In some embodiments, malaria-specific nanoparticles may also optionally be introduced into the host red blood cells. The laser pulses can cause rapid heating of the malaria-specific nanoparticles, but not of uninfected red blood cells or other host tissues. Liquid (such as water) around the malaria-specific nanoparticles can rapidly evaporate, leading to the generation of a transient vapor nanobubble.

The generation of transient vapor nanobubbles can be detected by optical detectors. A transient vapor nanobubble in a condensed media (such as liquid or skin or their mixture) can act as an optical reflector or scatterer as the vapor-skin boundary creates a relatively high gradient in the optical refractive index in the medium. Throughout the disclosure, scattering of light can refer to the scattering, reflecting, and/or deflecting of light. Therefore, a transient vapor nanobubble can scatter or reflect or deflect an incident (probe) light. The amount of scattered light can be determined by the maximal diameter of the transient vapor nanobubble. That is, the optical energy or power scattered by the transient vapor nanobubble follows the expansion and collapse dynamics of the transient vapor nanobubble. If the light scattered or reflected by such a transient vapor nanobubble is collected and detected as an optical signal, the signal can contain information about the expansion and collapse of the transient vapor nanobubble. A nanobubble-specific optical signal can include a signal time-shape reflecting the expansion and collapse of a transient vapor nanobubble during its lifespan. A transient vapor nanobubble, such as one generated around Hemozoin nanocrystals, can have a lifespan from about 10 ns to about 10 us.

The transient vapor nanobubbles can be generated using a laser pulse that optically excites the Hemozoin (HZ) in a liquid sample (such as blood, in particular peripheral blood, or urine) or skin. The Hemozoin-generated vapor nanobubbles in the liquid sample or the patient's skin can be detected by detecting the optical scattering of the probe light by the vapor nanobubbles. The optical detection examples disclosed herein can detect HZ-generated transient vapor nanobubbles in an optically turbid media (for example, the skin, blood, or otherwise).

In some embodiments, the transient vapor nanobubble-based malaria detection mechanism can detect a single Hemozoin nanoparticle. The transient vapor nanobubble-based optical malaria detection mechanism disclosed herein can be advantageous over the bulk photoacoustic optical scattering mechanism, which requires a large number of Hemozoin nanoparticles and high excitation optical energies to produce a detectable malaria-positive optical signal and may not be sensitive enough to detect a single parasite. In addition, a vapor nanobubble can produce much stronger optical scattering. The optical detection examples disclosed herein can detect Hemozoin-generated transient vapor nanobubbles at any type and/or stage of malaria at which the patient's body contains Hemozoin. The transient vapor nanobubble-based malaria detection mechanism disclosed herein can improve the sensitivity and/or selectivity of the detection of malaria parasites. The transient vapor nanobubble-based malaria detection mechanism disclosed herein can allow detection of malaria via a noninvasive and/or a non-contact manner. That is, the hardware of the optical detection system needs not contact the test sample, such as the patient's skin or a flow of blood.

The optical detection method can have advantages of the acoustic detection method, which is described in U.S. application Ser. No. 16/213,923. Advantage of optical detection over acoustic detection can include higher sensitivity and/or selectivity, lower noise, and/or false-positive signals. However, the optical detection systems and methods disclosed herein may also result in a reduction of the probed volume and therefore require increasing the number of tests in different locations, compared to the acoustic detection of Hemozoin-generated transient vapor nanobubbles.

In some embodiments, a non-invasive malaria sensor can use both acoustic (ultrasonic) and optical detection simultaneously.

A system configured to detect malaria noninvasively can comprise a laser pulse source configured to provide a laser pulse to a measurement site, the laser pulse configured to generate a transient vapor nanobubble around a malaria-specific optically absorbing nanoparticle, if present, located at a depth in the measurement site; a probe light source configured to provide a probe light to the measurement site, the probe light configured to be scattered, reflected, and/or deflected by the transient vapor nanobubble; and a photodetector configured to detect the scattered, reflected, and/or deflected probe light and output a nanobubble signal comprising characteristics of optical scattering, reflecting, and/or deflecting by the transient vapor nanobubble.

In some embodiments, the system can comprise one or more lenses configured to focus the probe light into the measurement site. In some embodiments, the system can comprise a plurality of free-space optics to direct paths of the laser pulse, the probe light, and the scattered, reflected, and/or deflected probe light. In some embodiments, the system can comprise a plurality of optical fibers to direct paths of the laser pulse, the probe light, and the scattered, reflected, and/or deflected probe light. In some embodiments, the laser pulse can be delivered to the measurement site in a multi-mode optical fiber. In some embodiments, the multi-mode optical fiber can have a core diameter of about 100 um to about 200 um. In some embodiments, the probe light can be delivered to the measurement site in a single-mode optical fiber. In some embodiments, the single-mode optical fiber can have a core diameter of about 5 um to about 10 um. In some embodiments, at least one of the optical fibers can comprise a distal tip engineered to concentrate optical energy into the measurement site through a lens, taper, a mirror, or any combinations thereof. In some embodiments, the laser pulse can have a wavelength of 671 nm or 672 nm. In some embodiments, the laser pulse can have a duration of about 300 ps. In some embodiments, the laser pulse can have an energy of about 20 uJ. In some embodiments, In some embodiments, the probe light source can comprise laser. In some embodiments, the probe light can comprise a non-coherent light. In some embodiments, the probe light source can comprise a super luminescent diode. In some embodiments, the probe light can have a wavelength of 1310 or 785 nm. In some embodiments, the characteristics of optical scattering, reflecting, and/or deflecting by the transient vapor nanobubble can comprise a dip or arch shape in the signal responsive to at least a first laser pulse. In some embodiments, the characteristics of optical scattering, reflecting, and/or deflecting by the transient vapor nanobubble can comprise a decay in the signal amplitude responsive to one or more laser pulses after the first laser pulse. In some embodiments, the characteristics of optical scattering, reflecting, and/or deflecting by the transient vapor nanobubble can comprise a malaria-positive threshold calculated based in part on sample-averaged metrics of the signals. In some embodiments, the system can be configured to detect malaria without any hardware of the system contacting the measurement site. In some embodiments, the system can have a sensitivity of being able to detect a transient vapor nanobubble of or smaller than 100 ns in lifetime. In some embodiments, the measurement site can comprise a patient's skin. In some embodiments, the depth can be about 200 um to about 500 um. In some embodiments, the measurement site can comprise a patient's physiological fluid including blood, urine, interstitial body fluid that has been drawn from the patient. In some embodiments, the system further can comprise a static filter for holding the physiological fluid. In some embodiments, the system further can comprise a microfluidic device configured to receive a flow of the physiological fluid.

An optical sensor configured to detect malaria noninvasively can include a laser pulse source configured to deliver a pump laser pulse to a measurement site to excite a malaria-specific nanoparticle at a depth of the measurement site to generate a transient vapor nanobubble around the malaria-specific nanoparticle; a first optical fiber configured to deliver a probe light to be scattered by the transient vapor nanobubble; a second optical fiber configured to collect and direct the scattered probe light; and a photodetector coupled to the second optical fiber at a location proximal to a distal end of the second optical fiber, the photodetector configured to detect the scattered/reflected/deflected probe light and output a nanobubble signal comprising characteristics of optical scattering by the transient vapor nanobubble.

In some embodiments, the sensor can comprise a sensor housing, wherein one or more of the optical fibers are enclosed within the sensor housing. In some embodiments, the sensor can comprise a third optical fiber configured to direct the laser pulse to the measurement site. In some embodiments, the pump pulse delivery optical fiber can be located within a sensor housing. In some embodiments, the third optical fiber can be configured to deliver the laser pulse to the measurement site. In some embodiments, the first or second fiber can be configured to direct the laser pulse to the measurement site. In some embodiments, the second optical sensor can comprise a lensed tip. In some embodiments, the second optical fiber can have a core diameter of about 200 um. In some embodiments, the second optical fiber can comprise a multi-mode fiber. In some embodiments, the first optical fiber can comprise a single-mode optical fiber. In some embodiments, the first optical fiber can have a core diameter of about 5 um. In some embodiments, the first optical fiber can comprise a lensed distal tip. In some embodiments, distal ends of the first and second optical fibers can be at a predetermined angle from each other. In some embodiments, one of the first or second optical fibers can comprise recess cladding to reduce the angle. In some embodiments, distal ends of the first and second optical fibers can run substantially parallel to each other. In some embodiments, the probe light can be emitted by a super luminescent diode. In some embodiments, the first and second optical fibers can comprise front input and front output. In some embodiments, the first and second optical fibers can comprise side input and side output. In some embodiments, the sensor can comprise a lens at an area of optical input and output. In some embodiments, the first and second optical fibers can be aligned such that an input light path and an output light path coincide. In some embodiments, the characteristics of optical scattering/reflection/deflection by the transient vapor nanobubble can comprise a dip or arch shape in the signal responsive to at least a first laser pulse. In some embodiments, the characteristics of optical scattering/reflection/deflection by the transient vapor nanobubble can comprise a decay in the signal amplitude responsive to one or more laser pulses after the first laser pulse. In some embodiments, the characteristics of optical scattering/reflection/deflection by the transient vapor nanobubble can comprise a malaria-positive threshold calculated based in part on sample-averaged metrics of the signals. In some embodiments, the sensor can be configured to detect malaria without contacting the measurement site. In some embodiments, the sensor can have a sensitivity of being able to detect a transient vapor nanobubble of or smaller than 100 ns in lifetime. In some embodiments, the measurement site can comprise a patient's skin. In some embodiments, the depth is about 200 um to about 500 um.

A method of detecting malaria noninvasively can comprise driving a laser pulse source to apply a plurality of laser pulses to a plurality of locations at a measurement site, the laser pulse configured to generate a transient vapor nanobubble around a malaria-specific optically absorbing nanoparticle, if present, located at a depth in the measurement site; driving a probe light source to apply a probe light to the plurality of locations, the probe light configured to be scattered, reflected, and/or deflected by the transient vapor nanobubble; receiving a plurality of optical signals from a photodetector detecting the probe light scattered, reflected, and/or deflected by the transient vapor nanobubble at the plurality of locations; and determining whether the measurement site is malaria-positive by: determining electronically a first signal amplitude or area of each of the plurality of optical signals responsive to a first laser pulse and a subsequent laser pulse at each location; calculating electronically a decay value between the optical signal responsive to the first laser pulse and the optical signal responsive to the subsequent laser pulse at each location; applying a statistical analysis to a distribution of the first signal amplitude or area and the decay value for the plurality of locations; and outputting a malaria-positive diagnosis threshold.

In some embodiments, the decay value can be calculated as a ratio of the first signal amplitude or area to a subsequent signal amplitude or area. In some embodiments, the optical signal can be analyzed in a pre-determined time window. In some embodiments, a ratio of two signal amplitudes or areas can be calculated for two pre-determined time-windows. In some embodiments, one of the plurality of locations can be 1.5 times of a diameter of the laser pulse away from another one of the plurality of locations. In some embodiments, the statistical analysis can comprise determining a preliminary threshold based on the distribution of the first signal amplitude or area and the decay value for the plurality of locations in known malaria-free samples. In some embodiments, the statistical analysis can comprise calculating a probability value of signals from known malaria-positive samples exceeding the preliminary threshold. In some embodiments, the statistical analysis further can comprise determining an amplitude or area threshold and a decay value threshold only for the signals in the known malaria-positive and malaria-free samples that exceed the preliminary threshold. In some embodiments, the statistical analysis further can comprise comparing the probability value, the amplitude or area threshold, and the decay value threshold for the signals from the known malaria-free samples and the signals from the known malaria-positive samples. In some embodiments, the amplitude or area of the signal can be determining after removing a background level.

A system for detecting malaria parasites or Hemozoin nanoparticles in a fluid from a patient, the fluid comprising the patient's blood, urine, interstitial fluid or other physiological liquid, can comprise a micro-fluidic device configured to receive a flow of the fluid from the patient; a laser pulse source configured to provide a laser pulse to the flow of the fluid from a first side of the micro-fluidic device, the laser pulse configured to generate a transient vapor nanobubble around a malaria-specific nanoparticle, if present, located in the patient's blood; a probe light source configured to provide a probe light to the flow from the first side of the micro-fluidic device, the probe light configured to be scattered, reflected, and/or deflected by the transient vapor nanobubble; and a photodetector located at a second side of the micro-fluidic device opposite the first side, the photodetector configured to detect the scattered, reflected, and/or deflected probe light and output a nanobubble signal comprising characteristics of optical scattering, reflecting, and/or deflecting by the transient vapor nanobubble.

In some embodiments, the micro-fluidic device can be connected to a pump with a syringe containing the fluid. In some embodiments, the pump can be configured to pump the fluid at a flow rate of about 0.2 uL/min to about 0.4 uL/min. In some embodiments, the micro-fluidic device can comprise a plurality of micro-cuvettes. In some embodiments, the pump laser pulse and the probe light can be directed to the flow of the patient's blood in the micro-cuvette. In some embodiments, the micro-cuvette can comprise a glass capillary having an inner diameter of about 50 um to about 100 um. In some embodiments, the laser pulse can have a wavelength of about 672 or 671 nm. In some embodiments, the pump laser pulse can have a fluence level of about 100 $mJ/cm^2$ to about 500 $mJ/cm^2$. In some embodiments, the probe light can comprise laser. In some embodiments, the probe light can comprise an incoherent light. In some embodiments, the probe light can be emitted by a super luminescent diode. In some embodiments, the probe light can have a wavelength of about 632.8 or 785 nm. In some embodiments, the probe light can have an energy level of about 1 to 30 mW. In some embodiments, the system can further comprise a single-mode optical fiber configured to deliver the probe light. In some embodiments, the characteristics of optical scattering, reflecting, and/or deflecting by the transient vapor nanobubble can comprise a dip or arch shape in the signal responsive to at least a first laser pulse. In some embodiments, the characteristics of optical scattering, reflecting, and/or deflecting by the transient vapor nanobubble can comprise a decay in the signal amplitude responsive to one or more laser pulses after the first laser pulse. In some embodiments, the characteristics of optical scattering, reflecting, and/or deflecting by the transient vapor nanobubble can comprise a malaria-positive threshold calculated based in part on sample-averaged metrics of the signals. In some embodiments, the system can have a sensitivity of being able to detect a transient vapor nanobubble of or smaller than 100 ns in lifetime.

BRIEF DESCRIPTION OF THE DRAWINGS

Various embodiments are depicted in the accompanying drawings for illustrative purposes, and should in no way be interpreted as limiting the scope of the embodiments. In addition, various features of different disclosed embodiments can be combined to form additional embodiments based on the present disclosure, which are part of this disclosure. Features in the drawings are not necessarily shown to scale.

FIG. 19A illustrates schematically a malaria detection system incorporating an example micro-fluidic device.

FIG. 19B illustrates an example micro-fluidic device of the system of FIG. 19A.

FIGS. 32A-34 (not drawn to scale) illustrate schematically example optical detection systems (sensors) with two vertical optical fibers.

FIG. 43A illustrates an example beam profile image exiting an optical fiber with the numerical aperture (NA) of 0.22.

FIGS. 43B-43E illustrate example pump laser beam profiles out of the optical fibers of different lengths and NAs when the example fiber mating device is used.

DETAILED DESCRIPTION

Figure 41:
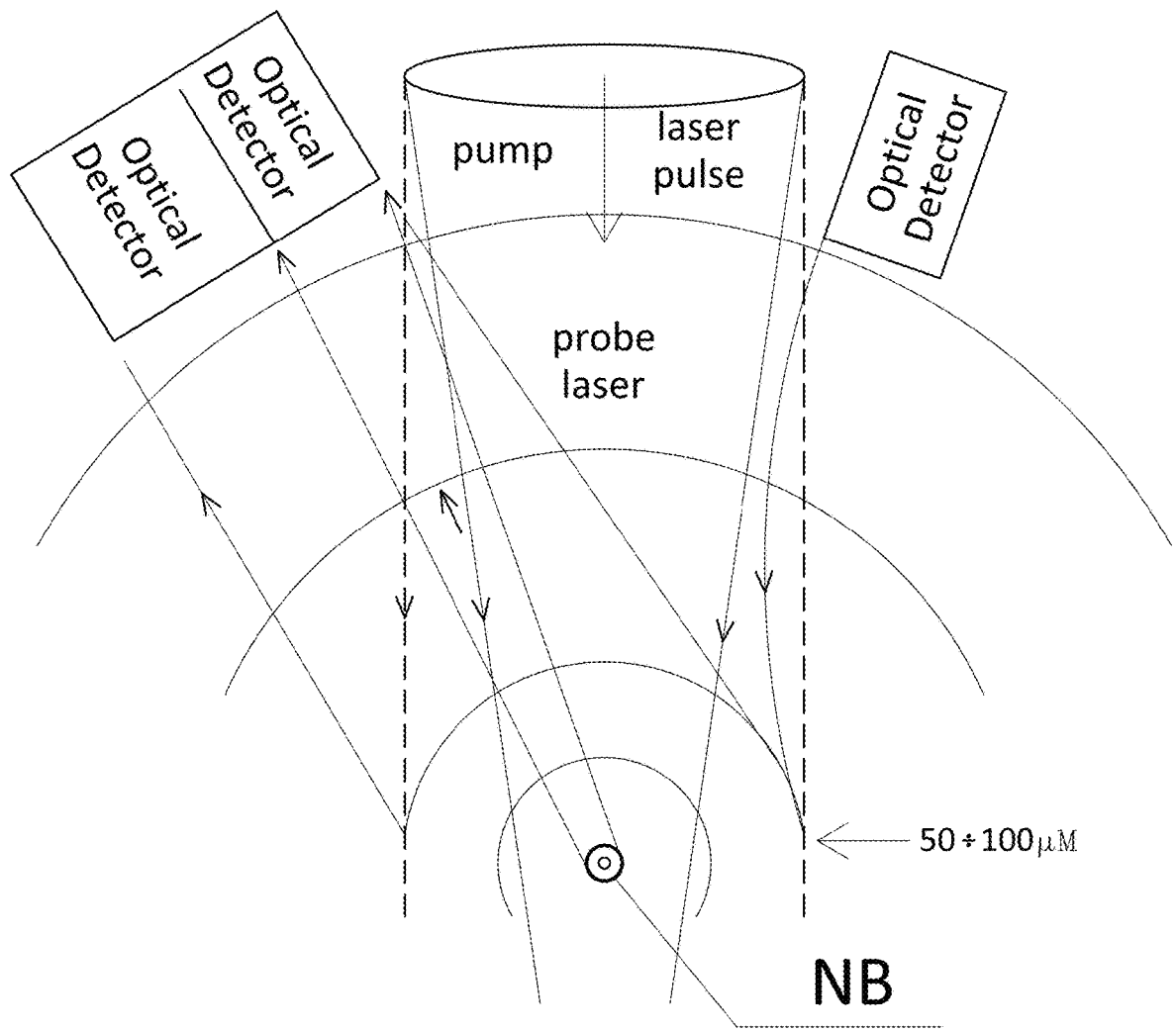
FIG. 41 illustrates schematically detection of a transient vapor nanobubble using optical scattering, reflecting, and/or deflecting detection (S1), and pressure pulse based optical (S2) and acoustic (S3) detections.

Overview of Example Systems and Processes of Detecting Transient Vapor Nanobubbles by Optical Detection A transient vapor nanobubble, such as a Hemozoin-generated vapor nanobubble, may be detected by detecting the optical scattering, reflecting, and/or deflecting by the vapor nanobubble (Signal S1 in FIG. 41), and/or by detecting pressure pulse of the vapor nanobubble, such as using optical detection methods (Signal S2 in FIG. 41), and/or using acoustic detection methods (Signal S3 in FIG. 41). The pressure pulse of a vapor nanobubble is the strongest near a parasite. This is where the highest sensitivity in the detection of parasite can be achieved. However, with acoustic detection, the probe cannot be brought to the site of the parasite (inside the skin). As a result, the remote detection of the acoustic pulse of the vapor nanobubble, as shown in FIG. 41, results in a relatively weak signal S3.

An optical detection of pressure gradients of acoustic waves generated by the vapor nanobubble is based on the related changes of optical refractive index of the skin as the acoustic pulse from a vapor nanobubble propagates through the skin. When a transient pressure gradient travels through the optically probed volume, the optical scattering of the pressure pulse will change due to the change in pressure-dependent optical refractive index. On the detector end, such change can produce a signal S2, which is a deviation from a baseline. S2 can be stronger than S3.

However, a better (stronger) signal S1 can be obtained through the direct optical detection of the vapor nanobubble: its vapor (inside a nanobubble)-skin (outside nanobubble) boundary scatters, reflects, and/or deflects the light much stronger than the acoustic wave. This is because such a boundary creates a stronger gradient of the optical refractive index than the gradient created by the acoustic waves (generated with any opto-acoustic method). Hence, the direct optical detection of a Hemozoin-generated vapor nanobubble can be a more sensitive approach for the malaria detection than the pressure pulse based detection methods. Since the excitation (pump) laser pulse can be delivered to a parasite, a continuous probe laser beam can also be delivered to the same parasite. A portion of the probed laser beam will be backscattered (including scattering, reflecting, and/or deflecting). The backscattered component, collected with a high numerical aperture (NA) lens, can be depth-specific so that it is possible to analyze the light backscattered within a specific focal volume (including a specific skin depth range). This backscattered light creates a baseline. A vapor nanobubble can enhance the optical scattering and produces a specific time-response signal. The present disclosure is related to the direct optical detection method of malaria.

Figure 1A:
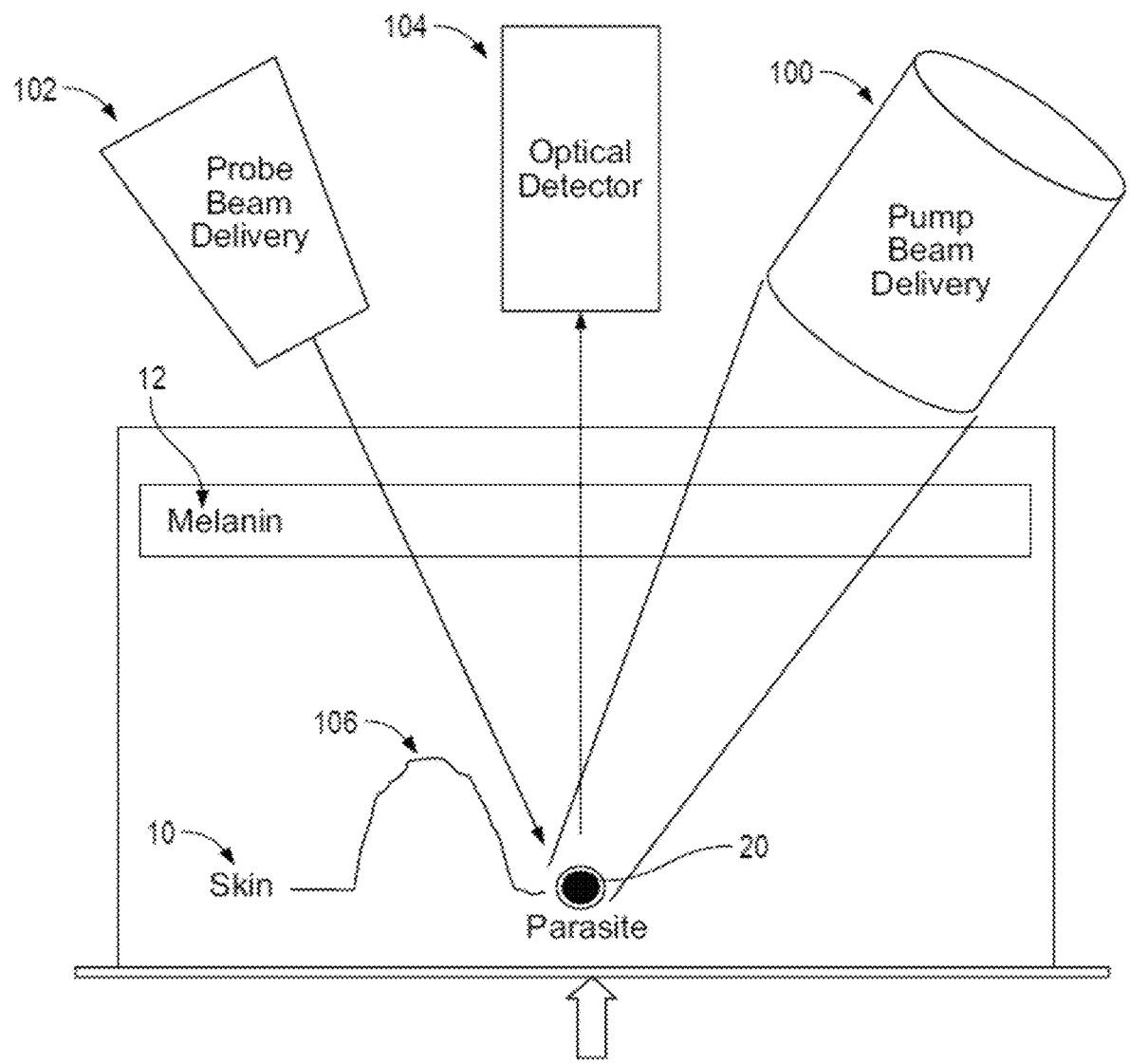
FIG. 1A illustrates schematically an example system of detecting a Hemozoin-generated vapor nanobubble using optical detection.

FIG. 1A illustrates schematically a malaria sensor, which can include a system for optically detecting a Hemozoin-generated vapor nanobubble. The system can have an optical source for providing a pump beam 100, which can include laser pulses (such as descried in U.S. application Ser. No. 16/213,923) to a test site, which can be a patient's skin tissue 10. As described above, the test site can also include a fluid (such as blood or urine or saliva or interstitial fluid) sample. As illustrated in FIG. 1A, the skin is not an optically transparent media. The skin is an optical turbid and absorbing media, for example, including at least a layer of melanin 12. The fluid sample, such as a blood sample, may also be optically turbid, such as due to the presence of the red blood cells.

If the skin tissue 10 is or has been infected by malaria parasites, the skin tissue 10 can contain the malaria parasite 20 or Hemozoin nanocrystals. The pump beam 100 can generate a transient vapor nanobubble around the parasite 20 or the Hemozoin nanocrystals. The pump beam can optionally be applied in sequence (in a series of pulses) to the skin tissue 10.

The system can have a second optical source to produce a probe beam 102, which may be another laser beam (continuous or pulsed), or a non-coherent light generated by a light-emitting diode, or otherwise. The probe beam 102 can be directed to the same location where the pump beam has been directed in the skin 10. An optical detectors 104, such as a photodetector, can be configured to detect the probe beam 102 scattered by the transient vapor nanobubble through the optical elements that collect the probe light scattered by Hemozoin-generated vapor nanobubble (HVNB). When a probe beam 102 is delivered to the skin, there can be a plurality of sources of optical scattering, which can include, for example, background scattering by the skin tissue, scattering by acoustic waves in tissue (which may be in different densities and therefore resulting in different pressure-induced gradients of refractive index), and/or optically scattering by the Hemozoin-generated vapor transient nanobubble. The boundary between the Hemozoin-generated vapor transient nanobubble and the tissue can result in a refractive gradient that causes an optical scattering in a stronger way than acoustic waves or thermal fields. The system disclosed herein can detect the optical scattering by the Hemozoin-generated vapor transient nanobubble in the skin.

The probe beam 102 can have a wavelength (for example, in the near-infrared region or otherwise) so as to penetrate through a certain depth of the skin (for example, up to 1 mm). The diameter of the probe beam 102 can be kept small, as will be described below, (thereby making the probe beam more focused) to improve the sensitivity of the optical detection system. A more focused probe beam with a more restricted focal volume, when optically coupled (that is, projected) into the plane of the optical detector, can help to reject all or substantially all of the scattering effects coming from outside of the focal volume. This can improve the selectivity of the HVNB detection in presence of a photothermal and photoacoustic background not related to malaria parasites and HZ, allowing such background to be spatially separated from the focal volume of the optical system.

As the delivery and collection of probe beam or light 102 occurs in a highly optically turbid and scattering medium, that is, the skin or blood, with significant losses in both illumination and collection optical paths, the medium can result in an optical noise in the optical signal. A combination of optical power in the probe beam sufficient to penetrate to and from the skin (such as in the order of milliwatts) with reduction in noise at both the light source and the optical detector can help to improve the signal-to-noise ratio and/or improve detection of nanobubble-induced deviation of the signal from its baseline, which is formed by the optical scattering by the skin tissue within the focal volume.

The system can have one or more signal processors and/or controller in electrical communication with the optical sources and/or the optical detector 104. The one or more signal processors can process optical signals 106 from the optical detector 104 to determine if the signals are indicative of transient vapor nanobubble(s) generation and thus for the presence of Hemozoin nanocrystals.

Figures 1B, 1C:
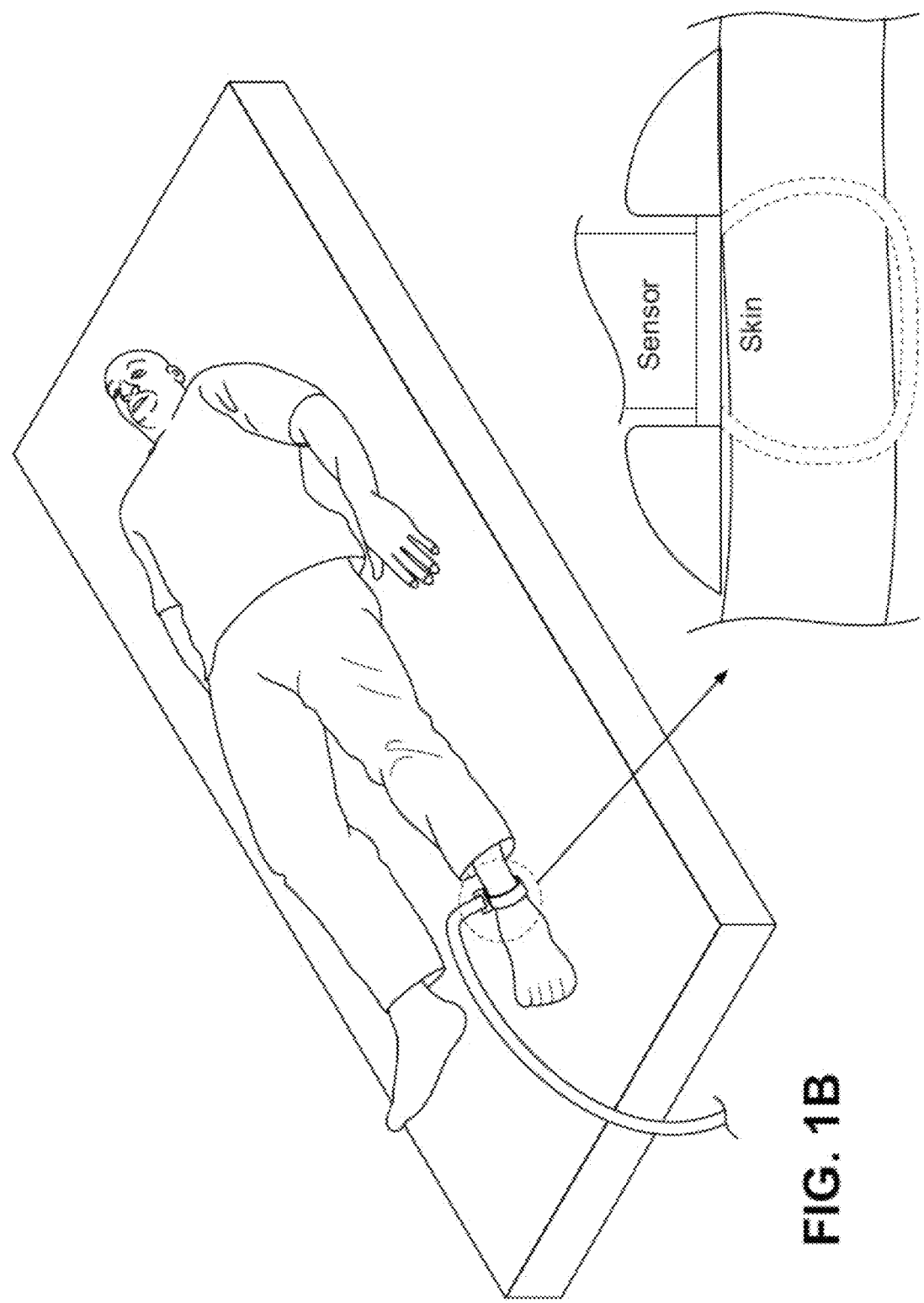
FIG. 1B illustrates schematically an example malaria sensor being used on a patient.
FIG. 1C illustrates schematically a view of an example malaria sensor being attached to a skin of a patient.

As shown in FIGS. 1B and 1C, the malaria sensor disclosed herein may be applied to a patient at a diagnostic location. Although the measurement site is illustrated as the ankle in FIG. 1B, the measurement location can vary, for example, at or near the ankle, hand, base of the tongue, or at any other suitable locations. The sensor can include an interface layer with the patient's skin at the measurement location. The interface layer can provide optical coupling between the malaria sensor and the patient's skin. In some embodiments, the interface layer can include an optically transparent and/or biologically safe material, such as optically transparent silicone resin (for example, Dowsil 1184 or Mastersil 151). The interface layer can be made of a conformable material to improve contact between the sensor and the skin. Such interface layer can provide about very high, for example, 99% optical transmission for the pump and probe beams at their respective wavelengths, and very high, for example, 90% acoustic transmission in the frequency range 1 KHz-50 MHz. Further, such interface layer can be in an optical and acoustic contact with both the skin surface and the sensor. The interface layer can be designed as a thin membrane (for example, about 10-200 um thick) or as a thicker layer up to several millimeters.

The sensor can be temporarily attached to the patient at the measurement site via any suitable coupling mechanisms, including but not limited to an elastic bracelet, straps, adhesives, clamps, suction device, and/or the like. The attachment can optionally include a reversible locking mechanism. The attachment can be different for various anatomical locations. The sensor and/or the sensor and the interface layer can be reusable. The temporarily attachment mechanism can optionally be a single use component. In some embodiments, the temporary attachment can allow the sensor to be used without an operator holding onto the sensor to maintain the contact and/or optical coupling between the sensor and the skin. The attachment can provide a pressure between the skin surface and the sensor, for example, in the range of about 10-200 grams. The attachment of the sensor and signal collection can be performed within 0.1-5 minutes, or within 1-2 minutes.

The malaria sensor may optionally have a sensor casing. The casing can make the sensor for durable, more suitable for repeated use, and/or protect the components of the sensor from the elements, infection, electromagnetic interference, and/or others. The casing can include a relieve for optical and/or electrical cables.

Figure 2A:
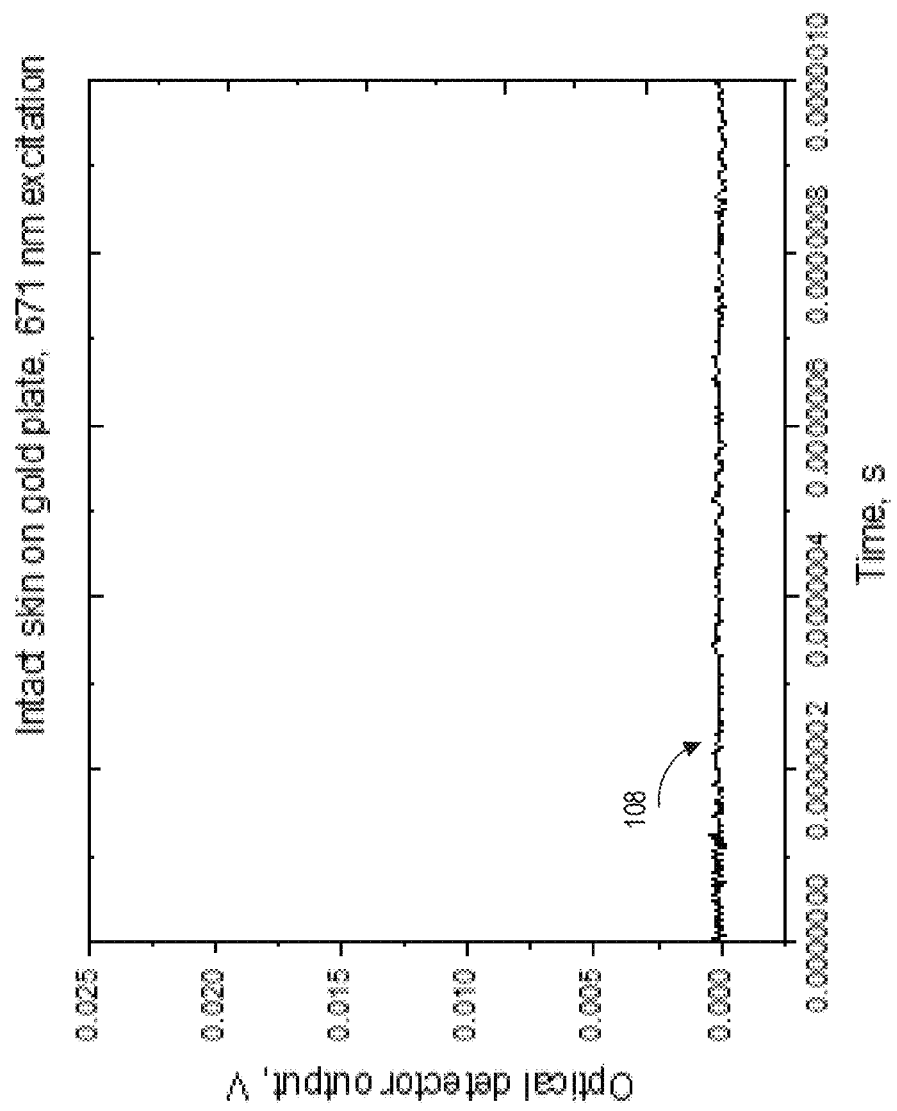
FIG. 2A illustrates an example optical signal from a malaria-free skin sample.
Figure 2B:
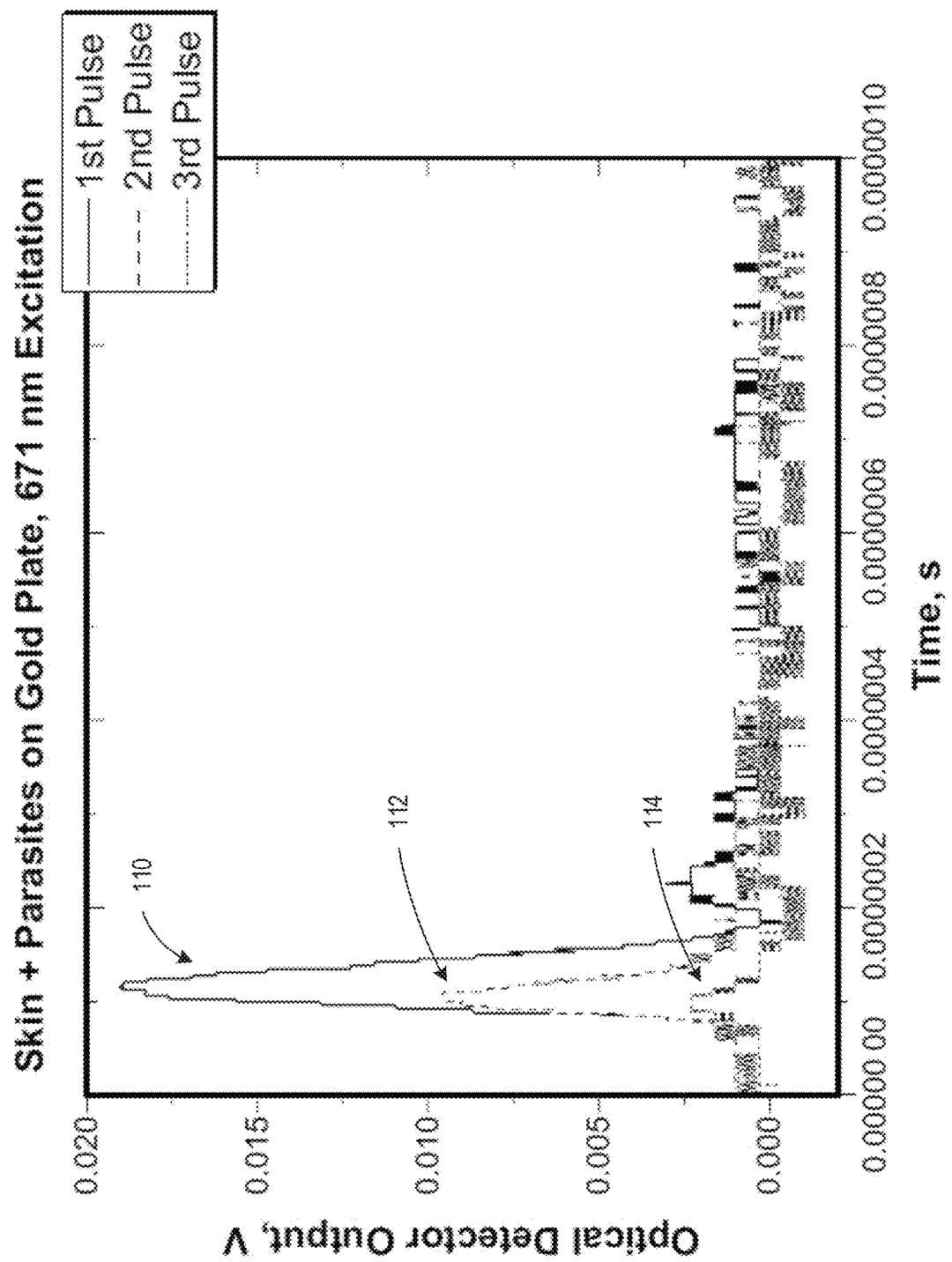
FIGS. 2B-2D illustrate example optical signals from malaria-positive skin samples.

FIGS. 2A-2D illustrate example signals that may be obtained using systems for optically detecting Hemozoin-generated vapor nanobubbles that implement the general setup as illustrated in FIGS. 1A-1C. As shown in FIG. 2A, when the test site was a malaria-free (intact) human skin sample and the pump beam was a laser pulse with a wavelength of 671 nm and an energy of 20 uJ (or the energy in the range 10-50 uJ), the optical signal 108 responsive to a first laser pulse was relatively flat. This baseline was formed from the optical scattering by the skin tissue within the focal volume of the probe beam. The signal 108 was relatively flat because no transient vapor nanobubble is generated to scatter the probe beam. In contrast, as shown in FIG. 2B, when the same pump beam (with a wavelength of 671 nm and an energy of 20 uJ) was directed toward a skin sample with malaria parasites in three subsequent pulses, the first 110, second 112, and third 114 signals, responsive to the first, second, and third pulses respectively, showed nanobubble-specific spikes of arch shapes. The nanobubble-specific time shape of the optical signal (that is, the arch shape which represents the expansion and collapse of a transient vapor nanobubble) can be used to detect Hemozoin-generated transient vapor nanobubbles in the background of other non-malaria, photo-thermal and/or and photoacoustic effects induced in skin by the excitation laser beam or the pump beam.

Figure 2C:
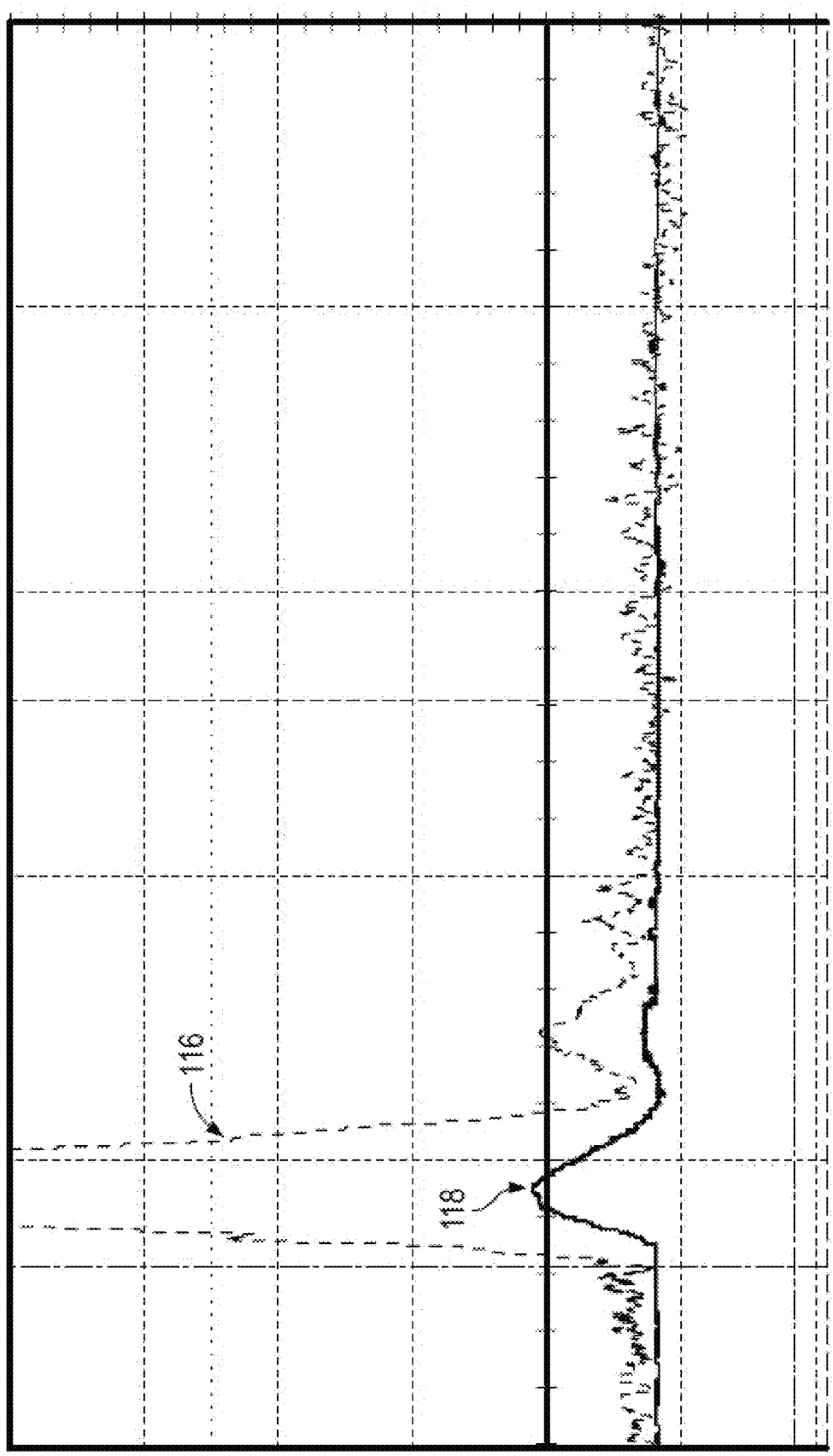

The signals 110, 112, 114 also showed decay in the amplitude of the malaria-specific signal spike after each consecutive laser pulse. Additional details about the example optical signals are provided below. FIG. 2C illustrates another example of applying two consecutive pump beam pulses at a human skin sample with malaria parasites. A nanobubble-specific spike is shown in the signal 116 responsive to the first pulse and a decay in the amplitude of the spike is shown in the signal 118 responsive to a second pulse.

Figure 2D:
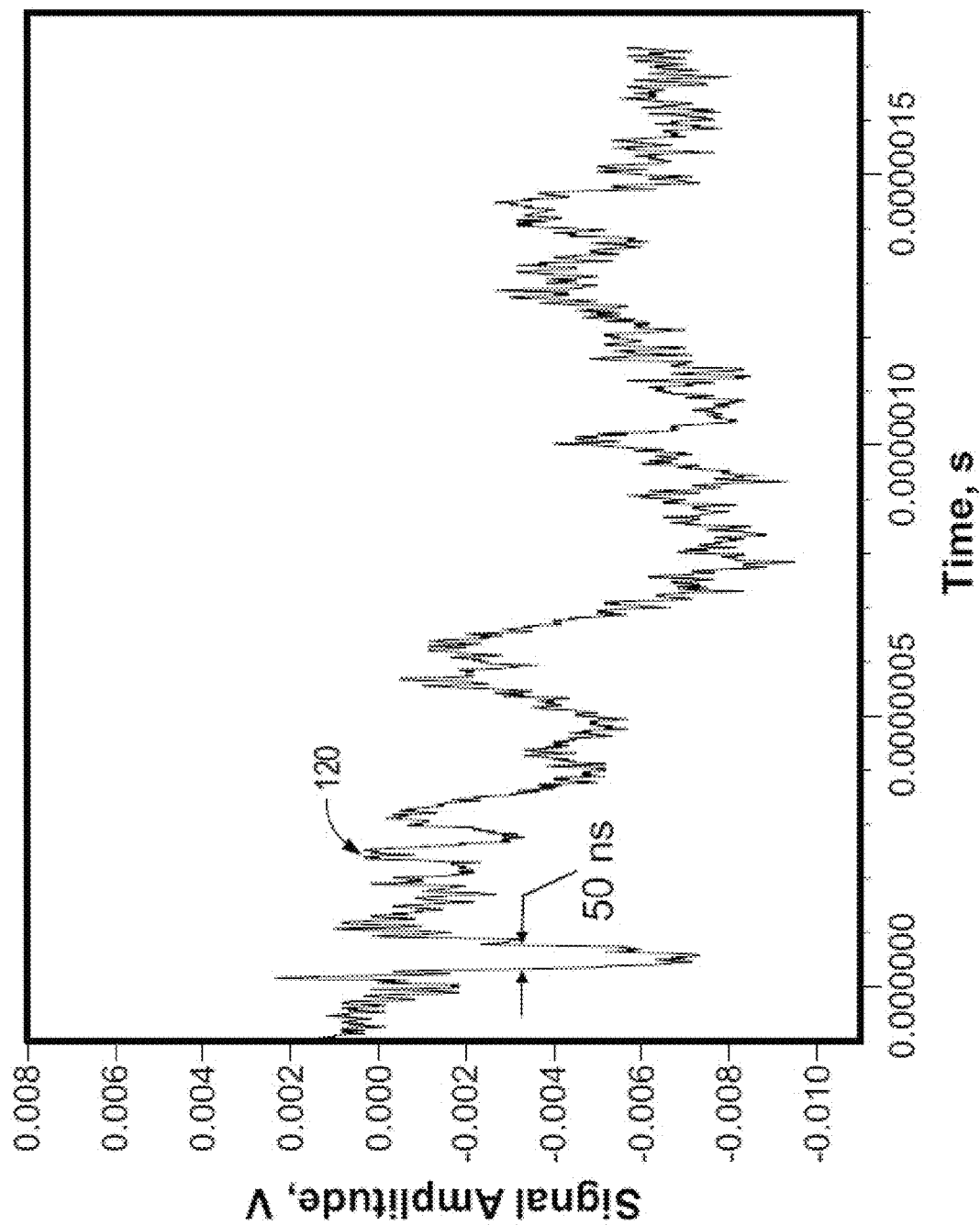

Turning to FIG. 2D, it can be observed from the optical signal 120 that a lifespan of a detectable Hemozoin-generated vapor nanobubble can be as small or as short as between about 20 ns to about 100 ns, or between about 50 ns to about 70 ns, or about 50 ns. The size (that is, lifetime) of optically detected transient vapor nanobubbles can be smaller than the acoustically detected nanobubbles. For example, the optically detected transient vapor nanobubbles can have a lifetime of about less than 0.1 us, whereas the acoustically detected nanobubble can have a lifetime of about 0.8 us to about 1.0 us as shown in U.S. application Ser. No. 16/213,923. A skilled artisan can appreciate based on the present disclosure that alternative parameters can be used in additional embodiments.

A combination of lenses (free space or combined with fiber optics) can be used to optically match the location of the skin volume of the transient vapor nanobubbles generation to the optical detector can improve the detection sensitivity of the Hemozoin-generated transient vapor nanobubbles and the rejection of the background photothermal effects. As will be described in greater detail below with reference to FIG. 3D, the signal may be more easily detected or stronger at the skin surface above the location of the transient vapor nanobubble generation. The lenses can direct the pump beam and the probe beams to the target location and/or direct the scattered probe beam to the optical detector. The pump beam and the probe beam can be delivered to the skin without a mechanical contact of the hardware with the skin (or blood), and the probe light scattered by the vapor nanobubbles in skin can also be collected in a non-contact manner. The optical detection system can also include a pair or more optical fibers for delivering the pump beam and probe beam to the target location and collecting the scattered probe beam from the target location, such as shown in FIGS. 32A-32B, 33-35, 36A-36C, 37, and 38, which will be described in greater detail below.

The pulsed pump beam and the probe beam can have different wavelengths. In some embodiments, the pump beam 300 can have a wavelength of about 671 nm or about 672 nm. In some embodiments, the probe beam can have a wavelength of about 1300 nm to about 1310 nm, or about 600 nm to about 1,000 nm, or about 700 nm to about 900 nm, or about 660 nm, or about 930 nm, or about 1310 nm. A skilled artisan can appreciate based on the present disclosure that alternative parameters can be used in additional embodiments. The probe beam wavelength can be selected so as to more easily propagate in the skin (or less attenuation) and to be closer to the excitation or pump beam wavelength to simplify management of hardware. The probe beam can be delivered constantly and/or in a train of pulses for periodic illumination. The laser pulses for Hemozoin-generated vapor transient nanobubble generation can be in the scale of nanoseconds or picoseconds. The signals relevant for detecting presence of malaria can therefore be significantly less affected or substantially unaffected by motion artefacts. In some embodiments, the probe beam can be emitted by an LED (that is, being non-coherent).

In some embodiments, the skin-specific focusing of the pump beam can be to a depth range of about 200 um to about 600 um to achieve an optical excitation volume having a diameter of about 20 um to about 100 um and/or a depth of about 20 um to about 500 um. In some embodiments, the skin-specific focusing of the probe beam can be to a depth range of about 100 um to about 500 um to achieve an optical detection volume having a diameter of about 5 um to about 50 um and/or a depth of about 100 um to about 500 um. Such an optical detection volume can be more optimal in rejecting potential false-positive signals generated by the photo-thermal or photoacoustic responses of non-malaria components in skin, such as melanin or otherwise. A skilled artisan can appreciate based on the present disclosure that alternative parameters can be used in additional embodiments.

To detect malaria parasites in skin, a sufficient number of skin locations may need to be probed, for example, up from 2-3 to several hundreds, to scan the total volume of skin from about 0.01 $uL^3$ to about 1 $uL^3$. The required scanning can be done through the optical scanning of the pump and probe beams across the sample (such as the skin or liquid surface). The scanning may be also performed mechanically by shifting of the probes temporarily and operably attached to the sample.

Examples of Optical Delivery

The delivery of the pump beam and the probe beam in an optical detection system can be configured to reduce background skin optical noise (such as due to melanin). The delivery of the pump beam and the probe beam can minimize the optical fluence and the associated thermal impact of the background (for example, the melanin located at the upper level of the skin) and/or maximize the optical fluence at the depth of parasites. The probe beam can be focused. The probe beam can also be launched at an angle to the skin surface, with the pump beam angled from one side and the probe beam angled from an opposing side, so that the background skin volume is spatially decoupled from the skin volume with Hemozoin and/or parasites.

The background source, such as the melanin, is usually located in the upper skin layer, whereas the parasites are usually located about 100 um to about 500 um deeper in the upper skin layers. Although the melanin layer still produces some photo-thermal and/or photoacoustic background signals, the source of such background signal is shifted away from the axis of the detection of the transient nanobubble signal. The amplitude of the background signal can also be reduced due to a reduced optical fluence of the pump beam, that is, the excitation laser beam, at the level of the melanin layer.

Such spatial decoupling of the target (Hemozoin) and background (melanin) was validated in dark human skin (rich with melanin) and human parasites placed at the depth of about 250 um to about 300 um below the skin surface. The improvement in the side and focused launch of the pump beam compared to the standard fiber launch from substantially directly above the probe beam, can include an about 3 fold (such as a 3.2 fold) suppression of the background signal amplitude, and/or an about 2 fold (such as 1.8 fold) increase in a second spike with amplitude indicative of Hemozoin-generated transient vapor nanobubble.

Figure 3A:
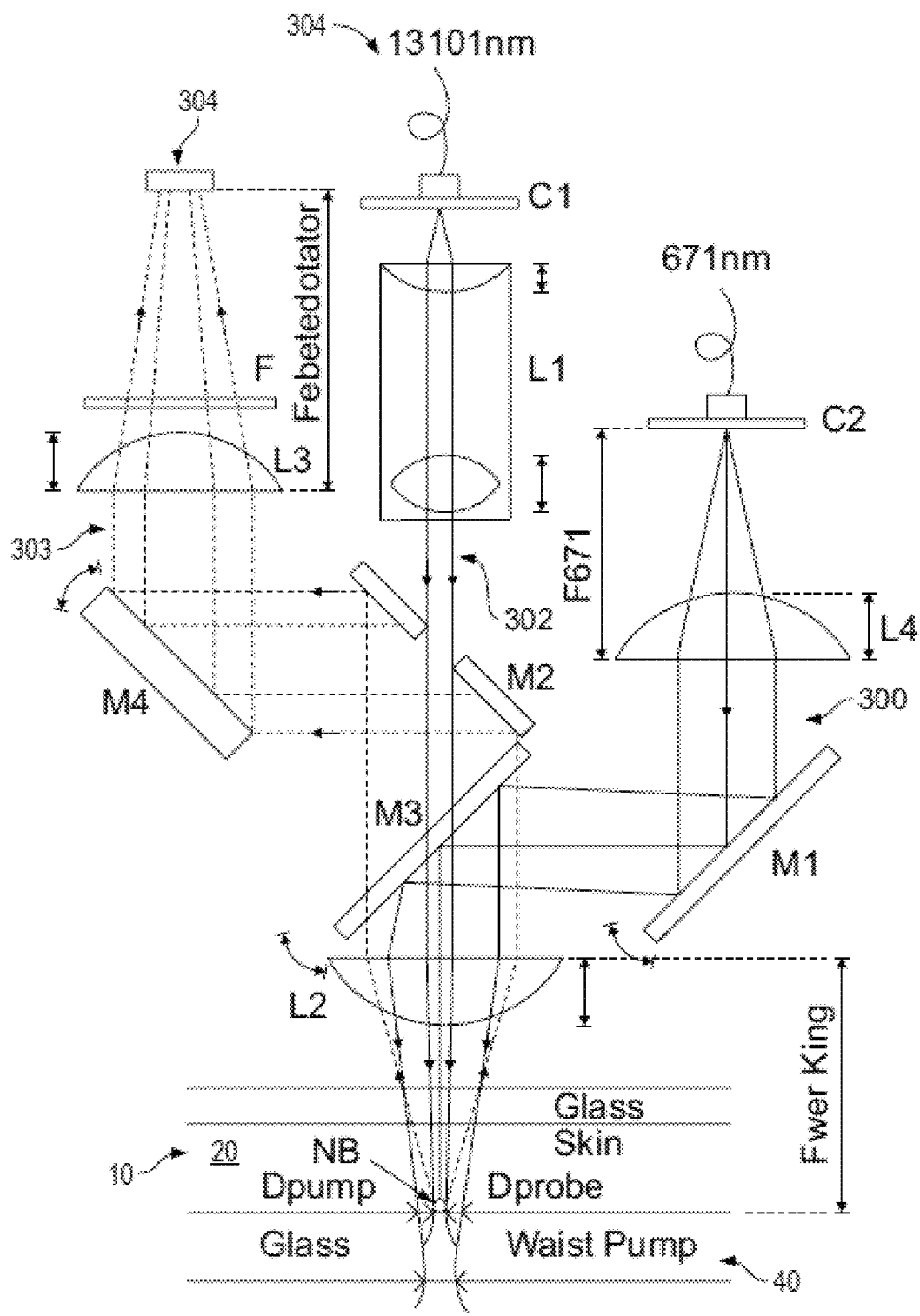
FIGS. 3A-3C illustrate schematically an example free-space optics setup for optically detecting a Hemozoin-generated transient vapor nanobubble.

An embodiment of the optical detection system disclosed herein can include free-space optics, fiber optics, and/or a combination of fiber optics and free-space optics. FIG. 3A illustrates schematically the optical paths between the various optics. The optics can include the lenses L1, L2, L3 for delivering the pump beam 300 and the probe beam 302, and the optical detector 304 respectively.

In some embodiments, the pump beam 300 path can optionally be delivered by an optical fiber (for example, a multimode fiber) connected to an FC/PC connector C2. The optical fiber for delivering the pump beam or pump laser pulse 300 can include a step index optical fiber. The pump beam optical fiber can have a core diameter of about 60 um to about 200 um. The selected core diameter can reduce optical damage to the pump beam fiber. An input optical coupler (that is, coupling lens(es)) can be defocused so the optical fiber tip is placed past the pump beam waist and receives a diverging beam. The pump beam diameter can be about 80% of the pump beam optical fiber core diameter when the pump beam 300 enters the optical fiber. Optionally, high-energy ferrules with air gap around the fiber tip can also be included.

Additionally, so called "hot spots" in the pump beam can cause additional false-positive signals generated by melanin. These hot spots can be suppressed to improve the optical delivery. The pump beam optical fiber, which can be a mulita-mode optical fiber, can have an increased length of about 12 m from about 1-2 m, which may improve homogenizing of the pump beam intensity profile at the fiber output so as to reduce hot spots in the pump beam. Additional details of the "hot spots" are described in U.S. application Ser. No. 16/213,923.

The pump beam 300, upon exiting the optical fiber, can travel though Lens L4 and be deflected to Lens L2 by the mirrors M1 and M3. Lens L4 can be a collimator configured to output the pump beam 302 as parallel collinear beams. The diameter of the pump beam 300 can be between about 40 um to about 50 um before arriving at the mirror M1. The mirror M1 can be a pump beam mirror. The mirror M3 can be a beam-mixing mirror. At the skin entrance plane, that is, after being deflected by the mirror M3, the diameter of the pump beam 300 can be about 150 um to about 200 um. Lens L2 can be a working lens that re-focuses the pump beam 300 to the target site, for example, where the parasite and/or Hemozoin is located, in the skin 10. Lens L2 can be a condenser lens. Lens L2 can be also an aspheric lens. If the malaria parasite and/or Hemozoin are present in the skin 10, a transient vapor nanobubble 20 can be generated. The pump beam can be focused at about 40 mm under a surface of the target site, such as when the target site is water.

In some embodiments, the probe beam 302 path can travel along another optical fiber. The optical fiber coupled to the probe beam 302 can include, for example, a single mode fiber with a core diameter of about 9.5 um (or from about 4 um to about 10 um), via the FC/PC connector C1. Upon exiting the single mode optical fiber, the probe beam 302 can travel though Lens L1, an opening in the mirror M2, and Lens L2. Lens L1 can be a probe beam collimator that can output the probe beam 302 as parallel collinear beams. Lens L1 can have an adjustable focal distance. The working Lens L2 can focus the probe beam 302 to the target site 20. If the vapor transient nanobubble has been generated, the nanobubble can scatter the probe beam 302 as described above. The probe beam 302 path can be adjusted through Lens L1 and the vertical position Z of the optical detection system.

The illumination of the volume in the test sample, such as in the skin or liquid, by the probe beam 302 can be increase or maximized to improve detection sensitivity. This can be achieved by focusing the probe beam 302 using the working Lens L2 and by positioning Lens L2 at a specific distance from the skin or liquid surface so that its focus is set at the depth of about 250 um to about 500 um, where parasites and Hemozoin are expected in the skin. The working focal distance, which can be from the vapor transient nanobubble to a flat surface of the working Lens L2, can be from about 5 mm to about 15 mm.

Figure 3B:
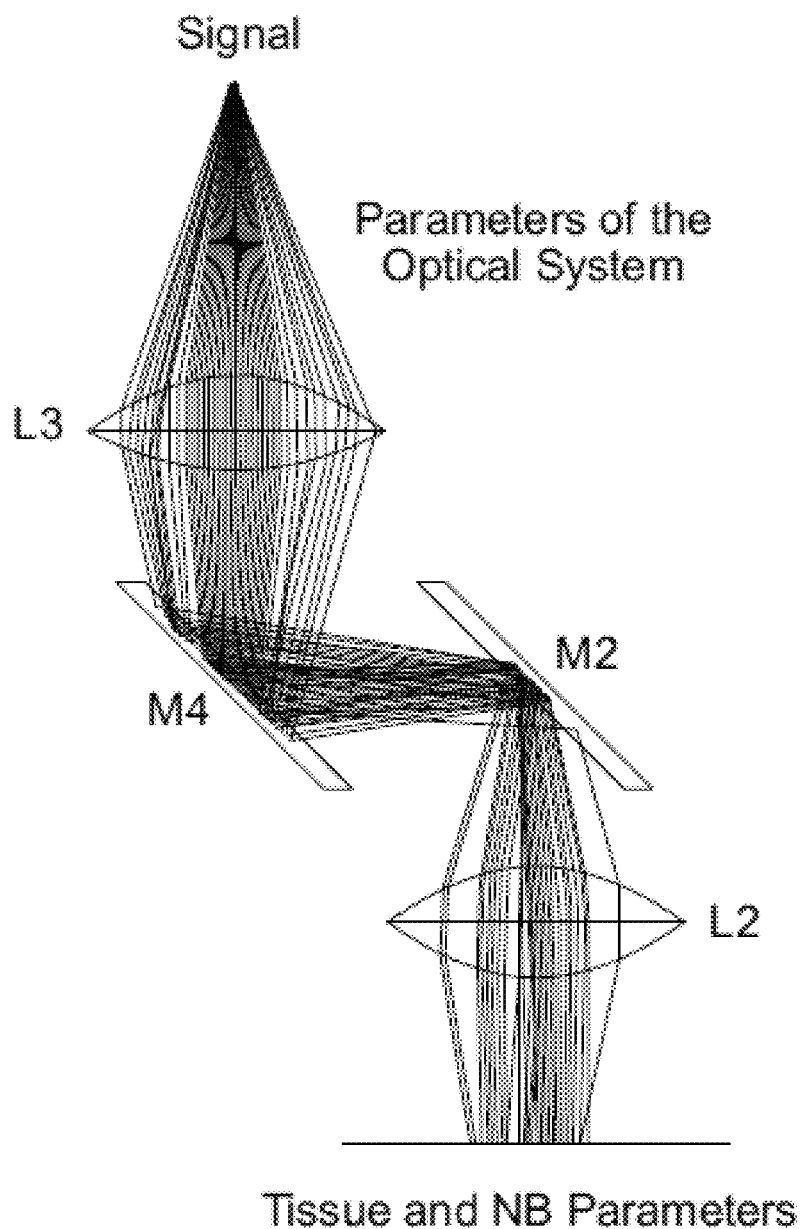

The collection path of the scattered probe beam 303, such as illustrated in FIGS. 3A and 3B, can travel through the working Lens L2 and be deflected by the mirrors M2 and M4 to the photodetector Lens L3 and the filter F before reaching the photodetector 304. That is, the focal point of the Lens L2 and the detector are not aligned in a straight line. As described above, the mirror M2 can include an opening at or about its center. The opening can have a diameter of about 3 mm. The collection path can be focused in the skin 10 and/or in water, with the focal points being different in the skin and in water. As described above, the working focal distance can be from about 5 mm to about 15 mm. In addition to detecting optical scattering by the transient vapor nanobubble, the photodetector can also detect optical scattering by the skin as the base level (background) signal.

Additional optional non-limiting specifications of the various optics components shown in FIG. 3A are summarized in Table 1 below. A skilled artisan can appreciate based on the present disclosure that alternative parameters can be used in additional embodiments.

TABLE 1

| Component | Diameter | Focal Distance | Other Optional Specifications |
| --- | --- | --- | --- |
| L1 probe beam collimator | N/A | 6-18 mm, adjustable | N/A |
| L2 Working lens | 25 mm | 15 mm | Numerical Aperture = 0.83, X, Y, Z drives |
| L3 Photodetector lens | 25 mm | 40 mm | Z-drive |
| Photodetector | 0.3 mm | N/A | Free space, FPD510-FS-NIR, DC-250 MHz, 50 Ohm output, low noise |

TABLE 1-continued

| Component | Diameter | Focal Distance | Other Optional Specifications |
|---|---|---|---|
| Mirror, 1310 nm/ 671 nm splitter | 25 × 36 × 1 mm | flat | Adjustable, mixes 671 and 1310 |
| Mirror, photodetector | 25 × 36 mm elliptical | flat | Sliver, adjustable |
| L4 pump beam collimator | 25 mm | 75 mm | Adjustable |
| M1 Pump beam mirror | 25 mm | flat | Adjustable |
| M2 Probe beam mirror | 25 × 36 × 1 mm | flat | 3 mm hole in the center |
| M3 Beam mixing mirror | 25 × 36 × 1 mm | flat | DMLP9900R: reflects 98% 671 nm, transmits 1310 nm, cutoff wavelength 900 nm, adjustable |
| M4 Probe collection beam mirror | 25 × 36 mm elliptical | flat | adjustable |
| Probe source, to be focused into a 12-16 um spot (e.g., in water) | 9.5 um SMF output, FC/PC connector | Super luminescent diode (SLD) via SM fiber | 1310 nm super luminescent diode (SLD) 30 mW, low noise (0.6% peak-to-peak) |
| Pump source, to be focused into 40 um spot (e.g., in water) | 105 um MM fiber output, FC/PC connector | Micro-laser via MM fiber | 671 nm, 300 ps, 20 uJ pulsed laser, Adjustable z position |
| F filter blocks 671 nm and 1342 nm wavelengths | 25 mm | flat | Transmission: max 1300 nm Rejection: max 671 nm, 1342 nm |

The collection of the scattered probe beam 303 can be improved directly by increasing and/or maximizing the collection of the probe beam scattered by the transient vapor nanobubble, and/or indirectly by reducing and/or minimizing the collection of background light scattered by the skin surface and the skin volume in the optical focus of the working lens L2. The direct improvements can be achieved by, for example, using a working Lens L2 with the maximal optical numerical aperture NA, and/or optically coupling the position of the photodetector and the transient vapor nanobubble so that both are located in matching optical foci of the optical collection system including Lenses L2 and L3. The indirect improvements can be achieved by using spatial filtering in the focus of the photodetector Lens L3, with an adjustable (x, y, z) pinhole having a diameter of about 10 um to about 100 um diameter in the focus of the lens L3 and/or in front of the photodetector.

Factors influencing the signal amplitude $A_{vnb}$ of a transient vapor nanobubble that is detected by the photodetector 307 can be related to the probe beam illumination, the collection, and/or the nanobubble size. The amplitude $A_{vnb}$ can be calculated using the formula $A_{vnb} = P_{led} \times K_{illumination} \times K_{collection} \times K_{nanobubble}$. In the formula, K denotes an optical coupling factor. $K_{illumination}$ can include the optical intensity delivered through the skin, which can depend on the skin depth H, and the diameter of the focal spot in water DO created by the working Lens L2 (the lens in front of the water or skin). $K_{collection}$ can include the numerical aperture of the collecting Lens L3, the skin or water depth H, and the optical coupling factor K (the efficacy of the projection of the nanobubble image to the photodetector 307). $K_{nanobubble}$ can include the maximal diameter of the transient vapor nanobubble $D_{vnb}$, and the diameter of the focal spot in skin Ds of the working Lens L2. The optical coupling factor K can be further determined by the alignment of the focal spots of the working Lens L2 and the photodetector Lens L3, the ratio of the focal spot of the photodetector Lens L3 to the diameter of the photodetector 307, and optical losses inside the system including losses due to the optical aberrations. Larger diameters of the focal spots Ds can reduce the influence of the nanobubble factors on the collection of optical scattering by the transient vapor nanobubble.

Factors influencing the background level (base level) I of the background signal can be related to the probe beam illumination $K_{illumination}$ the collection $K_{collection}$. Accordingly, one challenge of the optical detection systems disclosed herein can include reducing detection of the light scattered by skin and improving the relative sensitivity to detection of the light scattered by the transient vapor nanobubbles. Lower optical sensitivity to nanobubbles may be caused by poor optical delivery of the light from the transient vapor nanobubble to the photodetector in a high optical background created by the light delivered to the photodetector from the skin volume other than the transient vapor nanobubble. This may be caused by suboptimal optical properties of the working and the photodetector lenses L2 and L3, their suboptimal mutual alignment, and/or by too broad a probe beam spot at the transient vapor nanobubble plane.

Figure 3C:
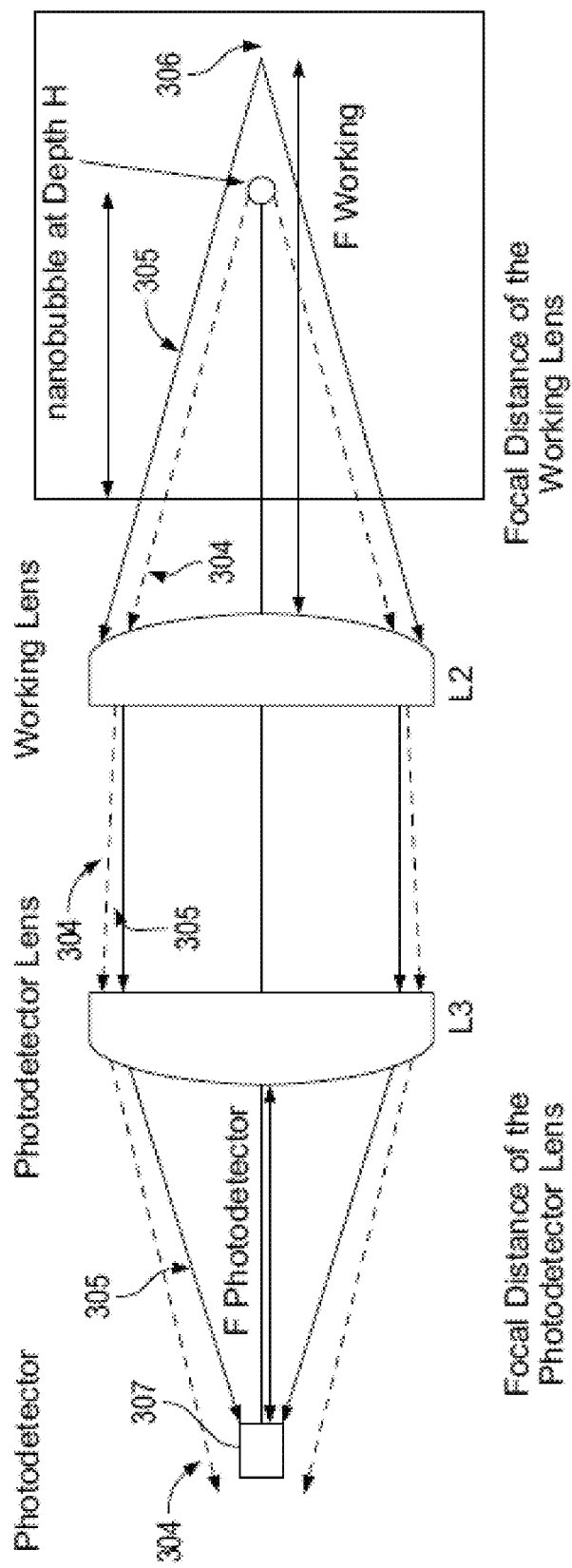

The polarity of the optical scattering signal of a transient vapor nanobubble depends upon the position of the transient vapor nanobubble relative to the source of the scattered background light. A positive polarity is associated with the light collection focus between the transient vapor nanobubble and the lens L2 (or at the transient vapor nanobubble). As shown in FIG. 3C, a negative polarity is associated with the light collection focus 306 behind the transient vapor nanobubble (that is, a transient vapor nanobubble being between the focus 306 and the Lens L2). FIG. 3C illustrates a simplified schematic diagram showing the collection path, the focal distance of the working Lens L2, and the focal distance of the photodetector Lens L3. In FIG. 3C, most of the collected scattered light comes from behind the transient vapor nanobubble, which disrupts the flux of scattered light by the tissue and thus causes a decrease in the absolute amount of light detected at the photodetector.

Figure 3D:
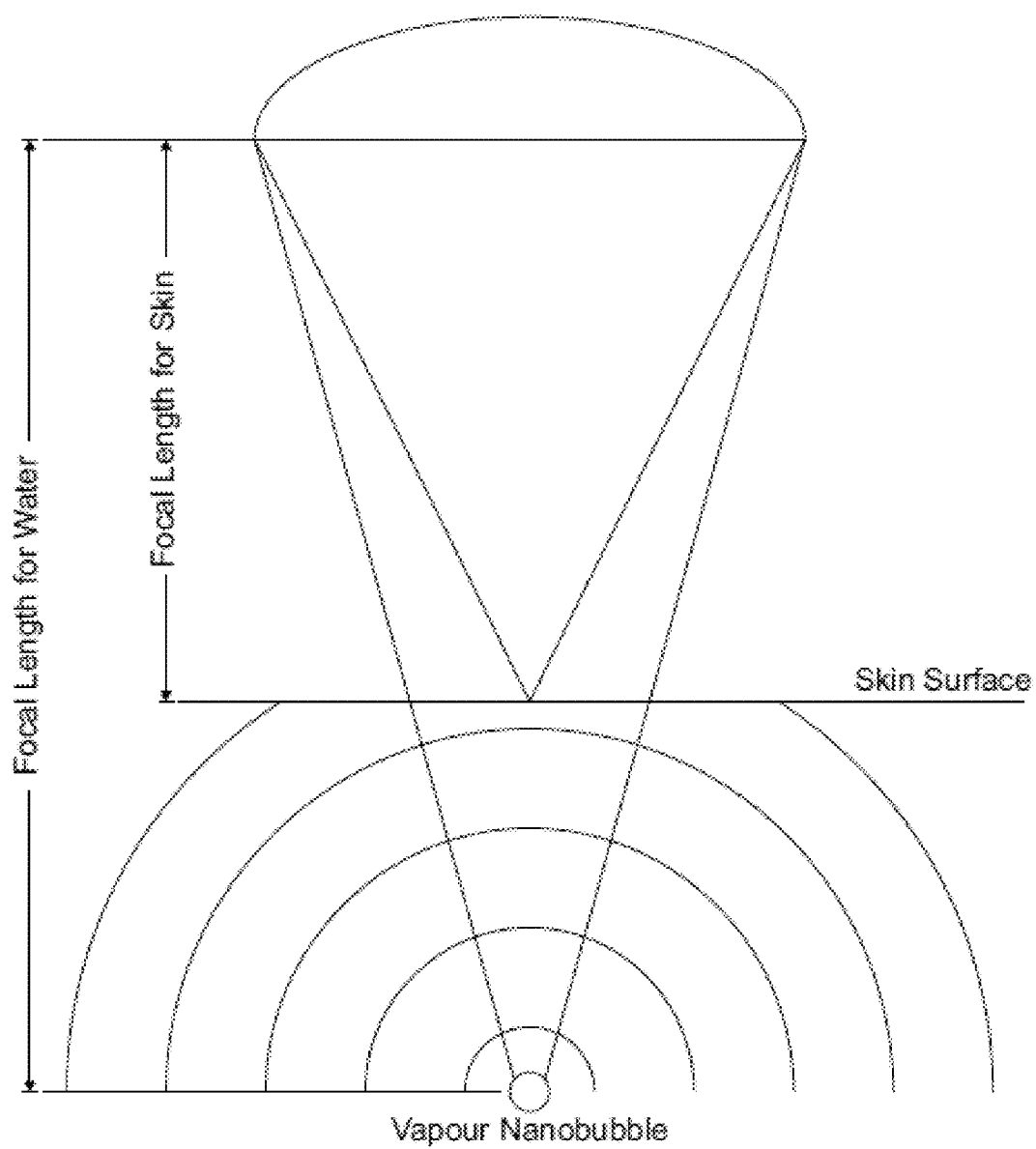
FIG. 3D illustrates focal lengths of a working lens of the free-space optical detection system for detecting transient vapor nanobubble in water and in skin.

As shown in FIG. 3D, when a transient vapor nanobubble is formed under the skin surface, an optical signal is detectable at the skin surface. Accordingly, the optimal focal length for detecting a vapor nanobubble generated in water is the distance from the base of the lens to the location of the vapor nanobubble. In contrast, the optimal focal length for detecting a vapor nanobubble generated underneath the skin is the distance from the base of the lens to the skin surface.

In the case when the malaria sensor include a plurality of optical fibers without free-space optics, the distal tip of the optical fiber delivering the laser pump bean can be directed at the angle of about 30 degree to about 45 degree to the measurement site. A curved surface of the distal fiber tip can act as a focusing lens that concentrates the optical energy at specific depth in the skin. The focal distance of the fiber can be defined as the distance from the surface of the fiber tip to the depth where the fluence reaches the maximal level, compared to that from the laser beam that propagates from the standard fiber with a flat tip. Optimal depth of the energy concentration can be about 250 um to about 350 um as measured orthogonally to the skin surface. To achieve such focal length in water, the radius of the fiber tip can be in the range 50-70 um. For fibers with the core diameter of 200 um and higher, this is lower than the radius of the fiber and hence some tapering of the fiber tip may be required. The fiber diameter can be recessed to that of the doubled radius of the curvature. In case of the angled launch, the focal distance can be increased to match the actual angle.

The diameter of the laser pump beam at the skin surface can be about 130-200 um. Smaller beams may lead to higher background signal caused by optical absorption be melanin. The effective focused diameter of the beam (defined as the diameter where the pulse fluence is above the vapor nanobubble generation threshold, which can be approximately 20 mJ/cm$^2$), can be about 50-60 um. Further increase of the beam diameter may result in the decreased laser fluence and thus fails to generate vapor nanobubbles.

Figure 4A:
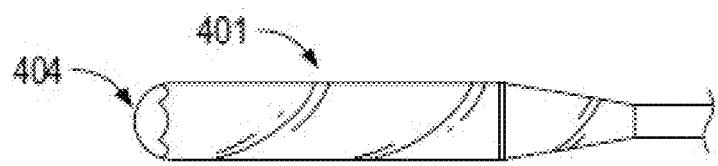
FIGS. 4A-4C illustrate example configurations of a distal tip of lensed optical fiber for delivering a pump beam.
Figure 4B:
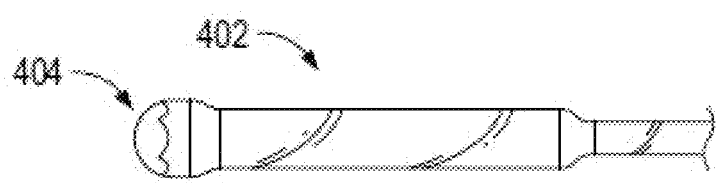
Figure 4C:

FIGS. 4A-4C illustrate various examples distal tips of an optical fiber 401, 402, 403 that can be used for delivering the pump beam. The optical fiber 401, 402, 403 can be multi-mode optical fibers. The optical fiber 401, 402, 403 can also be lensed fibers, which includes an optical fiber with a lens 404 on its distal tip. The lens 404 can optionally be an integral part of the optical fiber 401, 402, 403. In some embodiments, the lens 404 can be manufactured as a part of the optical fiber. The lensed optical fiber can include a step index multi-mode optical fiber, rather than a gradient index fiber, in order to avoid internal damage due to high local intensities, which forms inside a gradient index fiber.

Figure 4D:
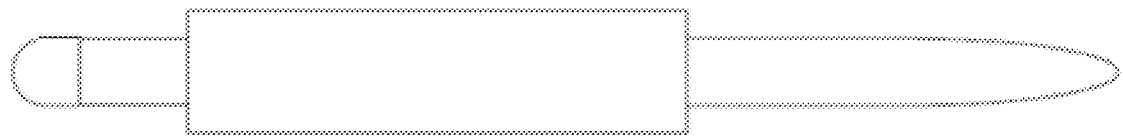
FIGS. 4D-4F illustrate additional examples of a lensed optical fiber.
Figure 4E:
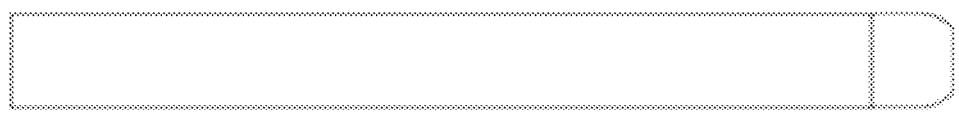
Figure 4F:
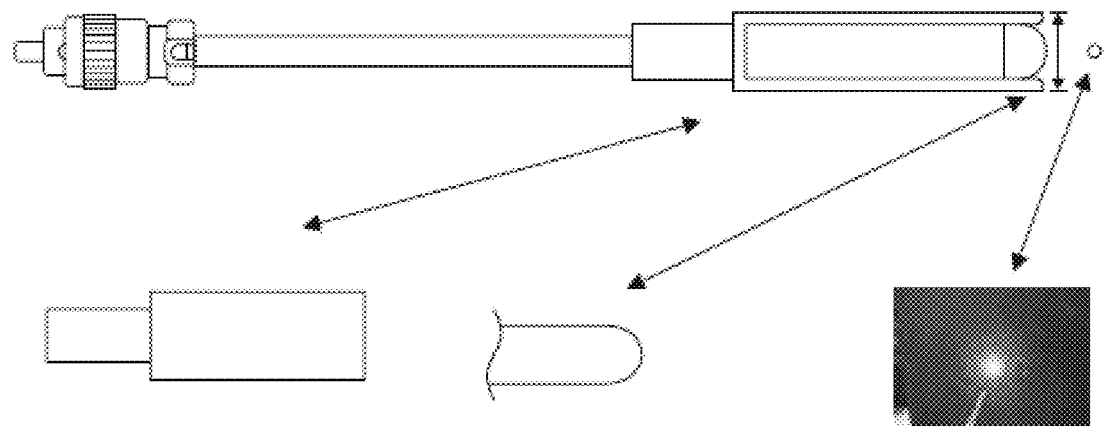
Figure 4G:
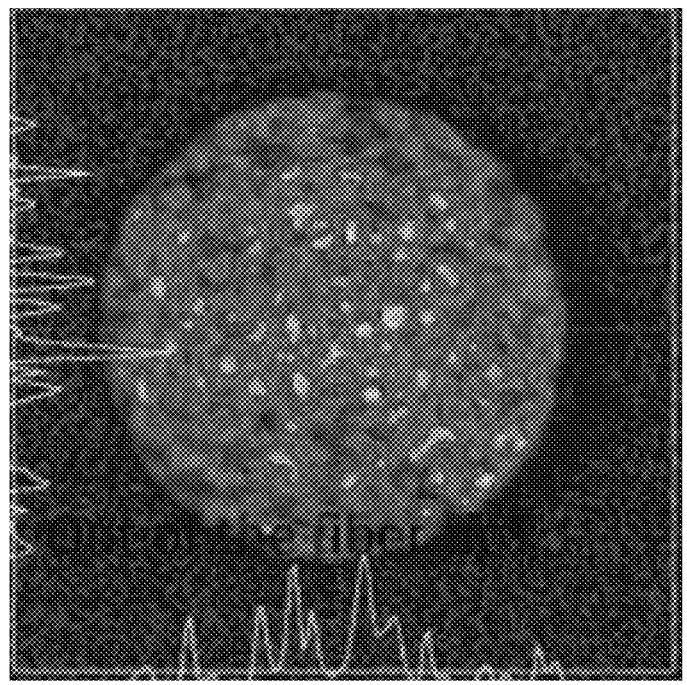
FIG. 4G illustrates an image of a light beam out of a tip of a short optical fiber having a length of 2 m.
Figure 4H:
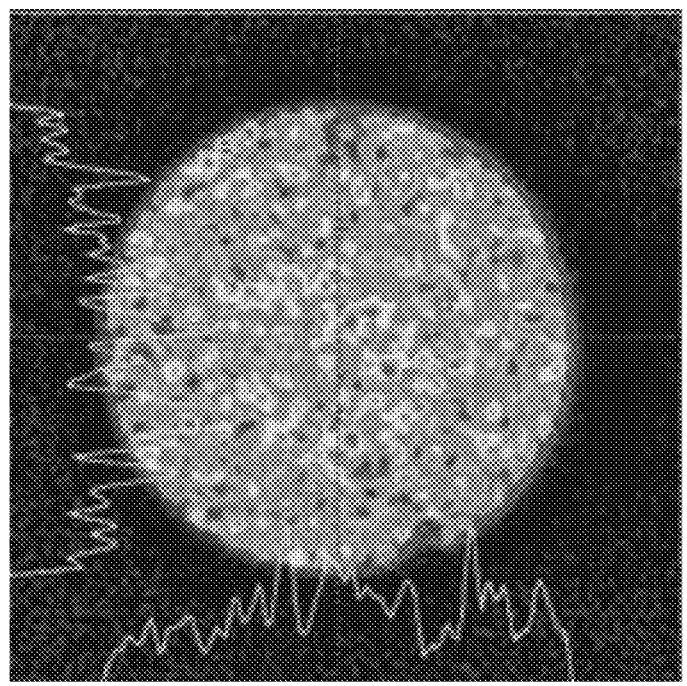
FIG. 4H illustrates an image of a light beam out of a tip of a long optical fiber having a length of 12 m.
Figure 4I:
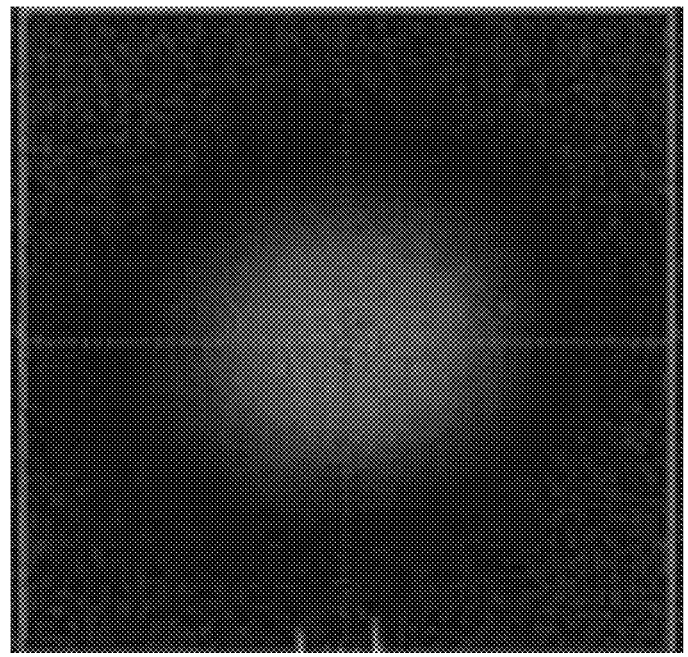
FIG. 4I illustrates an image of a light beam out of a skin sample of about 240 um to about 250 um in thickness via a tip of an optical fiber having a length of 2 m.
Figure 4J:
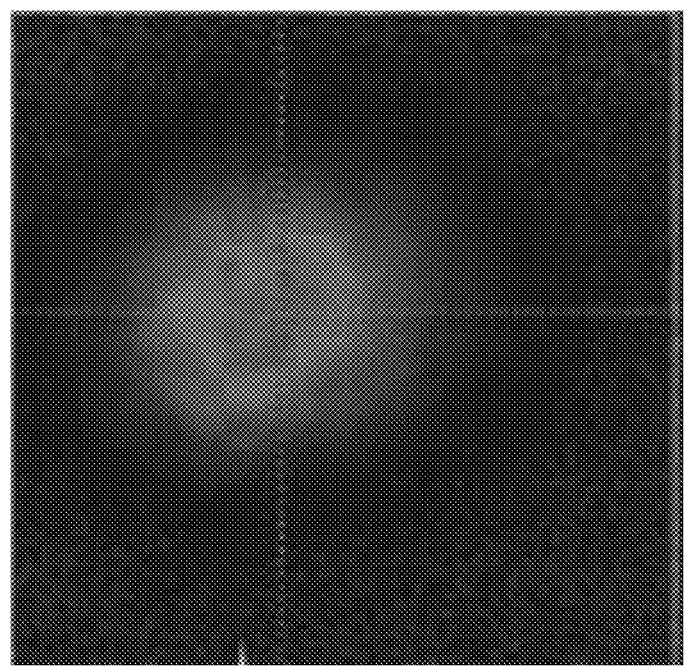
FIG. 4J illustrates an image of a light beam out of a skin sample of about 240 um to about 250 um in thickness via a tip of an optical fiber having a length of 12 m.

FIGS. 4D-4F illustrate other example lensed fiber tips. As shown in FIG. 4D, the lensed tip can include a half-dome lens on one side of the fiber. The lensed tip can include a conical lens on the opposite side of the fiber. The fiber can be covered with metal, such as nickel, silver, or otherwise. The metal can have a thickness of about 1-2 um. The conical lensed tip can be bare or in a ferrule. As shown in FIG. 4E, the lens can include a tapered tip with a polished flat end surface. As shown in FIG. 4F, the lens can include a Grin lens. The output diameter of the Grin lens can be about 140 um. The focal diameter or beam waist can be about 30-42 um. The Grin lens can have a length of about 7 mm. FIGS. 4G-4J illustrate example laser beam images using the multi-mode optical fiber disclosed herein.

The lensed optical fiber 401, 402, 403 can deliver a pump beam having a skin entrance diameter of about 150 um to about 300 um to a measurement site deep in the skin, such as to below skin surface. The skin entrance diameter of the pump beam can be chosen to reduce or minimize the melanin-generated background signal and/or false-positive signals. When focusing the pump beam into the skin, the focal spot of the pump beam can be at least 50 um in diameter (in the skin) and located at the skin depth of about 250 um to about 350 um. When focusing the pump beam into water, the focal spot of the pump beam can be at least 50 um in diameter and located at the depth of about 240 um to about 660 um below a surface of the water. Example data obtained using 10 different lensed fibers and a reference standard 105 um core diameter multi-mode step index fiber with a flat distal tip are summarized in Tables 2-4 (with Table 4 illustrating energy performance data of the sample tested lensed fibers when the input energy after the fiber collimator Lens L4 was 23.7 uJ) and the parameters are defined below:

Peak distance denotes the highest intensity peak distance from the fiber tip.

Peak width denotes the peak width as measured by the BeamMic software at the $1/e^2$ level.

Power in peak denotes the percentage of power in the peak (encircled by the $1/e^2$ level) relative to the total power.

Corrected intensity at the top of the peak denotes the ratio of power in a $10 \times 10$ $\mu m^2$ area (at the top of the peak) to the total power of the whole beam as measured by a CCD camera (with a 1000 multiplication factor).

Beam diameter at fiber tip denotes the beam width as measured by the BeamMic software at the $1/e^2$ level.

A skilled artisan can appreciate based on the present disclosure that alternative parameters can be used in additional embodiments.

TABLE 2

Figure 5A:
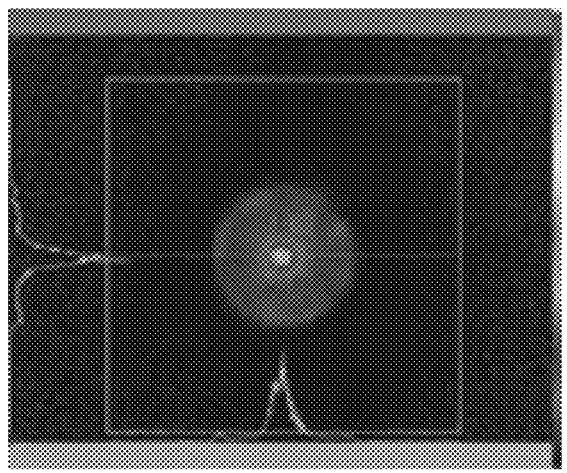
FIG. 5A illustrates an example pump beam image at peak intensity using a lensed optical fiber.
Figure 5B:
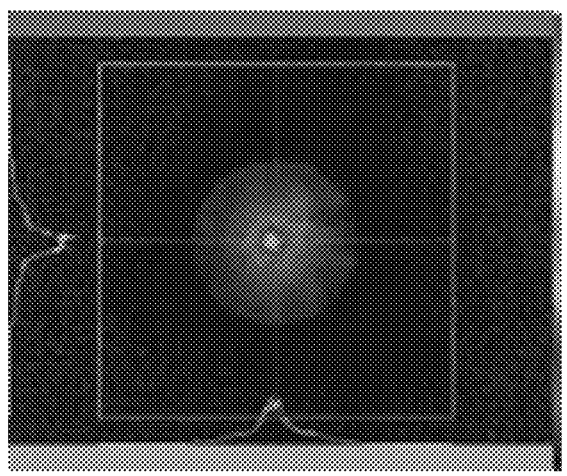
FIG. 5B illustrates an example pump beam image at a fiber tip using a lensed optical fiber.
Figure 6A:
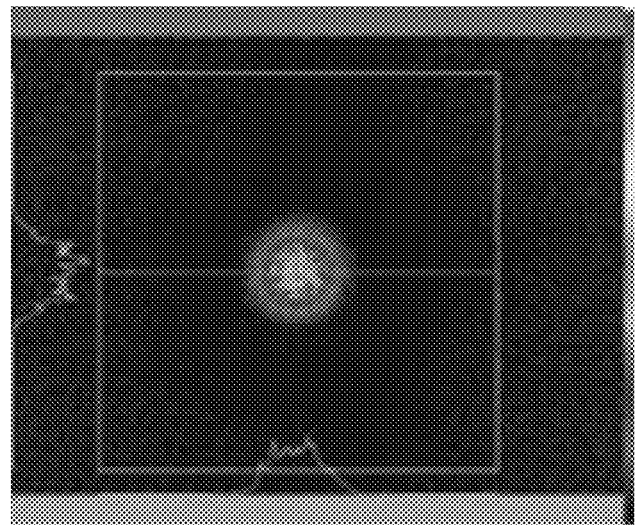
FIG. 6A illustrates an example pump beam image at peak intensity using a standard flat-tip optical fiber.
Figure 6B:
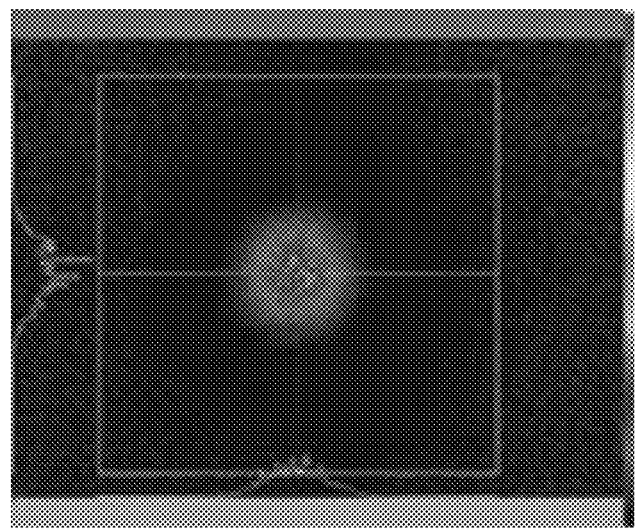
FIG. 6B illustrates an example pump beam image at a fiber tip using a standard flat-tip optical fiber.

| Parameters | Sample Lensed Fiber #B1 | Standard Flat Tip Fiber 1 | Standard Flat Tip Fiber 2 |
|---|---|---|---|
| Beam diameter at fiber tip $1/e^2$, μm | 122 | 122 | 128 |
| Peak distance, μm | 410 | 250 | 500 |
| Peak width $1/e^2$, μm | 59 | 108 | 124 |
| Power in peak, % | 24 | 81 | 733 |
| Corrected intensity at top of peak, a.u. | 20.4 | 13.5 | 10.9 |
| Beam image at peak intensity | FIG. 5A | FIG. 6A | FIG. 6B |
| Beam image at fiber tip | FIG. 5B | FIG. 6A | FIG. 6B |

TABLE 3

| Lensed Fiber # | Beam diameter at fiber tip $1/e^2$, μm | Peak distance, μm | Peak width $1/e^2$, μm | Power in peak, % | Corrected intensity at top of peak, a.u. |
|---|---|---|---|---|---|
| B1 | 122 | 410 | 59 | 24 | 20.4 |
| B2 | 128 | 600 | 31 | 19 | 50.6 |
| B3 | 290 | 450 | 52 | 24 | 32.7 |
| B4 | 123 | 560 | 36 | 21 | 42.4 |
| B5 | 334 | 410 | 31 | 9 | 24.2 |
| B6 | 189 | 240 | 88 | 40 | 21.4 |
| B7 | 93 | 340 | 47 | 24 | 26.7 |
| B8 | 102 | 400 | 58 | 26 | 23.4 |
| B9 | 97 | 620 | 35 | 15 | 33.9 |
| B10 | 112 | 540 | 36 | 18 | 34.9 |

TABLE 4

| Lensed Fiber # | Energy into air | | Energy into water | |
| --- | --- | --- | --- | --- |
| | Energy, μJ | Percentage | Energy, μJ | Percentage |
| B1 | — | — | — | — |
| B2 | 9.3 | 39% | 15.8 | 67% |
| B3 | 11.9 | 50% | 14.8* | 62%* |
| B4 | 10.2 | 43% | 15.7 | 66% |
| B5 | 13.8 | 58% | 15.4 | 65% |
| B6 | — | — | — | — |
| B7 | 14.4 | 61% | 16.9 | 71% |
| B8 | 14.6 | 61% | 16.7 | 70% |
| B9 | 11.2 | 47% | 16.1 | 67% |
| B10 | 10.3 | 43% | 16.6 | 70% |

(*Distance to energy head: 13 mm.)

In some embodiments, a laser pulse (671-674 nm wavelength, about 200-370 ps pule duration (or about 240-300, or about 250 ps, or about 300 ps, or about 370 ps), energy 10-50 uJ) can be delivered via a single multi-mode optical fiber. The fiber can be step index and made of silica. For the pulse energy 20 uJ and higher, the core diameter of the optical fiber can be 105 um or 200 um, with a numerical aperture of 0.2, or 0.1-0.22, or similar. The fiber can have a cladding diameter of 125 um or 225 um. Such a configuration can reduce optical delivery loses in the fiber, the fluence at the level of melanin, and better concentrate the pump laser energy. The optical fiber can have front input/front output, or be side-firing (side input/side output). A skilled artisan can appreciate based on the present disclosure that alternative parameters can be used in additional embodiments.

At the proximal end of the optical fiber for delivery the laser pump beam, the fiber can be coupled to a FC/PC connector. The fiber tip can be positioned beyond the focus of the coupling lens in order to launch the divergent beam, which can maximally fill the fiber aperture so the beam diameter is about 0.7 time of the fiber core diameter. This solution can reduce the probability of the optical damage to the fiber due to the high optical intensity of the pump laser pulse. The optical damage threshold may be 3 $GW/cm^2$ for a step index fiber. The total length of the fiber can be 12-14 m. Such a length provides better optical mixing of laser beam modes inside the fiber and thus reduces hot spots at the fiber output (see beam images in FIG. 4G as compared to FIG. 4H). Such length can be achieved with a single fiber which may optionally be a permanent part of the sensor, or with two parts, a shorter, 1-2 meter part permanently attached to the sensor, connected to a longer section via an optical mating sleeve. The sleeve can deliver into the next fiber up to 98% of the optical energy.

The distal tip of the optical fiber can be flat or focused (lensed). The taper lens can have a radius of about 70-100 um. The focal distance of the lensed tip can be about 250-350 um. The optical fiber can be placed orthogonal to the skin or at an angle to match the volume of the probe beam delivery and/or collection fibers.

In some embodiments, the lensed fibers disclosed herein may be used both for the delivery of the pump and/or probe beams into the test sample, and for the detection of the scattered light. In this case, a single lensed fiber can act as a sensor for the Hemozoin-generated transient vapor nanobubbles. As will be described below, multiple optical fibers can be used for the delivery of the pump/and/or probe beams, and for the collection of the scattered probe beam.

In some embodiments, the probe light delivery fiber can include any suitable single mode fiber that delivers a continuous probe light (600-640 nm, or 700-100 nm, or 785 nm in wavelength, 20 mW or other optical power) with a low intensity noise. A single mode fiber can include a 4-8 um or 5-25 um mode field diameter, 125 um cladding diameter, and/or a standard numerical aperture. The proximal end of the single mode fiber can be coupled to a FC/PC connector or other connector. Standard laser coupling, including the mating sleeve, can be used. Total length of the fiber can be about 2 m, or between 1-12 m, or another length needed to connect the probe light source to the malaria sensor. The distal end of the probe light delivery fiber can include a flat tip. The distal end of the probe light fiber can have front input/front output, or be designed side-firing. The probe light can be launched into the skin or another measurement site at an angle (for example, at about 20-45 degrees) and location that delivers the probe light into the focal volume of the excitation or laser pump pulse and into the focal volume of the probe light collection fiber. The probe light delivery fiber can also be a multi-mode fiber with 10-25 um core diameter. The multi-mode fiber can be used with a multi-mode probe laser. A skilled artisan can appreciate based on the present disclosure that alternative parameters can be used in additional embodiments.

In some embodiments, a probe light collection fiber (for collecting the scattered probe light) can include a multi-mode fiber. To collect more probe light from the skin surface, the fiber can have a core diameter of about 200-400 um, and/or higher NA (about 0.3-0.5 or higher). The fiber can have a cladding diameter of about 225 um or otherwise. The light collection performance of the fiber can be increased with a lensed tip. The fiber can be made of glass, a plastic, or another suitable material. The proximal end of the fiber can be coupled to a FC/PC or other connector. The fiber can include an in-line optical filter (for example, fibers made by Thorlabs with two insets) for improved suppression of the pump pulse wavelength. The proximal end can be operably connected to the photodetector (for example, the Menlo Systems 510 or similar for a maximal signal frequency of 20 or 50 MHz). Total length of the fiber can be about 2 m, or about 1-12 m, or another suitable length needed to connect the photodetector and optical filter to the sensor. The distal end of the probe collection fiber can include a flat or lensed tip with a maximal possible numerical aperture. If the tip includes a tapered lens with the radius of about 70-100 um, or a ball lens with a radius smaller than 200 um, the focal length can be about 300-700 um. The collection fiber can be applied to the skin or other measurement site orthogonally or at a zero angle. If a fiber with a flat standard tip is used, its axis can coincide with the volume of the focused pump pulse (that is, the volume where the vapor nanobubbles are generated) and with the illuminating probe light. If a lensed fiber is used, its focus can also coincide with the volume of vapor nanobubble generation. A skilled artisan can appreciate based on the present disclosure that alternative parameters can be used in additional embodiments.

Preliminary Example Results of Using Optical Detection Systems Incorporating the Lenses Example Simulated Results of Optically Detecting Particles Under the Skin FIGS. 7A-7D illustrate example differences between the optical detection of scattering by Silver-coated glass microparticles under a dark human skin sample and the optical detection of the background scattering by the dark human skin sample using an optical detection system incorporating the lenses described above. Here the particles or microparticles were used to simulate the transient vapor nanobubbles.

Figure 7A:
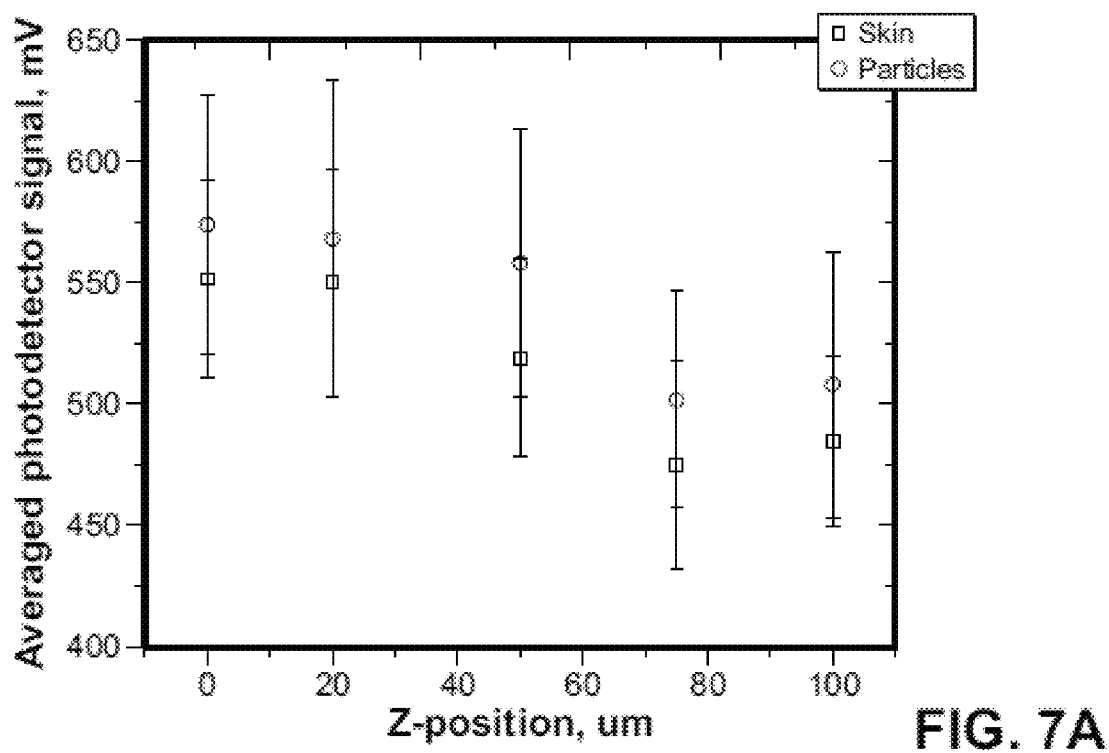
FIGS. 7A-7D illustrate example results of optically detecting micro-particles under a skin sample on a piece of glass.
Figure 7B:
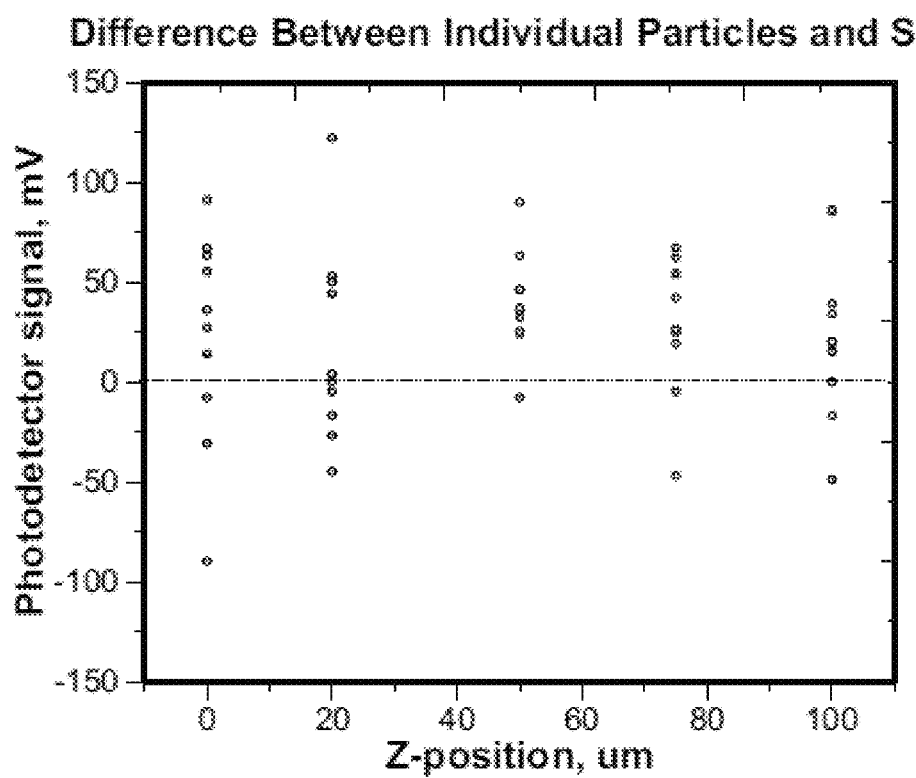
Figure 7C:
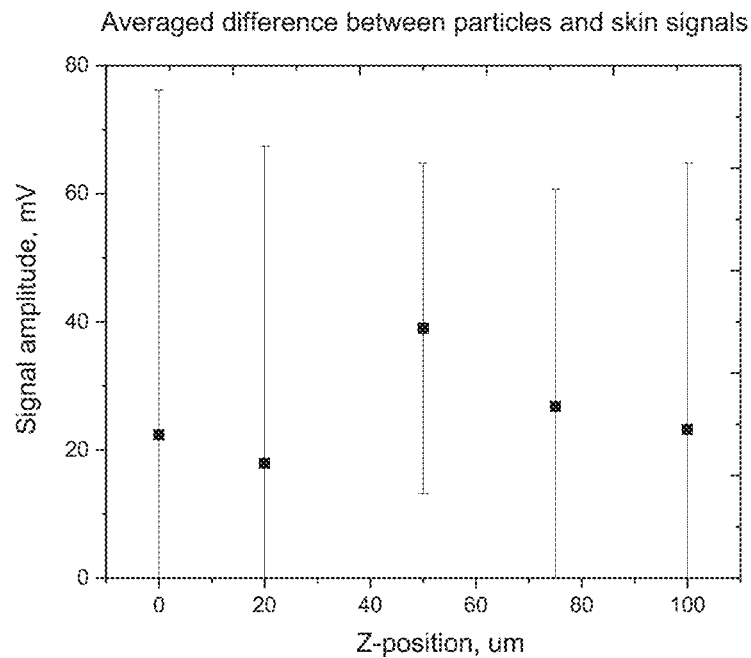

In FIGS. 7A-7C, the sample used a dark human skin and had a thickness of about 250 um. The skin sample was placed on a transparent glass slide. Silver-coated particles having an outer diameter of about 25 um were placed under the skin sample on the glass slide. The background signals level was measured for 10 different skin locations and 10 silver-coated particles were placed under the skin sample. Before data was collected, the distance between the lens (such as Lens L3 described above) and the photodetector in the probe beam collection pathway was optimized.

Figure 7D:
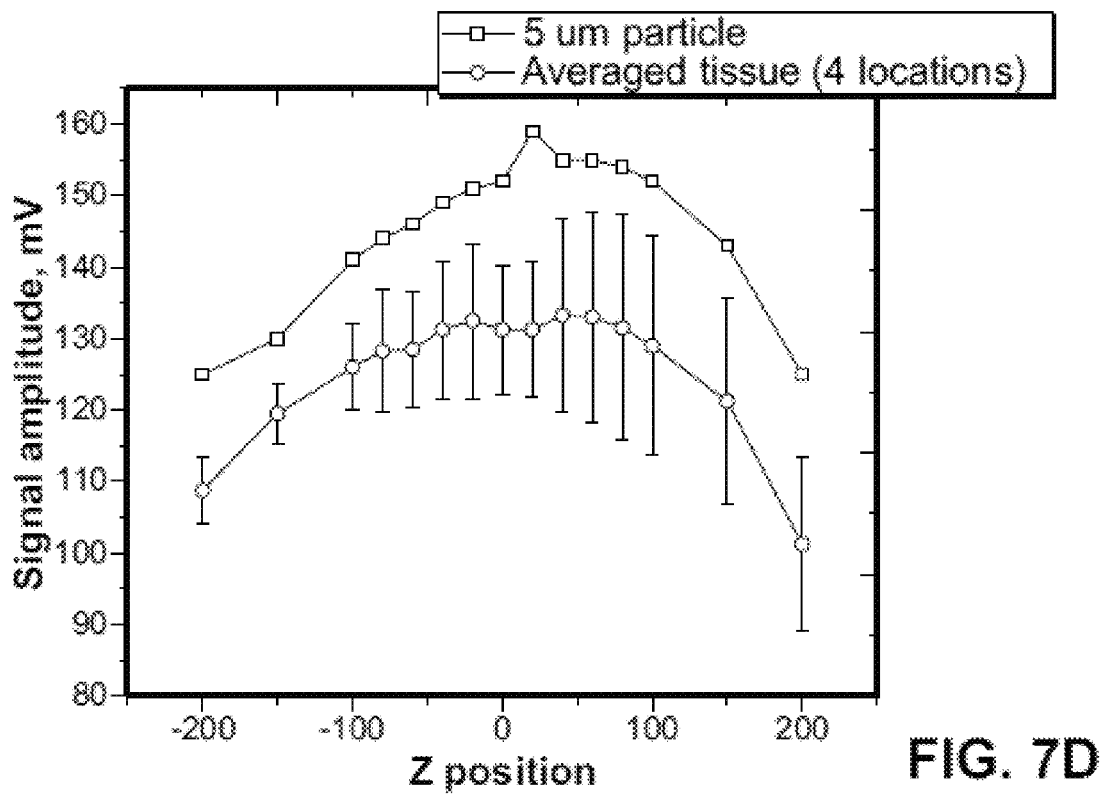

The optical detection process that was performed with the 25 um particles was repeated at four different skin locations with silver-coated micro-particles having an outer diameter of about 5 um. The difference between the micro-particle and the skin tissue is shown in FIG. 7D.

As illustrated in FIGS. 7A-7D, a smaller skin depth can result in a higher signal amplitude. This can explain an advantage of a positive Z position of the micro-particles (that is, also a positive Z position of a transient vapor nanoparticle). The zero Z position (also called the working plane) can be defined as the distance from the bottom of the Lens L2 frame to the microparticles. Although the maximum signal can be broad on the scale of the Z position, at least about 100 um to about 200 um of vertical space would be available in the optical detection system to detect the transient vapor nanobubbles.

Figure 8A:
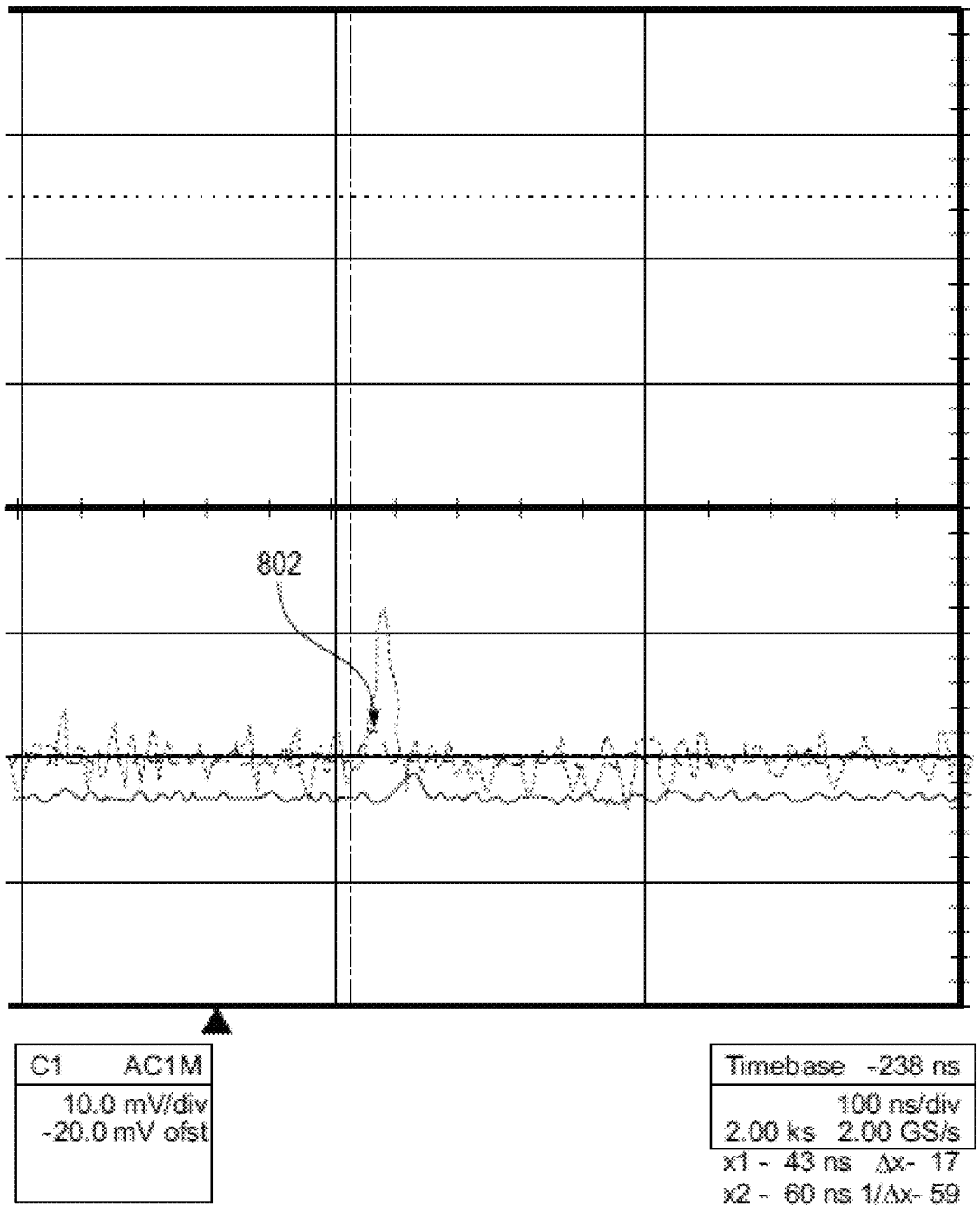
FIGS. 8A and 8B show signals that illustrate symmetrical expansion and collapse of a Hemozoin-generated transient vapor nanobubble.
Figure 8B:
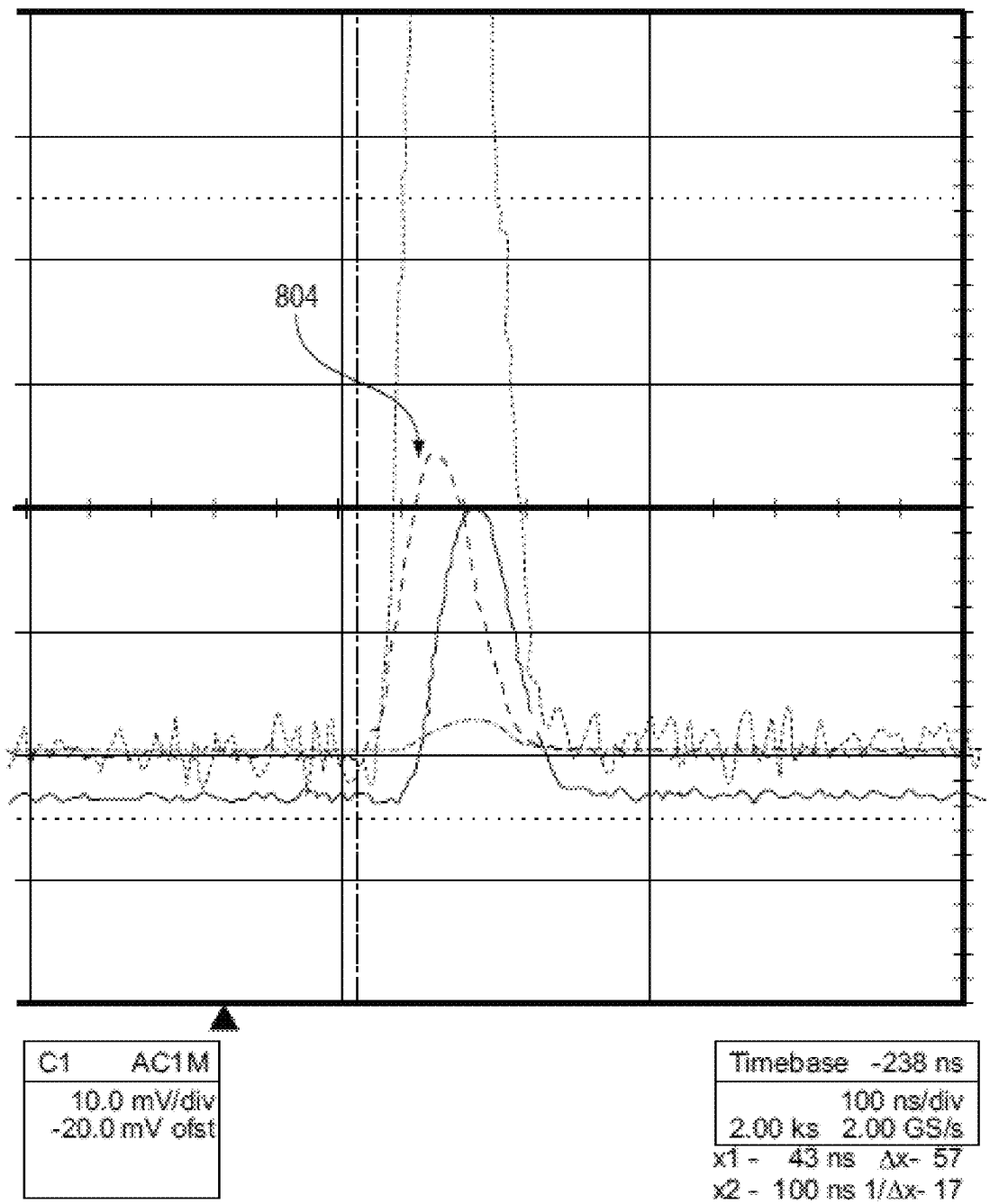

Example Results of Optically Detecting Gold-Generated Transient Vapor Nanobubbles When a transient vapor nanobubble is unrestricted (for example, when generated in water or other types of fluid), the expansion and collapse of the transient vapor nanobubble can be symmetrical. FIG. 8A illustrates optical scattering signals due to expansion and collapse of transient vapor nanobubbles in a bandwidth of 500 MHz before noise reduction was performed. As shown in FIG. 8A, the minimal signal 802 that was detected is indicative of a Hemozoin-generated transient vapor nanobubble having a lifetime of about 14 ns. FIG. 8B illustrates the signals after the noise reduction. As shown in FIG. 8B, the symmetrical expansion and collapse of the transient vapor nanobubble can be seen from a symmetrical or substantially symmetrical rise and fall of the amplitude of the signals 804. The symmetrical or substantially symmetrical shape of the signals follows the hydrodynamics of a vapor expansion and collapse in elastic media (such as water or other types of fluid) with low losses.

Figure 9A:
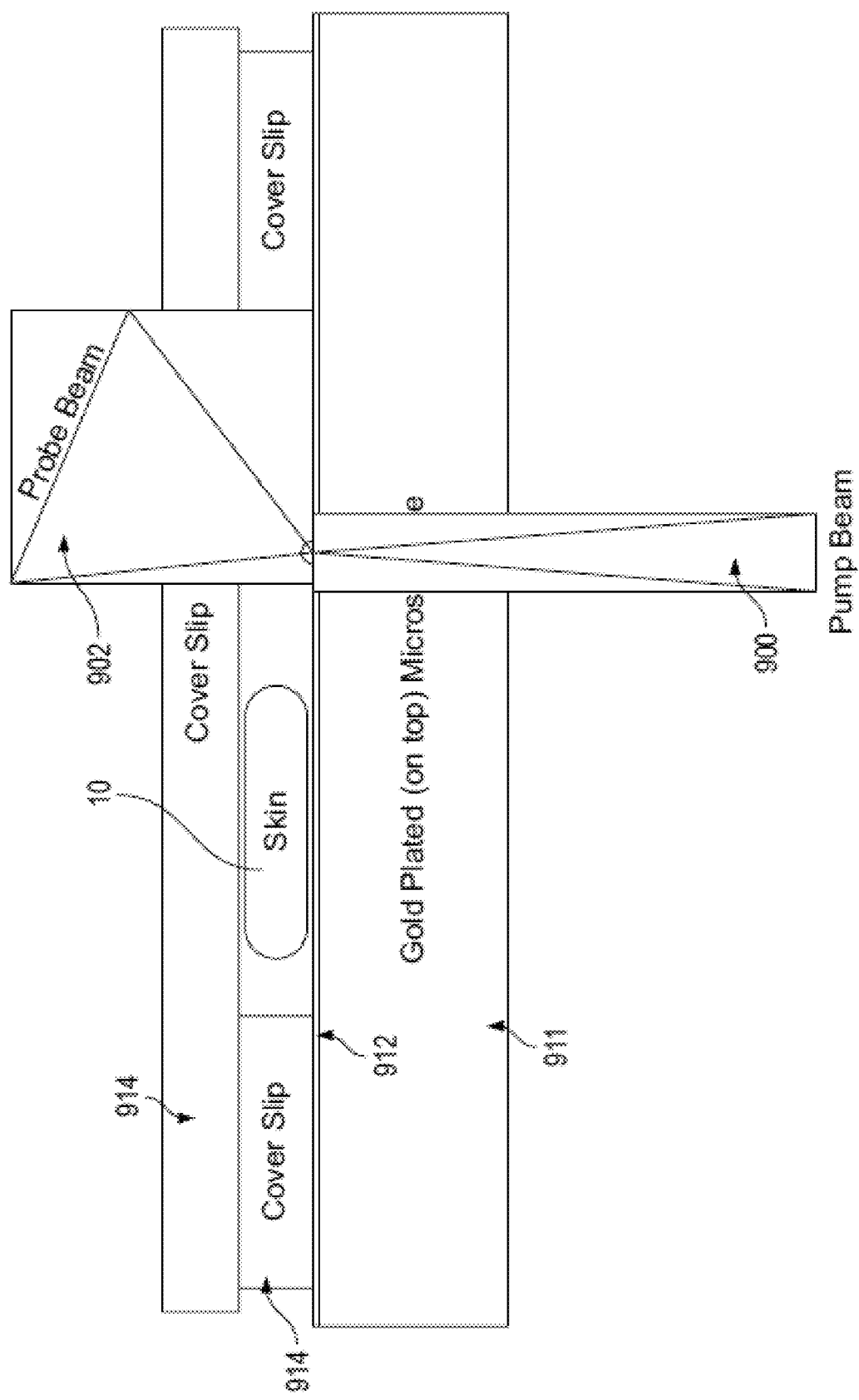
FIG. 9A illustrates schematically an experimental setup for optical detection of a gold-generated transient vapor nanobubble in water or skin.

However, in reality, the expansion and collapse of a transient vapor nanobubble, which may be in the patient's skin, may not be symmetrical due to the environment surrounding the vapor nanobubble. FIG. 9A illustrates an example experimental model that was used to generate a reproducible single transient vapor nanobubble at a specific location. The location of the transient vapor nanobubble was determined by a gold nanofilm 912 (about 50 nm to about 100 nm in thickness) in the Z direction and by the position of a focused pump beam 900 (which was pulsed laser with a wavelength of 532 nm), delivered from underneath a bottom side of the gold nanofilm 912 in the X-Y directions. The gold nanofilm 912 can be applied to on a top surface of a transparent microscopic slide 911 and the pump beam 900 can be delivered from under the slide 911. The transient vapor nanobubble was generated in human skin 10 (or in water) above the gold nanofilm 912. As shown in FIG. 9A, the skin 10 (or water) can be held in place above the gold nanofilm 912 by a plurality of cover slips 914 on the sides and/or above the skin 10 (or water). The probe beam 902 (having a wavelength of about 1310 nm) was delivered above the skin 10 (or water). The scattered probe beam 902 was filtered via a single mode optical fiber, which was connected to a photodetector with a relatively high noise level.

Figure 9B:
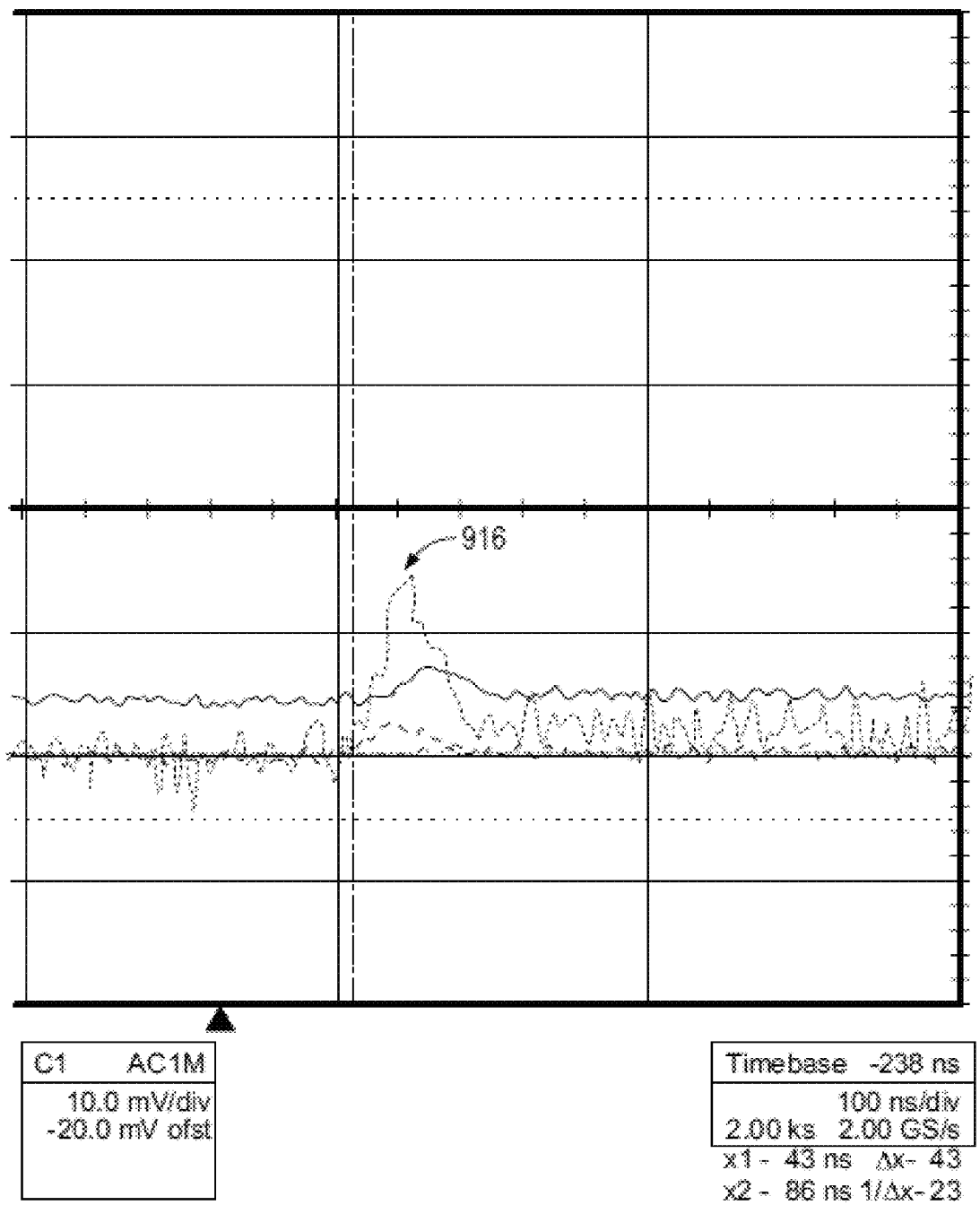
FIGS. 9B and 9C illustrate example signals of optical scattering by gold-generated transient vapor nanobubbles in a skin sample.
Figure 9C:
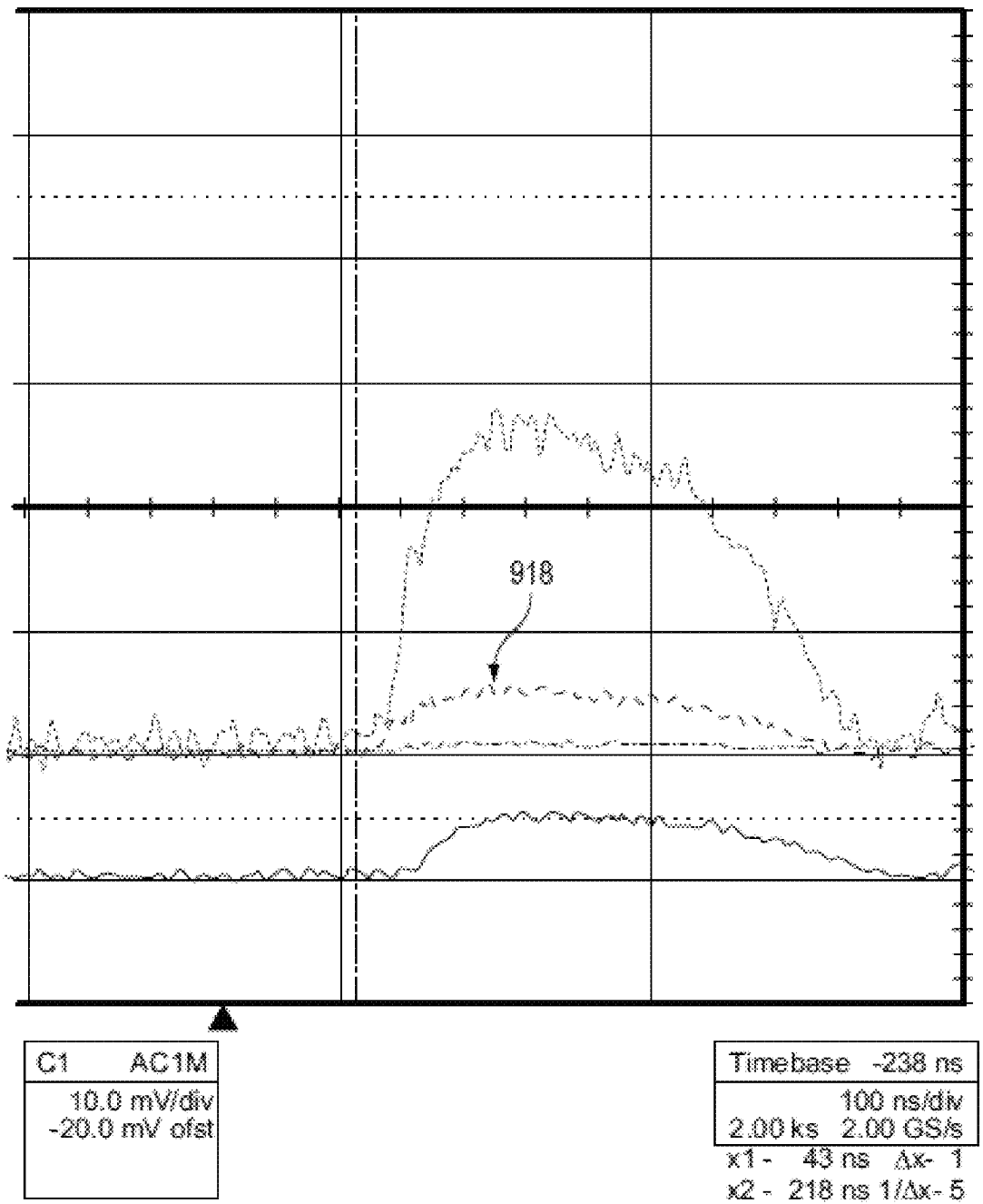

FIGS. 9B and 9C illustrate the optical scattering signals when a dark human skin sample 10 with a thickness of about 140 um was placed above the nanofilm 912. Transient vapor nanobubbles were generated by the gold nanofilm 912 under the skin sample 10. As shown in FIG. 9B, the minimally detectable signal 916 indicative of a single transient vapor nanobubble in or into the skin before the noise reduction had a lifetime of about 20 ns to about 30 ns, which is longer than an unrestricted transient vapor nanobubble signal as shown in FIG. 8A. The signal 916 also shows a delayed collapse phase compared to the expansion phase. As shown in FIG. 9C, which illustrates the optical scattering signals after the noise reduction, the signals 918 have a reduced amplitude compared to the signal 804 due to attenuation of the scattered probe beam by the skin tissue. The signals 918 also show asymmetrical signal shapes, that is, there is a delay of the transient vapor nanobubble collapse compared to its expansion, which can be due to the damping effect of skin. Compared to the nanobubble in water, such damping reduces the signal amplitude while the collapse delay also increases the nanobubble lifetime, which includes a full interval from the beginning of the expansion to the end of the collapse. The energy threshold of the transient vapor nanobubble generation in skin was also slightly higher compared to that in water.

Figure 10A:
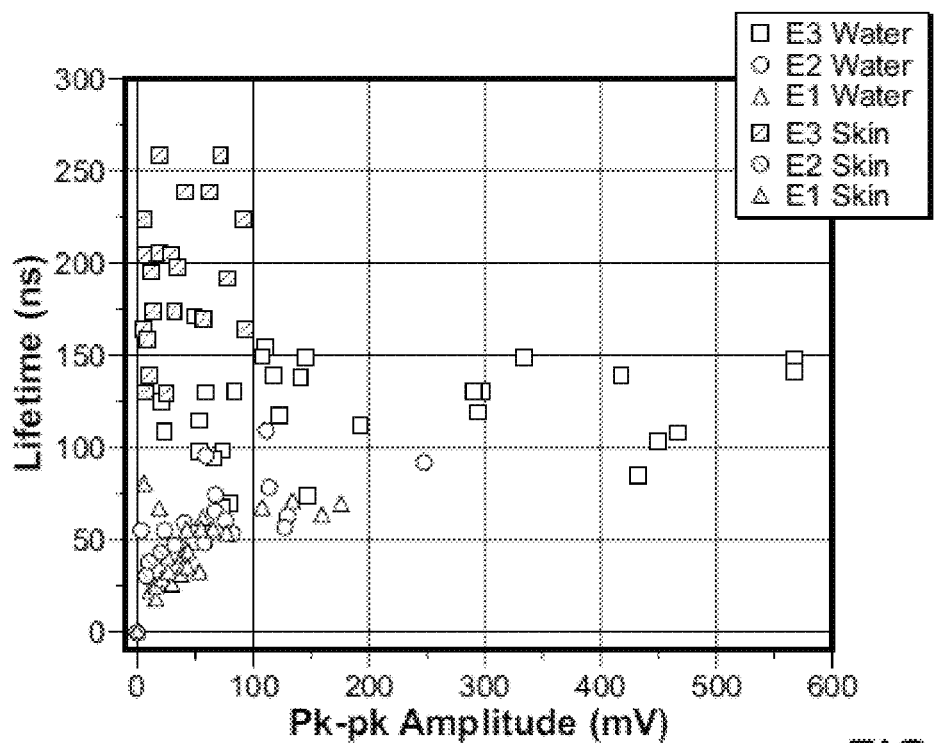
FIGS. 10A-10K illustrate example optical detection of vapor nanobubbles in water and human skin model with a gold nanofilm.
Figure 10B:
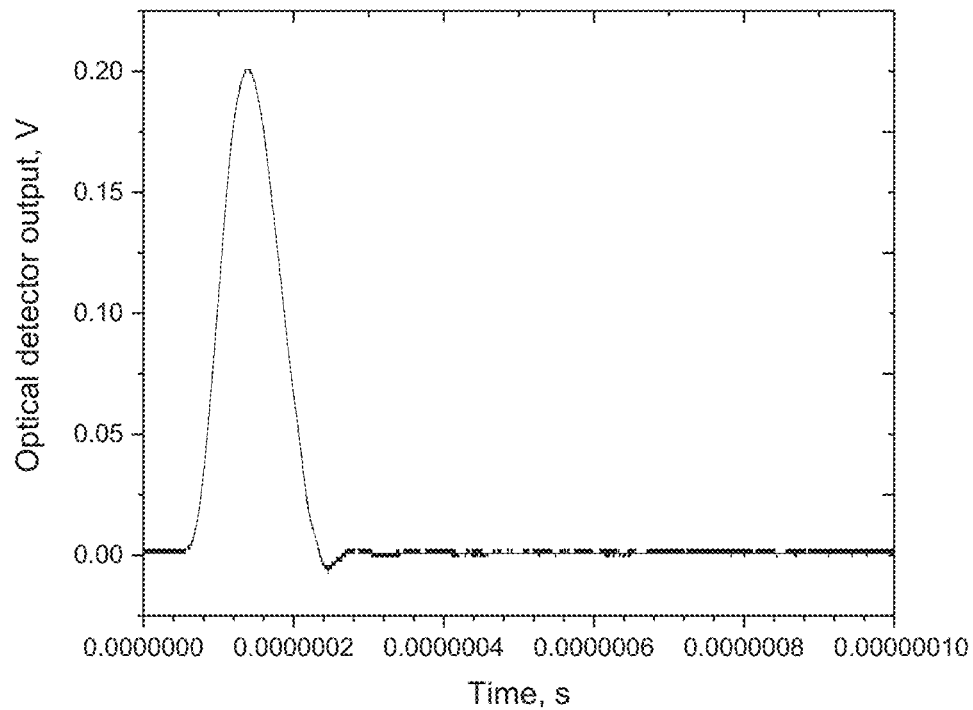

FIG. 10A illustrates the relationship between the transient vapor nanobubble lifetime and the peak-to-peak amplitude in water and in intact dark skin samples at three energy levels of a 532-nm pump laser pulse using the experimental setup shown in FIG. 9A. FIG. 10B illustrates another example of the photodetector signal for the unrestricted transient vapor nanobubble in water. The skin, compared to water, damps the nanobubble expansion (which can result in a decrease in the signal amplitude and/or an increase in the threshold energy of the nanobubble generation) and delays the nanobubble collapse (which can result in an increase of the lifetime of a relatively larger nanobubble in skin compared to those in water). The statistics of the experiments as shown in FIGS. 10A and 10B are summarized below in Tables 5-7. Table 5 illustrates the incidence rate of nanobubbles, in %. Table 6 illustrates the average signal peak-to-peak amplitudes and standard deviations, in mV. Table 7 illustrates the transient vapor nanobubble lifetimes and standard deviations, in ns. A skilled artisan can appreciate based on the present disclosure that alternative parameters can be used in additional embodiments.

TABLE 5

| | Energy level | | |
|---|---|---|---|
| | @E1 | @E2 | @E3 |
| Water, SLD current 200 mA | 100 | 100 | 100 |
| Skin, all signals, SLD current 600 mA | 3 | 20 | 73 |

TABLE 6

| | | Energy level | | |
|---|---|---|---|---|
| | | @E1 | @E2 | @E3 |
| Water, SLD current 200 mA | Average | 49.1 | 59.4 | 196.4 |
| | StDev | 41.6 | 47.4 | 166.7 |

TABLE 6-continued

|  |  | Energy level | | |
|---|---|---|---|---|
|  |  | @E1 | @E2 | @E3 |
| Skin, all signals, | Average | 0.2 | 3.3 | 24.3 |
| SLD current 600 mA | StDev | 0.9 | 9.8 | 28.4 |
| Skin, only signals with | Average | 5 | 16.3 | 33.1 |
| nanobubbles | StDev | 0 | 16.2 | 28.4 |

TABLE 7

|  |  | Energy level | | |
|---|---|---|---|---|
|  |  | @E1 | @E2 | @E3 |
| Water, SLD current 200 mA | Average | 43 | 57 | 119 |
|  | StDev | 15 | 17 | 28 |
| Skin, all signals, | Average | 2.7 | 19 | 142 |
|  | StDev | 14 | 64 | 92 |
| Skin, only signals with | Average | 80 | 93 | 194 |
| nanobubbles | StDev | 0 | 115 | 37 |

Figure 10C:
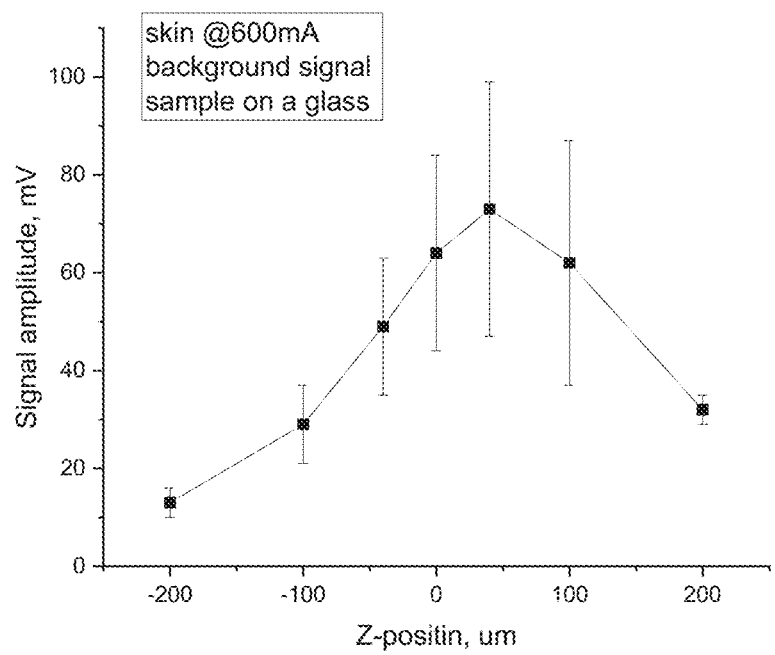
Figure 10D:
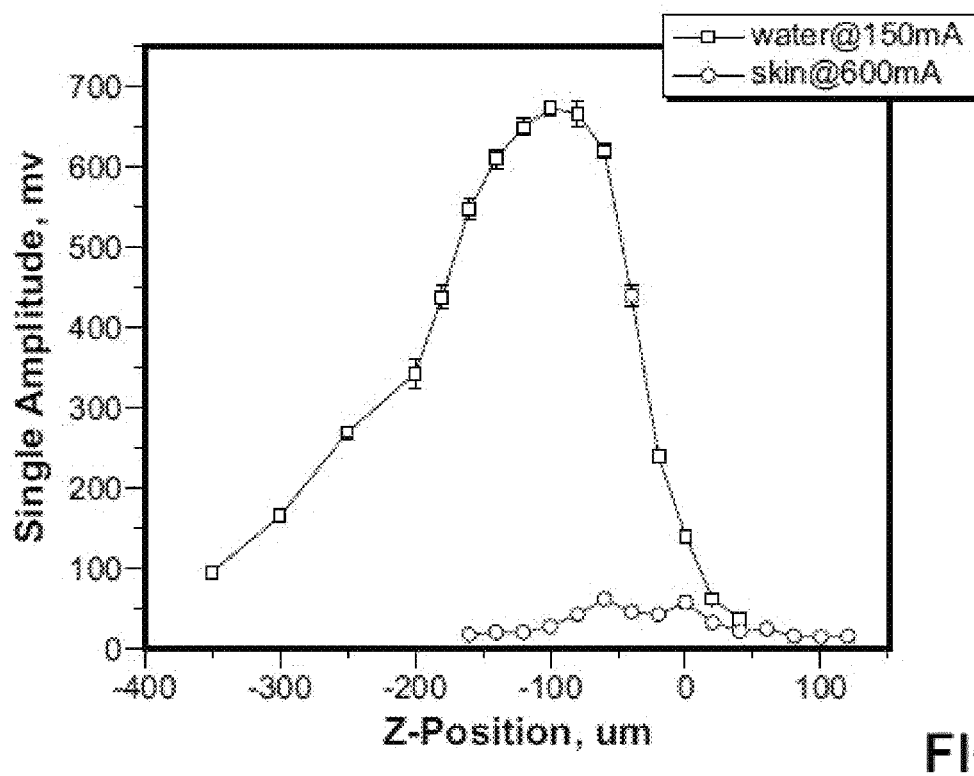
Figure 10E:
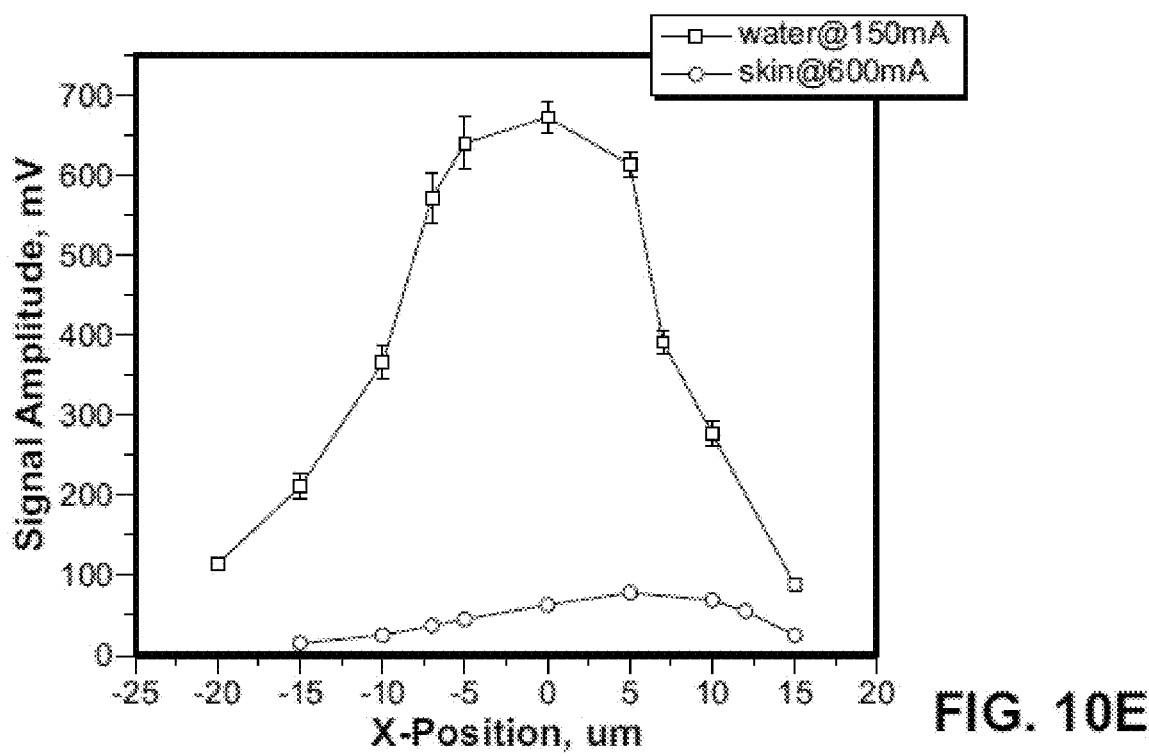
Figure 10F:
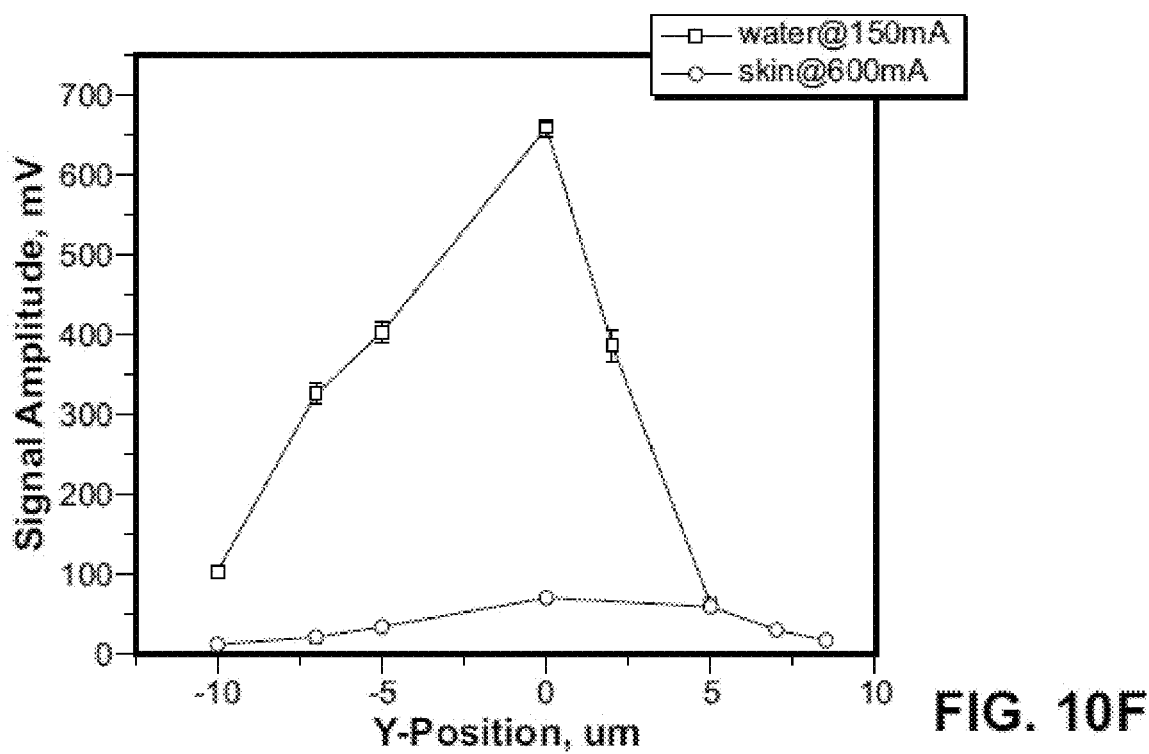

FIG. 10C illustrates the background level for the skin sample on the transparent microscopic glass slide that is not gold-plated. The information in FIG. 10C was superimposed onto transient vapor nanobubble signals in FIGS. 10D-10F to study the effect of the X, Y, and Z coordinates of the optical system on the amplitude of the transient vapor nanobubble signal in the skin. As shown in FIGS. 10D-10F, the optical system as shown in FIG. 9A can detect a transient vapor nanobubble within the volume of Z=100 um, X=15 um, and Y=15 um. A skilled artisan can appreciate based on the present disclosure that alternative parameters can be used in additional embodiments.

Figure 10G:
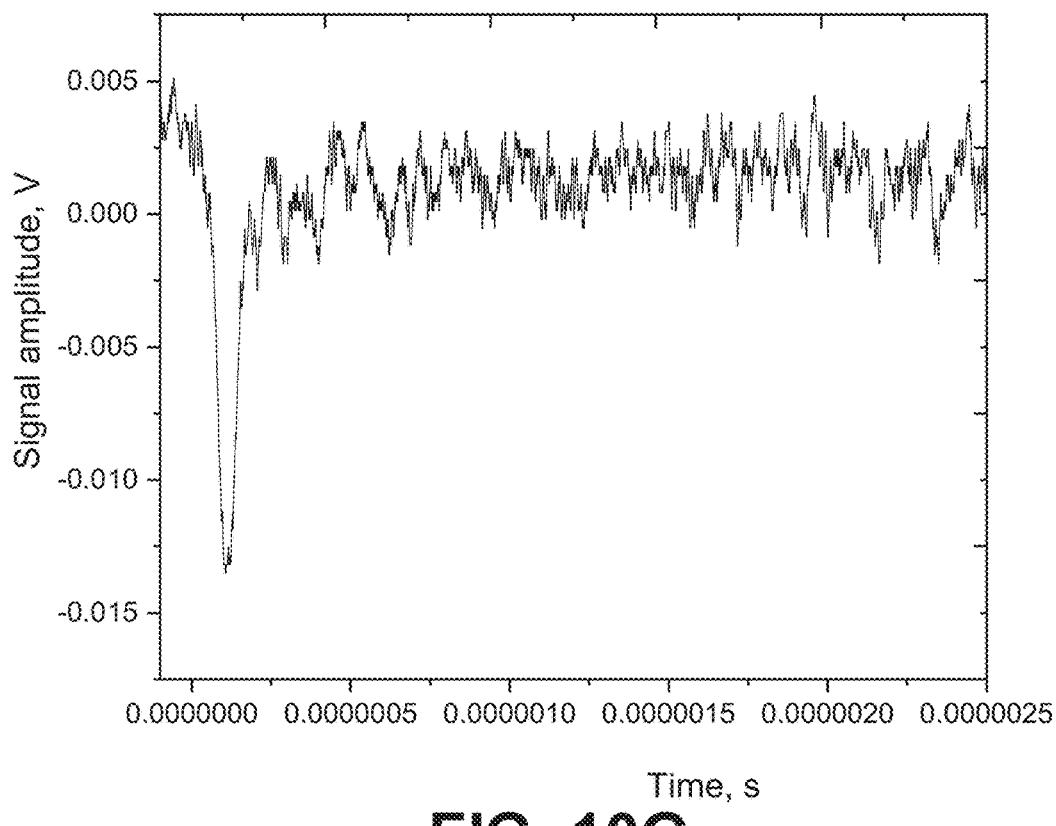
Figure 10H:
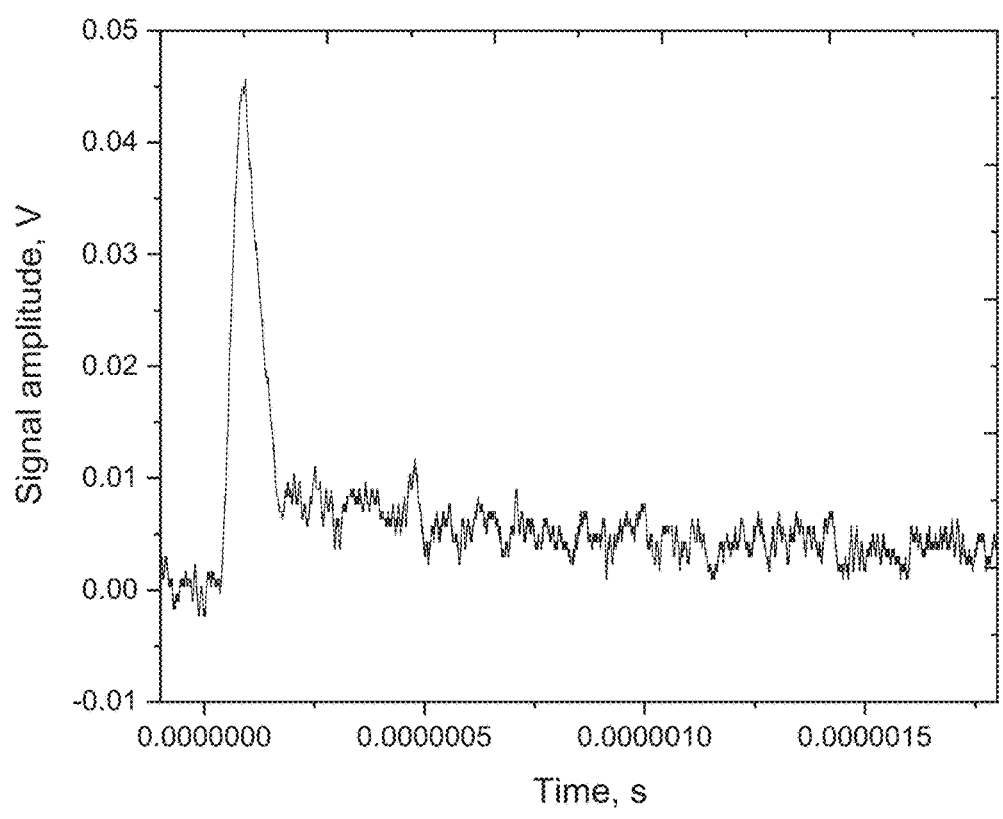
Figure 10I:
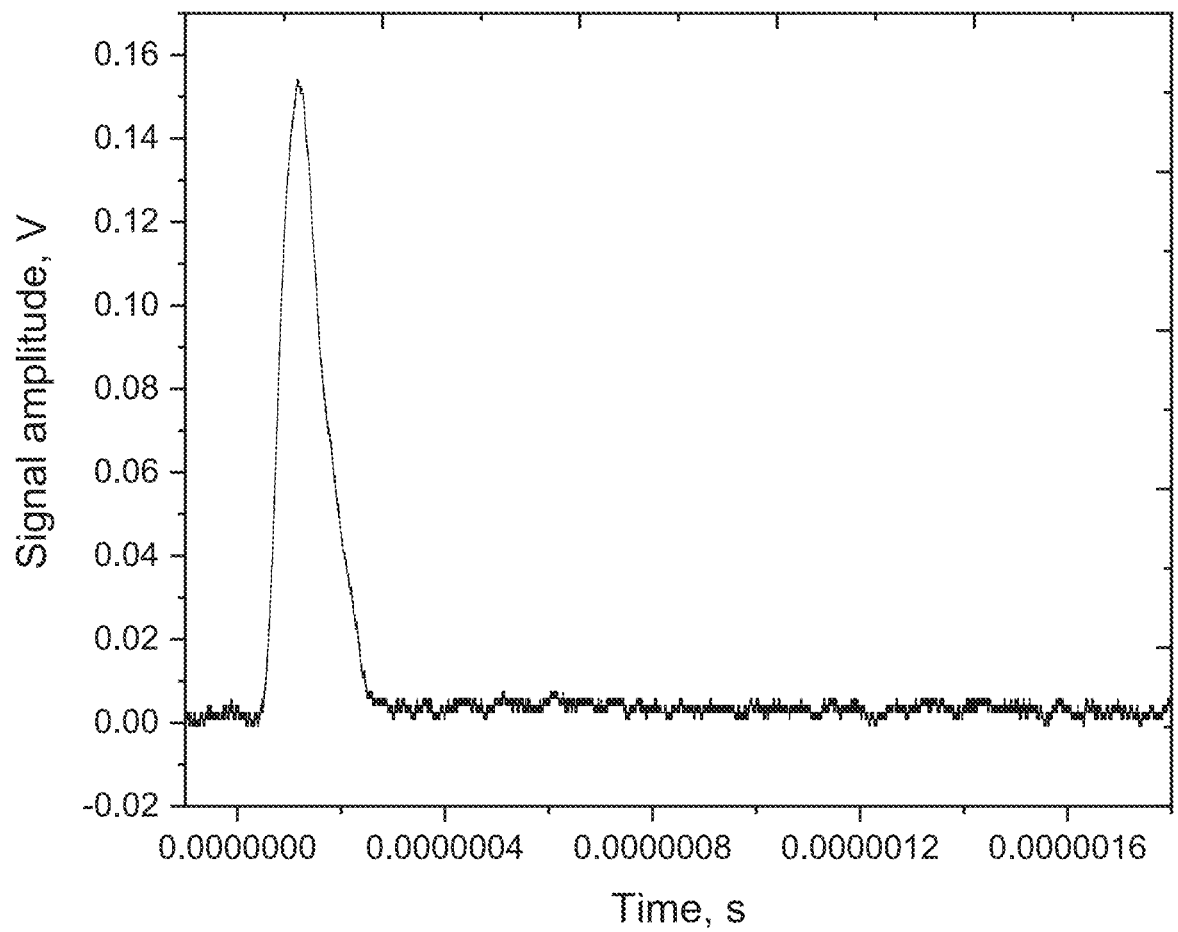
Figure 10J:
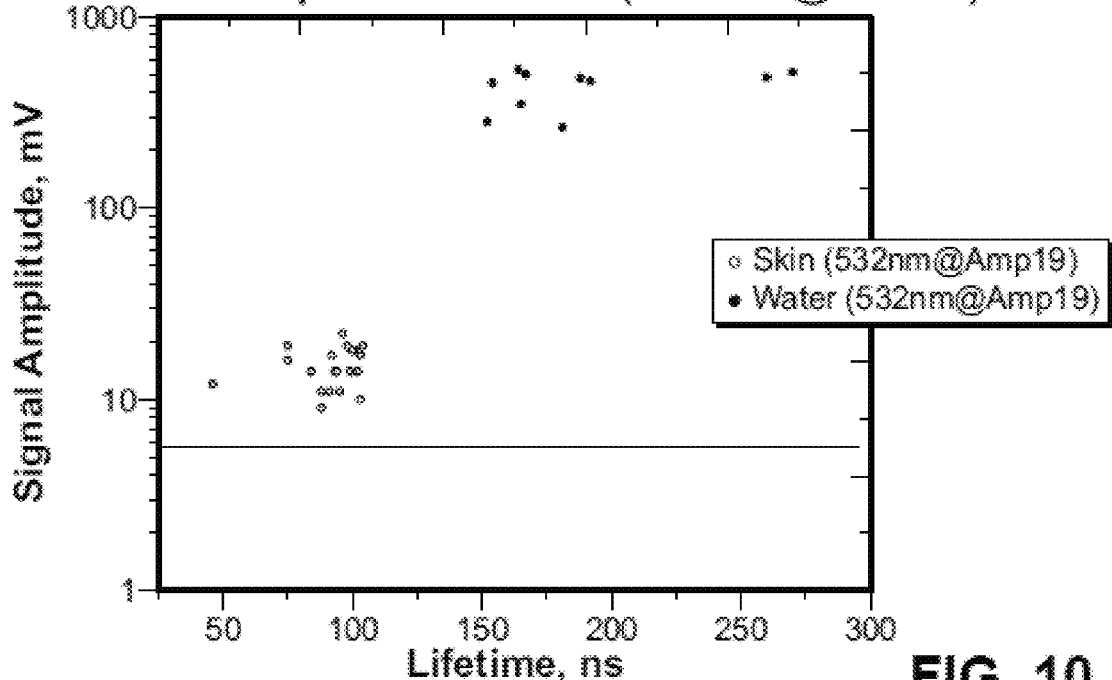
Figure 10K:
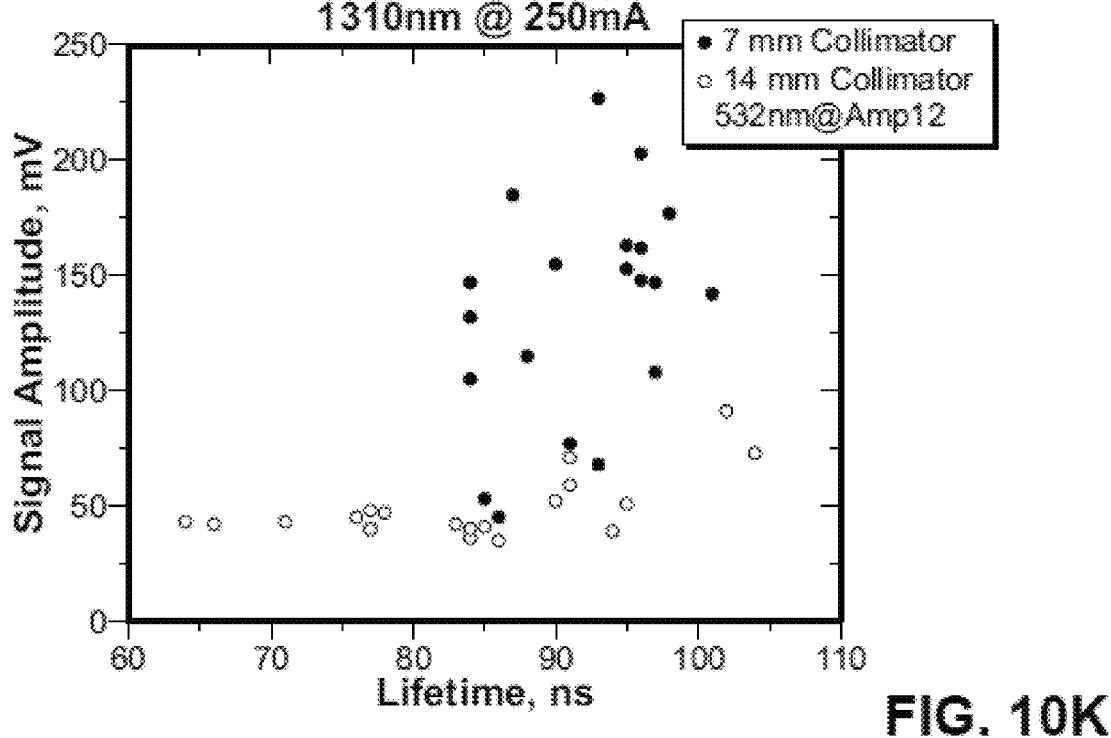

As described above, the skin significantly attenuates the transient vapor nanobubble signal compared to that in water. After optimizing the alignment of the optical system as illustrated in FIG. 9A, signals of the gold-generated transient vapor nanobubbles were compared for water and for skin sample (dark human, 250 um thick) for determining the alignment settings that are optimized for the skin. FIG. 10G illustrates an optimally detected signal due to transient vapor nanobubbles formed in the skin sample, using a collimator lens (such as L1 described above) having a focal distance of about 15 mm. FIG. 10G illustrates an optimally detected signal due to transient vapor nanobubbles formed in water, using a collimator lens (such as L1 described above) having a focal distance of about 14 mm. FIG. 10I illustrates another optimally detected signal due to transient vapor nanobubbles formed in water, using a collimator lens (such as L1 described above) having a focal distance of about 7 mm. FIG. 10J illustrates the signal amplitude of silver-generated transient vapor nanobubble in the skin sample and FIG. 10K illustrates the signal amplitude of silver-generated transient vapor nanobubble in water. As shown in FIGS. 10G-10K, the alignment settings for detecting the maximal or optimal nanobubble signals were found to be different for the skin and water.

The statistical summary for the water and the skin for the two different settings of the probe beam (L1) collimator is shown below in Table 8. A skilled artisan can appreciate based on the present disclosure that alternative parameters can be used in additional embodiments.

TABLE 8

Detection system optimized for bubble detection in water

|  | Water | |
|---|---|---|
|  | Collimator 7 mm @250 mA-large focal point, 16-17 um | Collimator 14 mm @250 mA, small focal point, 12 um |
| 532 nm pump beam laser amplification | 12 | 12 |
| Base level, p-t-p, mV | 473 | 643 |
| Vapor Nanobubble (VNB) lifetime, ns | 92 ± 5.4 | 84 ± 10.8 |
| Signal amplitude, mV | 136 ± 48.6 | 49 ± 14.3 |
| Base level noise, p-t-p, mV | 4.8 ± 0.7 | 5 ± 0.4 |
| Signal Noise Ratio (SNR) | 28 | 10 |

The optical system can be optimized for detecting transient vapor nanobubble in the skin in the following manner. A skilled artisan can appreciate based on the present disclosure that alternative parameters can be used in additional embodiments.

TABLE 9

Detection system optimized for bubble detection under the skin (250 um) Collimator 15 mm @560 mA

|  | Water | | Skin |
|---|---|---|---|
| 532 nm pump beam laser amplification | 12 | 19 | 19 |
| Base level, p-t-p, mV |  | 875 | 1007 |
| VNB lifetime, ns | 88 ± 8.9 | 189 ± 42.1 | 91 ± 13.6 |
| Signal amplitude, mV | 64 ± 14 | 431 ± 96.6 | 15 ± 3.6 |
| Base level noise, p-t-p, mV | 7 ± 0.4 | 9 | 5 ± 0.4 |
| SNR | 9 | 48 | 3 |

Under the current settings, small nanobubbles of 100 ns lifetime (smaller than those detectible acoustically where the minimal detectible nanobubble had 300 ns lifetime, see U.S. application Ser. No. 16/213,923) can be detected with a relatively poor SNR of 3. To improve the SNR, spatial filtering of the probe beam can be applied between the photodetector and the photodetector lens (L3). In early experiments in which a single mode optical fiber was used as a spatial filter to deliver the probe beam to the photodetector (the details of which are described below), the noise of the background was about 10-20 fold lower while the signal amplitude was comparable to that shown in the table above. However, using the single mode fiber may not be efficient because the core diameter of the single mode fiber, which is about 9 um, may be too small to collect enough light. In some embodiments, the diameter of a spatial filter can be designed to match the diameter of the probed zone, which is corrected by the factor $F_{photodetector}/F_{working}$. Accordingly, for a 20-um probed zone, the correction factor can be 2.6 (40 mm/15 mm). As a result, the diameter of the spatial filter would need to be close to a 50-um pinhole for the 20-um probed zone. A skilled artisan can appreciate based on the present disclosure that alternative parameters can be used in additional embodiments.

Figure 11B:
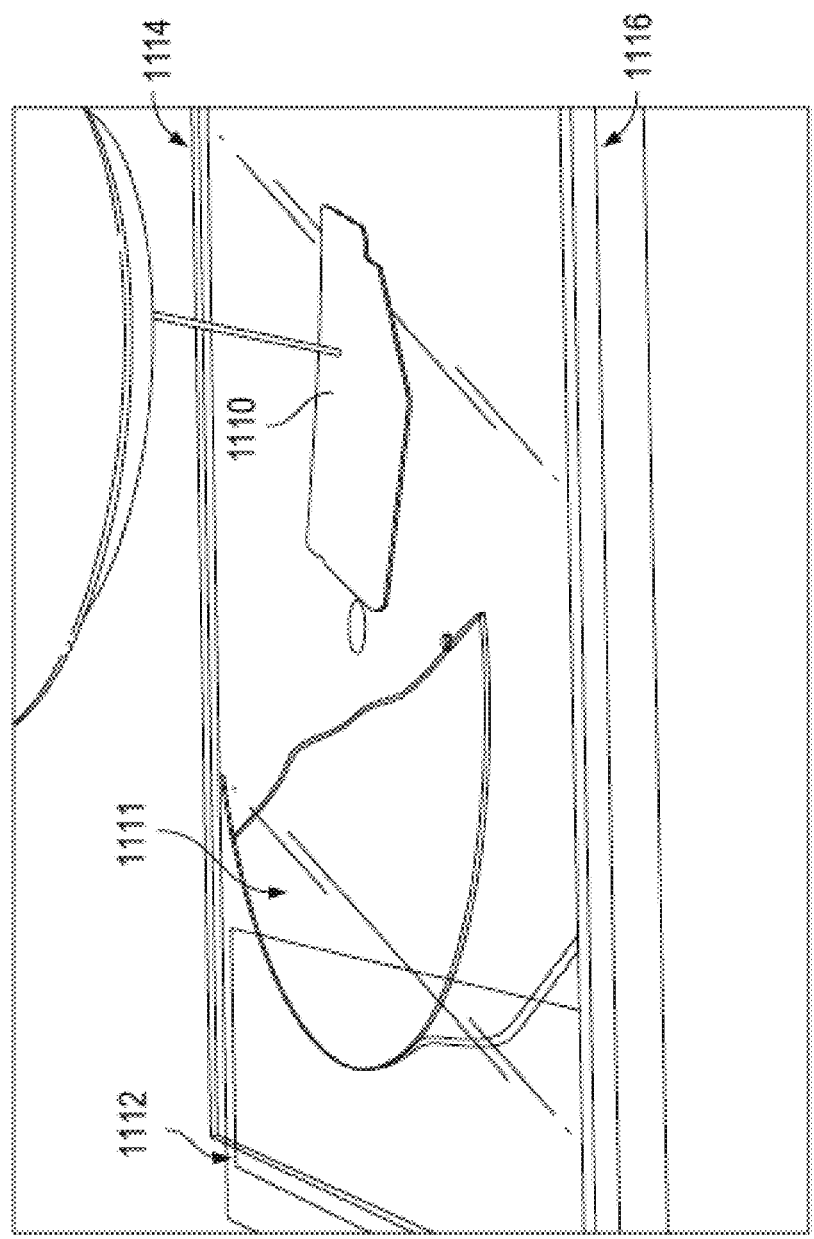
FIGS. 11A-11C illustrate an example experimental setup to detect optical scattering by Hemozoin-generated transient vapor nanobubbles in human skin and around human malaria parasites, with signals from transient vapor nanobubbles generated by gold particles as a positive control (the positive control was achieved by generating vapor nanobubbles in gold film with 532 nm laser pulses).
Figure 11A:
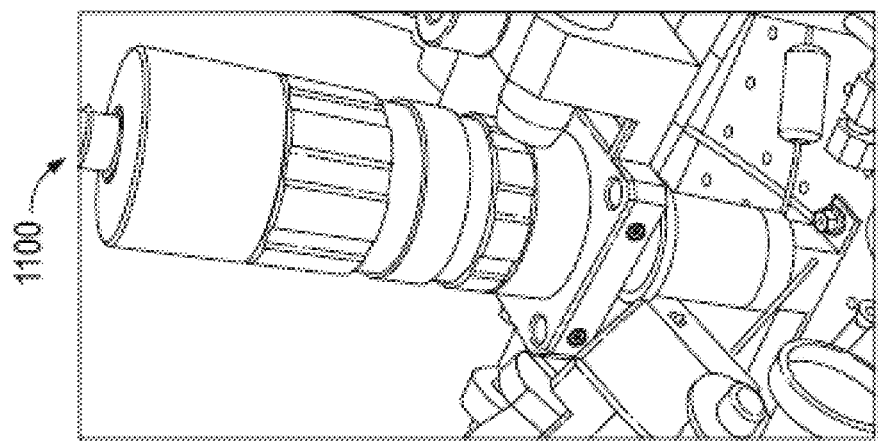

Example Experimental Results of Using an Optical Detection Experimental Setup to Detect Malaria Parasite in Skin Example Model with Single Mode Optical Fiber (9 Um Core Diameter) as a Spatial Filter FIG. 11A illustrates an example power source 1100 for the pump beam. The pump beam can include laser pulses having a wavelength of 671 nm or 532 nm or from about 670 nm to about 675 nm. FIG. 11B illustrates an experimental model for detecting malaria parasite in skin. The model can include a gold nanofilm 1112, and a testing sample between two microscopic glass slides 1114, 1116. The testing sample can include a skin sample (such as a piece of dark skin) 1110 without any malaria parasites, a sample of skin 1110 with malaria parasites (such as residue *Plasmodium falciparum* located in the bottom of the skin sample), or water 1111 with malaria parasites.

The malaria parasite excitation beam or pump beam can be delivered from above the model, through the glass slide 1114. The gold nanofilm 1112 does not absorb the pump laser pulse having a wavelength of 671 nm. Accordingly, no transient vapor nanobubble can be generated (see FIG. 1B, which illustrates the intact skin sample on gold plate signal in response to a laser pulse with a wavelength of 671 nm and energy of 20 uJ from above the gold nanofilm 1112 through the air). The gold nanofilm 1112 was used as a positive control (with vapor nanobubbles generated with the 532 nm laser pulse) for the detection of transient vapor nanobubbles from malaria parasites.

Additional laser pulses having a wavelength of 532 nm was also delivered directly to the gold nanofilm 1112 from a bottom surface of the model, through the glass slide 1116. The gold nanoparticles can absorb the laser pulse at that wavelength. Accordingly, the gold excitation pulse (that is, having a wavelength of 532 nm) can generate a single vapor nanobubble at the surface of the gold particles (see photodetector signals shown in FIGS. 11D (intact skin) and 11E (skin with parasite), which illustrate the skin signal in response to a laser pulse with a wavelength of 532 nm and energy of 20 uJ from below the gold nanofilm 1112 through the air).

Figure 11C:
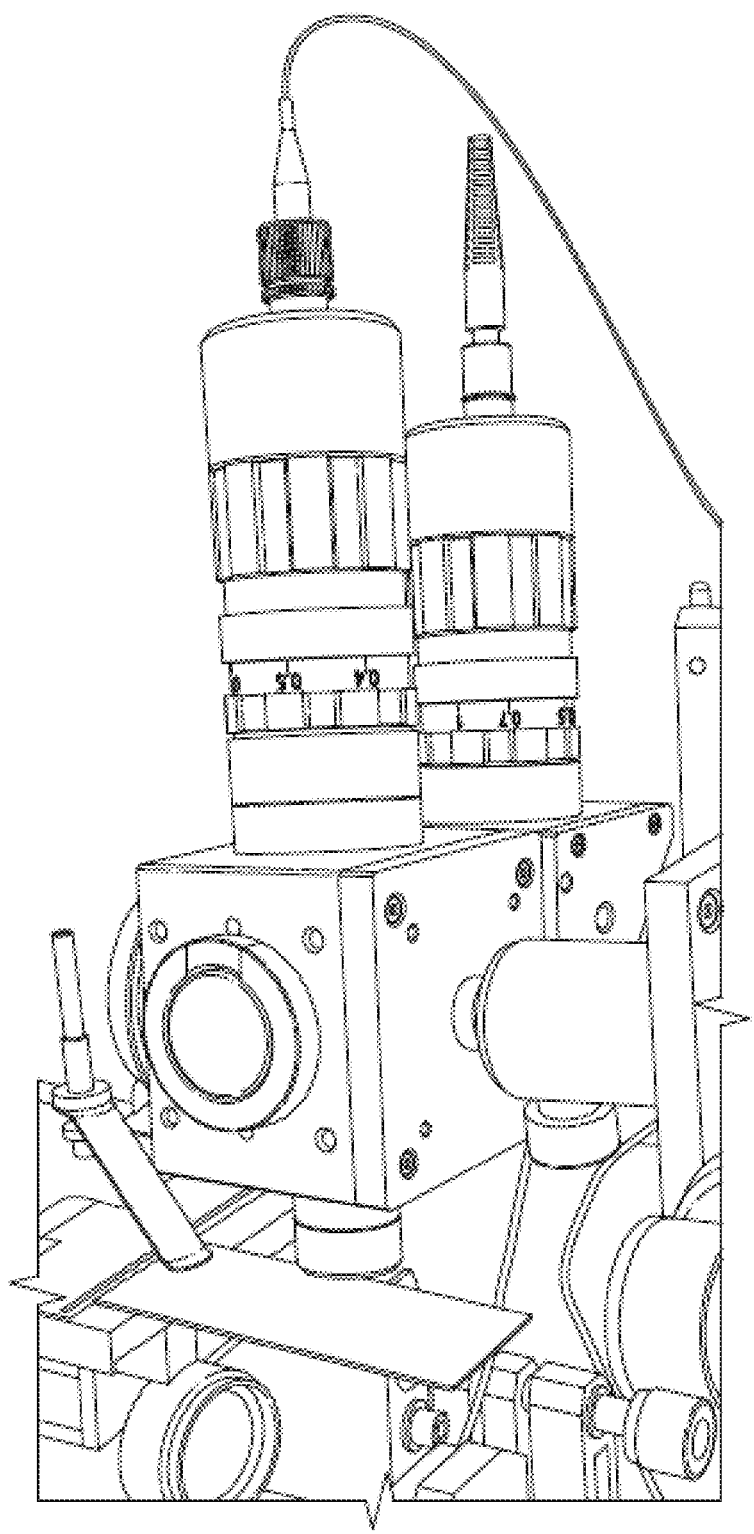
Figure 11D:
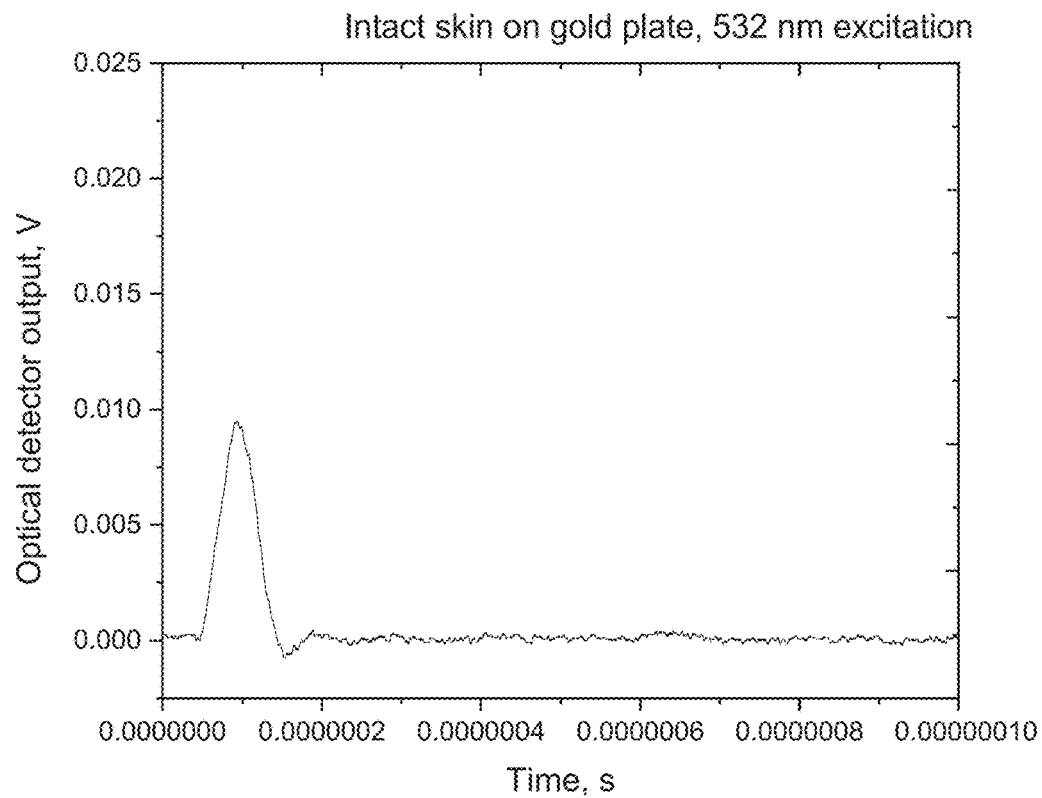
FIGS. 11D-11G illustrate example signals detected in the setup shown in FIGS. 11A-11C.
Figure 11E:
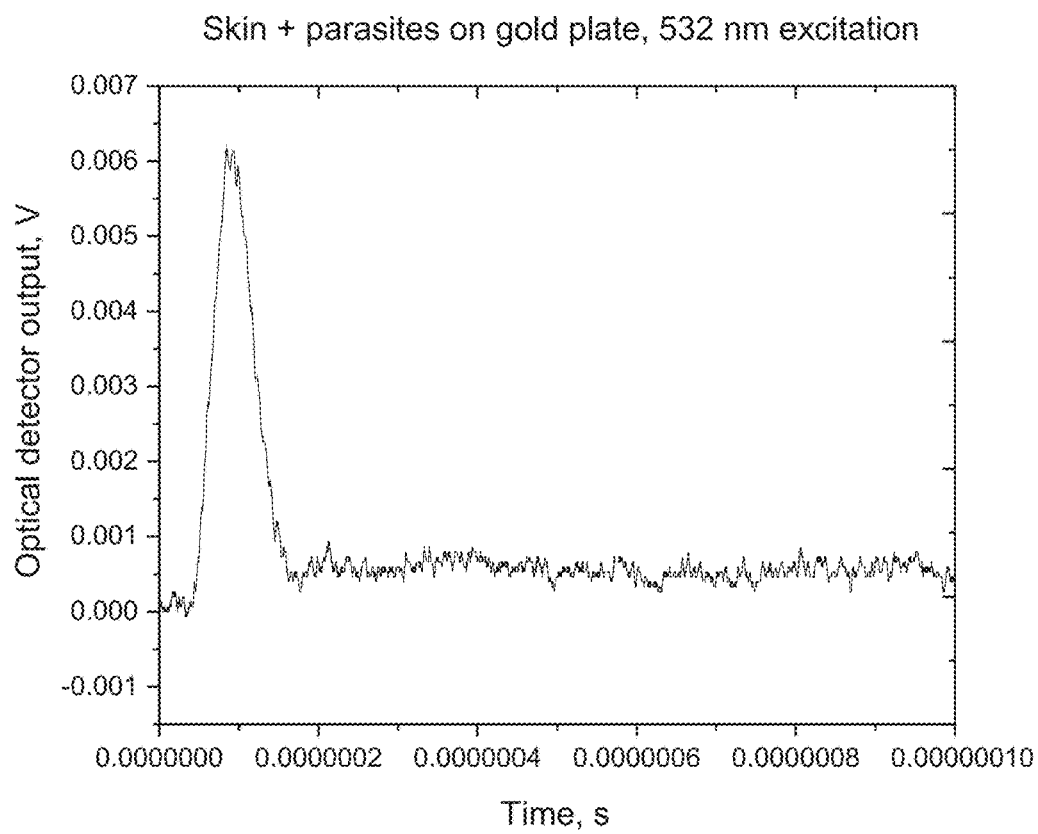

The optical excitation and detection were performed in a non-contact manner. The optical fibers for delivering the excitation (pump) laser pulses both terminate in the air and were not coupled to the test samples, including the glass slides 1114, 1116. The detection optics also terminated in the air and were not coupled to the test samples, including the glass slides 1114, 1116. The experimental setup as shown in FIG. 11C, which can employ the principle of the system described in FIGS. 1A and 3A, were optimized to increase the focal distance of the working Lens L2 and to reduce the numerical aperture of the Lens L2. The working lens can have a focal distance of about 15 mm. The changes can result in a larger probe zone, a lower sensitivity, and/or a low signal saturation threshold. An optical signal indicative of a Hemozoin-generated transient vapor nanobubble as small as about 100 ns in dark skin could be detected as positive. The signal could have an amplitude of about 4 mV to about 5 mV (with the noise level of about 0.3 mV). Therefore, the system shown in FIG. 11C may detect Hemozoin-generated transient vapor nanobubbles in skin that have a lifetime of 100 ns or more.

Further as shown in FIG. 2A, which illustrates the skin signals in response to three laser pulses each with a wavelength of 671 nm and energy of 20 uJ from above the skin through the air. The three signals show the transient vapor nanobubble-specific arch shape. Comparing the signal amplitude with the signal generated by the previous pulse, signal amplitude decays can be observed during the subsequent consecutive laser pulses.

Figure 11F:
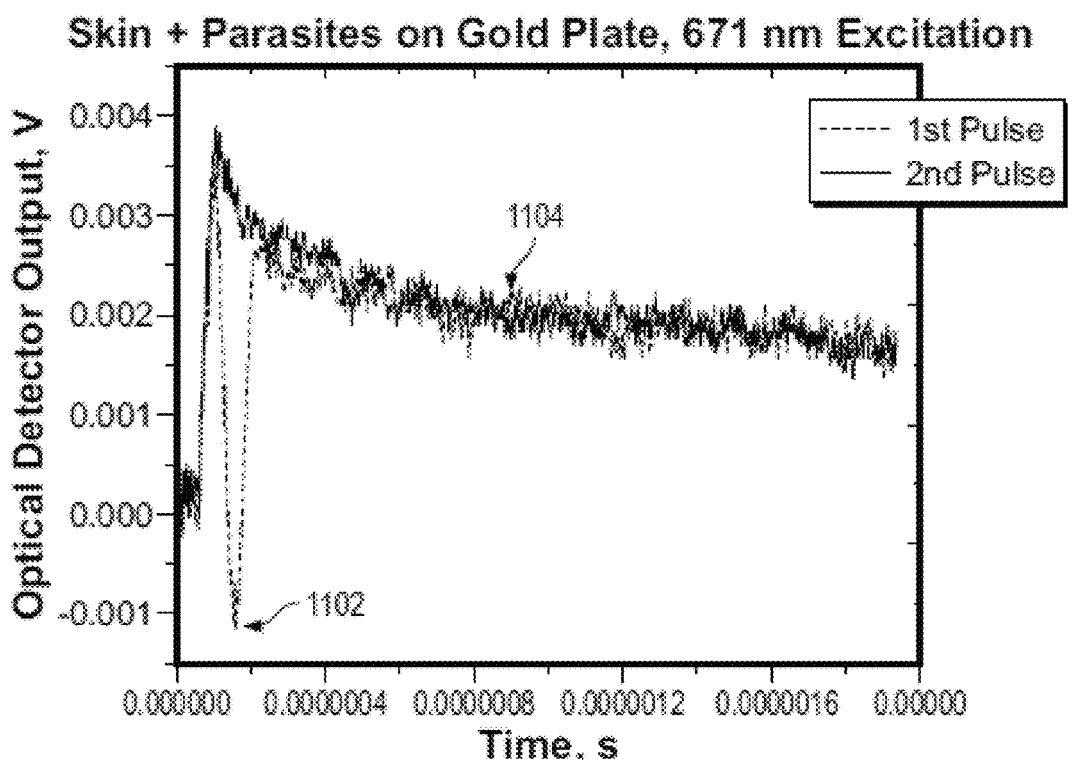
Figure 11G:
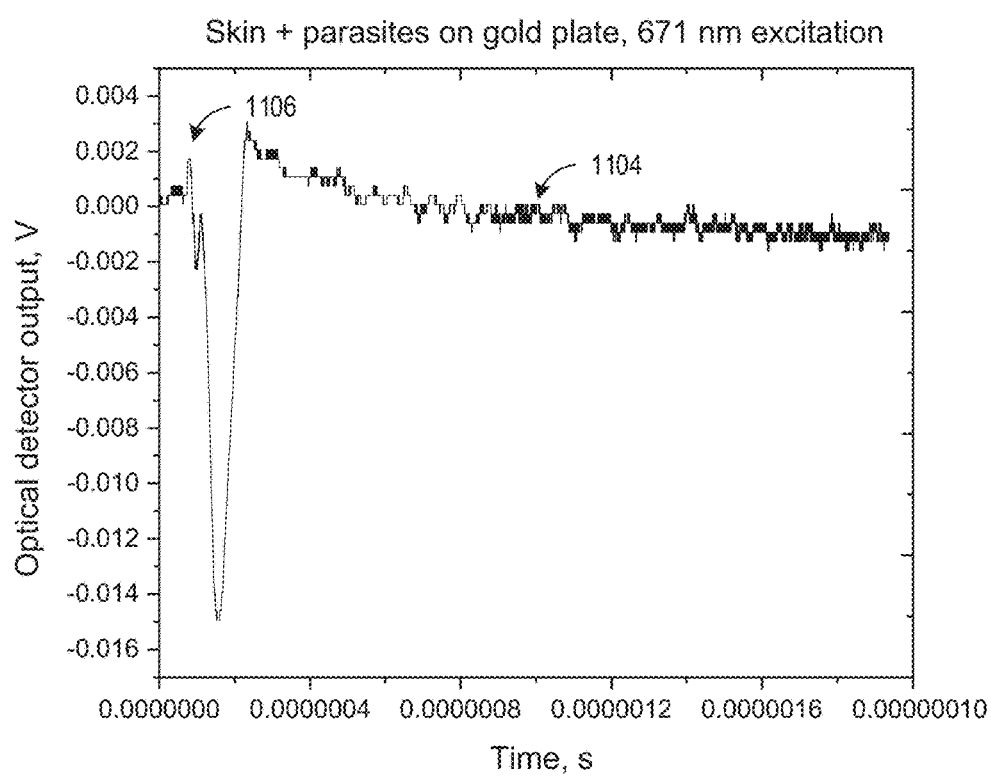

As shown by FIGS. 11F and 11G, different types of signals reflect the combination of several laser pulse-induced processes. In FIG. 11F, the transient vapor nanobubble signal responsive to the first laser pulse includes a negative arch 1102. However, this negative arch is not present in the signal responsive to the second laser pulse. The first signal can further include a sharp rise with a long exponential tail 1104. The tail 1104 can be reproducible during consecutive laser pulses (such as shown the signal responding to the second laser pulse). The tail 1104 can be due to photothermal heating. The signal in FIG. 11G also illustrates photothermal heating 1104 (a sharp rise with a long exponential tail). In addition, the signal in FIG. 11G also illustrates an acoustic transient 1106 (a short bipolar signal at the very beginning).

As shown above, the skin sample with the malaria parasites can deliver nanobubble-specific signals that are different for consecutive pump beam pulses. The signal can have an arch shape for the first laser pulse. The signal can show decaying of the amplitude and/or shape for the second and subsequent laser pulses.

In addition, vapor nanobubbles, photothermal effects (transient heating) and photoacoustic effects (pressure wave) all produce signals of different shape. The nanobubble signal shows the arch shape for the duration of the nanobubble lifetime (about 20 ns to about 2000 ns). The acoustic transient signal shows a bipolar spike for the duration of about 10 ns. The photothermal heating effect signal shows a step-like exponential signal for the duration greater than 1 microsecond.

An intact dark human skin sample of about 150 um in thickness does not produce any detectable signals when the focal volume was located at the depth of around 170 um. The signal observed at the photodetector may remain a flat line with the amplitude determined by the detector noise. A dark human skin sample of about 150 um in thickness with residual *Plasmodium falciparum* parasites at its bottom can produce all three types of the signals, including those due to Hemozoin-generated transient vapor nanobubbles.

Moreover, the optical scattering system such as shown in FIGS. 11A-11C can detect transient vapor nanobubbles, photothermal, and photoacoustic phenomena (induced by the pump laser pulse) generated within or close to the focal volume of the system. The optical scattering experimental setup such as shown in FIGS. 11A-11C does not detect transient vapor nanobubbles, photothermal, and photoacoustic phenomena (induced by the pump laser pulse) generated outside of the focal volume of the system.

The smallest detectable gold-generated transient vapor nanobubbles in a skin sample can be of 15-20 ns lifetime. This transient vapor nanobubble can be 20-fold smaller than the threshold of acoustic detection of transient vapor nanobubbles (which may be about 300 ns using a hydrophone as described in U.S. application Ser. No. 16/213,923, which may have a size of 0.4 mm). The smallest detectable parasite-generated nanobubbles in a skin sample can be of about 100 ns or less lifetime, with an SNR greater than 10. Compared to ultrasonic (that is, acoustic detection) data obtained for the same skin models in U.S. application Ser. No. 16/213,923, the optical detection systems disclosed herein may improve both the sensitivity and selectivity of the detection of parasites and also offer a possibility of non-contact detection.

The human skin can have a damping effect on the transient vapor nanobubble expansion and can also delay the transient vapor nanobubble collapse. The damping effects are not present in the transient vapor nanobubble signals generated under identical excitation conditions in water. Similar damping effects are also observed with acoustic detection of transient vapor nanobubbles.

In some embodiment, the current setup may be modified to include a coaxial and permanently aligned pump laser beam.

Example Optical Detection System Without Spatial Filter

As described above, the optical detection systems can also include no spatial filter (or optical fiber). FIGS. 12A-12G illustrate results of a first example experiment using such a system. In the first example experiment, the pump laser beam had a wavelength of 671 nm and a cross-sectional size of 61×49 um at the working plane. The pump beam was 176×184 um in cross-section at about 270 um up from the working plane. The pump beam was focused at about 79 um below the working plane. The probe laser beam had a wavelength of 1310 nm and a focal size of about 18×16 um at the working plane. The probe beam had an SLD current of 600 mA. A black marker under the skin on a microscopic glass slide was exposed to a 671-nm excitation laser pulse as a positive control sample. Intact skin on a microscopic glass slide was exposed to a 671-nm pump laser pulse as a negative control sample. A Skin sample was placed over malaria parasites dried on a microscopic glass slide as a test sample. The test sample was also exposed to a 671-nm pump laser pulse. The parasite concentration can be a 3 times reduced concentration compared to a typical parasite concentration in a malaria positive patient. A skilled artisan can appreciate based on the present disclosure that alternative parameters can be used in additional embodiments.

Figure 12A:
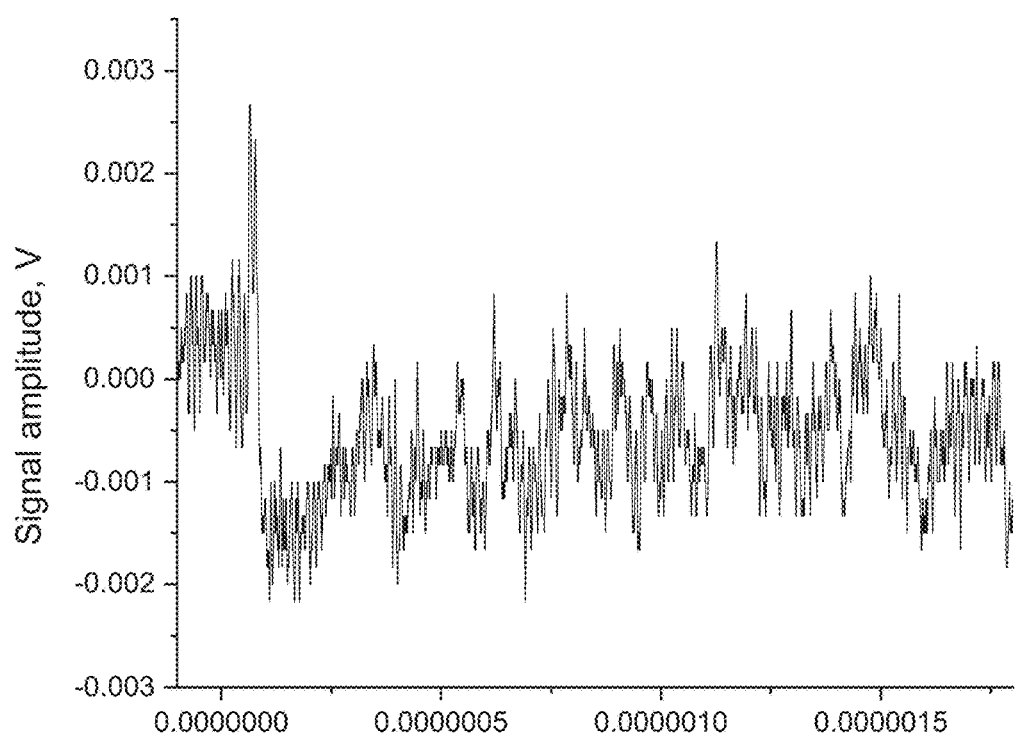
FIGS. 12A-14E illustrate example data using optical detection of malaria parasites in skin systems without spatial filtering.
Figure 12B:
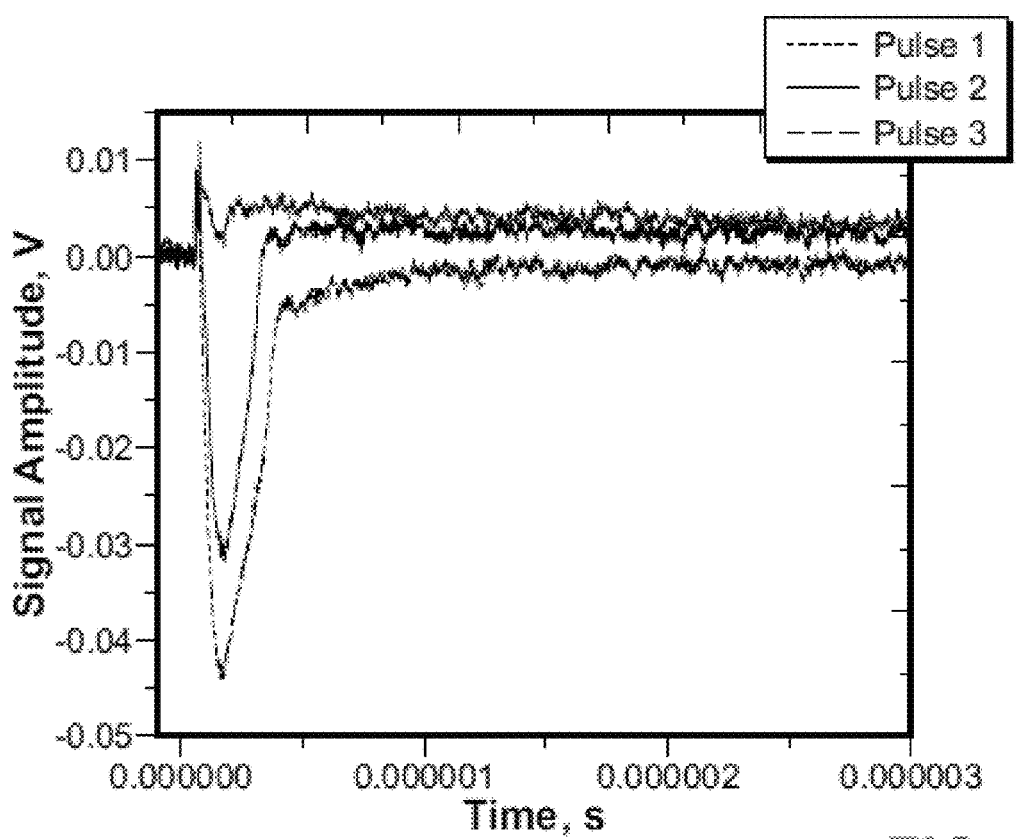

Transient vapor nanobubble detection under the skin was first verified using the positive control sample (that is, the black marker). Second, the negative control sample (that is, the intact skin) and the test sample (that is, skin with parasite) were tested under identical conditions. FIG. 12A illustrates the signal detected from the negative control sample. FIG. 12B illustrates the signal detected from the test sample. FIG. 12A shows the acoustic transient signal (a bipolar spike) and the photothermal heating effect signal (an exponential signal). FIG. 12B shows the nanobubble signal having an arch shape (negative in this case) for the first and second laser pulses, and a decay in the third pulse. The exponential tail of the signal can also be observed in all three signals in FIG. 12B. The bipolar spike can be observed in the signal responsive to the third laser pulse in FIG. 12B.

Figure 12C:
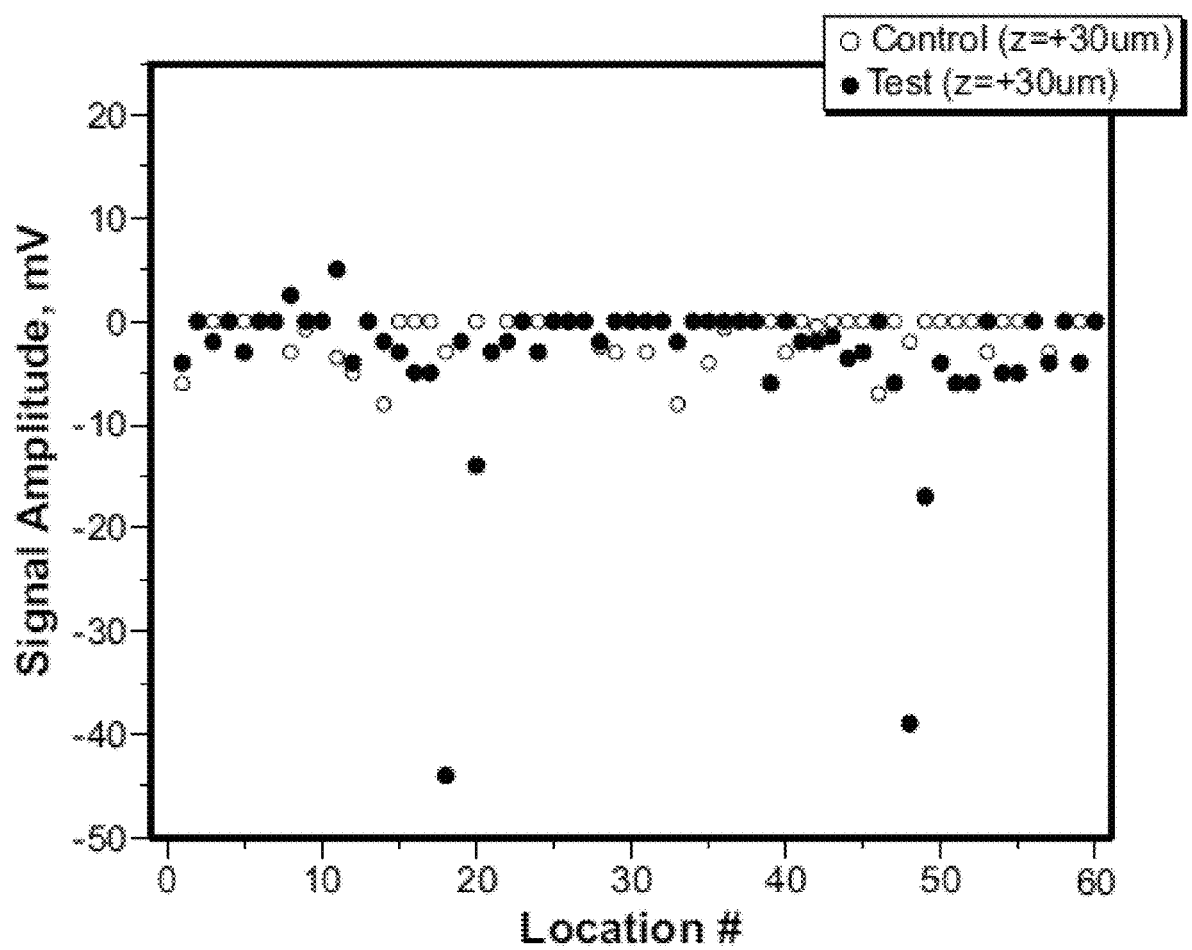
Figure 12D:
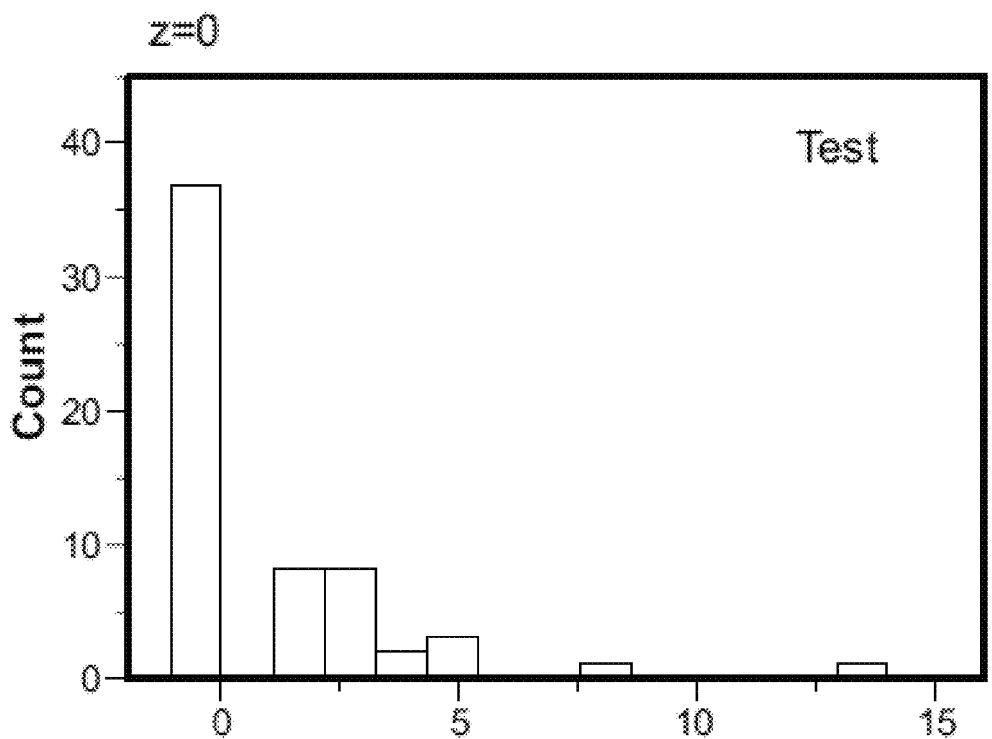
Figure 12E:
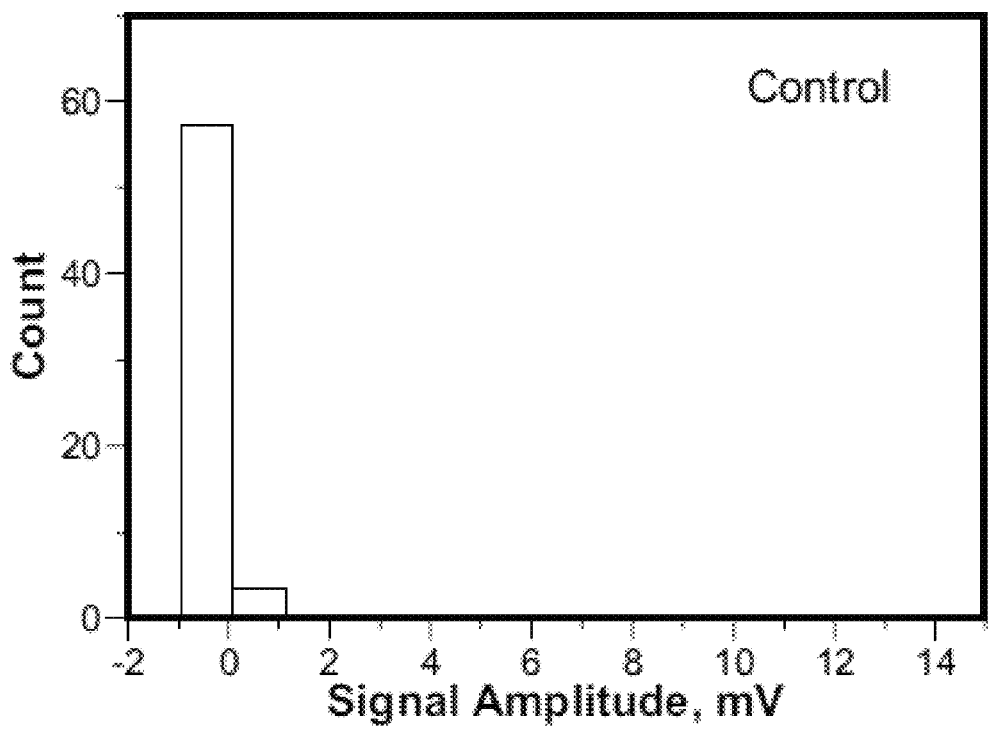
Figure 12F:
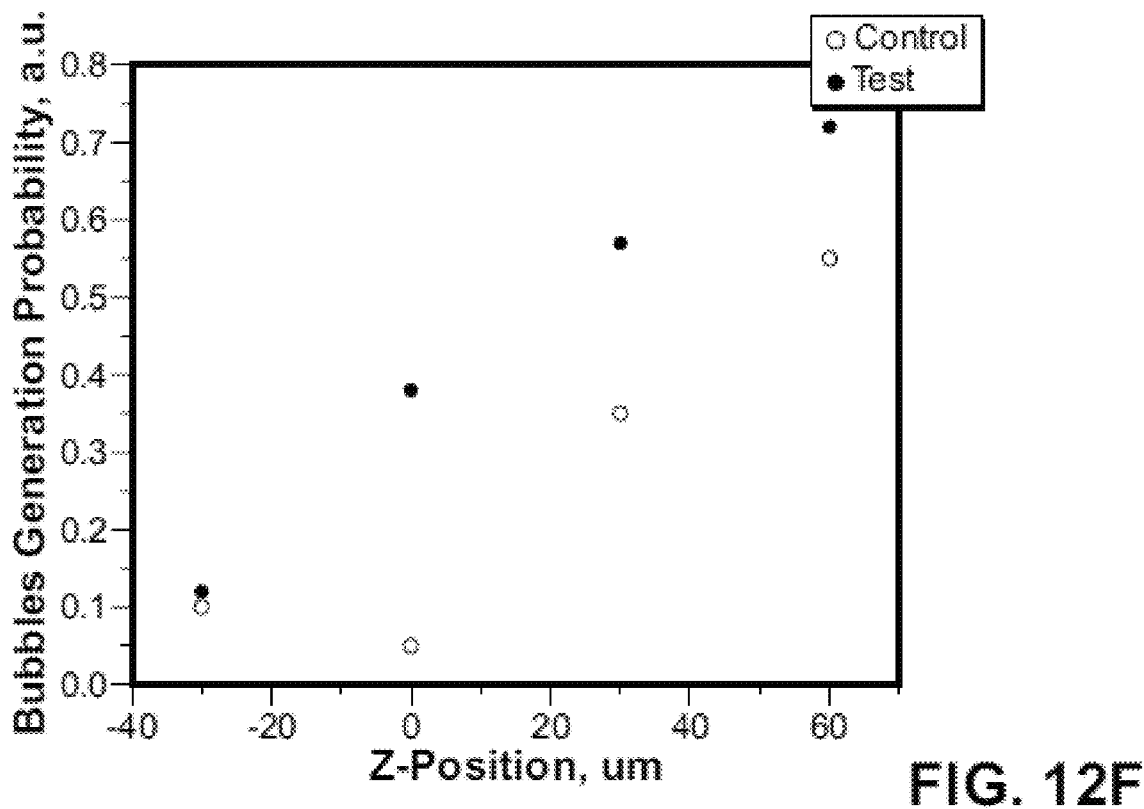
Figure 12G:
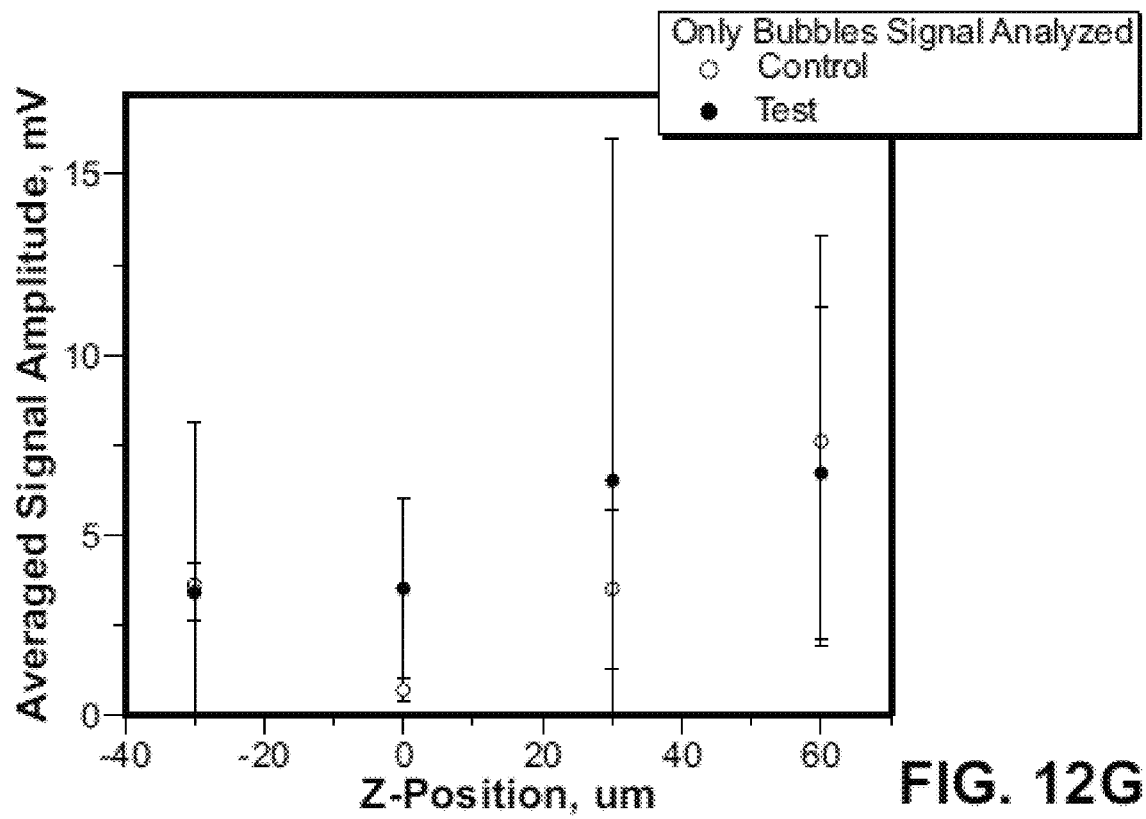

FIG. 12C illustrates signal peak-to-peak amplitudes for the negative control sample and the test sample by locations. FIGS. 12D (test sample) and 12E (negative control sample) illustrate the number of signals per signal peak-to-peak amplitude. FIG. 12D illustrates presence of nanobubble-specific signals, such as having an amplitude between about 2 mV to about 6 mV, which are not present in the negative control sample in FIG. 12E. FIGS. 12F and 12G illustrate the influence of the vertical (Z) position of the optical system on the diagnostic performance, such as the ability to detect the maximal transient vapor nanobubbles generated around malaria parasites underneath the human skin.

FIGS. 13A-13K illustrate results of a second example experiment using such a system. In the second example experiment, the pump laser beam had a wavelength of 671 nm. The pump beam had a cross-sectional size of 162×165 um at the Z position of about −270 um (that is, about 270 um above the working plane). The pump beam had a cross-sectional size of about 44×31 um at the Z position of 0 um (that is, at the working plane). The pump beam had a cross-sectional size of about 35×34 um at the Z position of about 31 um (that is, about 31 um below the working plane). The pump beam had a cross-sectional size of about 30×38 um at the Z position of about 50 um. The pump beam had a cross-sectional size of about 36×48 um at the Z position of about 100 um. Gold particles under the skin were exposed to a 671-nm excitation laser pulse as a positive control sample. Intact skin sample (negative control) on a microscopic glass slide was exposed to a 671-nm pump laser pulse as a control sample. Human skin sample with malaria parasites on a microscopic glass slide under the skin was exposed to a 671-nm pump laser pulse as a test sample. The parasite concentration can be a 3 times reduced concentration compared to the concentration in a malaria positive patient. A skilled artisan can appreciate based on the present disclosure that alternative parameters can be used in additional embodiments.

Transient vapor nanobubble detection under the human skin was first verified using the positive control sample (that is, the gold particles). Testing the positive control sample can ensure that transient vapor nanobubbles, if generated, were detected. Second, the control sample (that is, the intact skin) and the test sample (that is, skin with parasites underneath) were test under identical conditions. The probe laser beam had a wavelength of 1310 nm.

An L1 collimator having a focal distance of 7 mm was used. When a weak transient vapor nanobubble signal was detected, the base level was adjusted to maximize the amplitude of the detected signals. In the results shown in FIGS. 13A-13E, the base level was dropped to 130 mV from the maximum value of 300 mV.

Figure 13A:
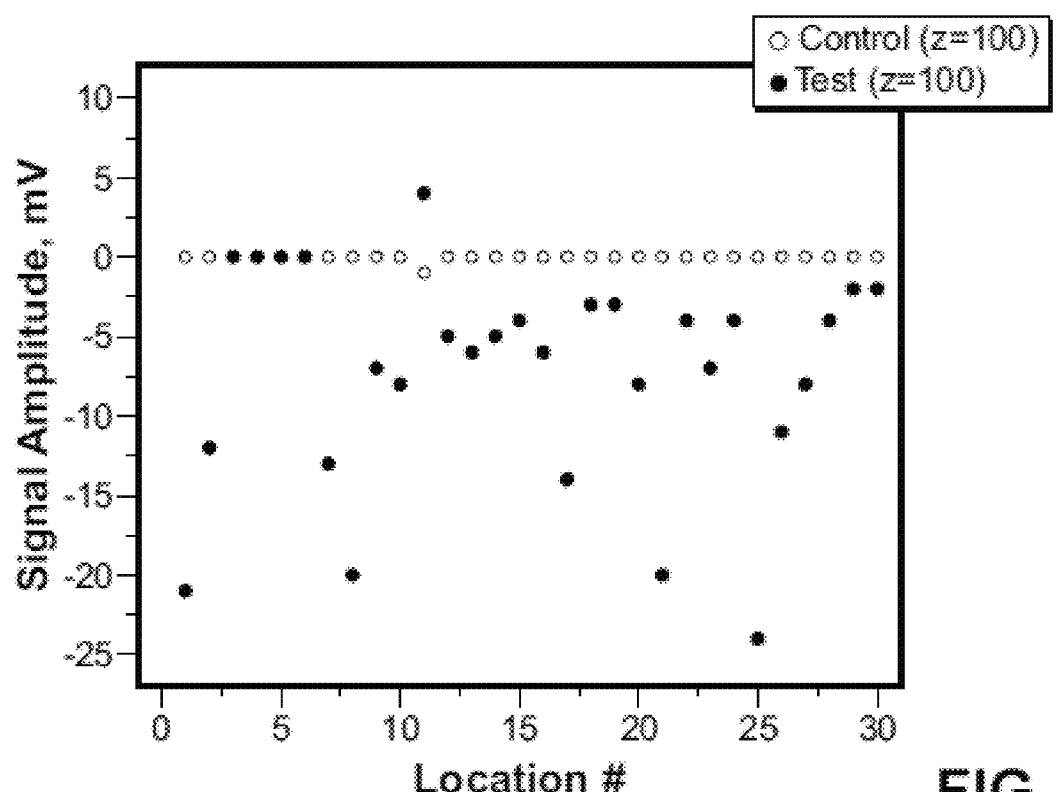
Figure 13B:
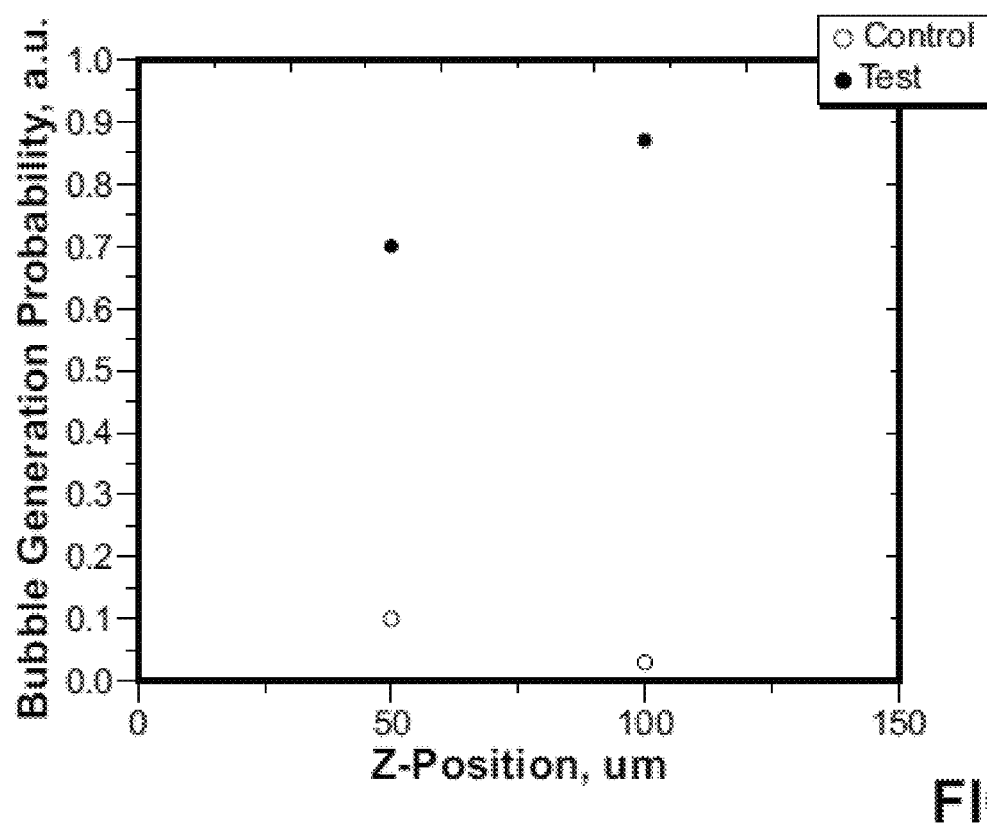
Figure 13C:
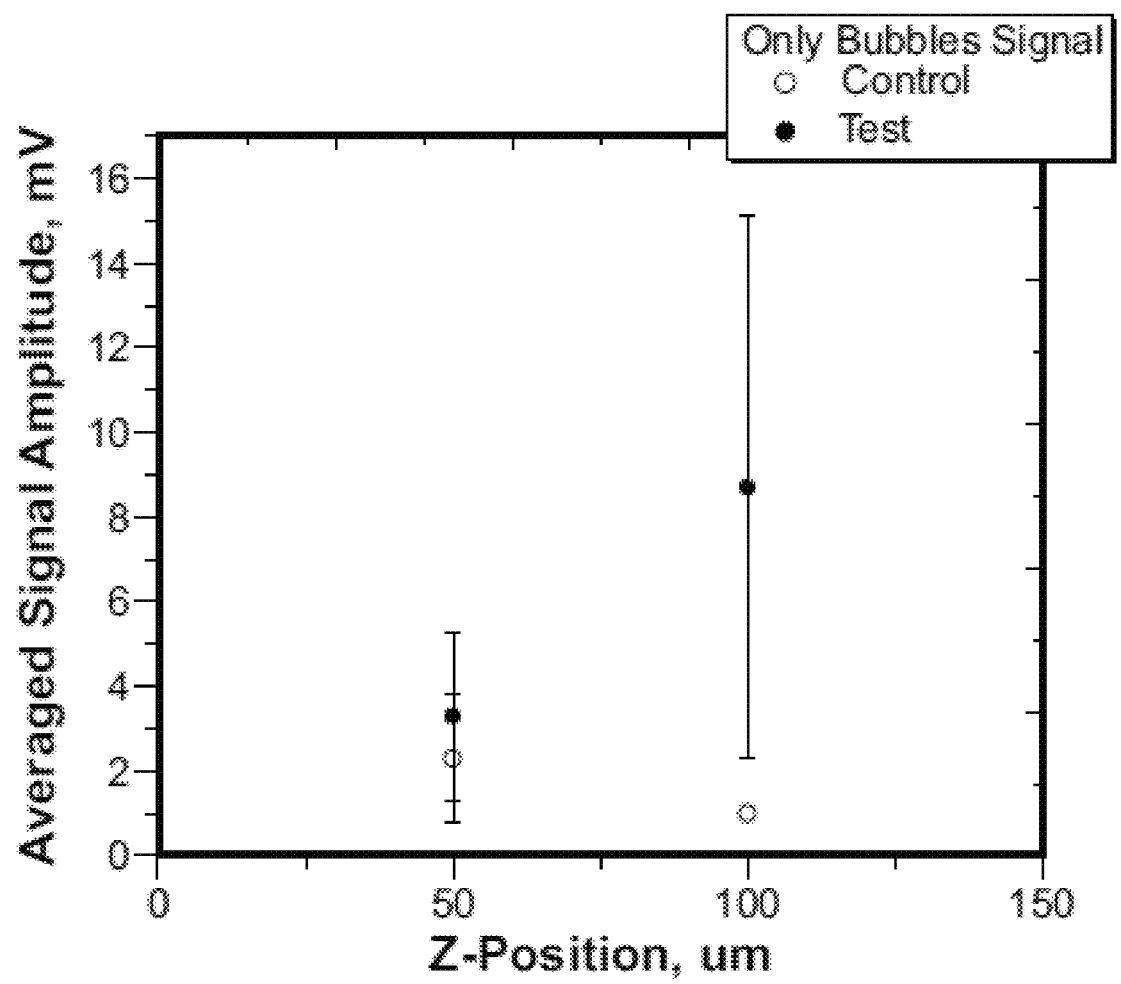
Figure 13D:
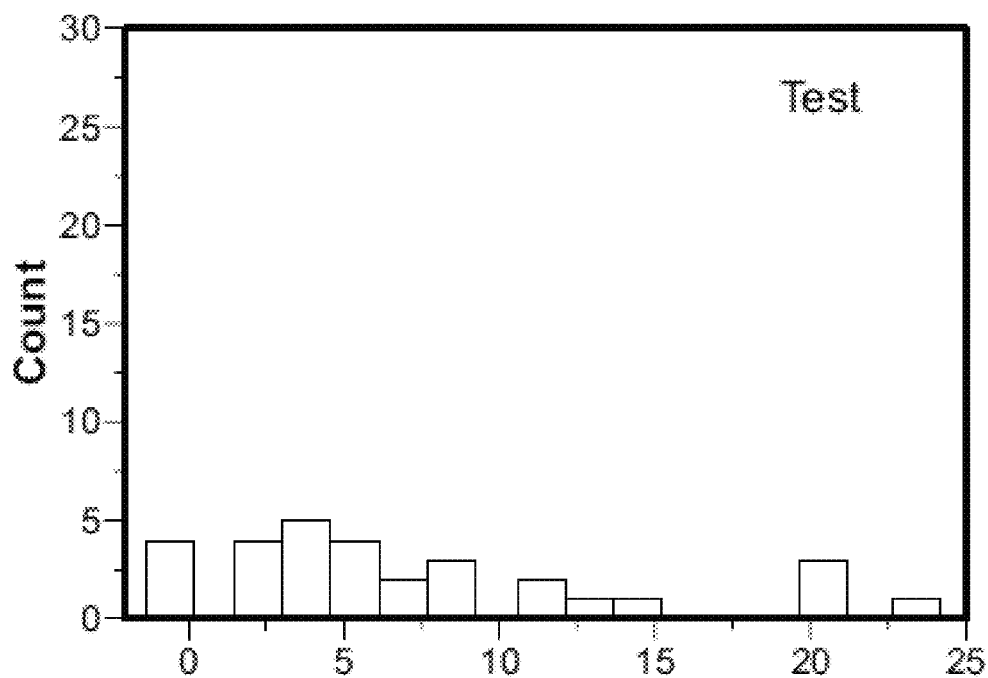
Figure 13E:
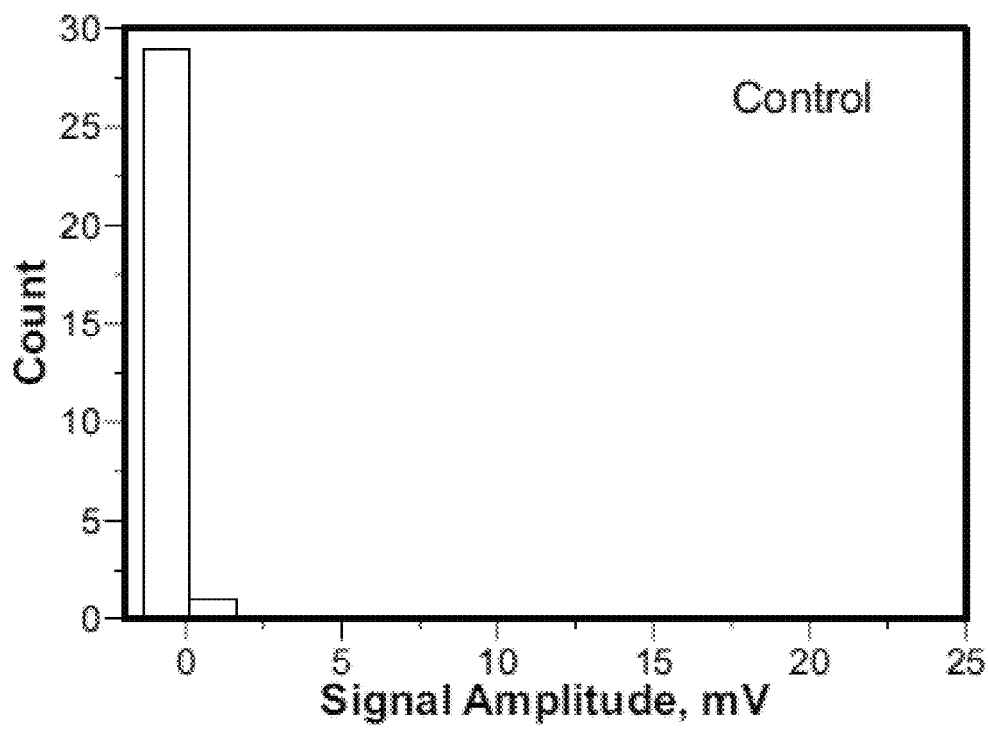
Figure 13F:
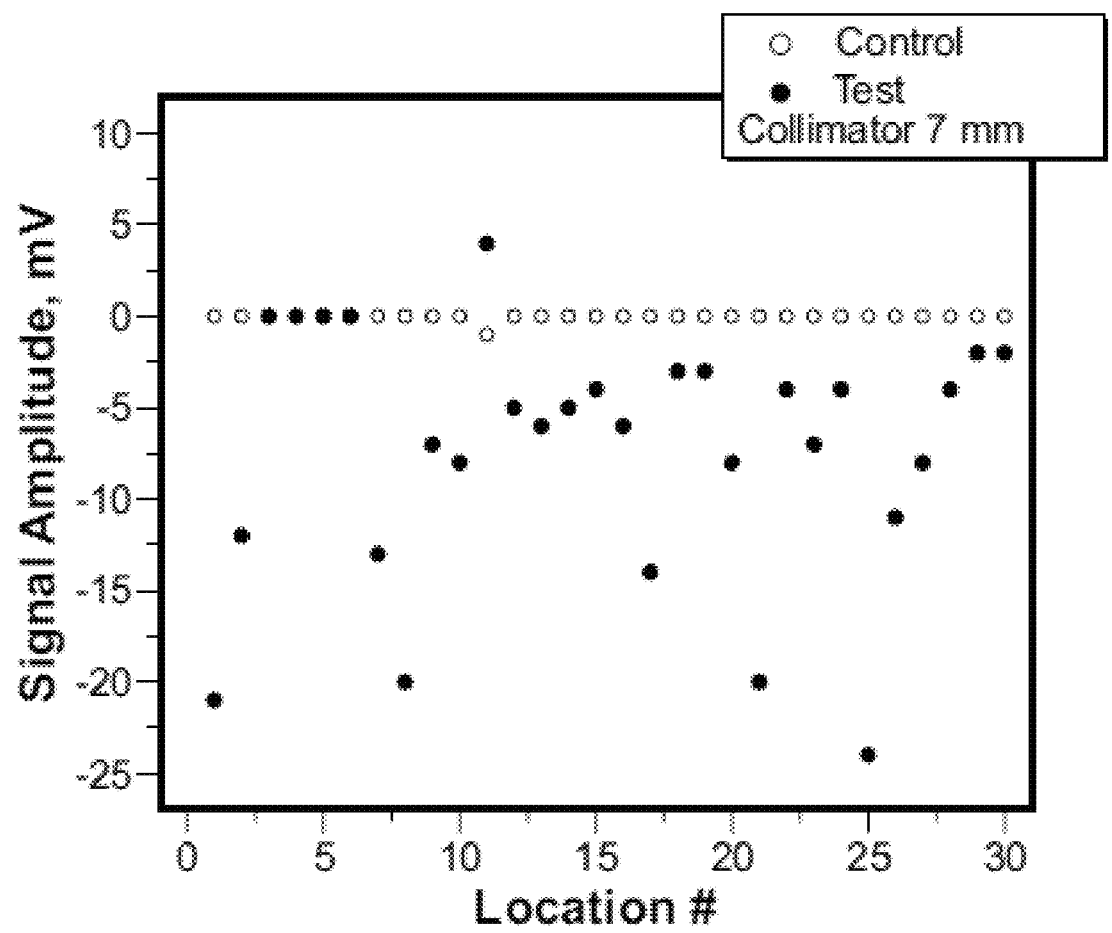
Figure 13G:
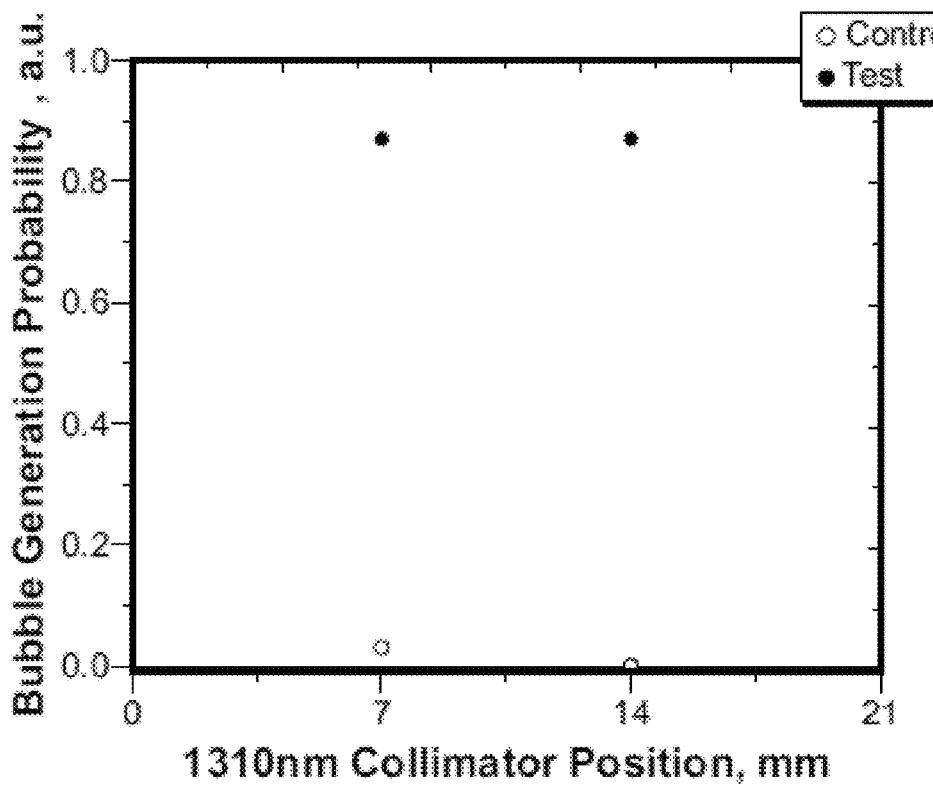
Figure 13H:
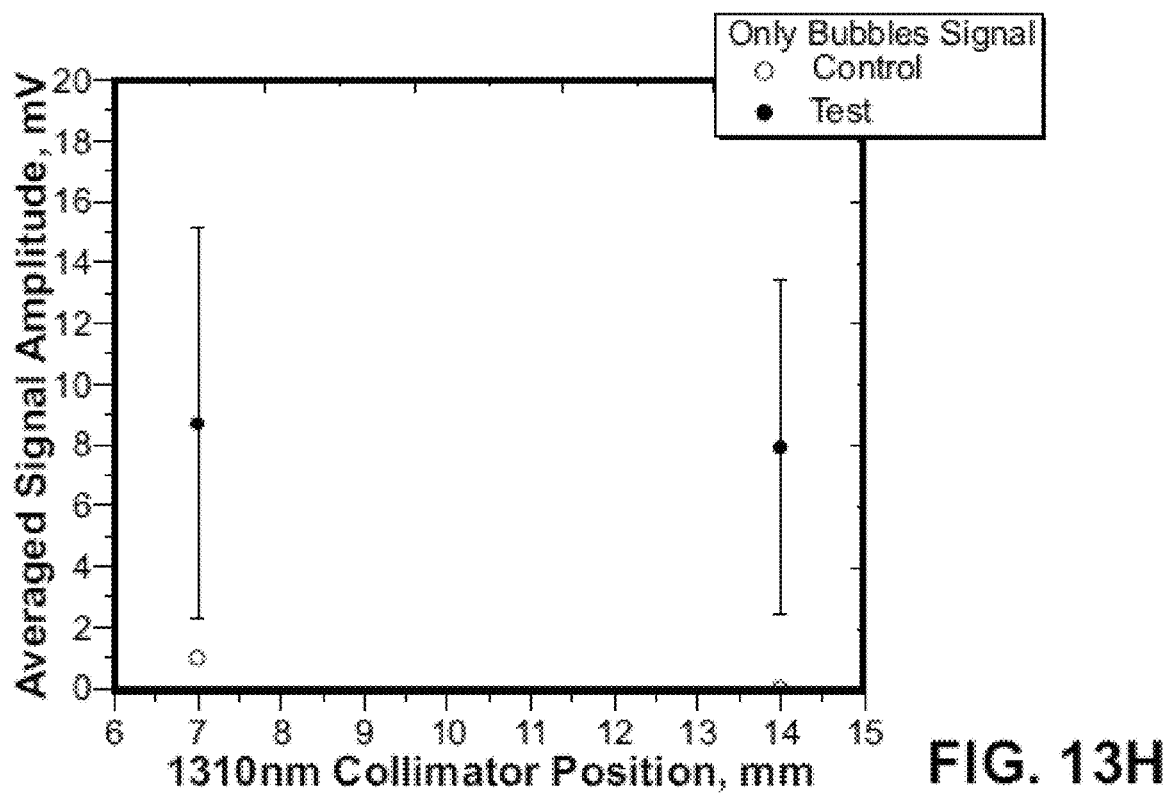

An L1 collimator having a focal distance of 14 mm was then used and the signals detected by the photodetector were collected at a Z position of 100 um. The detected signals and related data are shown in FIGS. 13F-13H.

Figure 13I:
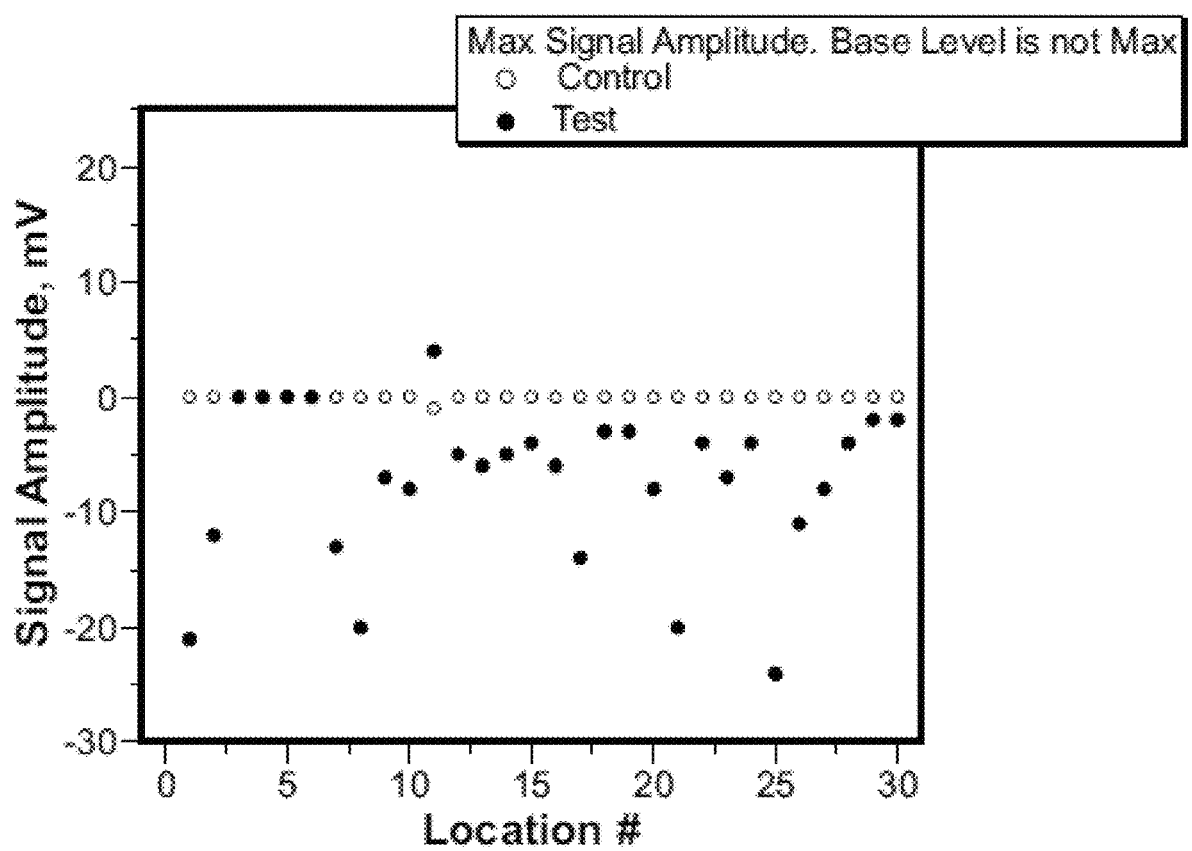
Figure 13J:
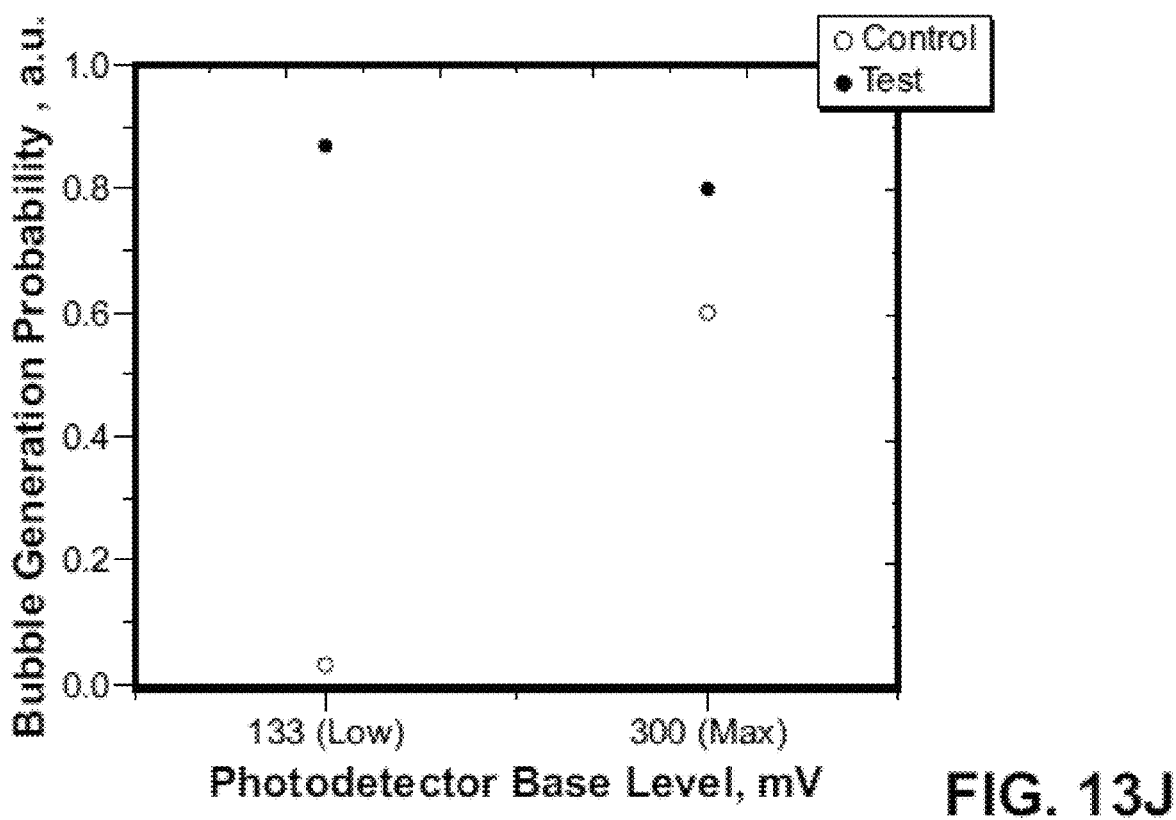
Figure 13K:
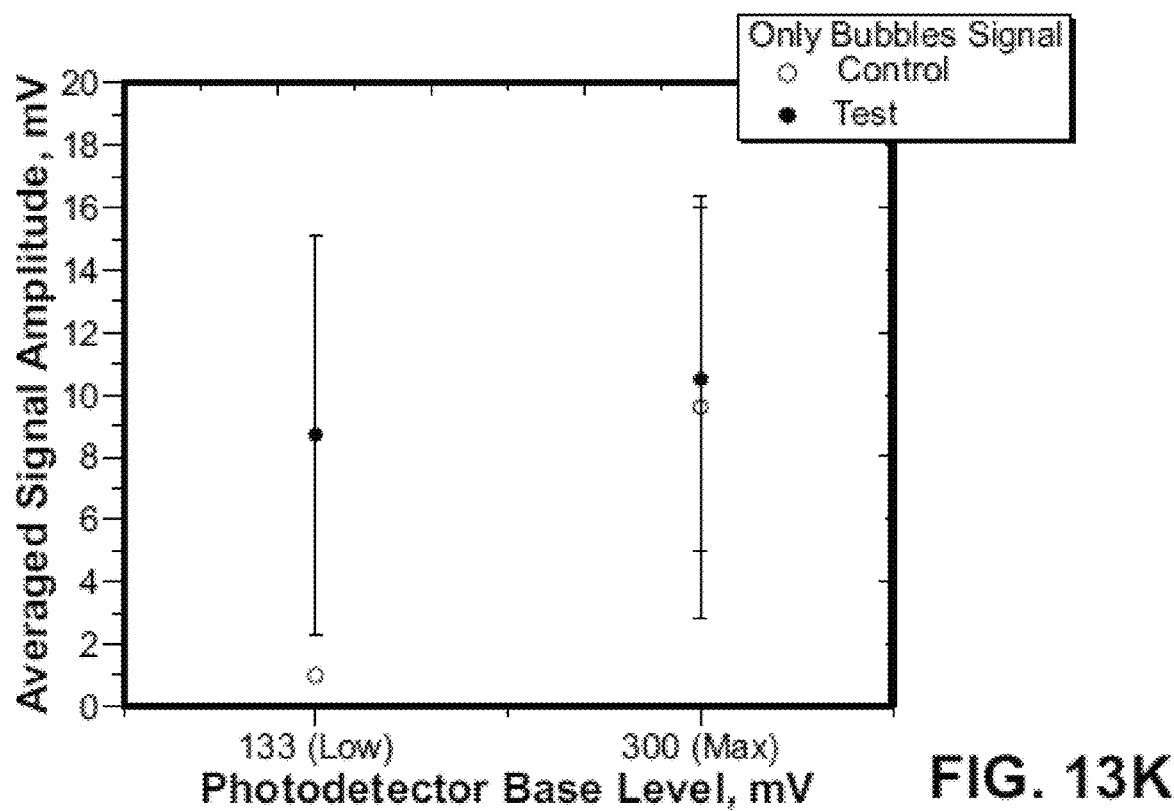

The L1 collimator having a focal distance of 7 mm was reused and the base level was re-adjusted back to the maximum value of 300 mV. FIGS. 13I-13K illustrate the signals detected by the photodetector were collected at a Z position of 100 um.

Figure 14A:
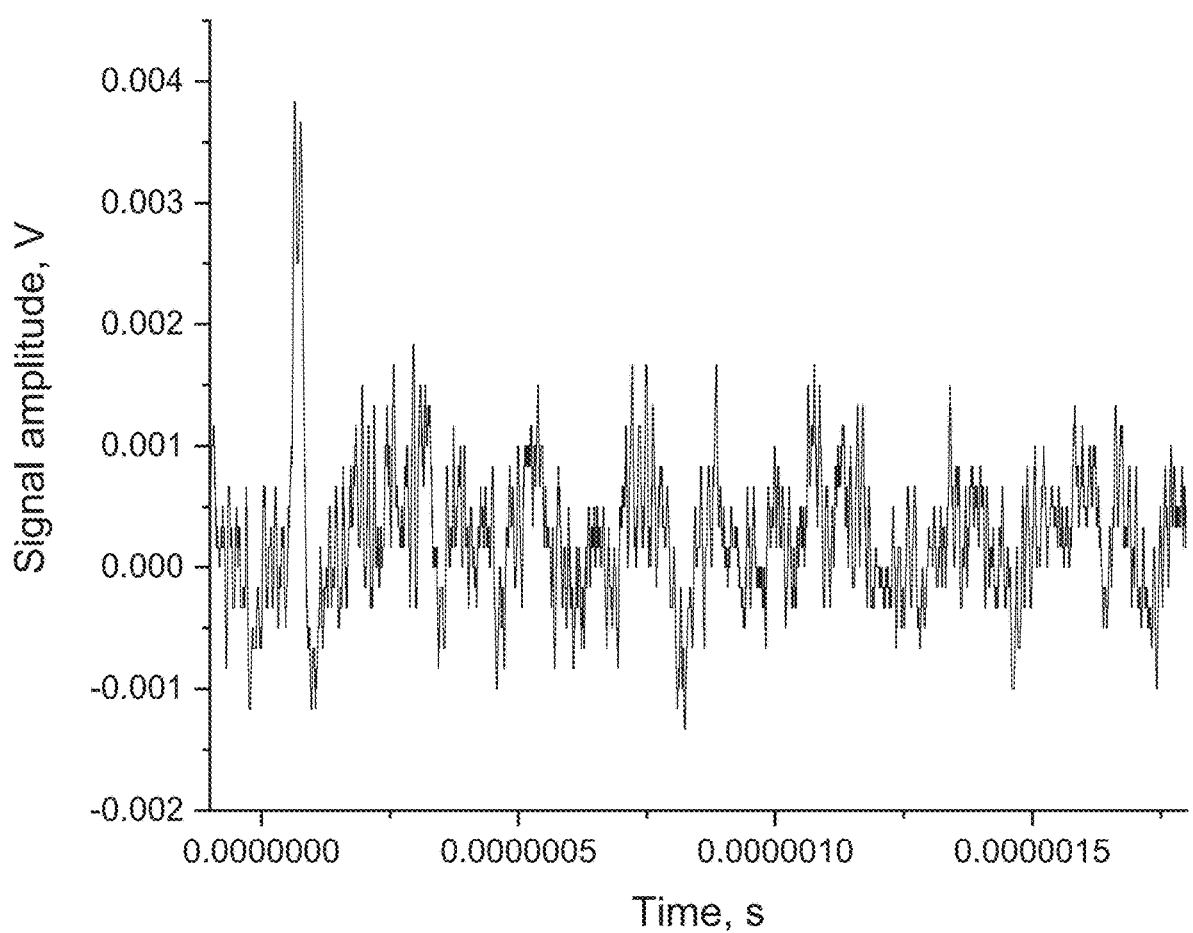
Figure 14B:
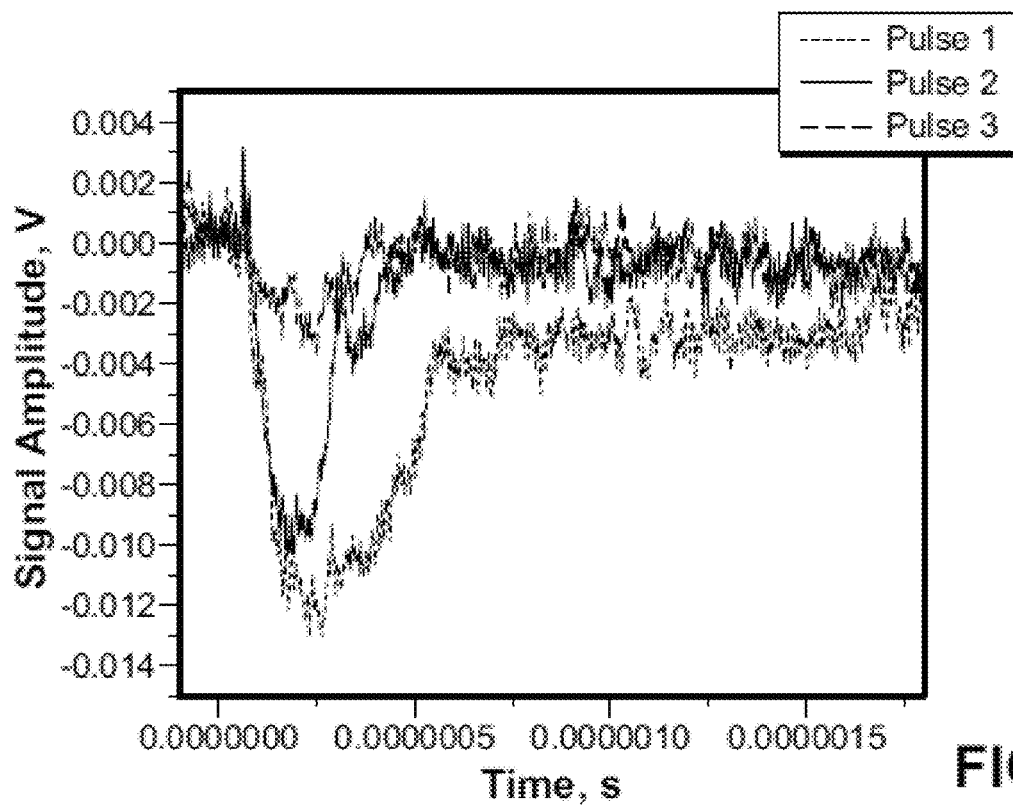
Figure 14C:
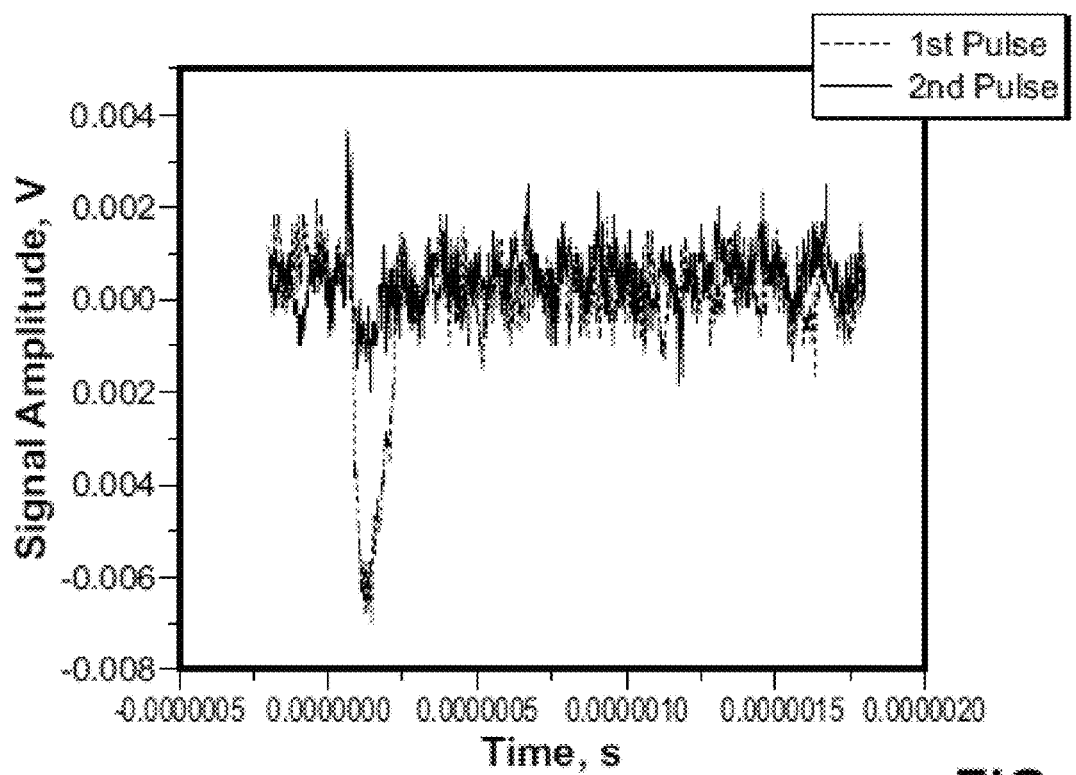
Figure 14D:
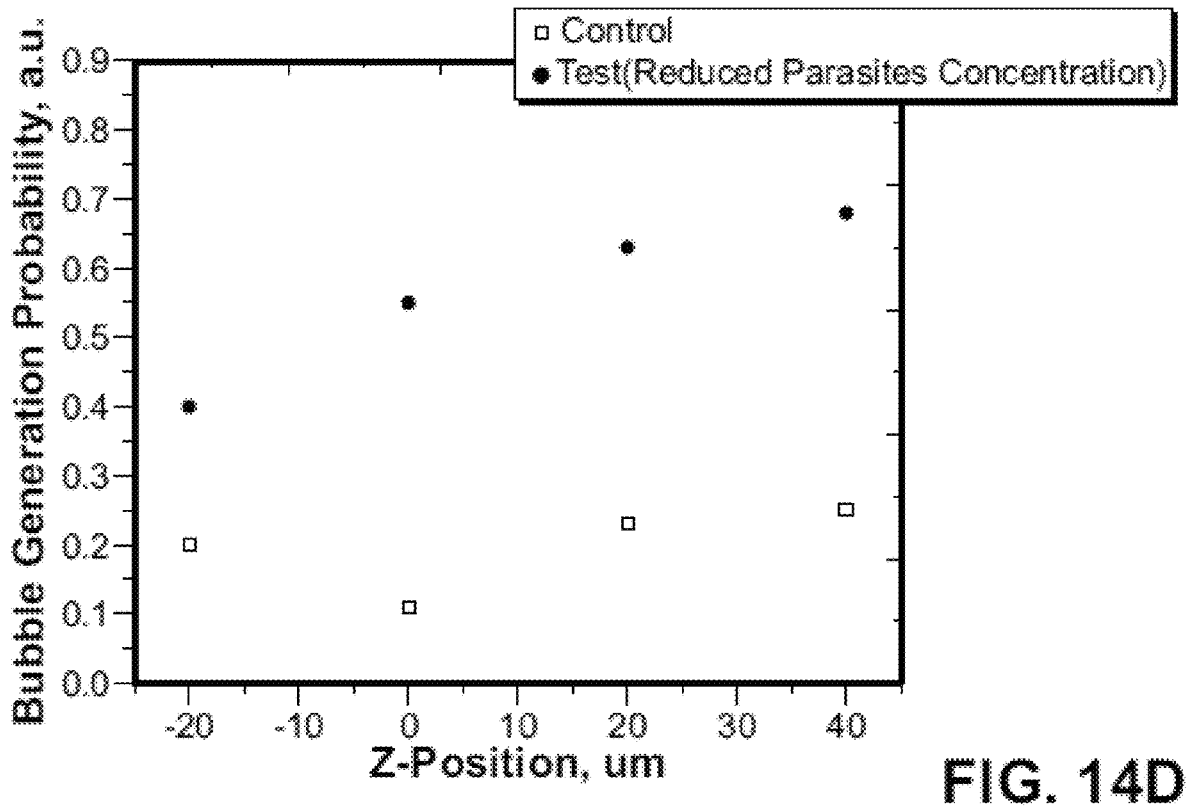
Figure 14E:
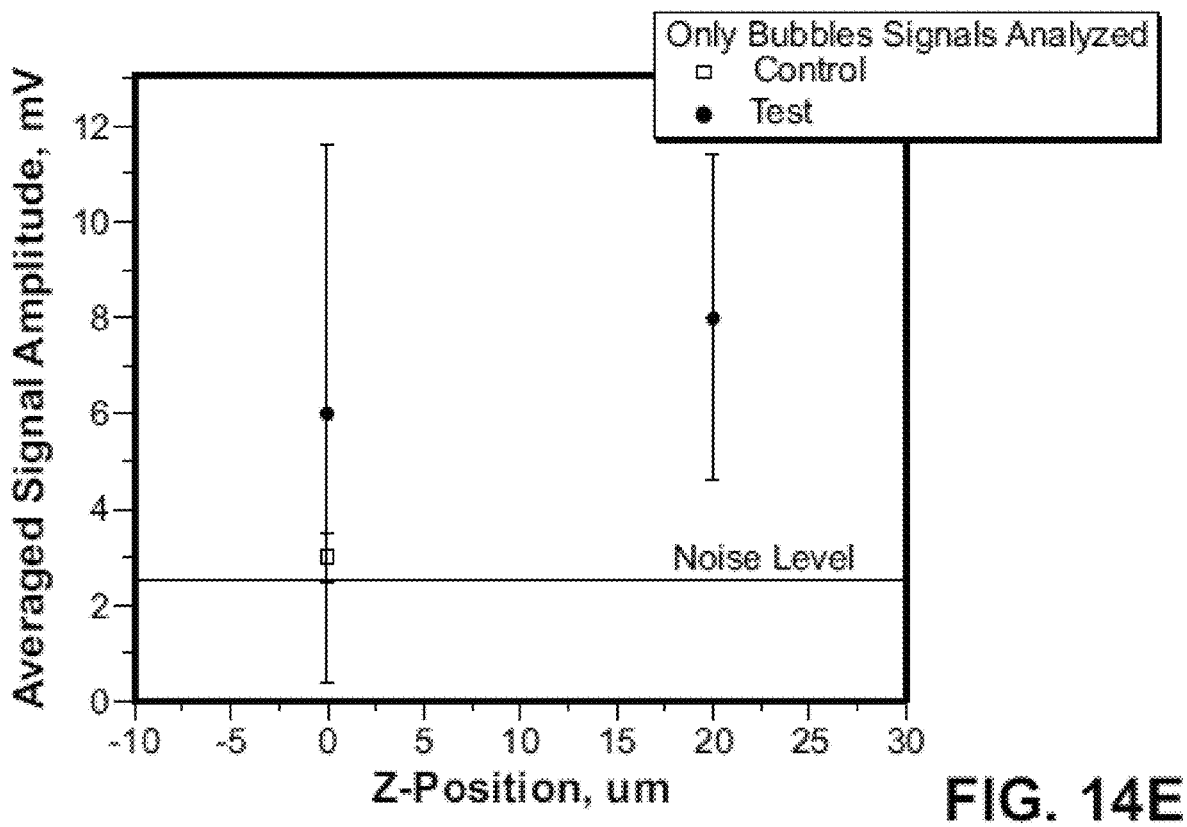

FIGS. 14A-14E illustrate results of a third example experiment using such a system under similar conditions as described above. FIG. 14A illustrates typical signals from a control sample (that is, an intact skin sample). FIGS. 14B and 14C illustrate typical signals from the test sample (that is, human skin sample with malaria parasites underneath) under consecutive pump laser pulses. FIGS. 14D and 14E illustrate the influence of the vertical (Z) position of the optical detection system when the control sample and the test sample were tested under the same settings.

As shown above, a total of six independent experiments in dark human skin with human malaria parasite models were performed with the example optical detection system without spatial filtering. In those experiments, the transient vapor nanobubble signals were observed mainly in the test sample (that is, dark human skin sample with malaria parasites underneath). That is, skin samples with the malaria parasites underneath delivered signals specific to transient vapor nanobubbles.

The polarity of Hemozoin-generated transient vapor nanobubble signals may often be negative, thus indicating that the transient vapor nanobubbles mainly form the signal by scattering the probe beam coming from some other source (such as the skin tissue) to the photodetector. The polarity of Hemozoin-generated transient vapor nanobubble signal also depends upon the relative position of the Hemozoin-generated transient vapor nanobubble and the optical focus of the collection system, as described above. When the Hemozoin-generated transient vapor nanobubble is between the optical focus and the working lens L2, the signal polarity would be negative.

Intact human skin samples may deliver some signals that appear to have characteristics specific to the transient vapor nanobubble. However, such signals were mainly observed when the focus of the excitation (pump) pulsed laser beam was lifted high enough so that melanin might have been present in the focused pump beam pathway. At a lower level of the Z position (closer to the bottom surface of the skin sample), there was a consistent significant difference in both the probability and the amplitude of nanobubble or nanobubble-like signals in intact and parasite skin samples studied.

The optical detection of transient vapor nanobubbles may require scanning the skin sample through about 60 locations or another number of locations, from 3 to 100 locations. Each of the locations is assumed not to have been previously exposed to the previous pump laser pulse(s). Compared to detecting the generation of transient vapor nanobubbles in water, detecting the generation of transient vapor nanobubbles in skin requires lifting the optical detection system in the Z position by about 50 um to about 100 um. This lift may indicate a shift of the optical collection focus in skin to a longer distance compared to that in water, for example, by about 50 um to about 100 um.

The diameter of the probe beam in the optical detection systems disclosed herein (as determined by the collimator L1 settings) may not noticeably influence the diagnostic performance of detecting the generation of transient vapor nanobubbles in skin. However, the sensitivity and/or selectivity of the optical detection system to detecting the transient vapor nanobubbles in skin can be improved if the probe beam is slightly shifted off-axis from the photodetector so that the background level is not at the maximum at the angle from which the probe beam is directed to the skin. This may indicate that a significant amount of background light comes from areas in the skin that are beyond or outside the boundary of the diagnostic volume. As described above, the background light outside the boundary of the diagnostic volume may be reduced and/or removed by using a spatial optical filter in front of the photodetector.

In some embodiments, the probe optical power required for the detection of Hemozoin-generated transient vapor nanobubbles in dark human skin at the depth of up to about 270 um can be in the range of about 5 mW to about 50 mW. The maximal size (that is, lifetime) of optically-detected transient vapor nanobubbles can be smaller than the size (that is, lifetime) of the acoustically-detected transient vapor nanobubbles in a similar model. In some embodiments, the optically-detected transient vapor nanobubbles can have a lifetime of about 0.1 us, whereas the acoustically-detected transient vapor nanobubbles can have a lifetime of about 0.8 us to about 1.0 us. Accordingly, the optical method may have a higher diagnostic sensitivity to that of the acoustic detection method of Hemozoin-generated transient vapor nanobubbles.

In some embodiments, the intensity noise of the probe beam source can be reduced to improve the diagnostic performance of the optical detection system. For example, an incoherent source, SLD, having a wavelength of 1310 nm and a noise level of 0.5% (peak-to-peak noise amplitude relative to the level of the background) may be replaced with the ultra-low noise laser, which may have much lower noise amplitude in the signal frequency range of about 50 kHz to about 20 MHz, which is the signal frequency range of interest. In some embodiments, additional frequency filters can be applied to the electric signal output of the photodetector. In some embodiments, an optical or electrical subtraction of the noise component can be used in the photodetector and/or in the signal processor. In some embodiments, a spatial filtering can be applied to reduce the background light without reducing the light backscattered by a transient vapor nanobubble.

Example Computational Modeling

Based on the performance of the optical detection system for detecting a transient vapor nanobubble in water, the data of which were measured experimentally, the performance of the optical detection system when used in on the human skin can be simulated. The measurements from experiments in water are summarized below in Table 10. A skilled artisan can appreciate based on the present disclosure that alternative parameters can be used in additional embodiments.

TABLE 10

| | 1310-probe beam (focused) | 671-pump beam (focused) |
|---|---|---|
| Experiments in water | | |
| Entry diameter, um | 30 | 150 |
| Diameter in the focal plane, um | 16 | 48 |
| Depth of the focal plane from the entry surface, um | 270 | 340 (lower than the focus of the probe beam) |
| Simulation in human skin (see the corresponding figures below the table) | | |
| Diameter in the focal plane, um (5 um) | 15-25 | — |
| Depth of the focal plane from the entry surface, um | 240 (30 um shorter than in skin) | — |
| Energy, uJ | — | 17 |

Figure 15A:
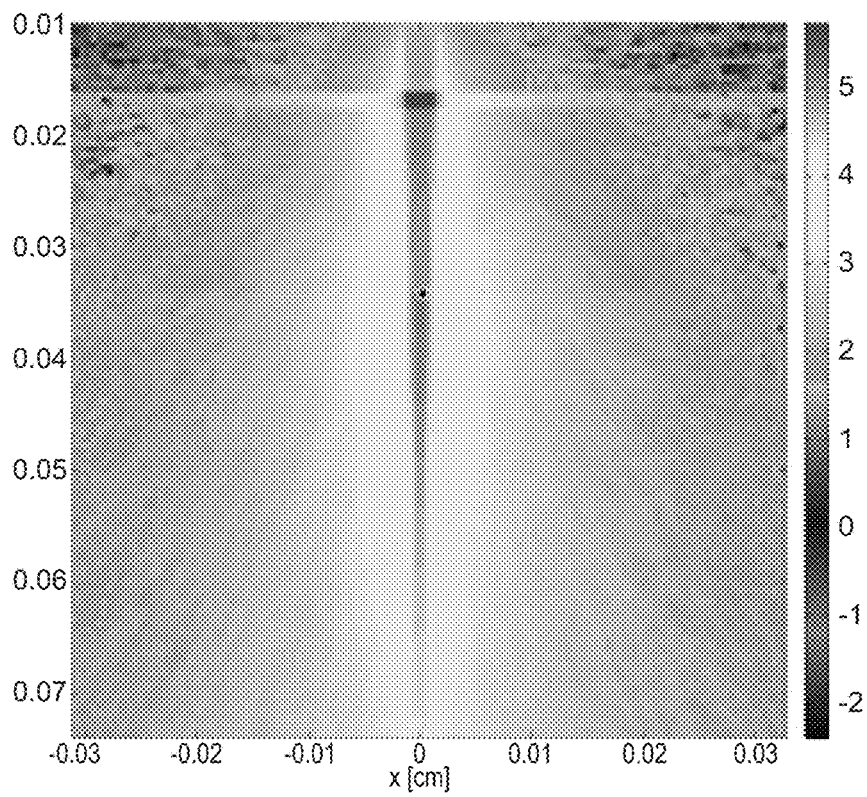
FIGS. 15A-15D illustrate example computer model simulation of optical propagation of laser beams in skin.
Figure 15B:
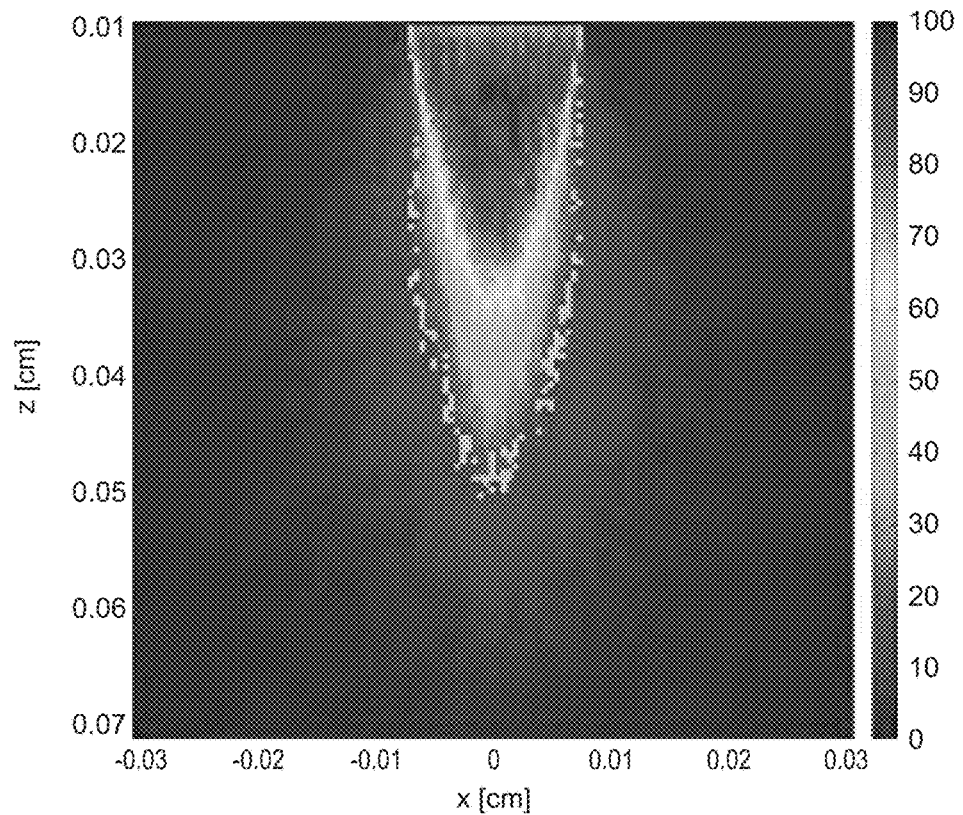
Figure 15C:
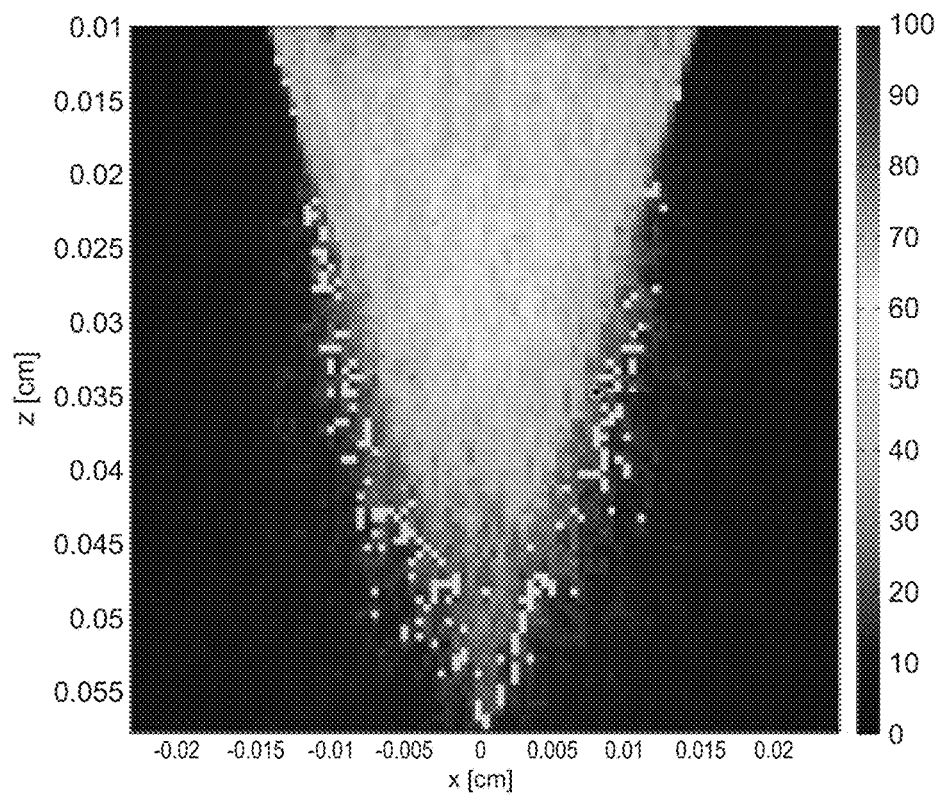
Figure 15D:
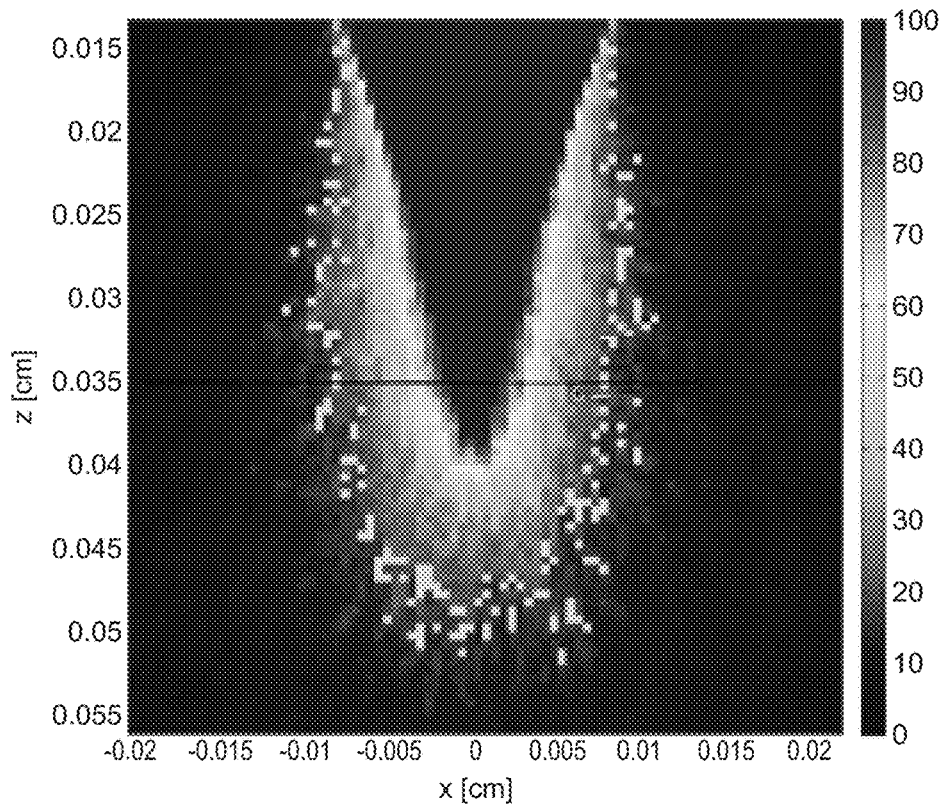

Example simulation results are shown in FIGS. 15A-15D. The skin simulations were performed for the lensed fibers that are described above. In particular, FIG. 15C illustrates the simulation for the B3 fiber and FIG. 15D illustrates the simulation for the B6 fiber.

Optical Detection Using Example Micro-Fluidic Method and/or Device

As described herein, the optical detection systems disclosed herein not only can be employed on the human skin in situ, but can also be applied to a sample of the patient's body fluid (for example, blood, urine, or otherwise). In some embodiments, the body fluid can be contained in a microfluidic device configured to allow the flow of fluid to receive the pump and probe beams.

When performing diagnose and/or mass screen on patients potentially having malaria and/or other life-threatening diseases, the standard malaria diagnostics (such as microscopy and RDT) may be inconclusive so that it is not possible to confirm or exclude such subjects from malaria diagnosis and treatment. Although PCR has higher sensitivity than the standard malaria diagnostics, PCR is much more expensive, a more complex process, and also more time-consuming. At the same time, the clinical condition of many such patients can be quite severe so that the patients may have a higher risk of fatality if not treated timely for malaria, although their blood may have such a low level of malaria parasites that they cannot be reliably detected by the standard methods mentioned above. It is also not advisable to prescribe malaria medications for patients who do not have the malaria parasites due to the undesirable side effects of those medications. The optical detection of malaria parasite and/or Hemozoin using the micro-fluidic device can have a higher sensitivity and be quicker and more reliable than standard malaria diagnostics.

Figure 16A:
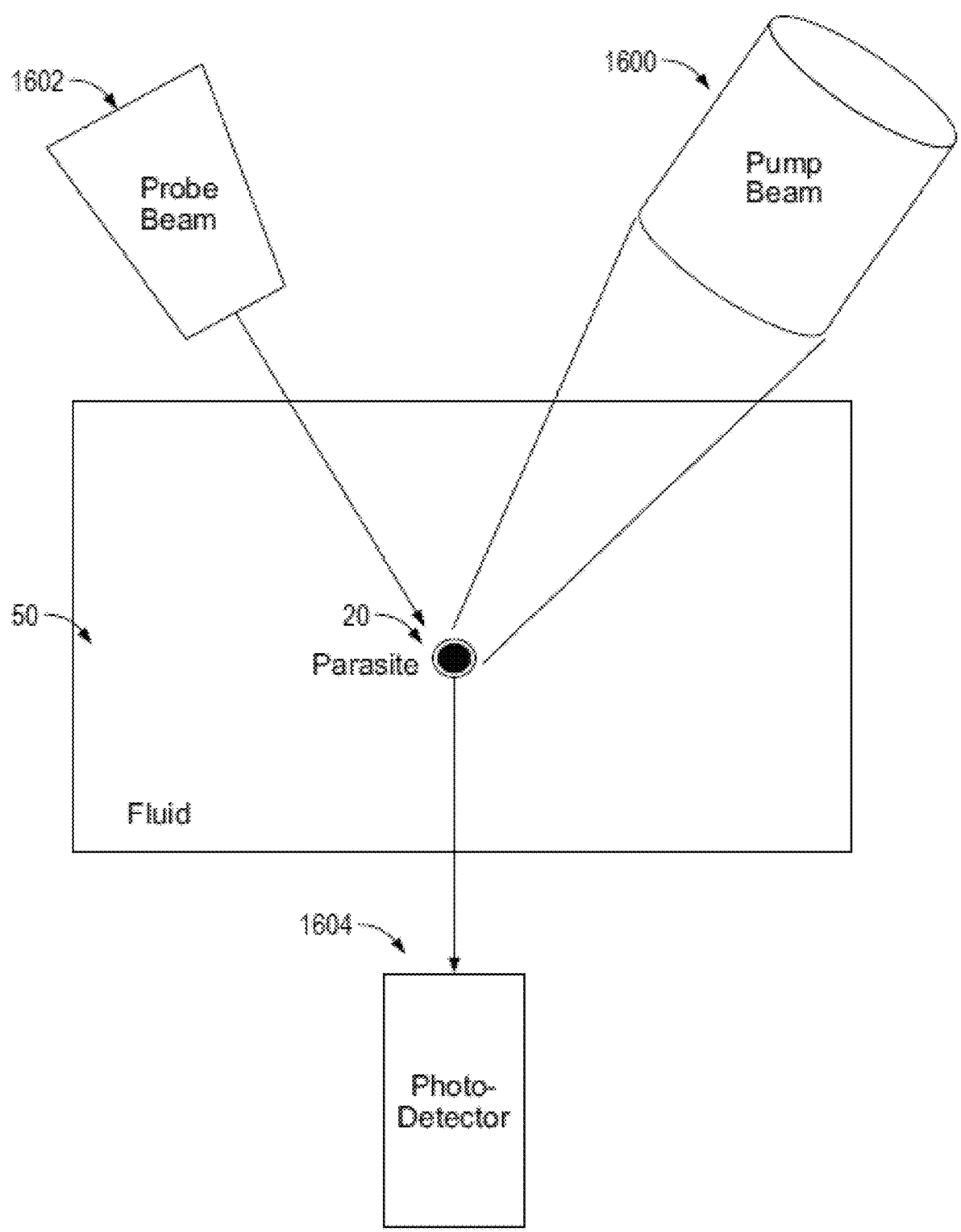
FIG. 16A illustrates schematically an example micro-fluidic device for optically detecting malaria parasite and/or Hemozoin in liquid sample.

As shown in FIG. 16A, the pump beam 1600 and the probe beam 1602 can be directed to the body fluid (such as but not limited to blood) in a micro-fluidic device 50 from a first side of the micro-fluidic device 50. In some embodiments, the pump beam 1600 and/or the probe beam 1602 can be side-focused as described above so that the pump beam 1600 and/or the probe beam 1602 can be at an angle on two sides of the malaria parasite 20. The photodetector 1604 can be located on a second side that is opposite the first side of the micro-fluidic device 50. The photodetector 1604 can be located such that light scattered by a Hemozoin-generated transient vapor nanobubble can travel substantially perpendicular to a longitudinal axis of the micro-fluidic device 50 (that is, along the direction of the fluid flow) between the transient vapor nanobubble (that is, where the parasite 20 is located) and the photodetector 1604.

Figure 16B:
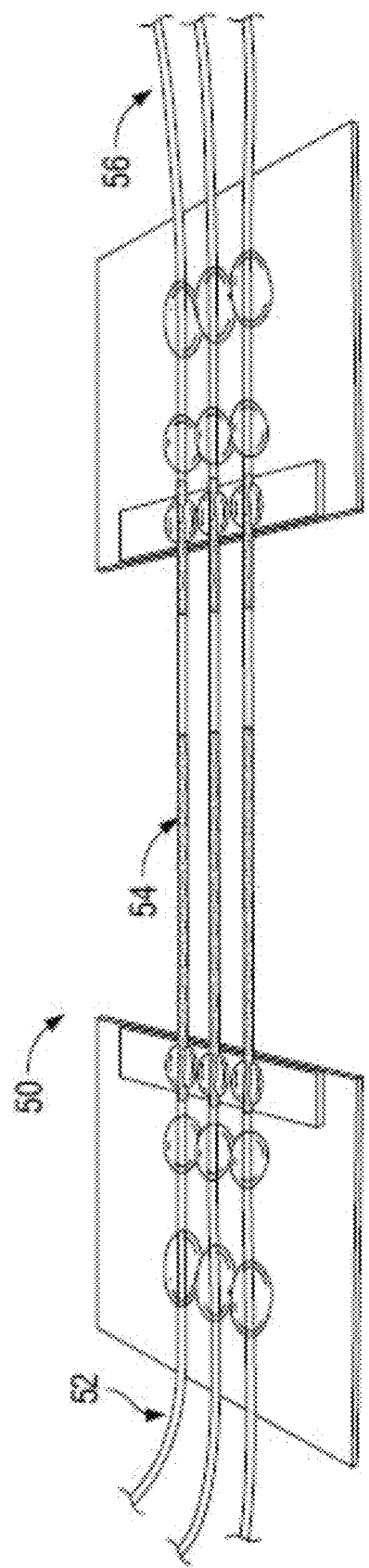
FIG. 16B illustrates a perspective view of an example micro-fluidic device.

In some embodiments, such as shown in FIG. 16B, the micro-fluidic device 50 can include or be coupled to a pump (for example, a mechanical pump, an electrical pump, or otherwise) with a syringe containing a sample fluid. The fluid can flow from the syringe into a tubing 52 coupled to a micro-cuvette 54, which is in turn coupled to a waste container via another tubing 56. The micro-fluidic device 50 can include a plurality of pathways for the fluid, each of the pathway including a micro-cuvette 54 coupled to the tubing 52, 56 on opposite ends of the micro-cuvette 54. In some embodiments, the micro cuvettes 54 can include glass capillaries. In some embodiments, the capillaries can include a square hollow lumen. In some embodiments, the capillaries can have an internal diameter of about 0.100 mm. In some embodiments, the capillaries can have an outer diameter of about 0.200 mm. In some embodiments, each of the capillaries can have a length of about 50 mm.

In some embodiments, the pump beam 1600 can include pump laser pulses with a duration of about 28 ps and a wavelength of about 672 nm. The pump beam 1600 can have a cross-sectional diameter of about 46 um. The pump beam 1600 can have a fluence of about 500 mJ/cm$^2$. The probe beam 1602 can include a laser beam. In some embodiments, the probe laser beam can be continuous. In some embodiments, the probe laser beam can be pulsed. The probe laser beam can have a wavelength of about 632.8 nm or otherwise. In some embodiments, the probe laser beam can have an energy of about 1 mW. Alternatively, the probe beam can include an incoherent light emitted by an SLD. The probe beam 1602 can be focused into the center of the micro-cuvette 54. The diameter of the focal spot of the probe beam 1602 can be about 10 um. In some embodiments, the transmitted probe laser beam can be coupled into a single mode optical fiber, which is in turn connected to an amplified photodetector 1604. The optical fiber can have a mode field diameter of about 5 um.

The flow of fluid in the micro-cuvette can form a parabolic velocity profile which, coupled to the length of the micro-cuvette, can result in partial hydrodynamic focusing of the particles (including malaria parasites and Hemozoin) in the axis of the flow. This focusing effect can concentrate the generation of Hemozoin-generated transient vapor nanobubbles in the center of the flow that is exposed to the probe beam, which can improve the detection of malaria parasite and/or Hemozoin particles.

Figure 16E:
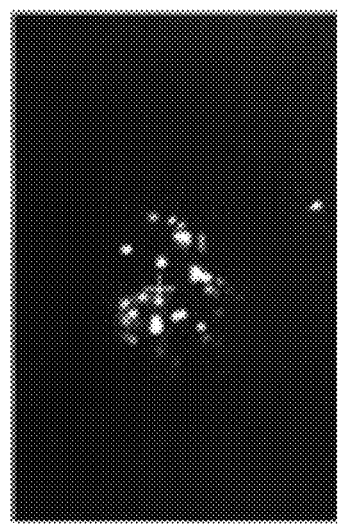
FIGS. 16C-16E illustrate various microscopic images of fluid in a micro-fluidic device.
Figure 16D:
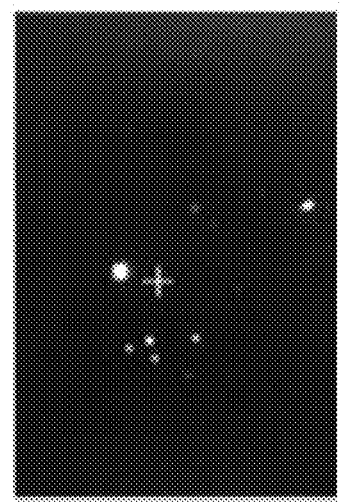
Figure 16C:
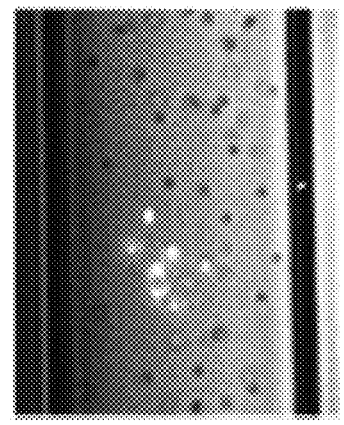

FIGS. 16C-16E illustrate the effect of hydrodynamic focusing of flowing nanoparticles to the center of the cuvette, by using the optical scattering by polystyrene particles introduced into the flow. The images were captured in the center of the micro-cuvette during the optical scattering of the probe laser pulse in flow conditions and in static conditions. FIG. 16C illustrates a white light image when the flow rate was zero. FIG. 16D illustrates the optical scattering image when the flow rate was zero. FIG. 16E illustrates the optical scattering image when the flow rate was greater than zero. Significantly more particles (33 particles in FIG. 16E vs. 5-6 particles in FIG. 16D) were concentrated within the center of the micro-cuvette and exposed to a single laser pulse when the flow rate was greater than zero (that is, in a non-static condition).

Figure 17A:
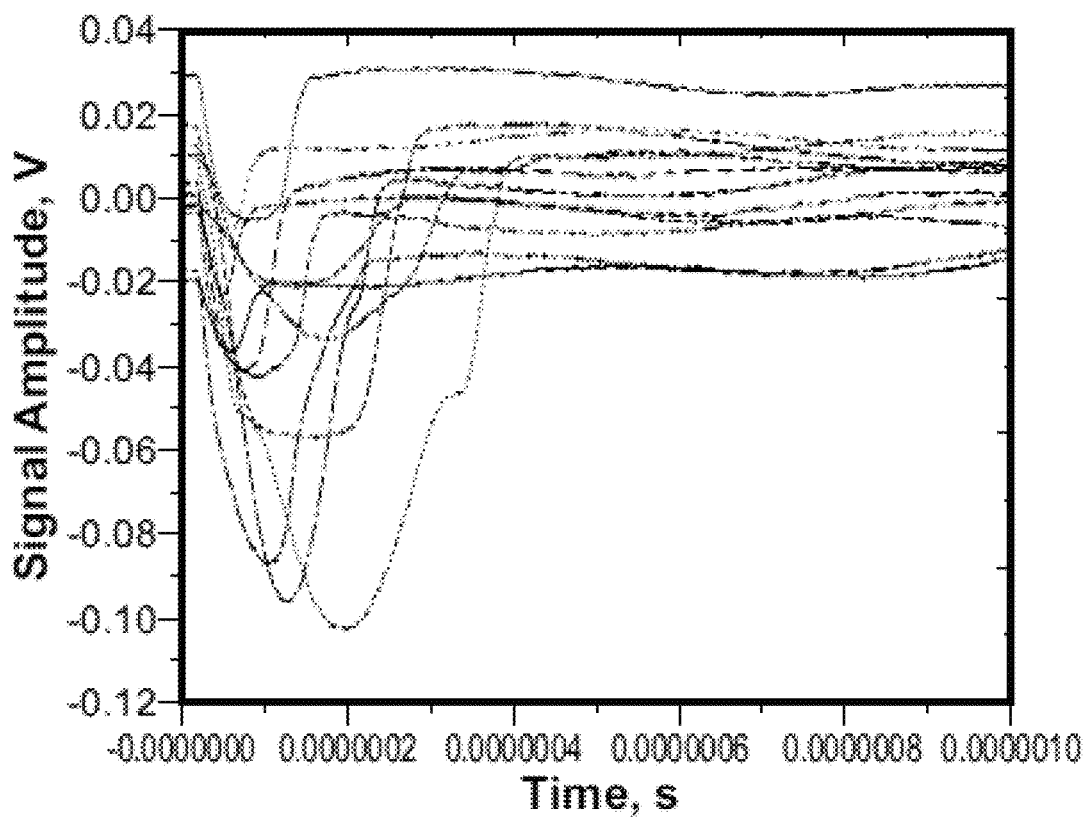
FIGS. 17A and 17B illustrate optical scattering signals from malaria parasites and HZ by Hemozoin-generated transient vapor nanobubbles generated in a micro-fluidic device.
Figure 17B:
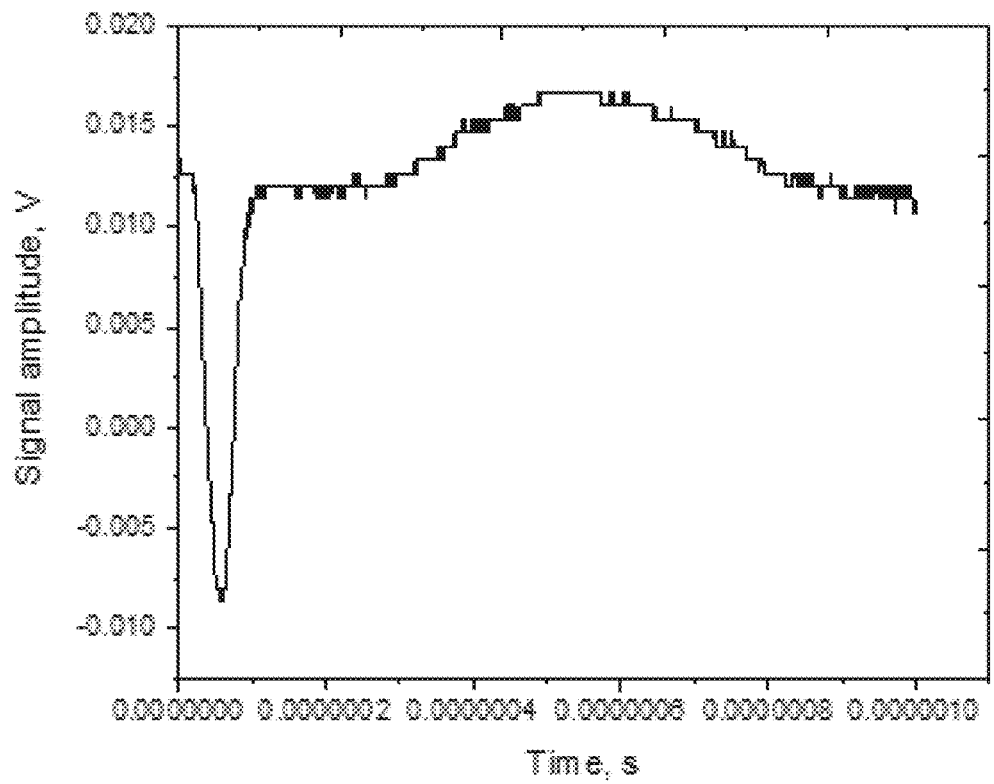
Figure 17C:
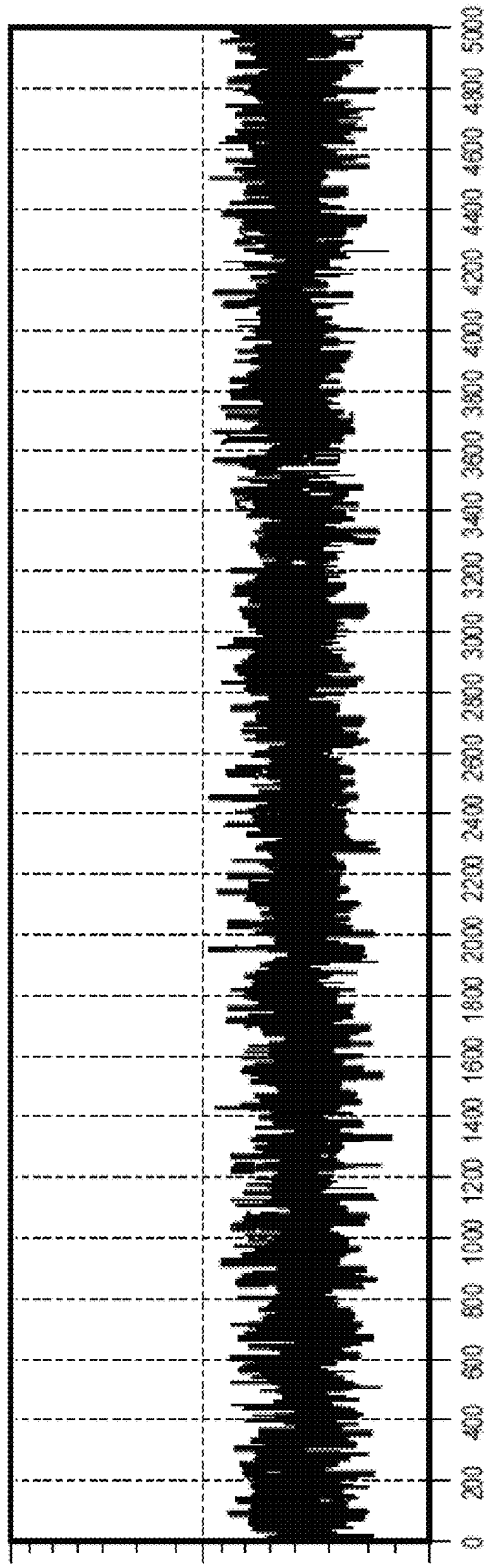
FIGS. 17C and 17D illustrate optical scattering signals from Hemozoin-free samples using a micro-fluidic device.
Figure 17D:
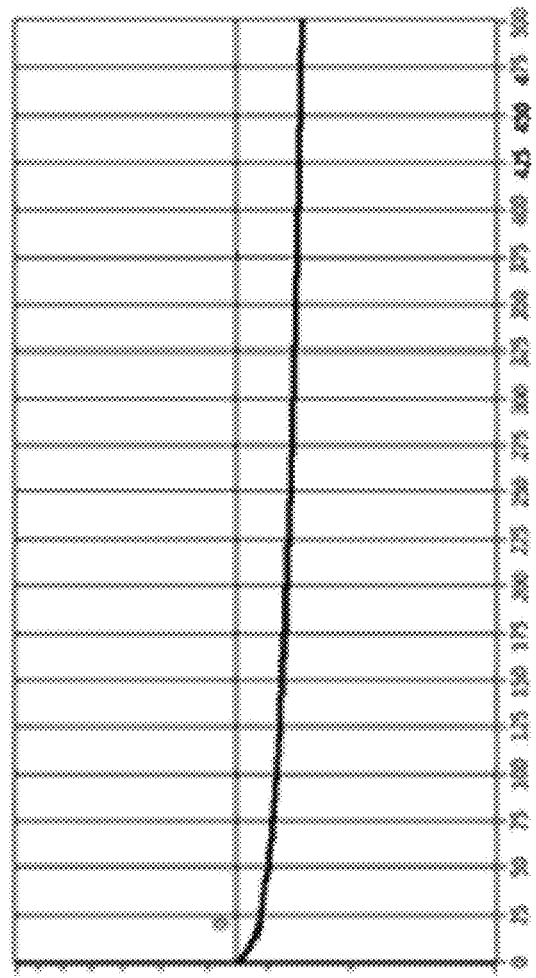
Figure 17E:
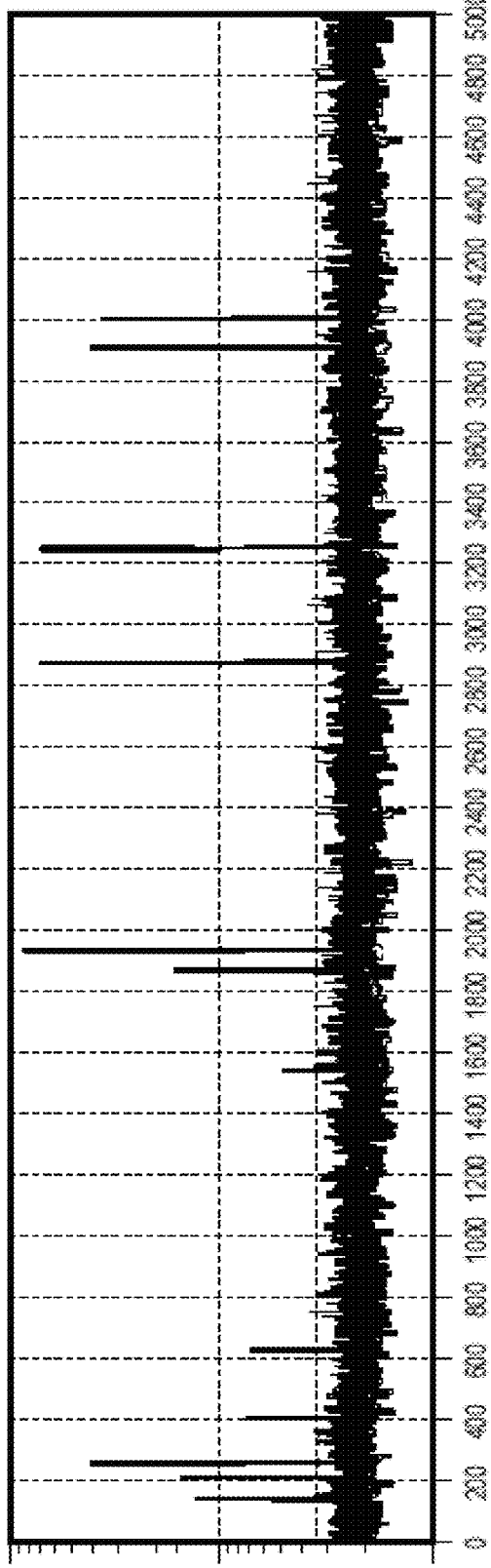
FIGS. 17E-17H illustrate optical scattering signals from Hemozoin-positive samples using a micro-fluidic device under different test conditions.
Figure 17F:
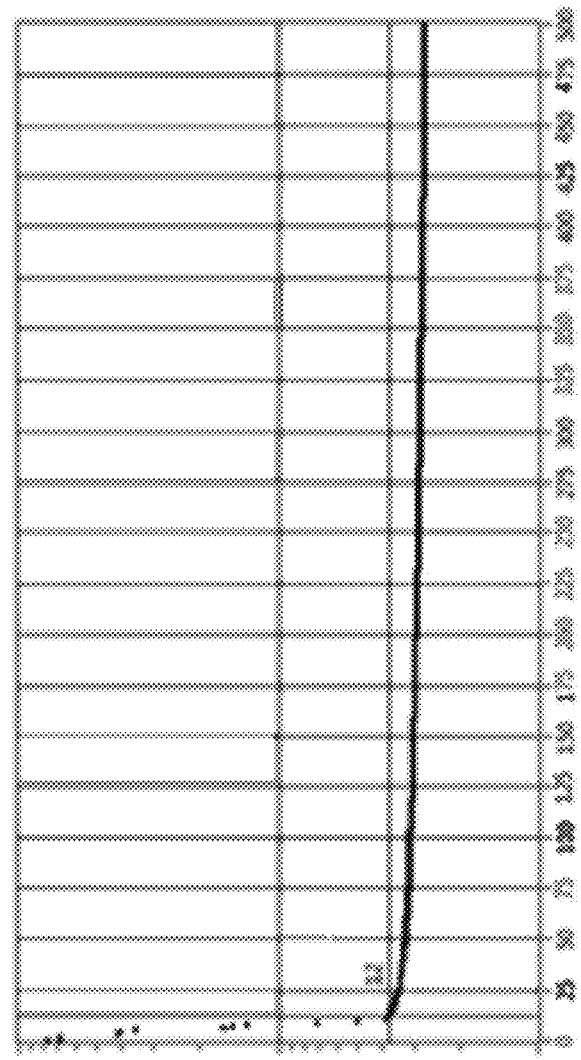
Figure 17G:
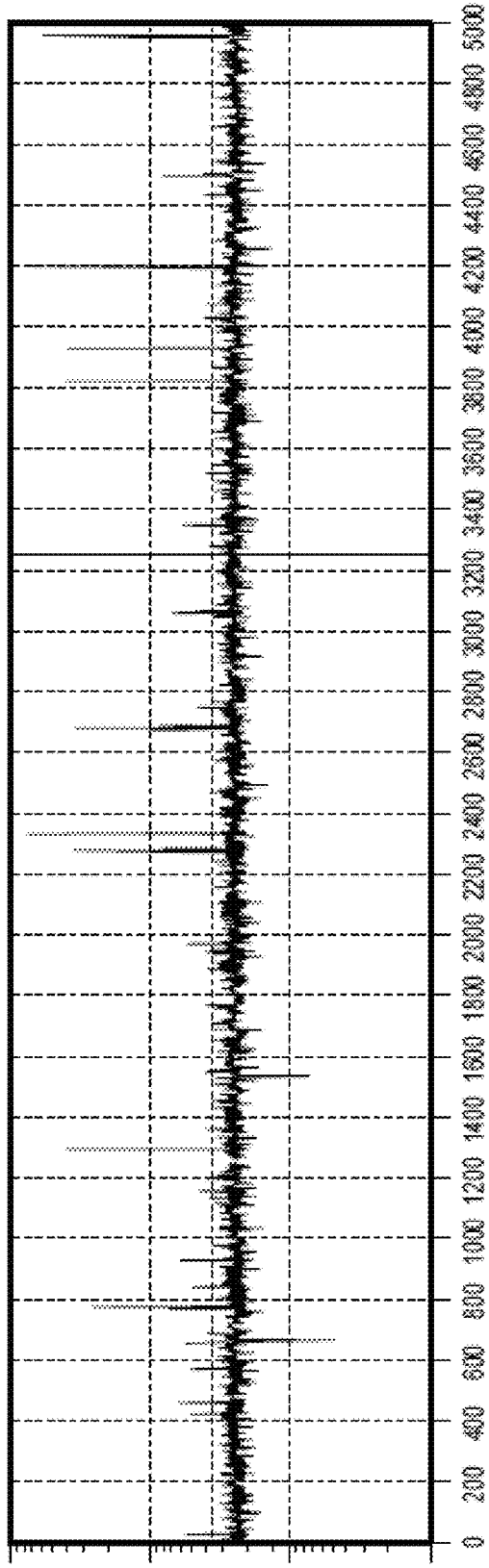
Figure 17H:
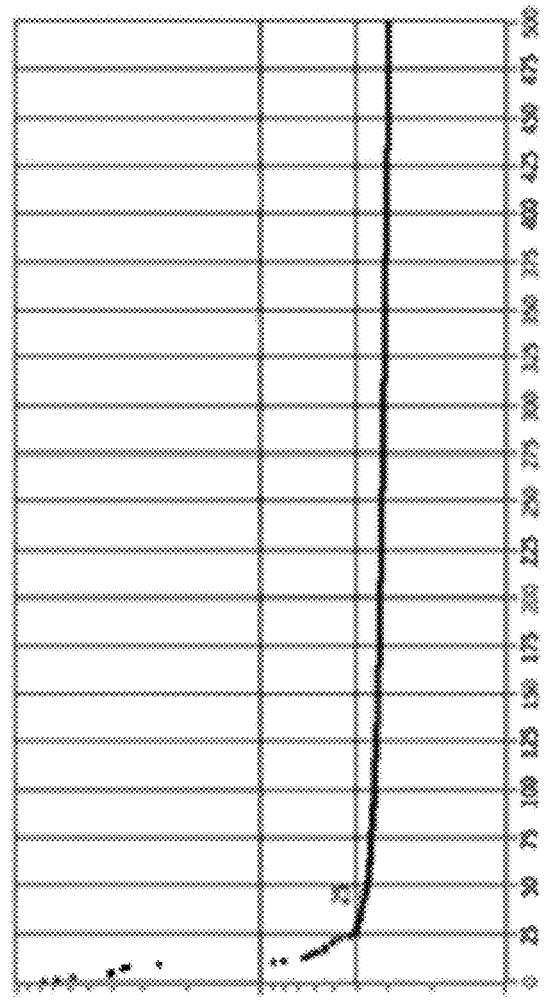

Several parameters of the optical detecting system using a micro-fluidic device were studied in example experiments with Hemozoin and malaria parasites, which were prepared from blood of malaria positive patients. FIGS. 17A and 17B illustrate the signals detected by the photodetector of the optical detection system shown in FIG. 16A when the fluid sample contained Hemozoin. The detected signals show a time-shape that is typical or specific to Hemozoin-generated transient vapor nanobubbles. For example, all the signals showed an arch shape indicating the expansion and collapse of transient vapor nanobubbles. The signals also show a typical negative polarity for the configuration shown in FIG. 16A with a passing probe beam 1602. The smallest transient vapor nanobubble detected had the lifetime of about 30 ns. 5,000 to 10,000 signals were obtained during the flow. In FIGS. 17C-17H, the transient vapor nanobubble signals, which have higher maximal amplitudes compared to the nanobubble-free signals, were logged as positive events. FIGS. 17C and 17D illustrate signals from Hemozoin-free samples. No signals indicative of transient vapor nanobubbles were detected. FIGS. 17E and 17F illustrate signals from Hemozoin-positive samples. The concentration of the Hemozoin nanoparticles was about 2 parasites per uL. The micro-cuvette was 75 um in inner diameter. Transient vapor nanobubble events can be seen as the high amplitude spikes. A total of 12 positive events were observed out of 5000 pump pulses. FIGS. 17G and 17H illustrate signals from Hemozoin-positive samples under different testing conditions. The concentration of the Hemozoin nanoparticles was about 8 parasites per uL. The micro-cuvette was 100 um in inner diameter. Transient vapor nanobubble events can be seen as the high amplitude spikes. A total of 25 positive events were observed out of 5000 pump pulses. A skilled artisan can appreciate based on the present disclosure that alternative parameters can be used in additional embodiments.

Influence of Cuvette Size

Figure 18A:
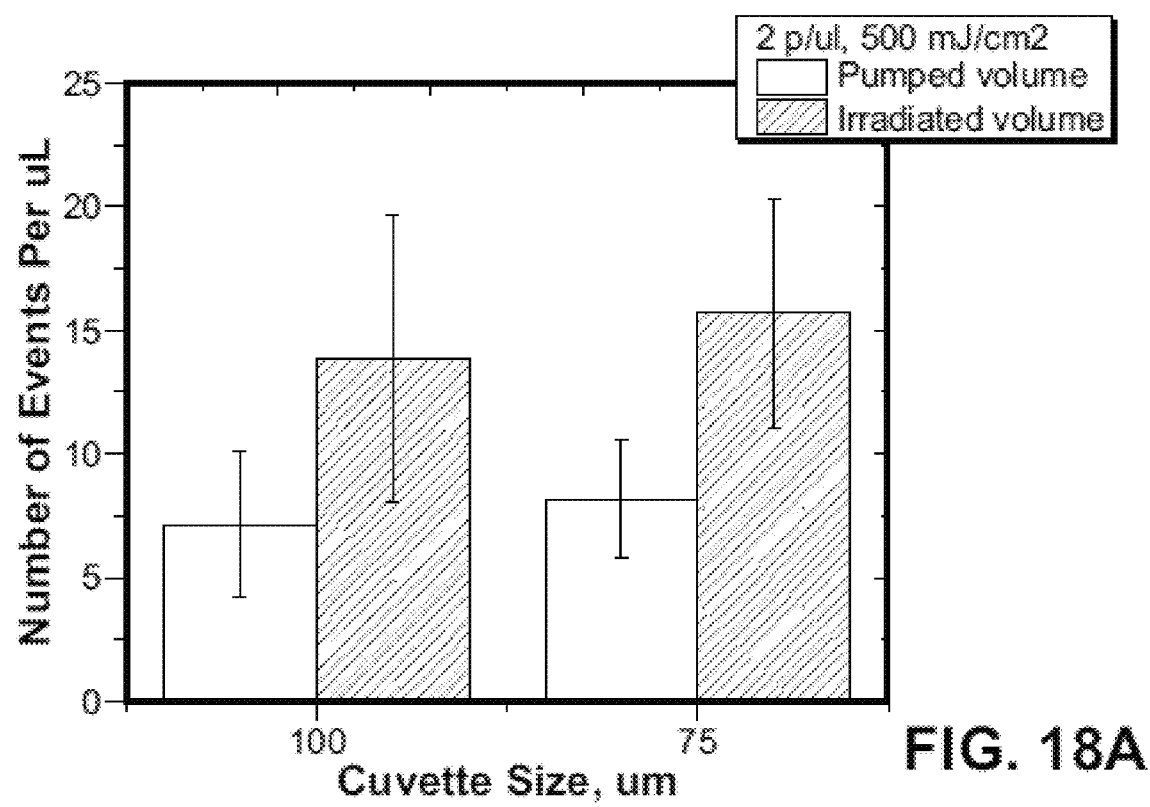
FIGS. 18A-18G illustrate influence of various design parameters on the efficacy of the optical detection using a micro-fluidic device.

FIG. 18A illustrates the number of positive events for optical detection experiments using two different types of the micro-cuvette. Both types of micro-cuvettes have a length of 50 mm. The first micro-cuvette has an internal diameter of 0.100 mm and an outer diameter of 0.200 mm. The second micro-cuvette has an internal diameter of 0.075 mm and an outer diameter of 0.307 mm. The tubing coupled to the micro-cuvette includes medical platinum cured silicone micro tubing. The tubing has an internal diameter of 0.31 mm and an outer diameter of 0.64 mm.

The flow rate in the 0.1-mm ID micro-cuvette was set at 0.442 uL/min (with the measured flow rate being 0.385 uL/min). The flow rate in the 0.075-mm ID micro-cuvette was set at 0.249 uL/min (with the measured flow rate being 0.217 uL/min). The laser pump beam applied to the fluid flow in both micro-cuvettes had a pulse duration of 28 ps and a focal spot of about 46 nm. The laser pulse had a wavelength of 672 nm and a fluence of about 500 mJ/cm$^2$.

As shown in FIG. 18A, the micro-cuvette size, within the range of 75 um to 100 um, did not show any significant influence on the sensitivity of the optical detection of transient vapor nanobubbles. A skilled artisan can appreciate based on the present disclosure that alternative parameters can be used in additional embodiments.

Influence of Centrifugation of the Blood Sample During Sample Preparation

Figure 18B:
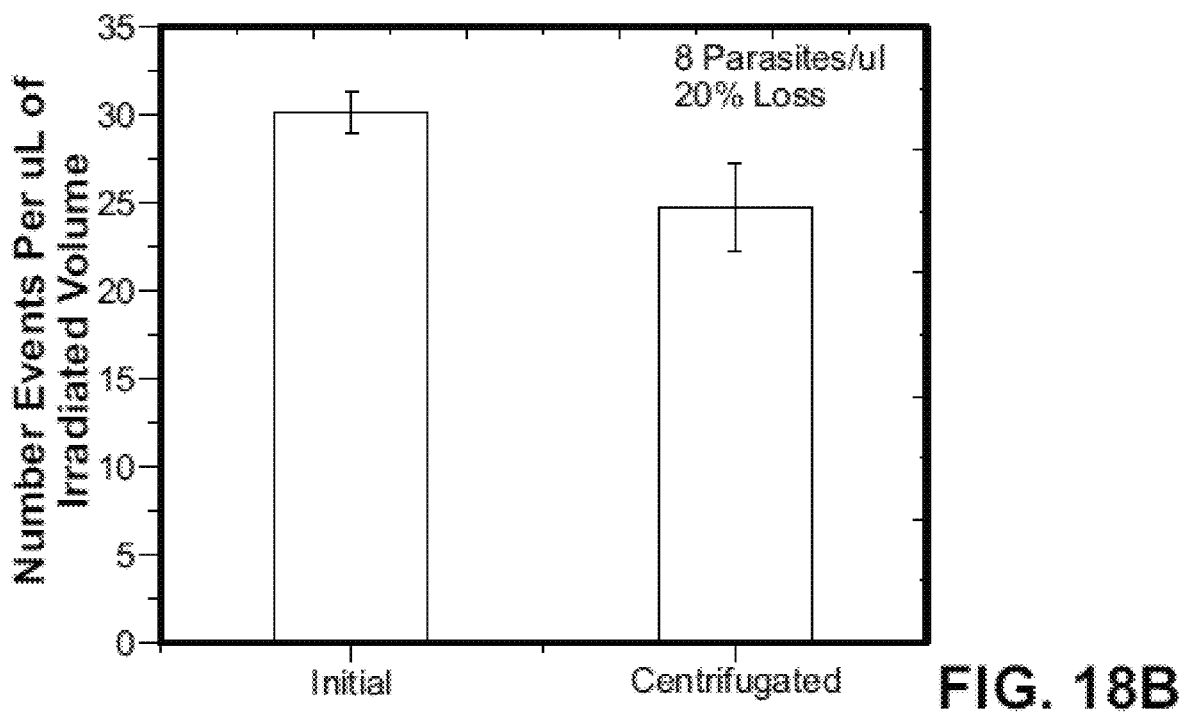

FIG. 18B illustrates the number of positive events for optical detection experiments when a blood sample was not centrifuged and when a blood sample was centrifuged, respectively. The micro-cuvette in both samples had an internal diameter of 0.100 mm and an outer diameter of 0.200 mm. The micro-cuvette had a length of 50 mm. The tubing coupled to the micro-cuvette includes medical platinum cured silicone micro tubing. The tubing has an internal diameter of 0.31 mm and an outer diameter of 0.64 mm.

The flow rate was set at 0.442 uL/min (with the measured flow rate being 0.385 uL/min) in both micro-cuvettes. The laser pump beam had a pulse duration of 28 ps and a focal spot of 46 nm. The laser pulse had a wavelength of 672 nm and a fluence of about 500 mJ/cm$^2$. Both blood samples had about 8 parasites per uL. The blood sample that was centrifuged was centrifuged once at 14,000g for 10 minutes.

As shown in FIG. 18B, centrifuging the blood sample slightly reduced the amount of detectable Hemozoin by about 20% compared to the blood sample that was not centrifuged. A skilled artisan can appreciate based on the present disclosure that alternative parameters can be used in additional embodiments.

Influence of Flow Rate

Figure 18C:
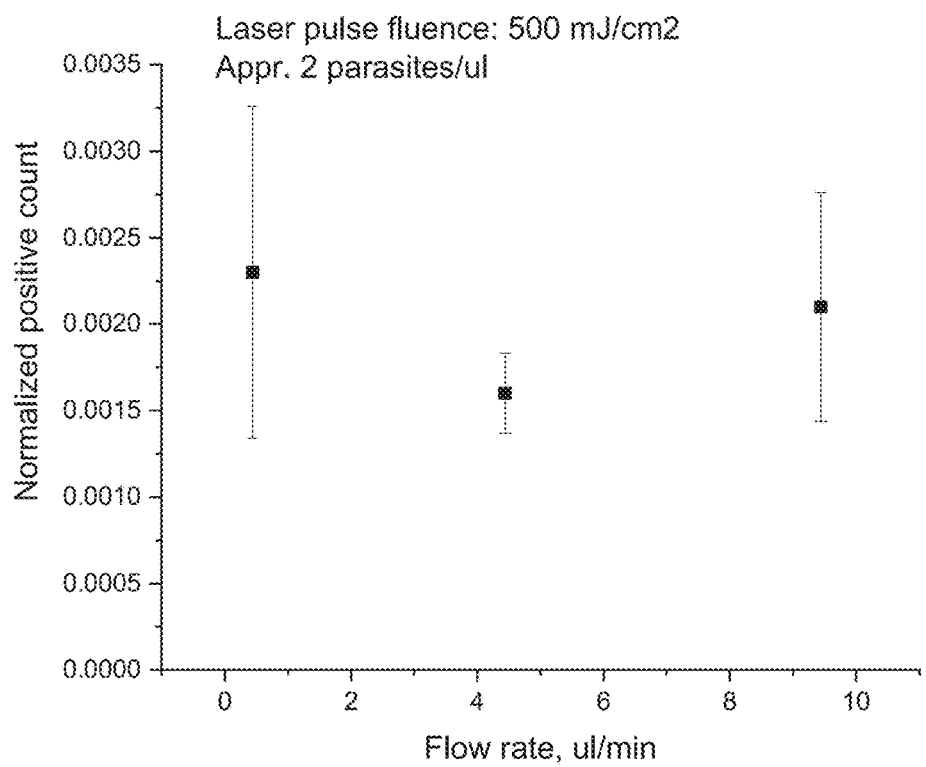

FIG. 18C illustrates the number of positive events for optical detection experiments at different flow rates. The micro-cuvette had an internal diameter of 0.100 mm and an outer diameter of 0.200 mm. The micro-cuvette had a length of 50 mm. The tubing coupled to the micro-cuvette includes medical platinum cured silicone micro tubing. The tubing has an internal diameter of 0.31 mm and an outer diameter of 0.64 mm.

The flow rate was set at between about 9.442 uL/min to 0.442 uL/min (with the measured or real flow rate being less than the set flow rate by about 13%). The laser pump beam had a pulse duration of 28 ps and a focal spot of 46 nm. The laser pump pulse had a wavelength of 672 nm and a fluence of about 500 mJ/cm$^2$. The blood samples had about 2 parasites per uL.

As shown in FIG. 18C, the flow rate, within the error margins, did not have a significant influence on the sensitivity of the optical detection. A skilled artisan can appreciate based on the present disclosure that alternative parameters can be used in additional embodiments.

Influence of Laser Pulse Parameters

FIGS. 18D-G illustrate the number of positive events for optical detection experiments using different pump laser pulse parameters. The micro-cuvette had an internal diameter of 0.100 mm and an outer diameter of 0.200 mm. The micro-cuvette had a length of 50 mm. The tubing coupled to the micro-cuvette includes medical platinum cured silicone micro tubing. The tubing has an internal diameter of 0.31 mm and an outer diameter of 0.64 mm.

The flow rate was set at about 0.442 uL/min (with the measured or real flow rate being about 0.385 uL/min). The laser pump beam had a pulse duration of 28 ps and a focal spot of 46 nm. The laser pulse had a wavelength of 672 nm. The fluence of the laser pulse was varied between about 200 mJ/cm$^2$ to about 500 mJ/cm$^2$. The laser beam was located at about 35 mm from the beginning of the micro-cuvette.

Three test samples were prepared. The first sample included water. The second sample included water with polystyrene nanoparticles having an outer diameter of about 1 um. The third sample included a solution of Hemozoin at a concentration of about 9.97 pg/uL, which was equivalent to approximately 17 parasites per uL. A skilled artisan can appreciate based on the present disclosure that alternative parameters can be used in additional embodiments.

Figure 18D:
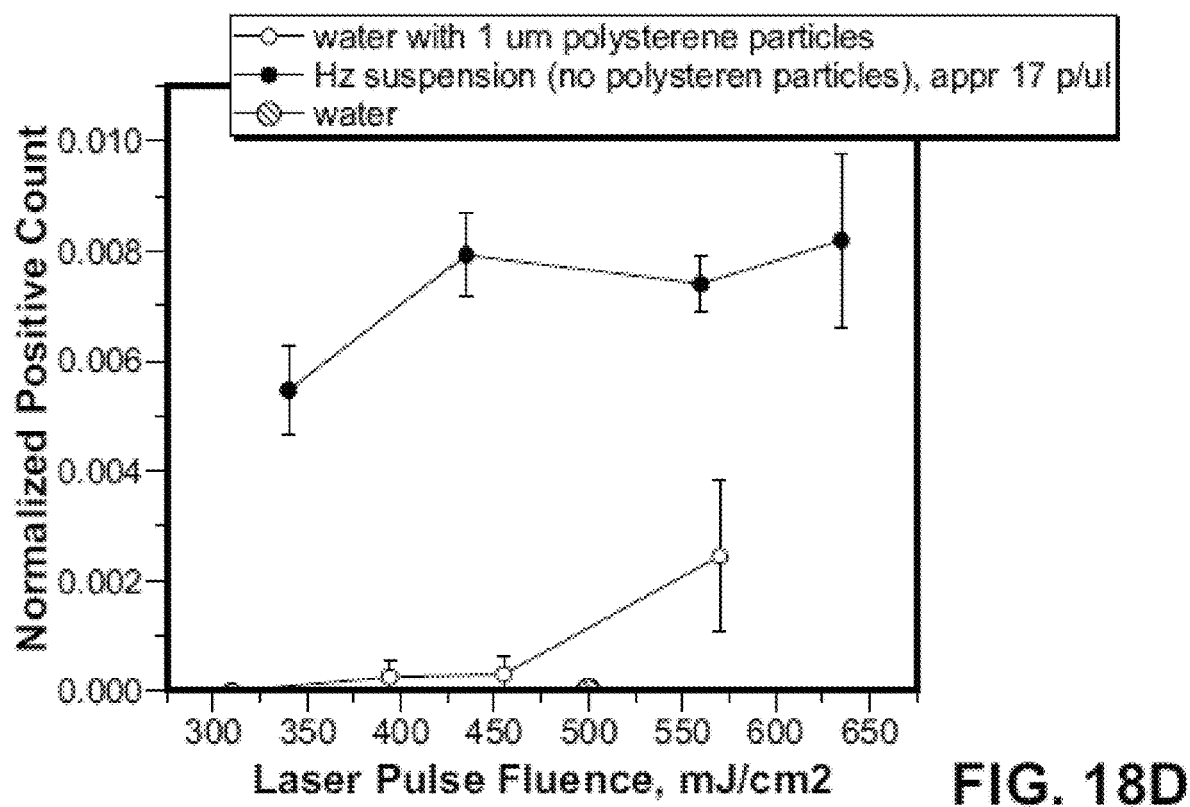
Figure 18E:
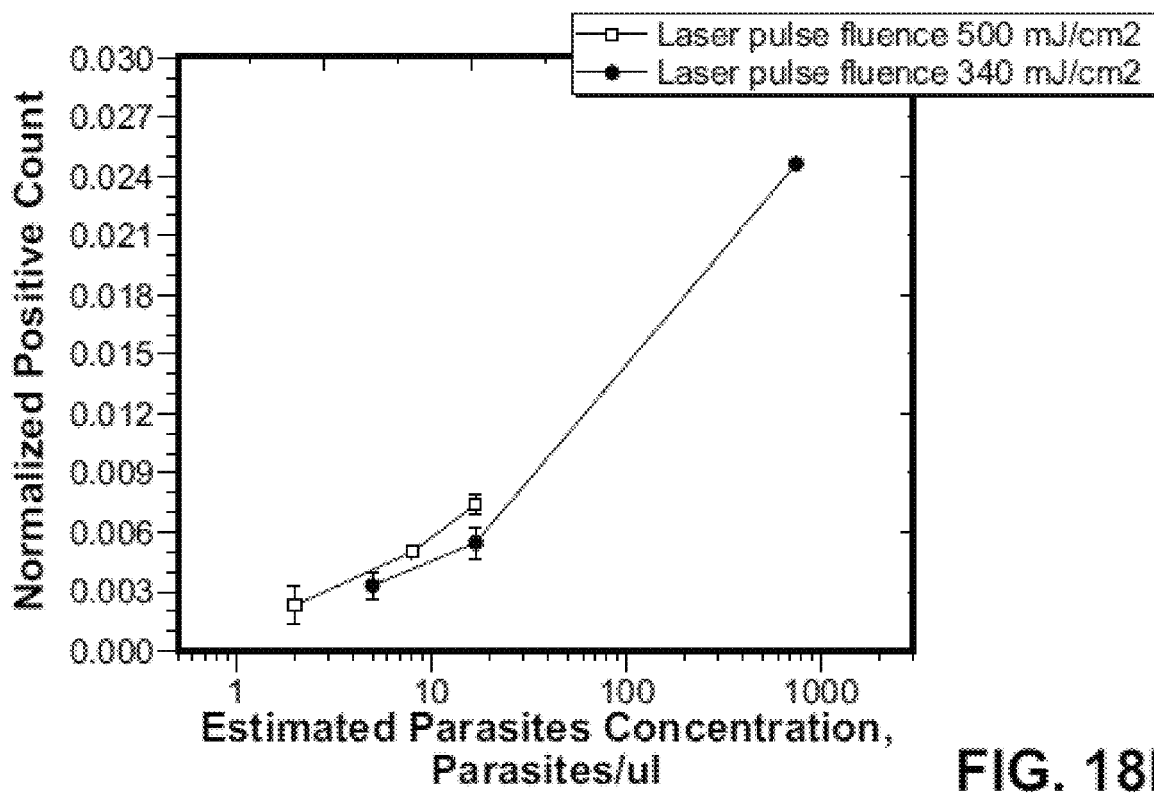

As shown in FIG. 18D, the number of positive events increased generally with an increase in the laser pulse fluence until a saturation point is reached for the second and third samples. The laser fluence can influence the sensitivity of the optical detection set up to the detection of single particles of Hemozoin in the purified sample. At the fluence level of 450 mJ/cm$^2$, the detection of Hemozoin-generated transient vapor nanobubbles appears to be at the maximum. As shown in FIG. 18E, which illustrates the relationship of the number of positive events and the estimated parasite concentration, a higher laser pulse fluence can improve the detection of Hemozoin and/or malaria parasites at a lower concentration. Of note, the Hemozoin nanoparticles in malaria parasites are usually clustered and such clusters can have a much lower fluence threshold of the Hemozoin-generated transient vapor nanobubble generation compared to individual Hemozoin nanoparticles suspended in a solution, which come from the sample preparation and purification.

Figure 18F:
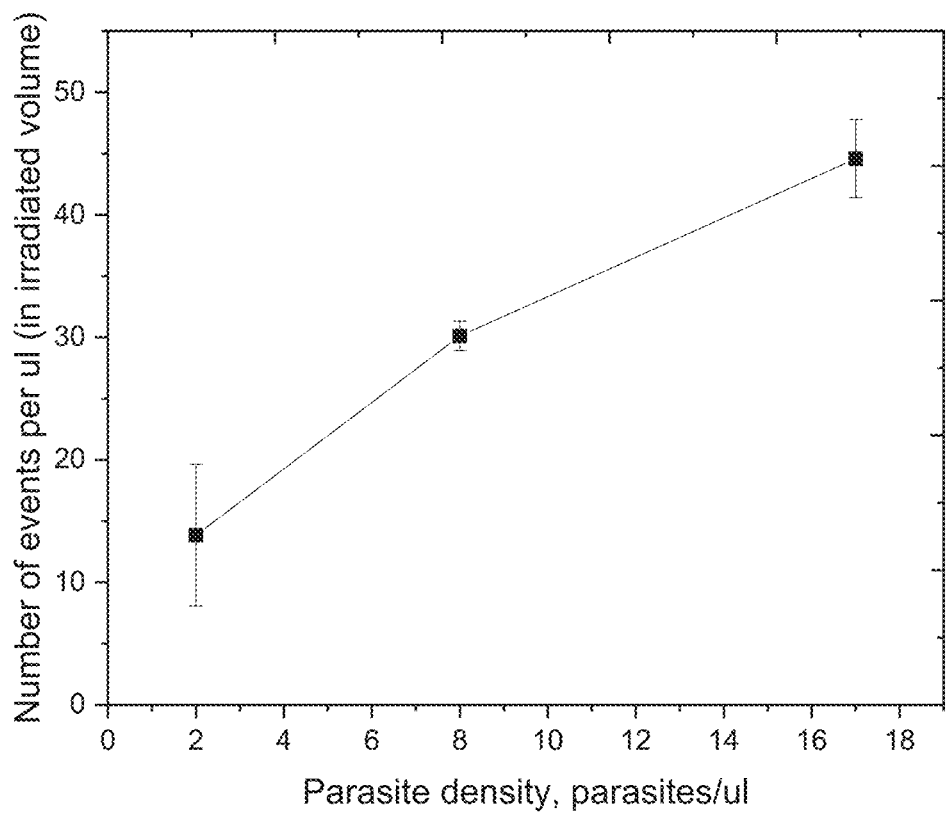
Figure 18G:
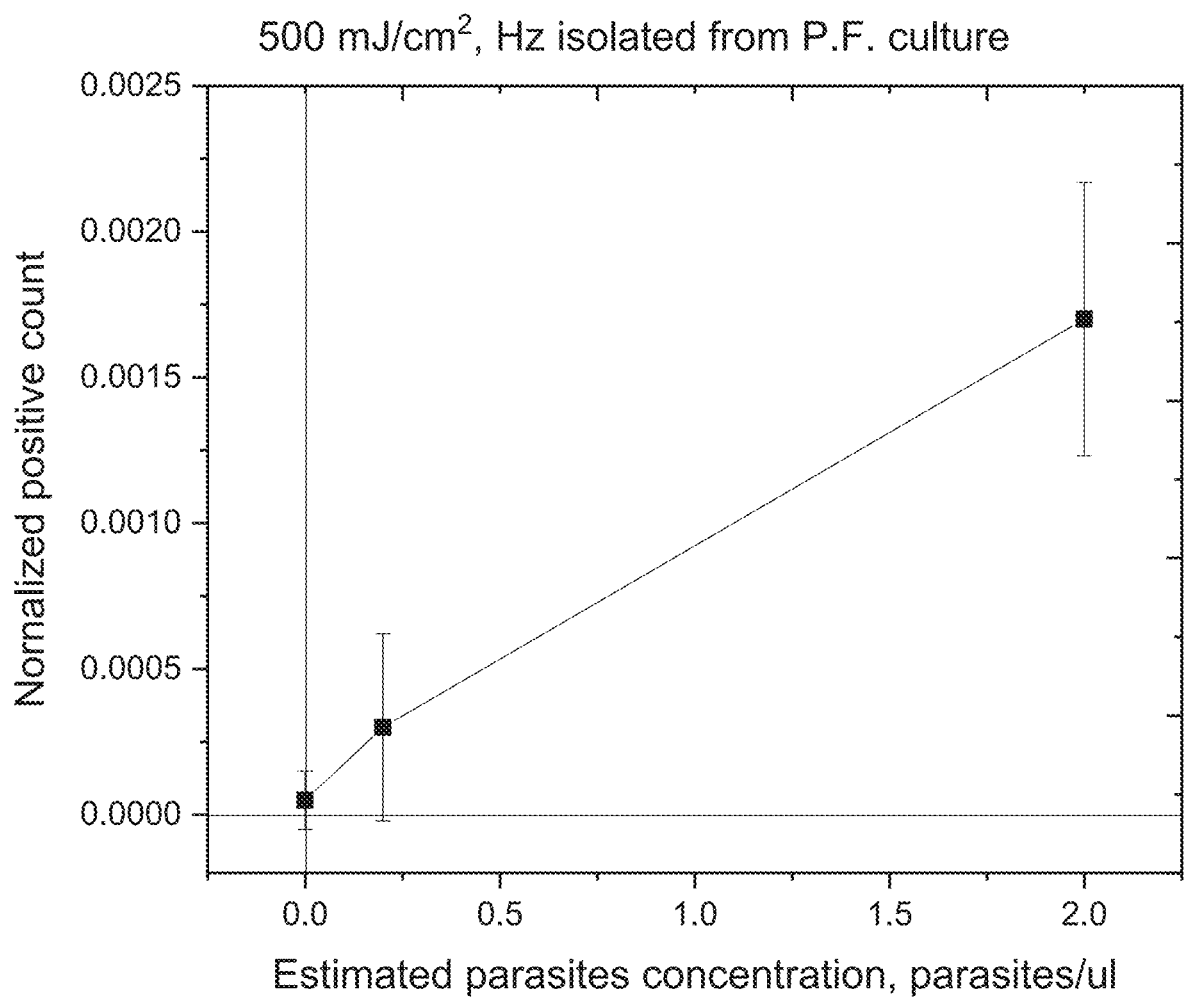

Studies have also been conducted to establish the basis for optimizing the Hemozoin detection in the micro-fluidic device for Hemozoin nanoparticles at a lower concertation. In those studies, the malaria-specific laser pump pulse had a wavelength of 671 nm and a fluence of 500 mJ/cm$^2$. Three samples were prepared. The first sample included water. The second sample included a solution of Hemozoin isolated from a *Plasmodium falciparum* culture having a parasite concentration equivalent to about 2 parasites per uL. The third sample included a solution of Hemozoin isolated from a *Plasmodium falciparum* culture having a parasite concentration equivalent to about 0.2 parasites per uL. Hemozoin is purified from the whole blood using standard published methods. FIGS. 18E-G illustrate the number of positive counts at different parasite densities or concentrations. As shown, a parasite density equivalent to about 0.2 parasites uL could still be detected. The above data illustrate the high-sensitivity and rapid (diagnosis time of about 5 minutes) detection of Hemozoin in blood samples using an optical detection system incorporating a micro-fluidic device.

FIGS. 19A and 19B illustrate another example micro-fluidic device 1950 that can be used in a malaria detection system based on Hemozoin-generated vapor nanobubble. The device 1950 can have any features of the device 50 described above except the differences described with reference to FIGS. 19A and 19B. The malaria detection system can have any features of the malaria detection systems described above, except the differences described with reference to FIGS. 19A and 19B. The device 50 and the malaria detection systems described above can have any features of the micro-fluidic device 1950.

As described above in FIG. 16B, the flow path of the liquid sample along the micro-cuvette 54 may be perpendicular to the direction of the probe beam and/or the pump beam. This flow path is illustrated by dashed lines in FIG. 19A. In contrast, the micro-fluidic device 1900 in FIGS. 19A and 19B can have a capillary tube 1954 that runs in a direction generally parallel (in other words, collinear) to the direction of the probe beam 1902 and/or the pump beam 1900 from a laser source (not shown in FIG. 19A). A fluid sample 1955 can enter the capillary tube 1954 at a fluid inlet 1952, flow through the capillary tube 1954 generally collinear to the direction of the probe beam 1902 and/or the pump beam 1900, and exit the capillary tube 1954 at a fluid outlet 1954. In some embodiments, the inner diameter of the capillary tube 1954 can be between about 20 um and about 80 um, or between about 30 um and about 70 um, or about 50 um. The capillary tube 1954 can have a length between about 50 mm and about 200 mm, or between about 80 mm and about 160 mm, or between about 100 mm and about 130 mm.

The capillary tube 1954 can include optical flange windows 1958, 1960 on or near opposite ends of the tube 1954 along its length. The capillary tube 1954 can act as an optical light guide, similar to that of an optical fiber. The optical flange windows 1958, 1960 can allow a passageway for the beams 1900, 1920 along the length of the capillary tube 1954. The pump and probe beams 1900, 1902 can propagate inside the flow 1955 along a length (or a portion thereof) of the capillary tube 1954 and fill or substantially fill the whole cross-section of the capillary tube 1954. The beams 1900, 1902 can propagate due to internal reflection from the inner capillary wall. The refractive index of the capillary tube 1954, which may be made of glass or polymer, can higher than that of the liquid sample. The propagation can be at such low angles of incidence that both beams 1900, 1902 may propagate in the flow 1955 for some distance before leaving the capillary tube 1954, for example, via the flange window 1960. As shown in FIG. 19A, after the flange window 1960, the probe beam 1902 can be coupled into the photodetector 1904. The probe beam 1902 and the pump beam 1900 can exit the capillary tube 1954 and be directed to a photodetector 1904, which can output a signal 1905 based on the detected probe beam 1902. Any optical scattering event in the probe beam path, such as by the Hemozoin-generated vapor nanobubbles, diverts more light to the nearest walls at higher angles of incidence, and such light escapes the capillary tube 1954. The optical scattering event reduces the amount of light at the photodetector 1904, which can be used to detect a cumulated effect of all the Hemozoin-generated vapor nanobubbles. That is, while some probe beam 1902 may end up propagating through the capillary tube 1954 and exit via the flange window 1960 due to the total internal reflection by the inner wall of the capillary tube 1954, local optical scattering caused by Hemozoin-generated vapor nanobubbles should result in optical losses detectable at the photodetector 1904, with the losses reflected in the output signal 1905 of the photodetector 1904.

This collinear flow-beam arrangement if FIGS. 19A and 19B can increase the laser-probed volume, for example, by a one to two orders of magnitude. As a result, a single pump laser pulse 1900 can irradiate more parasites, if present in the flow 1954, and generate more Hemozoin-generated vapor nanobubbles. This arrangement can increase the probability of detecting a parasite under a low concentration of parasites and can improve the detection of Hemozoin-generated vapor nanobubbles. Therefore, the micro-fluidic device 1950 can improve the Hemozoin-generated vapor nanobubbles detection threshold and/or consistency.

In some embodiments, the micro-fluidic device 1950 as shown in FIG. 19B can be adapted from an optical fiber or capillary tubing used in gas spectroscopy.

Figure 19C:
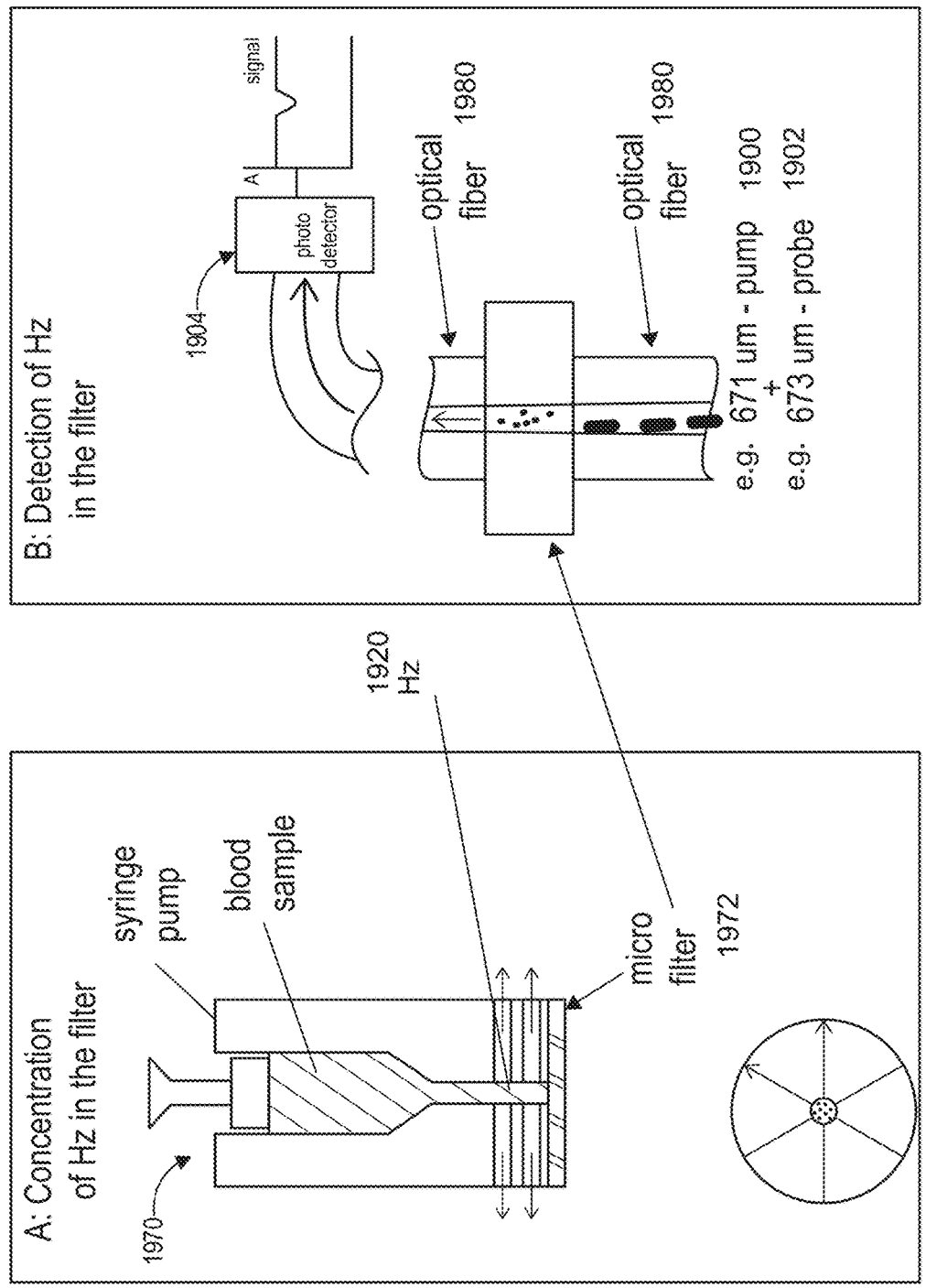
FIG. 19C illustrates an example two-step incorporation of a filter in a malaria detection system.

In some embodiments, installing filters of a specific size along or at the output of the flow of a liquid sample from a light guide, such as an optical fiber or the capillary tube 1954 described above, may allow further concentration of parasites and/or Hemozoin inside the light guide or at the output of the light guide. If the pump and/or probe laser beams enter the light guide in the direction opposite to that of the liquid flow (such as shown in FIG. 19A), the highest concentration of parasites and/or hemozoin would be nearer to the capillary tube end that is the optical entrance for the pump and probe laser beams. In this case, the probability of Hemozoin-generated vapor nanobubbles generation is expected to be the highest at the optical entrance, and expected to be increasing over time with the continuing buildup of the local concertation of parasites. In some embodiments, a separate liquid sample preparation device and/or method can prepare very high concentration of Hemozoin. In this case, the liquid sample can be static for malaria detection. A static sample in the filter can be analyzed as shown in FIG. 19C.

In FIG. 19C, the fluid sample preparation and analysis can be separated into two procedures (Steps A and B), using different devices. In Step A, a liquid sample can prepared with a preparation device 1970 that includes a filter 1972 to accumulate the Hemozoin 1920. In Step B, the filter 1972 can be removed from the preparation device 1970 and installed into an optical device 1980, which can be any optical devices disclosed herein, such as the micro-fluidic devices in FIG. 16A or FIGS. 19A-B, with the pump-probe laser beams 1900, 1902 routed through the filter 1972. The Hemozoin-generated vapor nanobubbles can be detected and quantified through the photodetector 1904, which analyses the probe beam 1902 exiting from the filter 1970.

Example Statistical Analysis for Optically Detecting Malaria

Figure 20A:
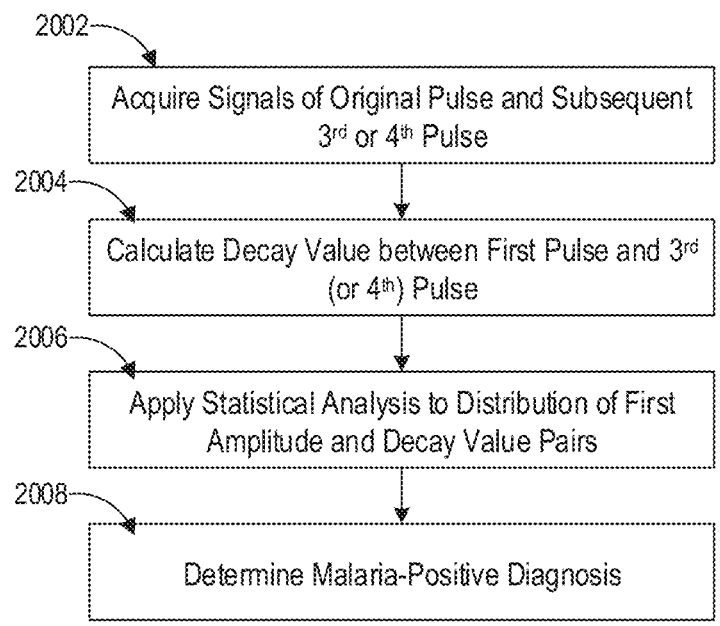
FIGS. 20A-20E illustrate example processes for optically detecting malaria parasite and/or Hemozoin-generated transient vapor nanobubbles using a signal processing, signal-specific metrics and their statistical analysis, with FIG. 20D illustrating schematically a theoretical signal.

In some embodiments, the optical detection data can be analyzed statistically to provide additional confirmation that malaria parasite and/or Hemozoin has been detected. The statistical analysis can follow the steps in FIG. 20A. At step 2002, signals of the original or first laser pulse and signals of the subsequent (such as the second, the third, and/or the fourth) laser pulses can be acquired. At step 2004, a processor or controller in communication with the photodetector can process the signals from the photodetectors and calculate a decay value between the first pulse and the third (or second, or fourth) pulse. At step 2006, the processor or controller can apply a statistical analysis to a distribution of the first signal amplitude and the decay value pairs. At step 2008, the processor or controller can determine a malaria-positive diagnosis.

The concept of the signal decay will be described using results from an experimental model. In this model, a layer of dermis tissue (about 750 um thick) was covered by a layer of dark skin (about 250 um thick) so that a total thickness of the sample about 1 mm. A *Plasmodium falciparum* parasites suspension was applied to the top of the dermis layer and incubated for about 15 minutes before the dermis layer with parasites was covered by the skin layer so that the parasites are between the dermis and the dark skin to create a test sample.

One of the optical detection systems disclosed herein was applied to the test sample. The pump laser beam had a wavelength of 671 nm and an energy of 17 uJ. The pump beam had a focal point at 380 um (in water). The pump beam had a cross-sectional diameter of about 120 um at the surface of the test sample and a cross-sectional diameter of about 150 um at a depth of about 250 um, that is, at the depth of the malaria parasites in the test sample. A skilled artisan can appreciate based on the present disclosure that alternative parameters can be used in additional embodiments.

Figure 20B:
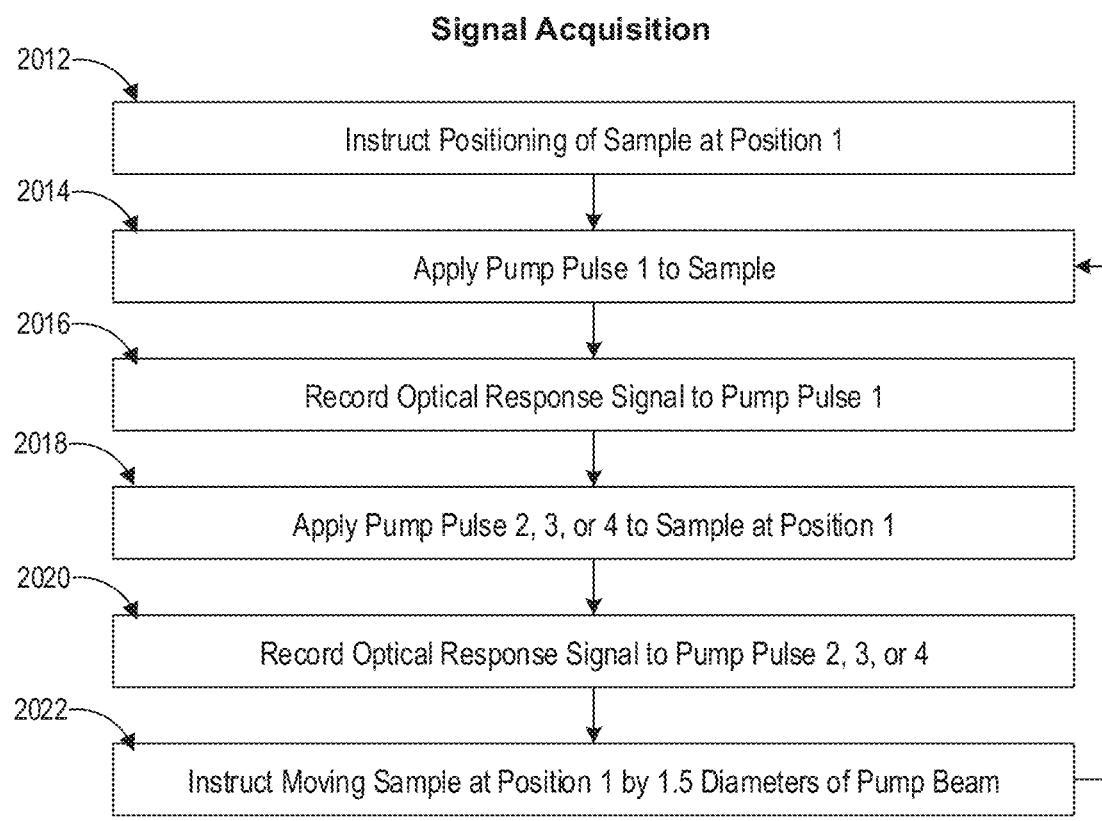

Signal acquisition was performed according to the following steps shown in FIG. 20B. At step 2012, the position of the test sample was fixed. At step 2014, the first pump laser pulse was applied. At step 2016, the signal was recorded to show the initial response of the target (that is, the parasites) to the pump pulse. At step 2018, several consecutive pulses, include the second, the third, and/or the fourth pulses, were applied to the same location when the position of the test sample was still fixed. At step 2020, the signal was recorded for the second, third, and fourth pulses to show the response of the residual target (that is, the parasites after the first pulse) to the pump pulses.

The diagrams shown in FIGS. 21A-21H compare the amplitudes of the signal responsive to the first laser pulse to that of the signal responsive to the second laser pulse. The laser pulses had an energy of about 17 uJ to about 18 uJ. The parasites and/or Hemozoin can be destroyed by the mechanical impact of vapor nanobubbles. As a result, the parasites and/or Hemozoin may not produce the vapor nanobubble signal after the first laser pulse or after a few laser pulses because no more vapor nanobubbles of a detectable size can be formed after the parasites and/or Hemozoin were destroyed (see FIGS. 21A-21D). In contrast, native skin targets do not usually deteriorate as quickly as the malaria parasites and/or Hemozoin under exposure of several consecutive laser pulses. Therefore, the signals due to optical scattering by the skin may be similarly shaped after several laser pulses (see FIGS. 21E-21H).

As described above, compared to intact skin, Hemozoin-generated transient vapor nanobubble signals can demonstrate apparent decay, that is, the decrease (often to zero) in the signal amplitude in response to consecutive laser pulses applied to the same location. However, many large Hemozoin-generated transient vapor nanobubbles can still return non-zero signals during consecutive laser pulses because of the large amount of Hemozoin involved. The greater the concentration of Hemozoin in the parasite, the longer or more laser pulses it takes to destroy such Hemozoin nanoparticles. As a result, the decay value can be analyzed as the ratio of signal amplitudes for the first verses the third and/or fourth laser pulses applied to the same location.

With continued reference to FIG. 20B, at step 2022, the position of the test sample can then be changed by about 1.5 times the diameter of the pump beam (by about more than 220 um). A plurality of laser pulses can be applied to the second location according to the steps 2014-2020 until a specific number N of signal pairs (the first amplitude and the decay value) were obtained.

Figure 22A:
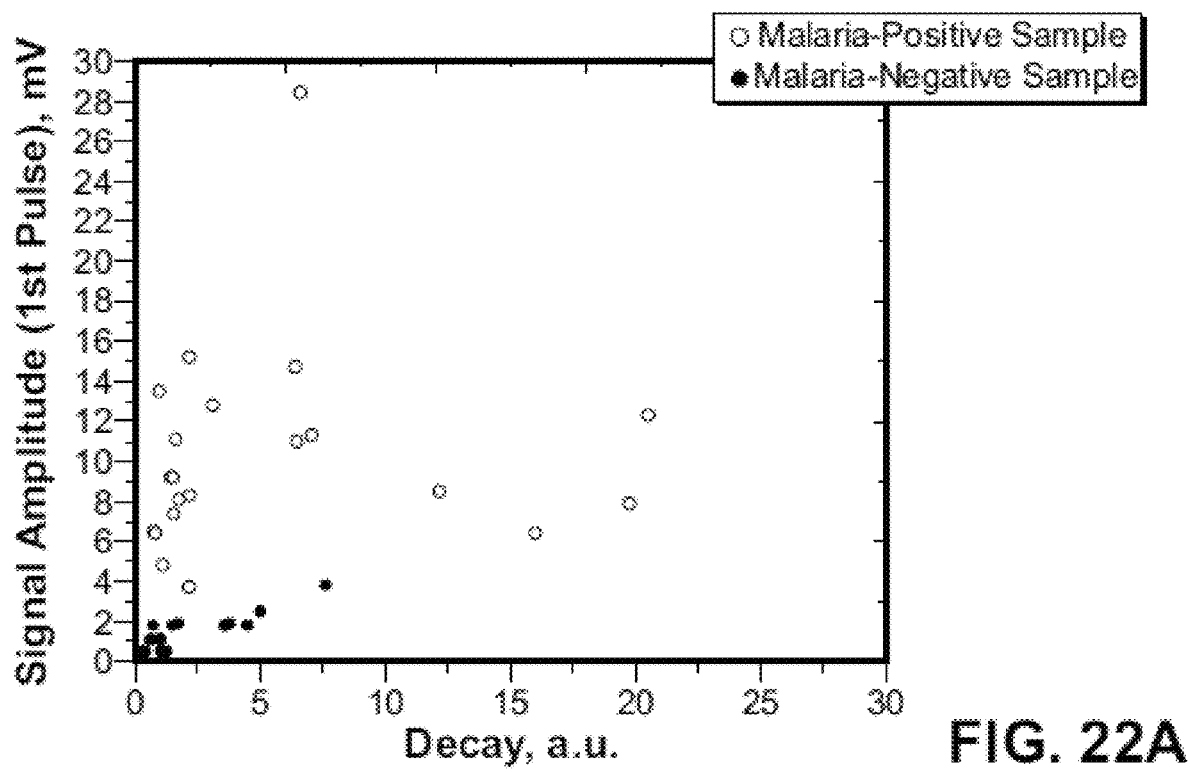
FIGS. 22A and 22B illustrate example Amplitude-Decay (A-D) diagrams for the optical scattering signal amplitude A and the decay D at each individual probe location for the malaria-negative and -positive human dark skin samples.
Figure 22B:
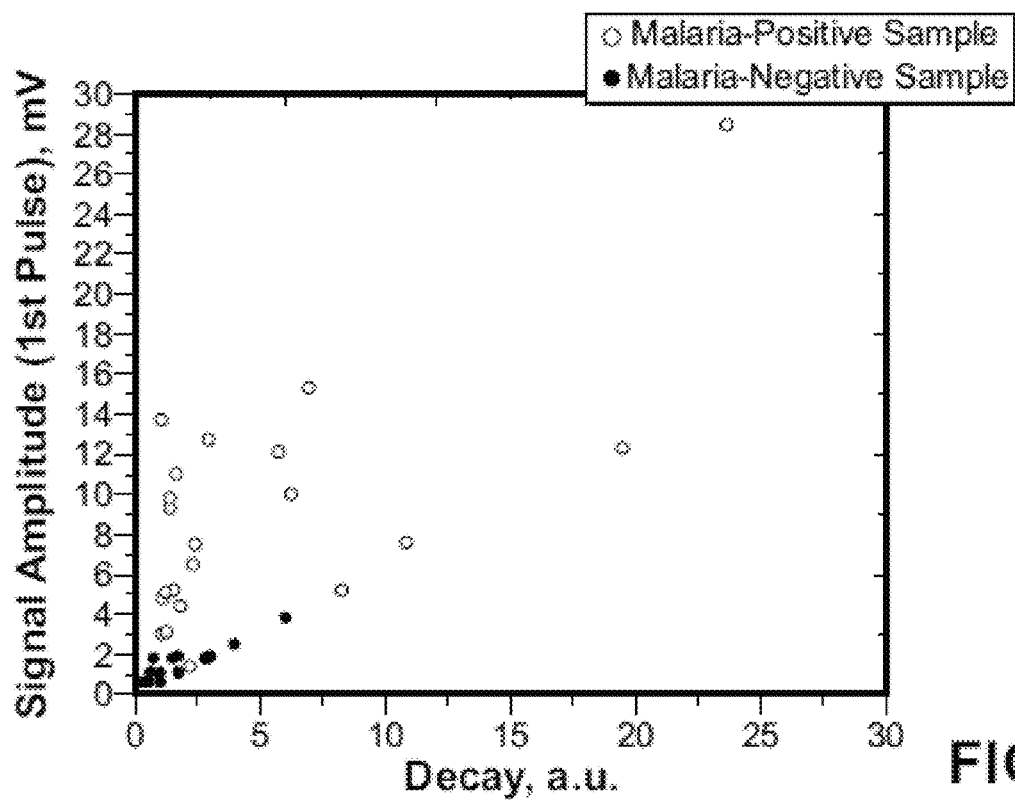

A value pair of amplitude of the first signal A and the decay value D can be obtained, such as shown in FIGS. 22A and 22B. The window in FIG. 22A shows the metrics obtained for the full signal time window, without limitations to the minimal value of the signal amplitude (for example, zero amplitude was allowed). The window in FIG. 22B shows the metrics calculated under the parameters as described below with reference to FIG. 20C.

Figure 20C:
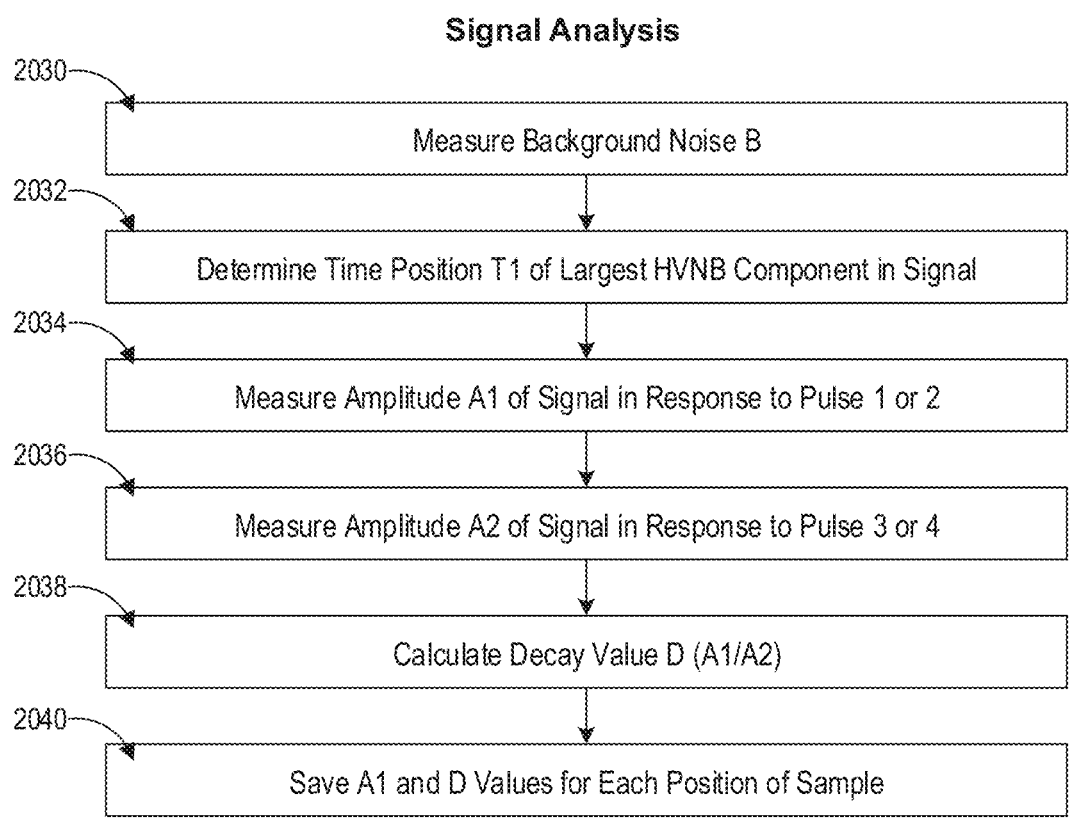

FIG. 20C illustrates an example signal analysis process. At step 2030, after having acquired the signals from the photodetector, the background noise B (see FIG. 20D) can be measured. At step 2032, a time position T1 (see FIG. 20D) of the largest Hemozoin-generated transient vapor nanobubble component in the signal can be determined. The background or signal nose B can be measured as an average peak-to-peak value from the time window before the trigger time point. If several Hemozoin-generated transient vapor nanobubble components were found, the one with the highest peak-to-peak amplitude and the one closest to the trigger time point T1 can be used. In some embodiments, the typical nanobubble signal shape can also be distorted by the optical system with the peak of the signal turning into the spike of an opposite polarity. A time window Tnb, which determines the time position of the maximal signal amplitude for the maximal possible vapor nanobubble generated under the laser fluence in skin, can be applied. For example, the time window Tnb can start with 1.0 us for the maximal possible duration of Hemozoin-generated transient vapor nanobubble having a lifetime of about 2 us so the signal peak would be within half of the Hemozoin-generated transient vapor nanobubble lifetime.

At step 2034, the processor or controller in communication with the photodetector can measure an amplitude A1 (see FIG. 20D) of the signal in response to the first and/or second laser pulse. In some embodiments, A1= [peak-to-peak value in the time window from T1 to T1+Tnb]−B. As the minimal value of A cannot be smaller than one digitation level: Amin, mV, which can be calculated as [oscilloscope voltage range, mV]/256, this excludes zero values of A (A min=0.63 mV for 20 mV/div).

At step 2036, the processor or controller can measure an amplitude A2 (see FIG. 20D) of the signal in response to the third and/or fourth laser pulse. In some embodiments, A2= [peak-to-peak value in the time window from T1 to T1+Tnb]−B. A2 also cannot have a zero value.

At step 2038, the processor or controller can calculate the decay value D as a ratio of A1 to A2. At step 2040, the processor or controller can save A1 and D values for each position of the test sample, for example, on a memory device in communication with the processor or controller. In some embodiments, the processor or controller can form a table of N pairs of A and D, available for graphical presentation and/or for the calculation of the statistical analysis.

Figure 20D:
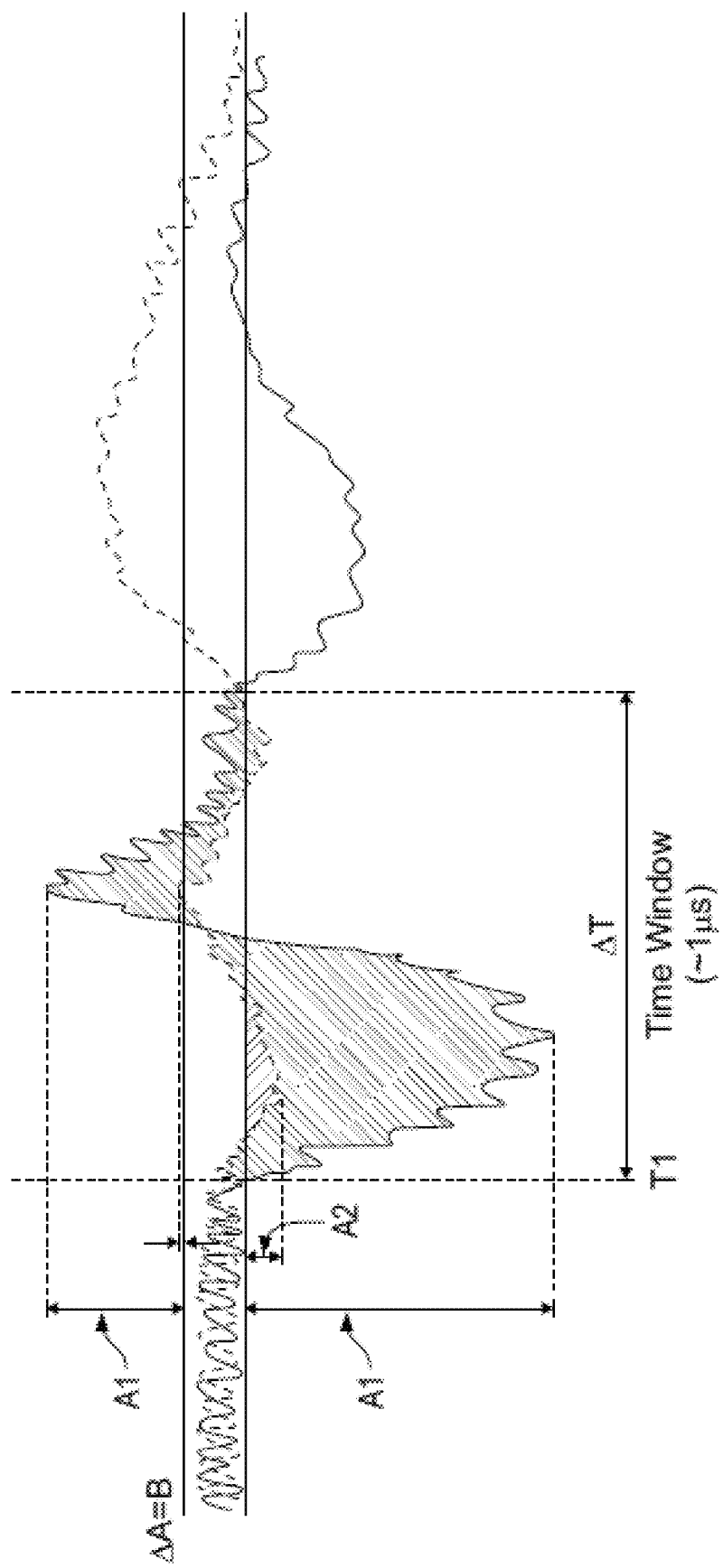
Figure 20E:
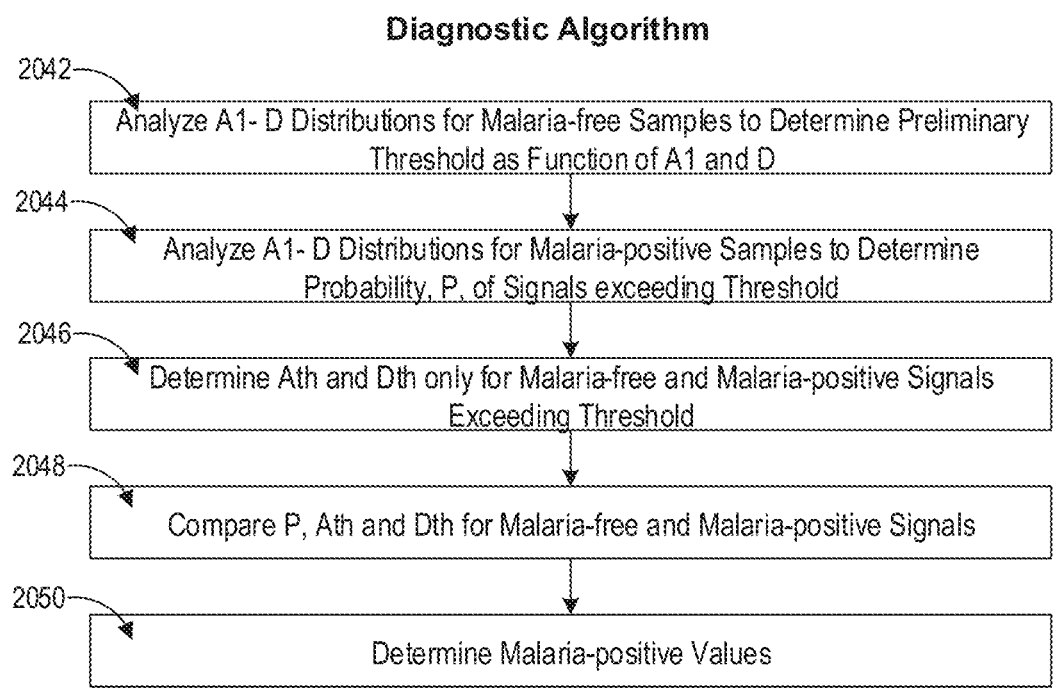
Figure 21A:
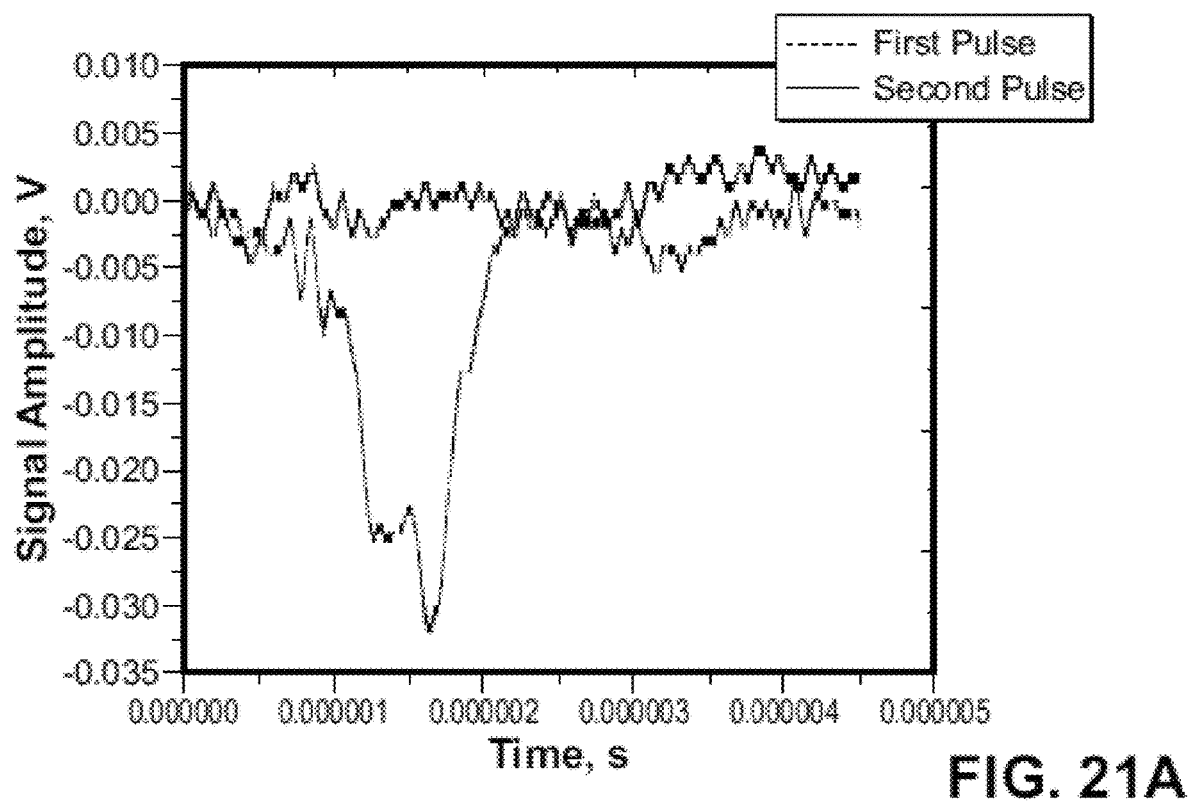
FIGS. 21A-21D illustrate example signals from human dark skin samples with malaria parasites in response to the first pump laser pulse and the second pump laser pulse.
Figure 21B:
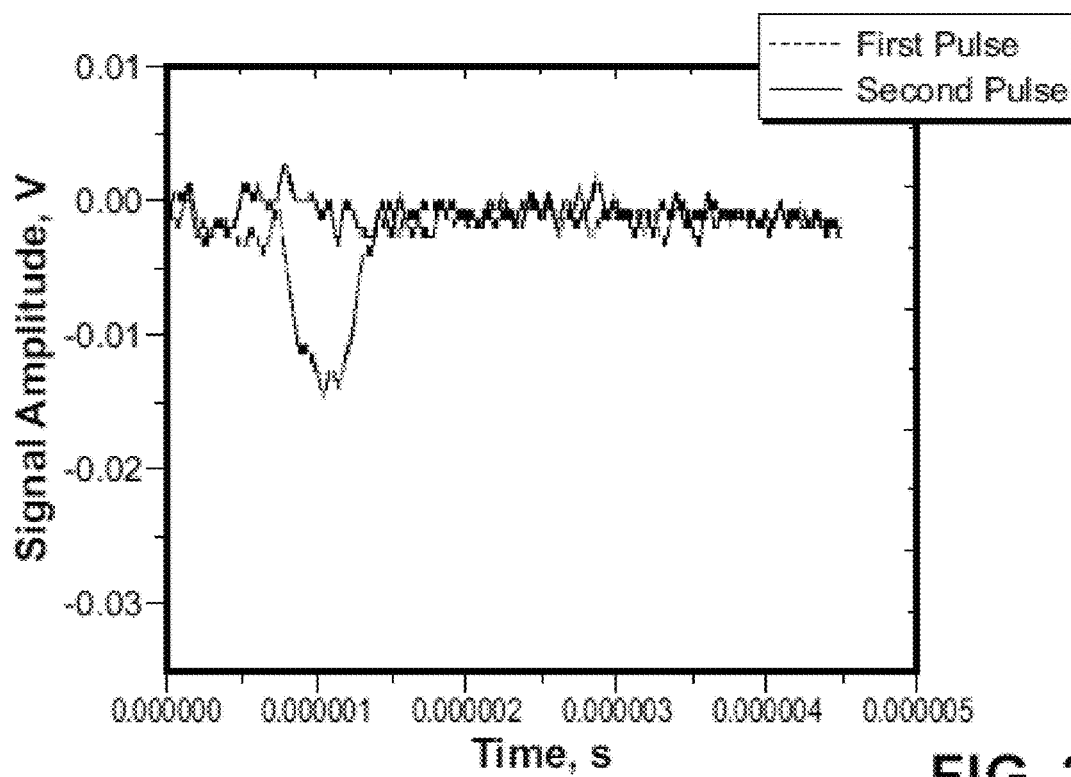
Figure 21C:
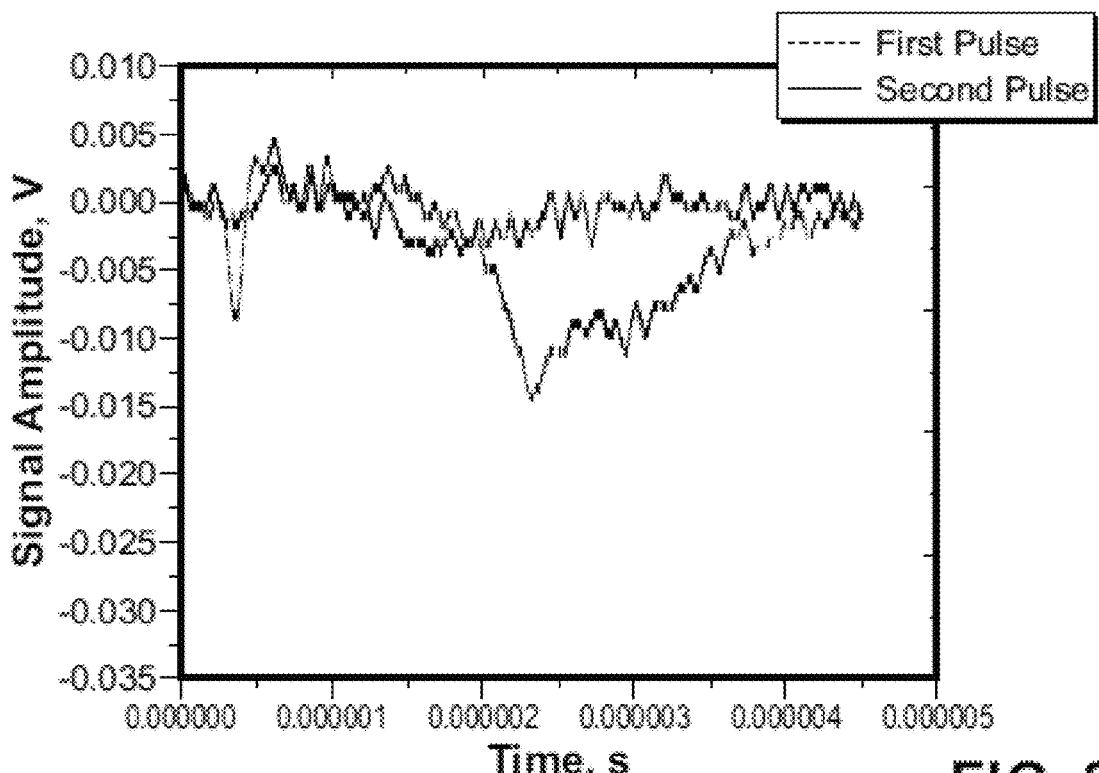
Figure 21D:
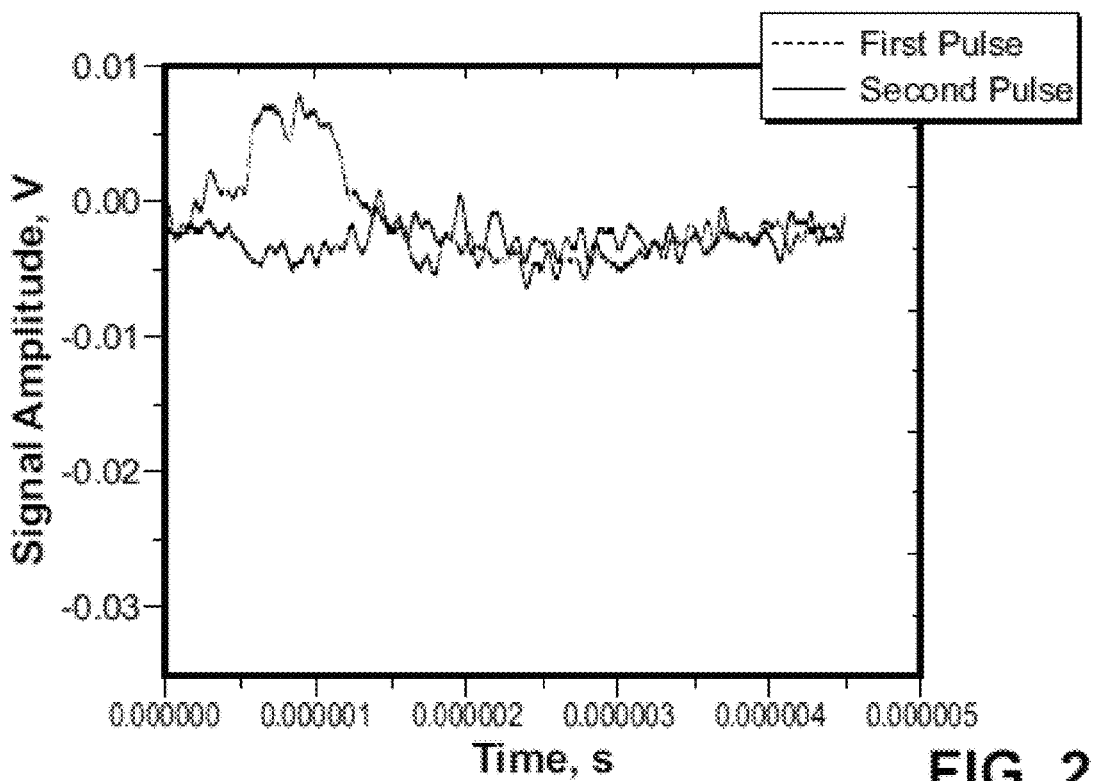
Figure 21E:
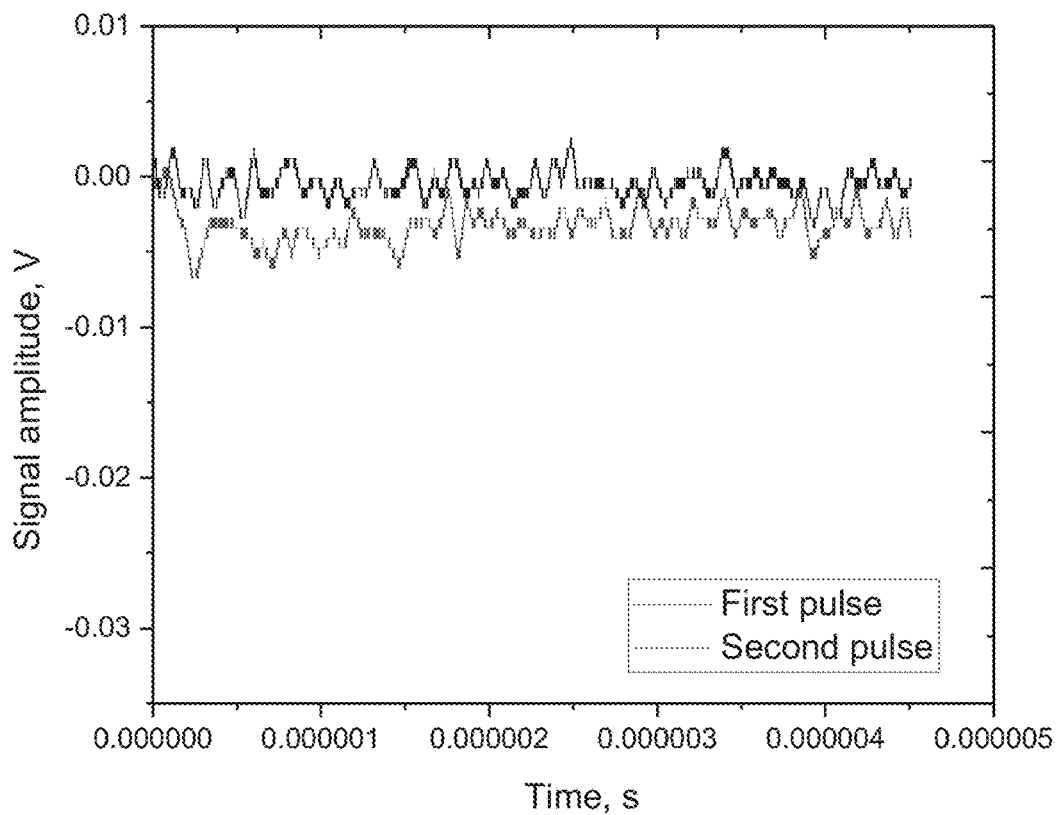
FIGS. 21E-21H illustrate example signals from intact dark skin samples in response to the first pump laser pulse and the second pump laser pulse.
Figure 21F:
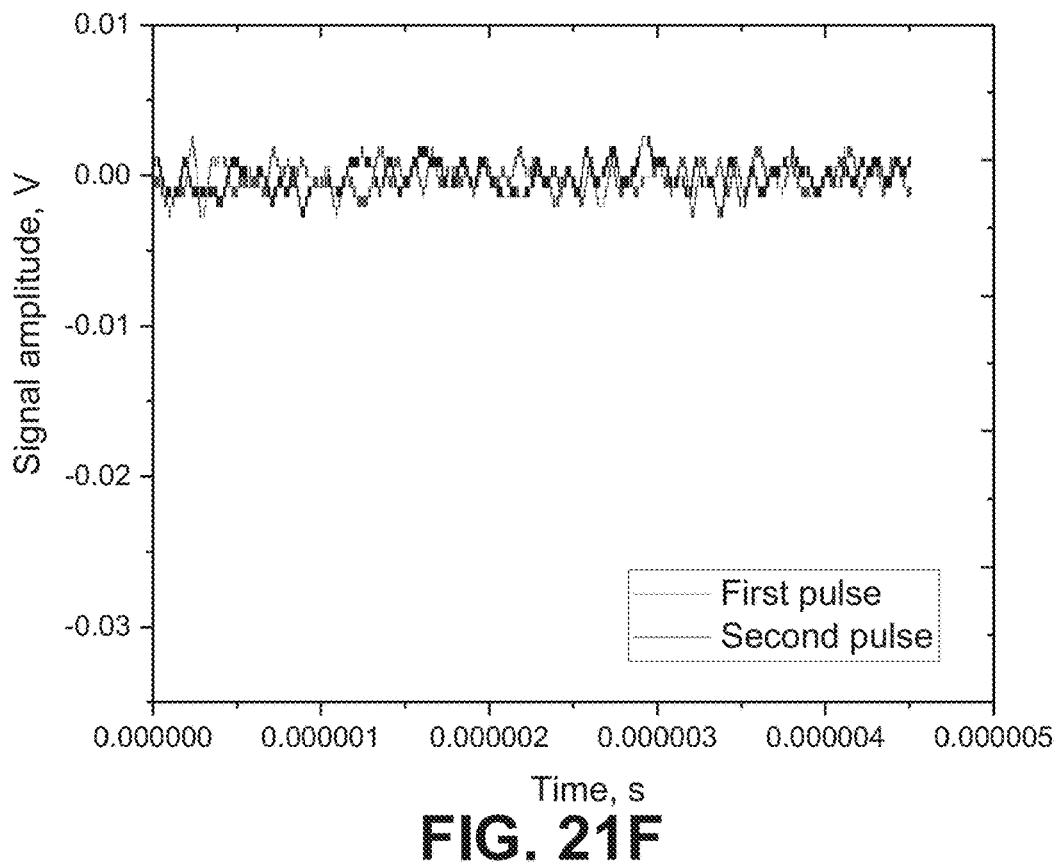
Figure 21G:
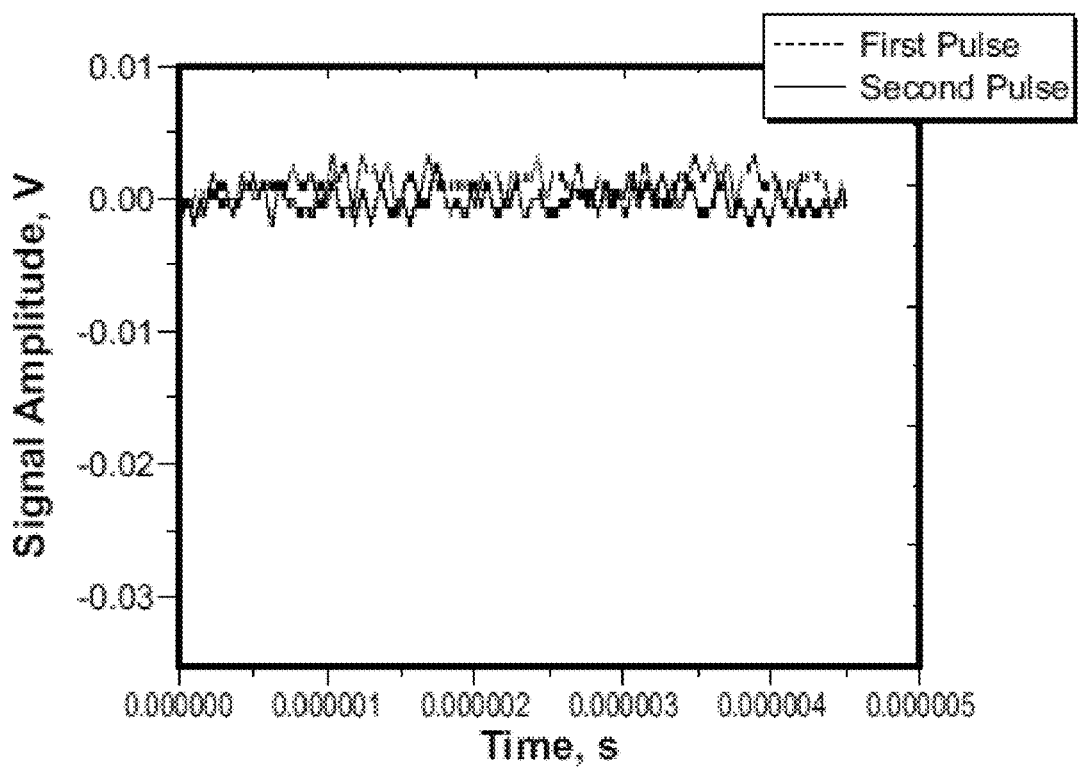
Figure 21H:
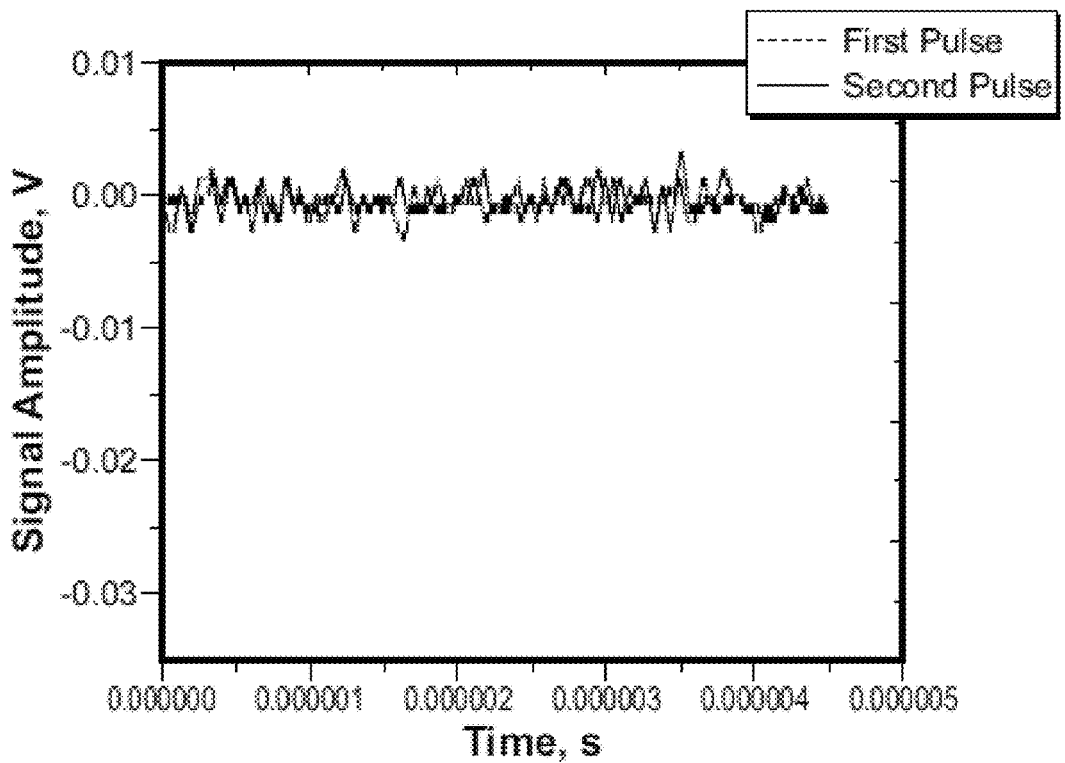

The A1-D pairs can be used to make a malaria-positive diagnosis, such as using the diagnostic algorithm shown in FIG. 20E. At step 2042, the processor or controller can analyze the A1-D distribution for malaria free samples to determine a preliminary threshold as the values or borders for signal metrics. In some embodiments, the preliminary threshold can be expressed as a function of A1 and D.

At step 2044, the processor or controller can analyze the A1-D distribution for malaria-positive samples to determine the relative change in metrics values and the relative level (which can be expressed as a probability P) of the malaria-positive signals whose metrics exceed the preliminary threshold determined in step 2042. In some embodiments, the probability P can be calculated as:

$$N(\text{signals above the preliminary threshold})/N(\text{total number of signals}).$$

At step 2046, the processor or controller can determine an amplitude threshold Ath and an decay threshold Dth only for the malaria-free and malaria-positive signals that exceed the preliminary threshold determined in step 2042. At step 2048, the processor or controller can compare the values of P, Ath, and Dth for the malaria-free and malaria-positive signals. At step 2050, the processor or controller can determine the malaria positive values based on the comparison in step 2048. In some embodiments, the preliminary thresholds and/or malaria positive values can be determined manually. In some embodiments, the preliminary threshold and/or malaria positive values can be determined using a mathematical model and/or neural network model trained to perform the statistical analysis on the optically detected signal.

Figure 22C:
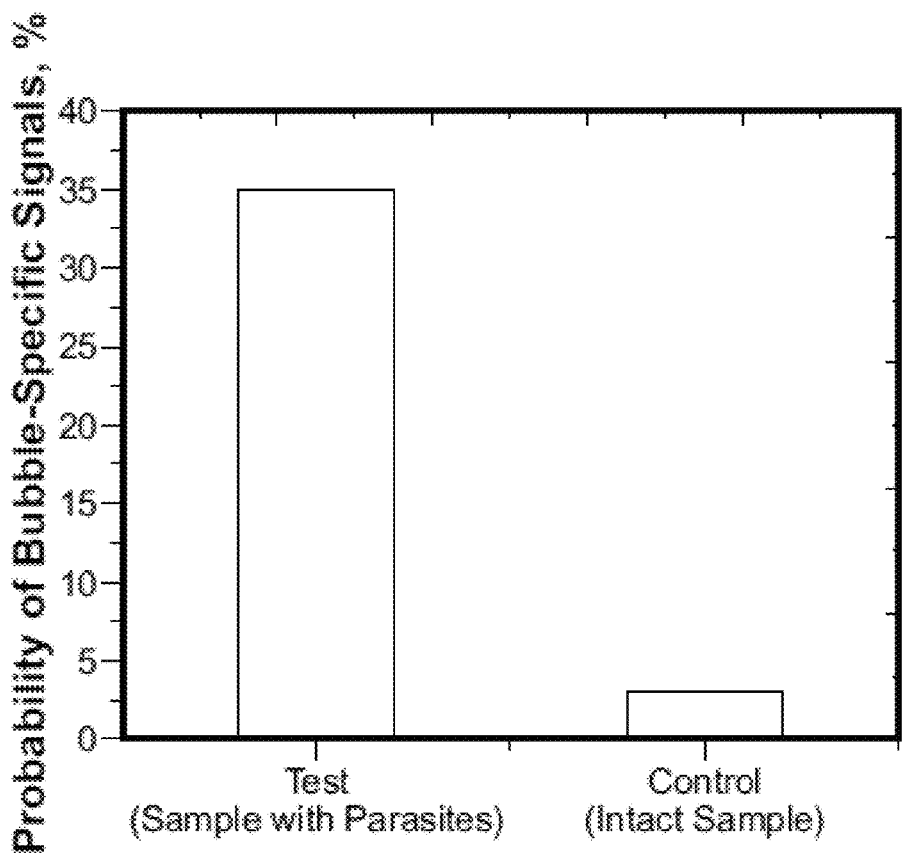
FIGS. 22C and 22D illustrate example sample-averaged signal metrics when performing a statistical analysis of the data using the optical detection method disclosed herein.
Figure 22D:
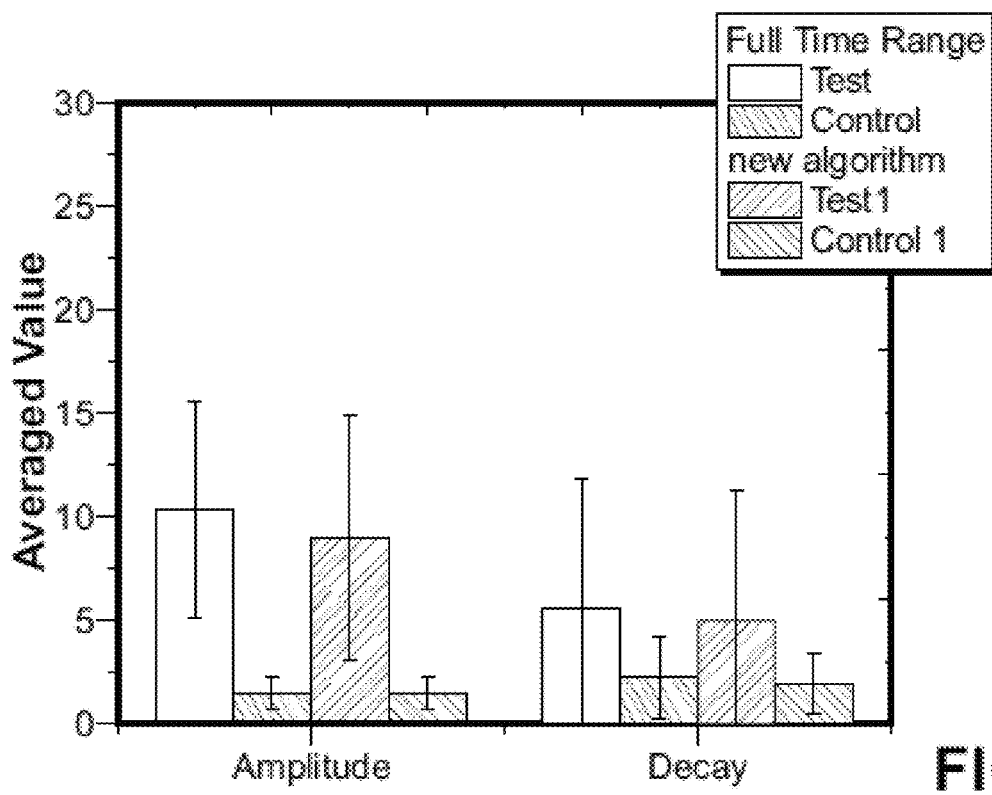

FIGS. 22C and 22D illustrate example sample-averaged signal metrics. The malaria-negative samples were used as a control. The malaria-positive samples were used as test samples. FIG. 22C illustrates the example probability P of the nanobubble specific signals. FIG. 22D illustrates the example amplitude A and the example decay D. Some locations in intact sample also produce nanobubble-like signals and thus contribute to "false-positives." The false positives can be further filtered out by using the decay metric in combination with the amplitude of the signal in response to the first laser pulse.

As described above, the polarity of the Hemozoin-generated transient vapor nanobubble signal may be both negative and positive depending upon the vertical position of the vapor nanobubble. "Upper" vapor nanobubbles (those formed in the upper skin layer) scatter the light "returning" from backscattering by the skin. Therefore, those nanobubble signals produce a negative signal. "Lower" vapor nanobubbles (those formed in the lower skin layers) scatter the incident probe light. Therefore, those signals produce a positive signal. Multiple Hemozoin-generated transient vapor nanobubbles may create one or several different signals in response to a single pump laser pulse.

In one experiment using the experimental model described above, no significant time-shift was observed for all Hemozoin- or malaria-positive signals. All the Hemozoin-generated transient vapor nanobubble spikes began at about 100 ns to about 200 ns time-point.

Figure 40A:
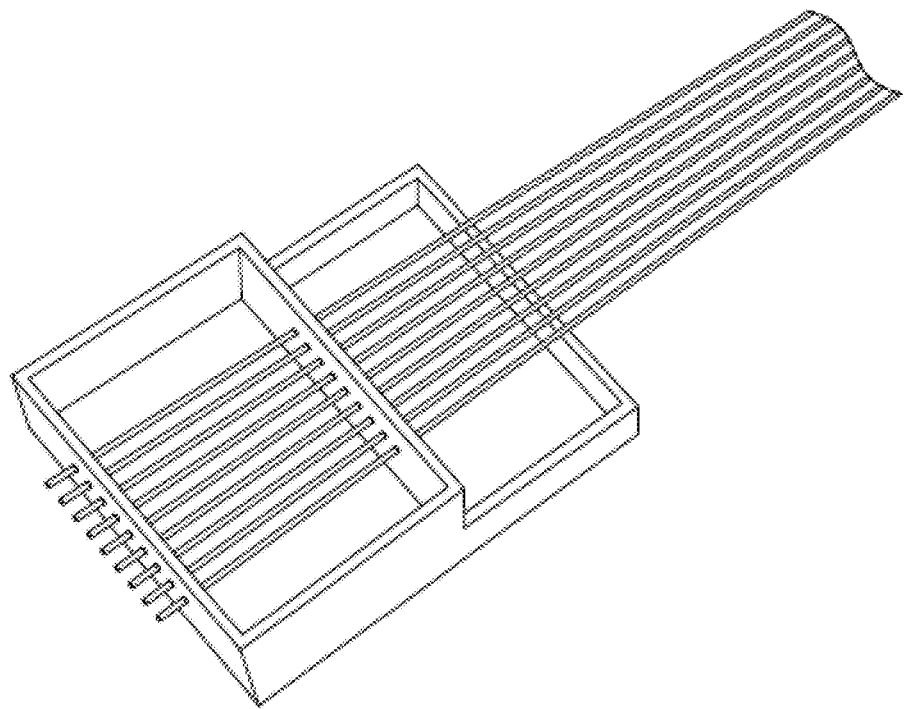
FIG. 40A illustrates an example array of optical fibers for optical detection of malaria.
Figure 40B:
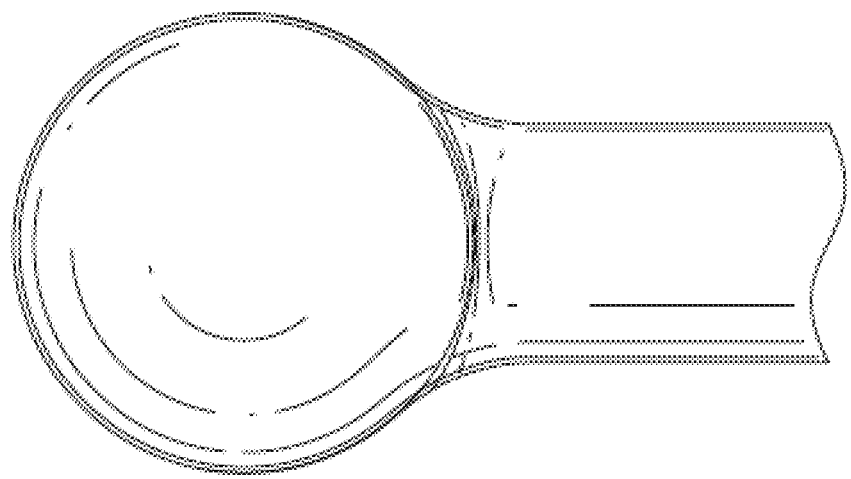
FIG. 40B illustrates a lensed tip of one of the optical fibers in the array of FIG. 40A.

In some embodiments, the malaria sensor can include an array of optical fiber bundles (which are described in greater detail below), with each bundle capable of detecting malaria optically in one location of the measurement site. FIG. 40A illustrates an example fiber array and FIG. 40B illustrate individual fiber bundle. The array can include about 10 to 20 bundles. In some embodiments, the laser beam can be sequentially switched so that the bundles can sequentially probe different locations (for example, 10-20 close locations at about 100 um per location) in the same measurement site.

Distortion of Optically Detected Transient Vapor Nanobubble Signals

Figure 24A:
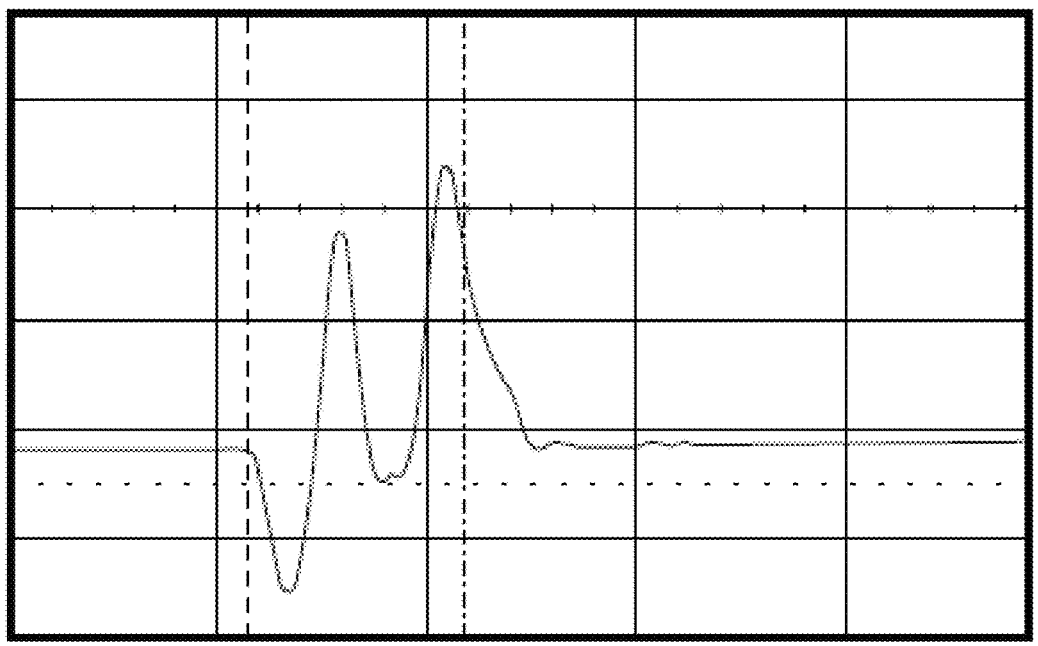
Figure 24B:
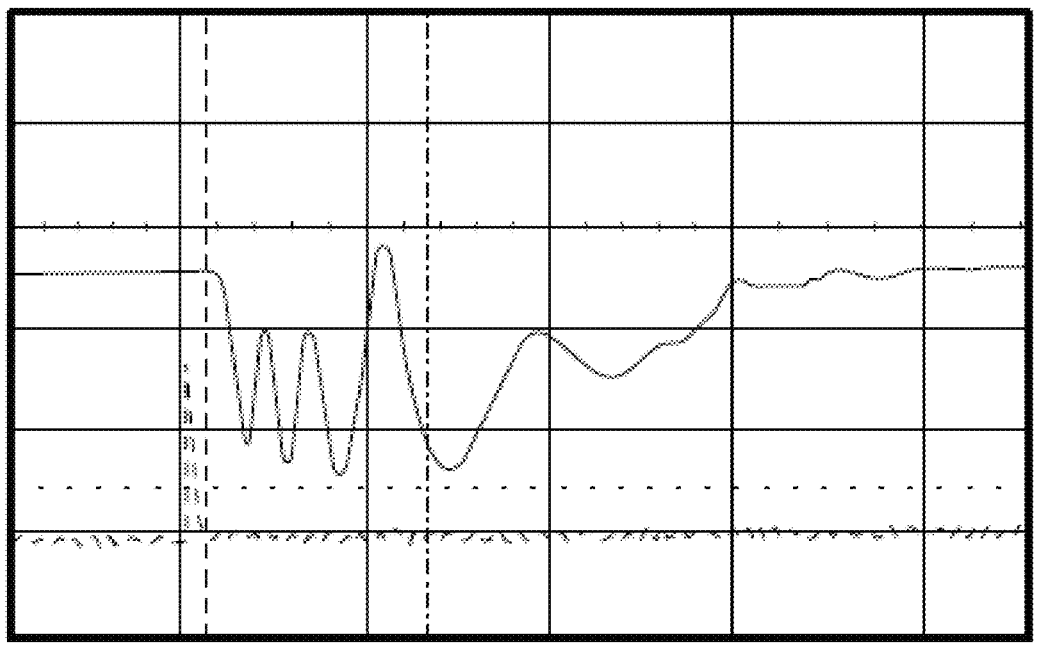
FIG. 24B illustrates example raw signals of optical scattering from an experimental model including gold nanoparticles in water by a plurality of transient vapor nanobubbles generated at a specific location.
Figure 25A:
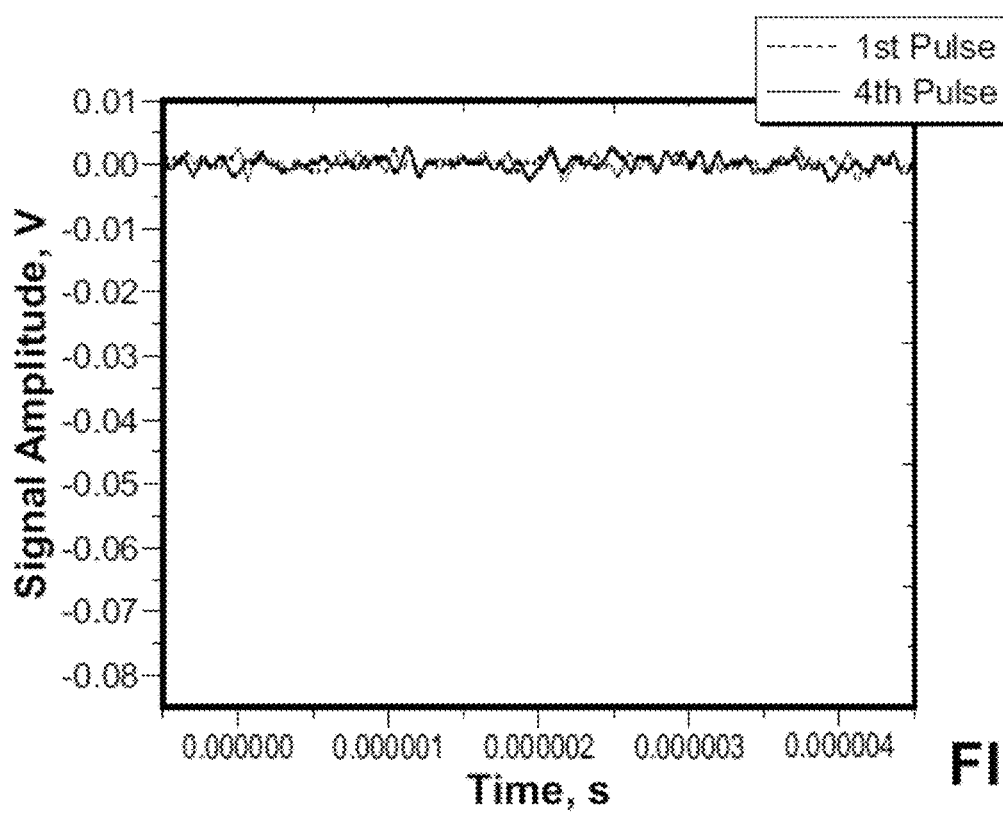
FIGS. 25A-25D illustrate example raw signals of optical scattering by transient vapor nanobubbles generated in response to the first (red) and the fourth (black) laser pulses in malaria-negative and malaria-positive human dark skin samples.
Figure 25B:
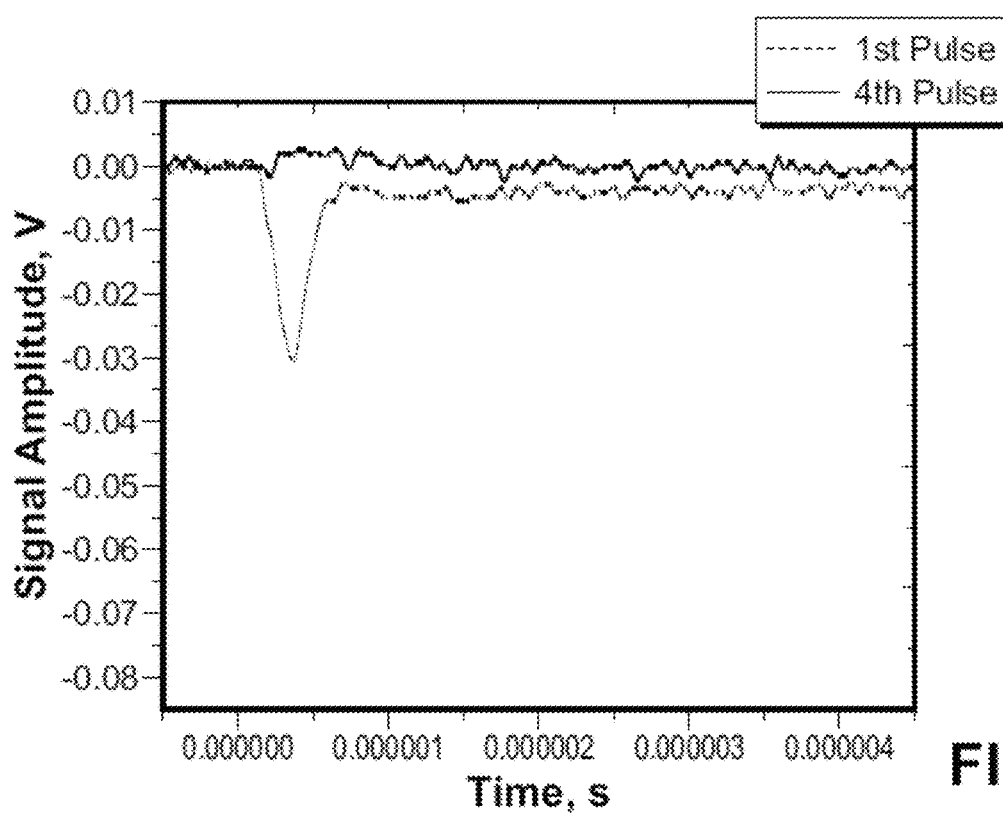
Figure 25C:
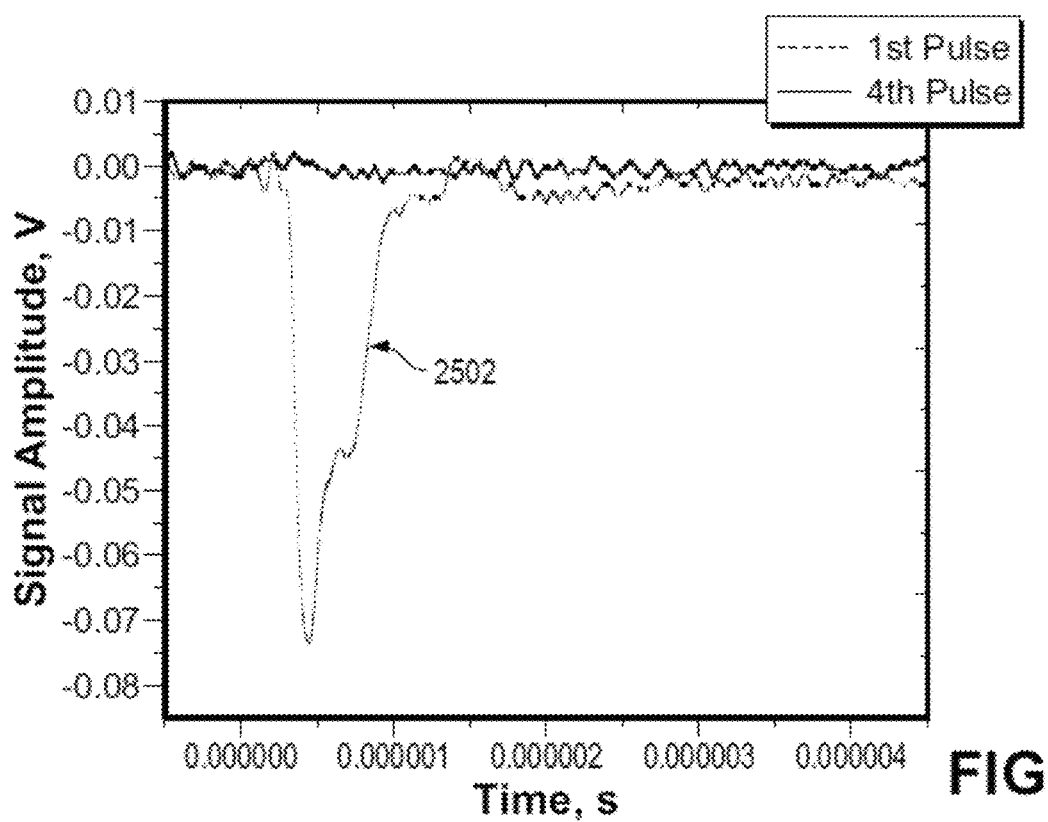
Figure 25D:
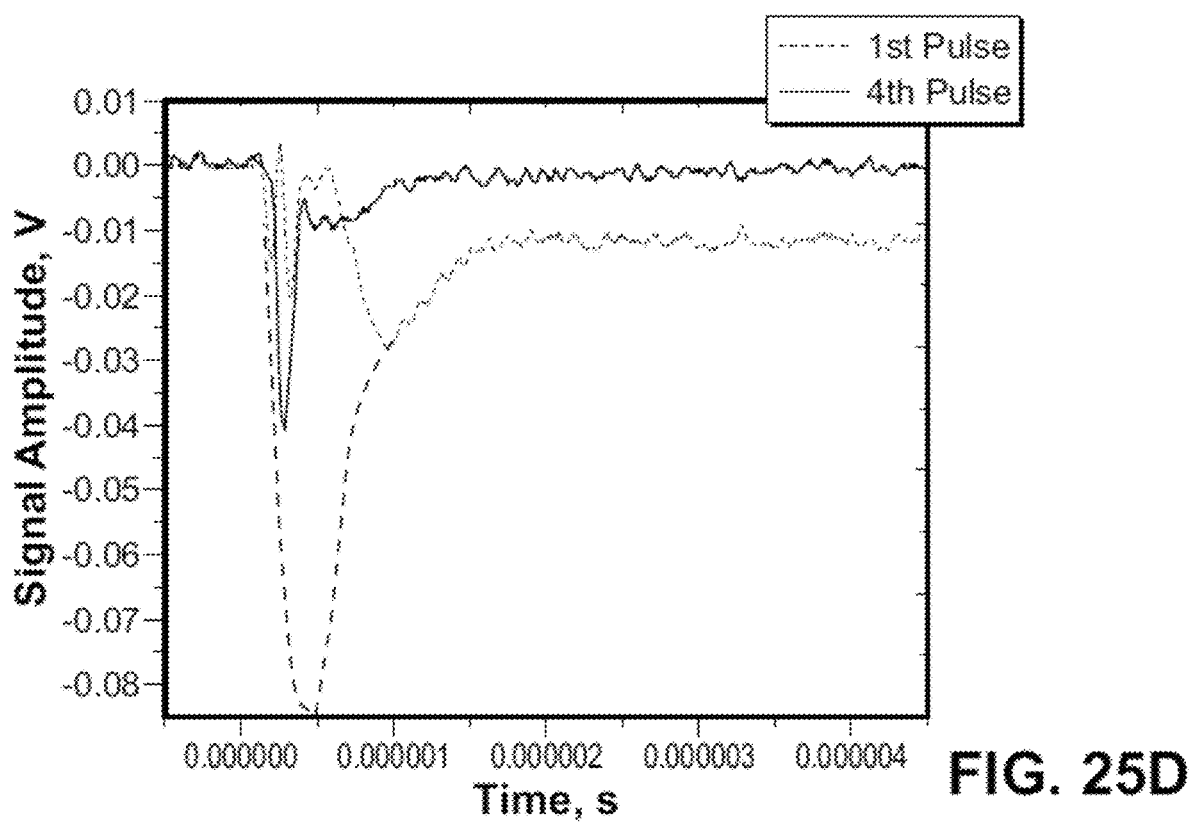

In some embodiments, not all the transient vapor nanobubble signals that are detected by the photodetector exhibit a dip-shape, such as shown by the yellow dash line 2506 in FIG. 25D. The dash line illustrates a hypothetical undistorted optical signal by a transient vapor nanobubble. One or more parameters of the optical detection system can distort the nanobubble signal, for example, into having multiple peaks, such as shown in FIGS. 24A and 24B. The parameters can include but are not limited to, the location of the malaria parasite and/or Hemozoin relative to the center of the probe beam (or how much the transient vapor nanobubble is shifted from the probe beam), the size of the pump beam relative to the size of the probe beam, the energy level of the pump beam, and/or the concentration of the parasite in the probed volume. A skilled artisan can appreciate based on the present disclosure that alternative parameters can be used in additional embodiments.

A gold particles in water experimental model was used to study the effects of two cases of a lateral shift of a transient vapor nanobubble relative to the aperture of the probe beam when the probe beam diameter was about 20 um, the energy level of the pump beam, and the relative sizes of the pump beam and the probe beam.

In the first case, a single transient vapor nanobubble in one specified location was generated with a pump laser pulse having a wavelength of 532 nm. In this case, the lateral position of the probe beam was varied by moving the optical system relative to the location of the single transient vapor nanobubble. FIGS. 23A-C and 24A illustrate the signals obtained in the first case.

Figure 23A:
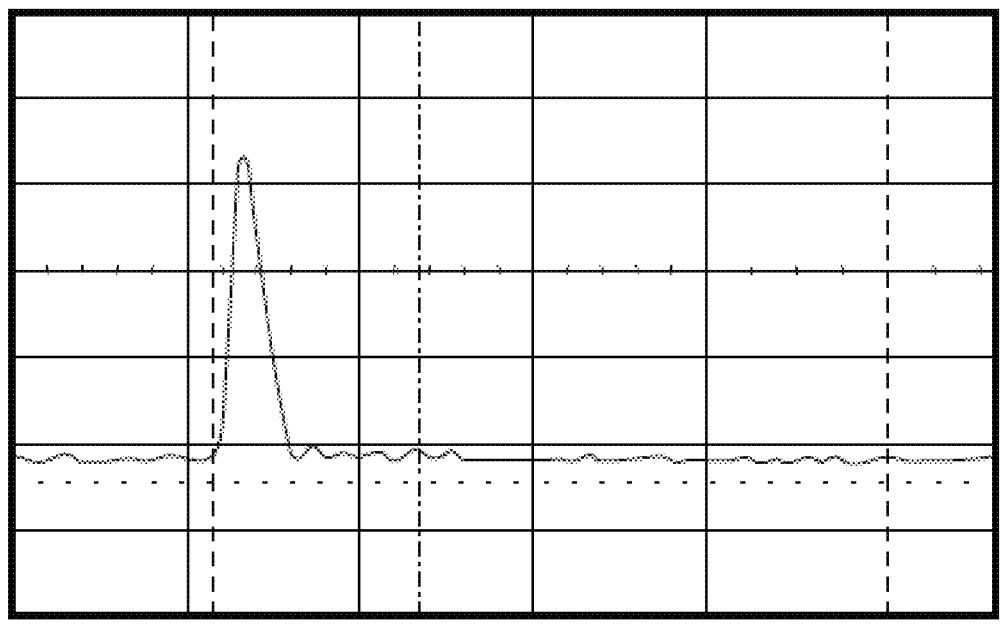
FIGS. 23A-23C and 24A illustrate example raw signals of optical scattering from an experimental model including gold nanoparticles in water by a single transient vapor nanobubble generated at a specific location.
Figure 23B:
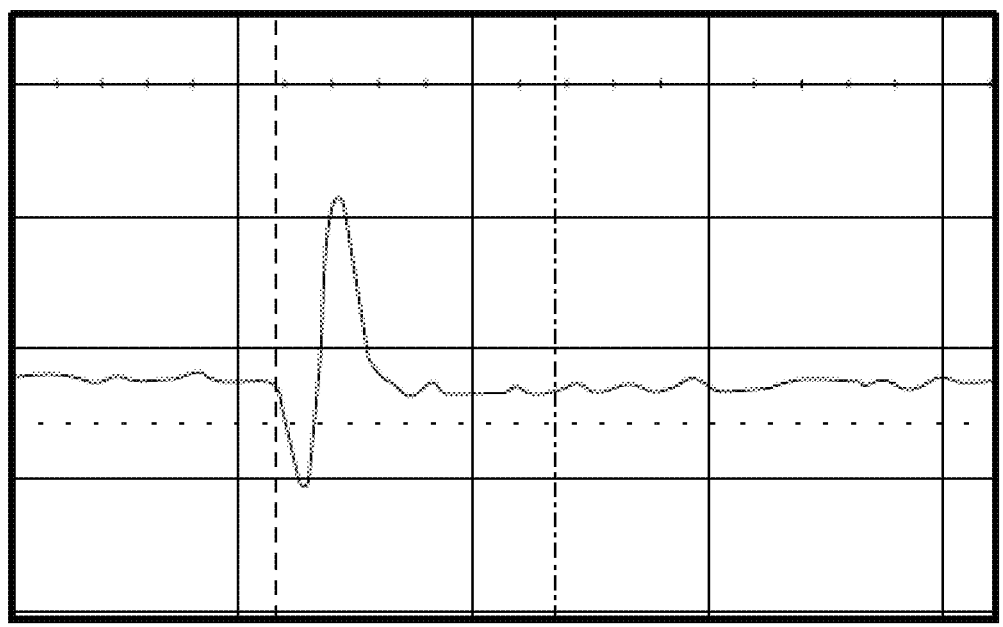
Figure 23C:
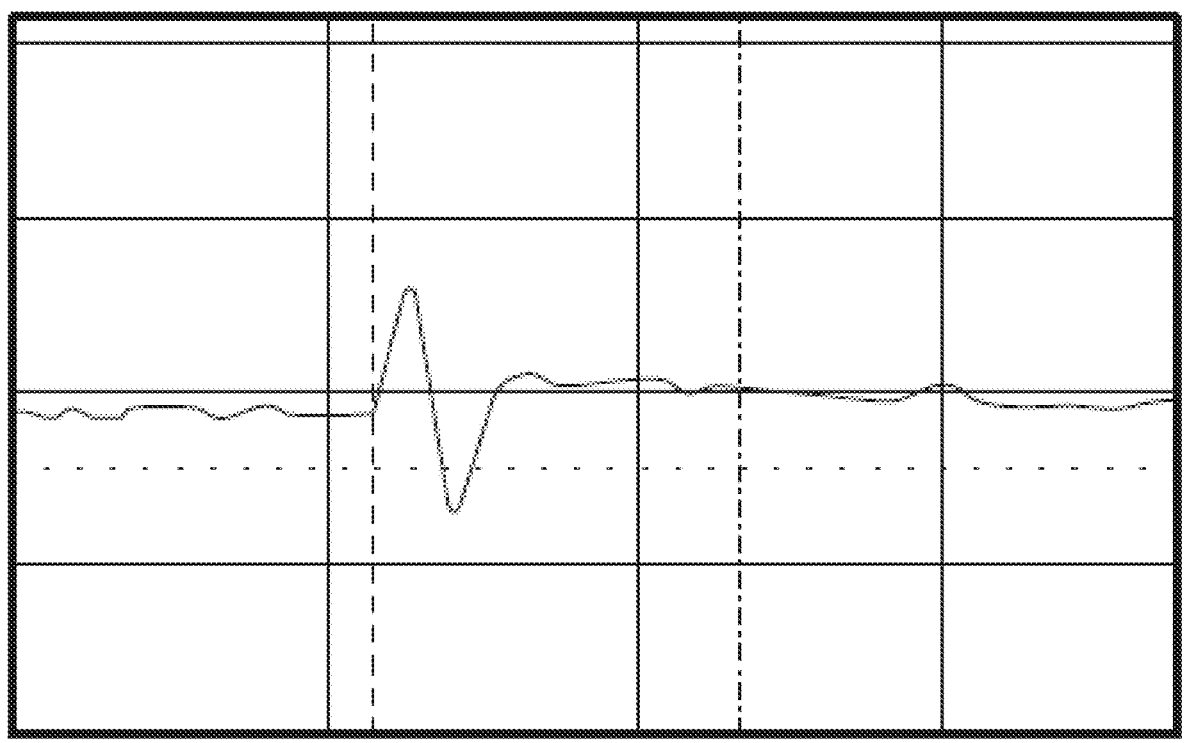

For the signals in FIGS. 23A-23C, the laser pulse had an energy level of about 11 uJ (lower than the energy level of the pump beam that produced the signal in FIG. 24A). Accordingly, the transient vapor nanobubble generated had a relatively small lifetime and/or size. In FIG. 23A, the transient vapor nanobubble was generated in the center of the probe beam. In FIG. 23B, the probe beam was shifted laterally in a first direction by 25% of its diameter (the shift was about 4 um to about 5 um). In FIG. 23C, the probe beam was shifted laterally in a second direction that is opposite the first direction by 25% of its diameter (the shift was about 4 um to about 5 um). Relatively, the transient vapor nanobubbles were shifted laterally by 25% on each side of the center of the probe beam to produce the signals shown in FIGS. 23B and 23C. The shift in the lateral position of a transient vapor nanobubble can significantly influence the shape and/or amplitude of transient vapor nanobubble signal, as shown in FIGS. 23A-23C. For example, a shift by 25% of the probe beam aperture resulted in a bipolar signal in FIGS. 23B and 23C, which are not typical for transient vapor nanobubble-specific signals. As described above, the nanobubbles typically produce a dip-shaped or arch-shaped signal when the transient vapor nanobubble was in the center of the probe beam.

For the signal in FIG. 24A, the laser pulse had an energy level of about 17 uJ (higher than the energy level of the pump beam that produced the signals in FIGS. 23A-23C) and a wavelength of about 532 nm. The pump laser pulse was also tightly focused. Accordingly, the transient vapor nanobubble generated had a relatively larger lifetime and/or size than the nanobubbles generated with the 11-uJ energy level. However, the signal in FIG. 24A shows multiple peaks with an amplitude that is not noticeably greater than those of the signals in FIGS. 23A-23C. Instead of the steady growth of a signal trace for a single transient vapor nanobubble, the signal shows multiple crests and troughs so that instead of showing a single dip-shaped signal with a high amplitude, the resulting signal shows a saw tooth-shaped signal of a lower amplitude. The design or setting of the optical detection system used for producing the signals in the first case limits the signal amplitude and distorts the shape of the signal. Therefore, the optical design or settings of the optical detection path may hinder correct detection of large transient vapor nanobubbles.

As shown in FIGS. 23A-23C and 24A, the signal shape is more likely to show the typical "dip" pattern for a transient vapor nanobubble as shown in FIG. 23A as the maximal diameter of the transient vapor nanobubble decreases and/or as the transient vapor nanobubble is positioned more precisely in the center of the probe beam.

In the second case, one large transient vapor nanobubble or many transient vapor nanobubbles were generated within an aperture of the pump beam that is about 2-3 fold larger than the aperture of the probe beam. The pump laser pulse had a broad pump beam having a diameter of about 30 um to about 40 um. The area of transient vapor nanobubble generation was larger than the aperture of the probe beam. This situation was similar to the Hemozoin-generated transient vapor nanobubble excitation and detection in situ at a patient's skin. The lateral position of the probe beam remained the same in the second case since the pump pulse was delivered through the same optical system as a probe beam. The pump beam was a laser pulse having a wavelength of 671 nm pulse.

FIG. 24B illustrates the signals obtained in the second case. As shown in FIG. 24B, a similar, if not larger, distortion of the transient vapor nanobubble signal as the signal in FIG. 24A was observed for a delocalized generation of transient vapor nanobubbles over the area that is outside the aperture of the probe beam. A saw tooth pattern with the lower or more limited amplitude was observed instead of typical dip-shaped signals for the transient vapor nanobubbles.

Signals observed in FIGS. 23A-C and 24A-B were similar to many signals observed in malaria parasite-positive skin samples (which will be described below). This similarity can be explained by the following. In skin samples with a non-uniform spatial distribution of parasites and a large aperture of the pump beam (which may be at, for example, 50 um or otherwise and about 1.5-2 fold larger than the aperture of the probe beam), the transient vapor nanobubbles are generated, almost always, off the center of the probe beam. There can also be multiple transient vapor nanobubbles of different maximal diameters when exciting the malaria parasites or Hemozoin in the human skin.

The maximum amount of lateral shift of the probe beam may be limited to about 10 um or about 50% of the probe beam aperture before the transient vapor nanobubble signal becomes undetectable. Regardless how much the lateral shift of the probe beam is (within the maximum amount of shift) and/or how much larger the excitation area of the pump beam is, time-shifts of transient vapor signals may not be significant. The maximal time-shifts in the first and second cases disclosed herein did not exceed about 100 ns for the detectable transient vapor nanobubble signals.

The distortion effect of the parasite concentration on the transient vapor nanobubble signal was also studied using malaria-free and malaria-positive skin samples. This experiment used three malaria-positive skin samples, each 1 mm in thickness. The first sample was an intact malaria-negative skin sample. The second and third samples each included parasites in the depth range of between about 230 um to about 500 um under the skin surface. One of the malaria-positive samples, the second sample, included a skin sample with a typical concentration of parasites for a malaria patient. The second one of the malaria-positive samples, the third sample, included a skin sample with residual parasites (that is, parasites were added to an intact skin sample in a very low concentration, such as being 1-2 orders of magnitude lower than the parasite concentration in the second sample). Laser pulses of an energy level of about 15 uJ were applied to all three samples. Four pulses were applied to each location, for 20 different locations in each sample. The probe beam had a diameter of about 120 um at the skin surface or entrance. The probe beam had a focal depth of about 370 um in water. At the laser pulse energy level of about 15 uJ and when coupled with a focused probe beam geometry, relatively larger Hemozoin-generated transient vapor nanobubbles were generated around the malaria parasites in the second and third skin samples.

FIG. 25A illustrates example signals from the intact malaria-free skin sample. Most of the signals collected for the intact (malaria-negative) samples (19 out of 20) showed no NB components. As shown in FIG. 25A, the signals responsive to the first and the fourth laser pulses were similar and did not differ much from the background level.

FIG. 25B illustrates example signals from the sample with a lower or reduced concertation of the malaria parasites. The sample with the lower concentration of the parasites returned some first pulse signals at some locations (but not all) with the typical transient vapor nanobubble signal shape (that is, the dip-shape). The signals quickly decayed to the background level during consecutive laser pulses.

FIGS. 25C and 25D illustrate example signals from the sample with a higher concentration of the malaria parasites. The sample with the higher concentration of the parasites returned most of the first pulse signals which were interpreted as being indicative of a transient vapor nanobubble, although some of the first pulse signals were distorted in the time region of the assumed maximal amplitude. FIG. 25C illustrates a substantially undistorted transient vapor nanobubble signal 2502 with a typical dip shape responsive to the first pump laser pulse. FIG. 25D illustrates a distorted transient vapor nanobubble signal 2504 responsive to the first pump laser pulse. Compared to the hypothetical dip shape for the same transient vapor nanobubble shown by the yellow dash line 2506, the first pulse signal 2504 was distorted in the time region of its highest amplitude such that the highest amplitude is smaller than the hypothetical highest amplitude and the signal 2504 included multiple peaks until the collapse stage of the transient vapor nanobubble. In FIG. 25D, the first 2504 and fourth 2508 pulse signals both showed a residual signal portion that is offset of the baseline. The residual signal portion can be due to possible residual quasi-stationary small residual vapor nanobubbles and/or the thermal effect.

In FIG. 25D, the distorted shape of the transient vapor nanobubble signals was similar to the signals obtained for vapor nanobubbles generated in the gold nanoparticles in water model with a single laterally shifted transient vapor nanobubble (see FIG. 24A). The distorted shape was also similar to the signals obtained for transient vapor nanobubbles generated in the gold nanoparticles in water model to under the excitation with a broad pump beam (see FIG. 24B). However, the distorted shape in FIG. 25D also includes a relative increase (instead of a typical decrease) of the signal amplitude from the first signal 2508 to the fourth signal 2504 for the initial component of the transient vapor nanobubble signal. This example shows that the maximal amplitude of optically-distorted transient vapor nanobubble signal may be misleading and hence other metrics may need to be used to quantify the signal decay, which are described in greater detail below.

To make the signals more representative of the transient vapor nanobubbles and their relative sizes, the optical collection and detection paths can be optimized so that signals of the largest transient vapor nanobubbles have the highest amplitude and do not reverse into signals with low amplitude and/or an irregular shape. The settings of the collection optical path of the system can be modified to widen the dynamic range with the highest sensitivity for the small transient vapor nanobubbles generated in the center of the probe beam. The collection and the scattered light can also optionally be improved in other embodiments to better detect transient vapor nanobubbles generated further from the center of the probe beam and/or to have a higher dynamic range to correctly report any large transient vapor nanobubbles.

Figure 26A:
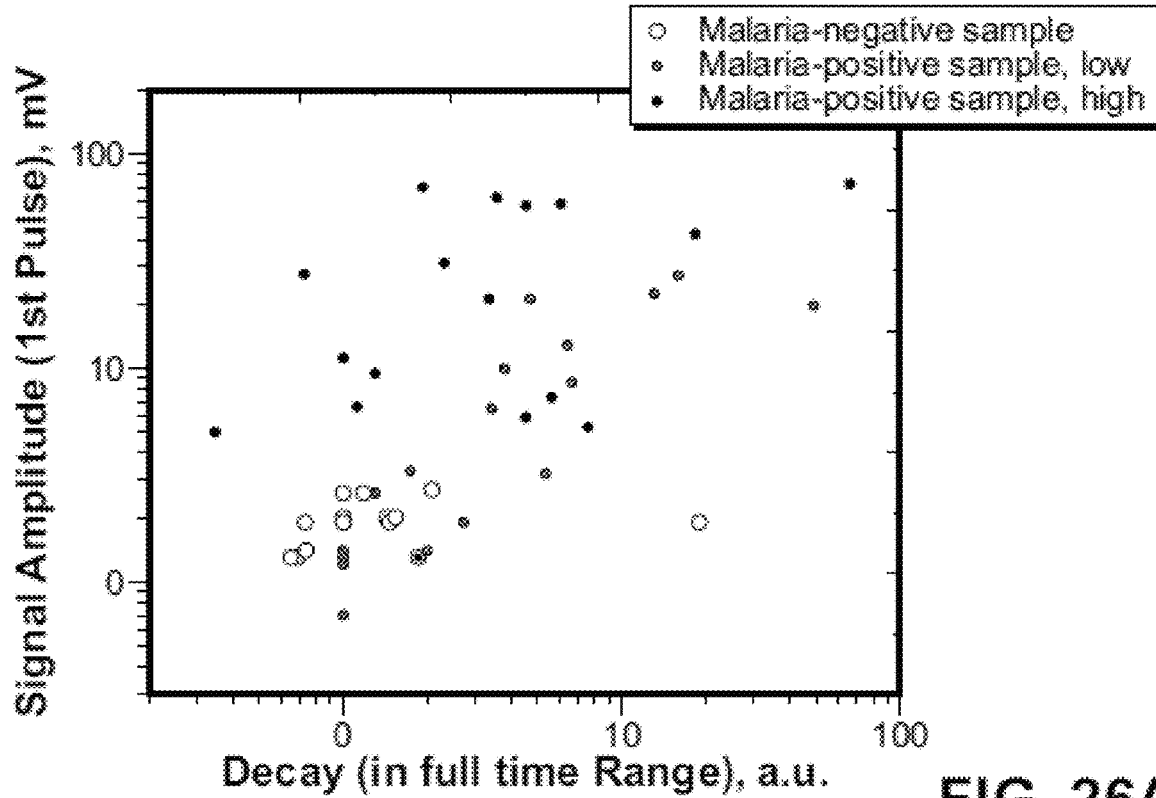
FIGS. 26A and 26B illustrate example A-D (optical signal amplitude-decay) diagrams for the signal amplitude A and the decay D at each individual probing location in malaria-negative and malaria-positive human dark skin samples.
Figure 26B:
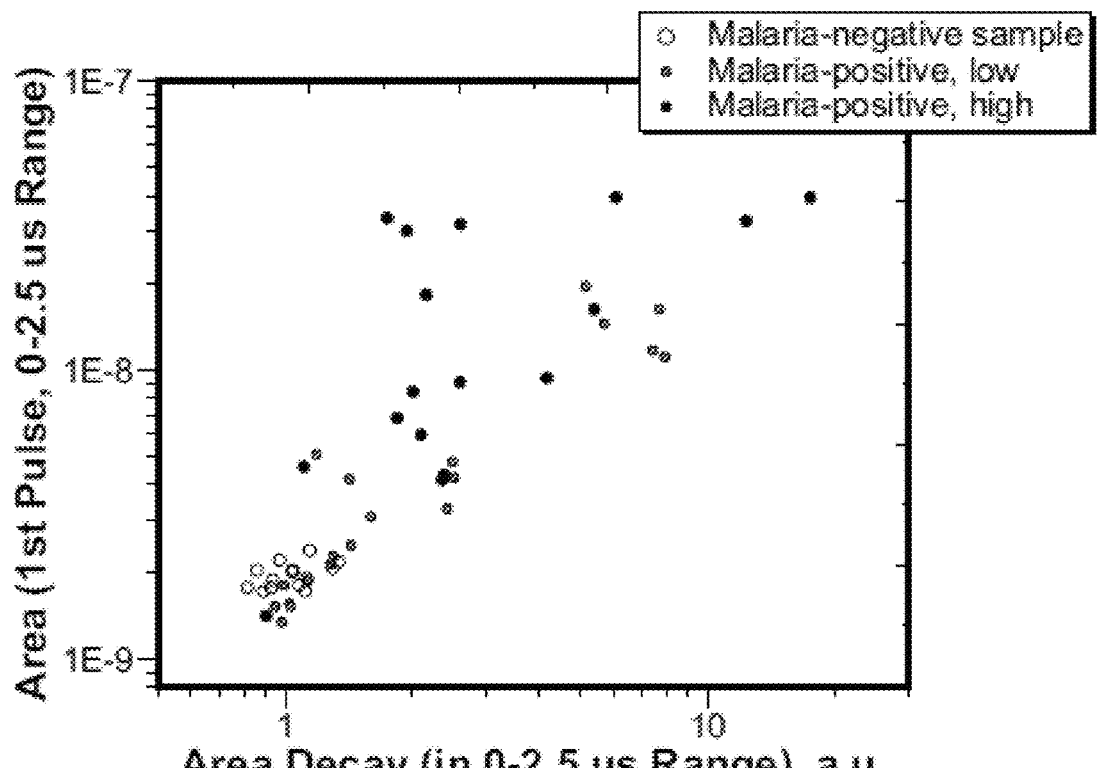

In addition, the A-D diagram described above can be used to further improve the accuracy of the optical detection of the transient vapor nanobubbles. The A-D diagram can be in the form of a signal amplitude-based A and D or a signal area-based A and D. A transient vapor nanobubble optical scattering signal can increase in its amplitude and duration with an increase in the diameter of the transient vapor nanobubble. As a result, the area of the signal (which can be calculated as the amplitude integrated over the duration of the transient vapor nanobubble component of the signal) may be more representative of an indicator than its amplitude in indicating the size and/or lifetime of the transient vapor nanobubble, especially when the amplitude may have been compromised (reduced and/or distorted) by suboptimal optical collection of the nanobubble-scattered light. FIG. 26A illustrates the A-D diagram for the three skin samples described above by calculating the signal amplitudes. FIG. 26B illustrates the A-D diagram for the three skin samples by calculating the signal areas. The data in FIG. 26B included the noise and/or background level. By comparing the distribution of data points in FIGS. 26A and 26B, it can be observed that data points for the same type of skin sample appear to be more clustered in FIG. 26B than in FIG. 26A.

Figure 27A:
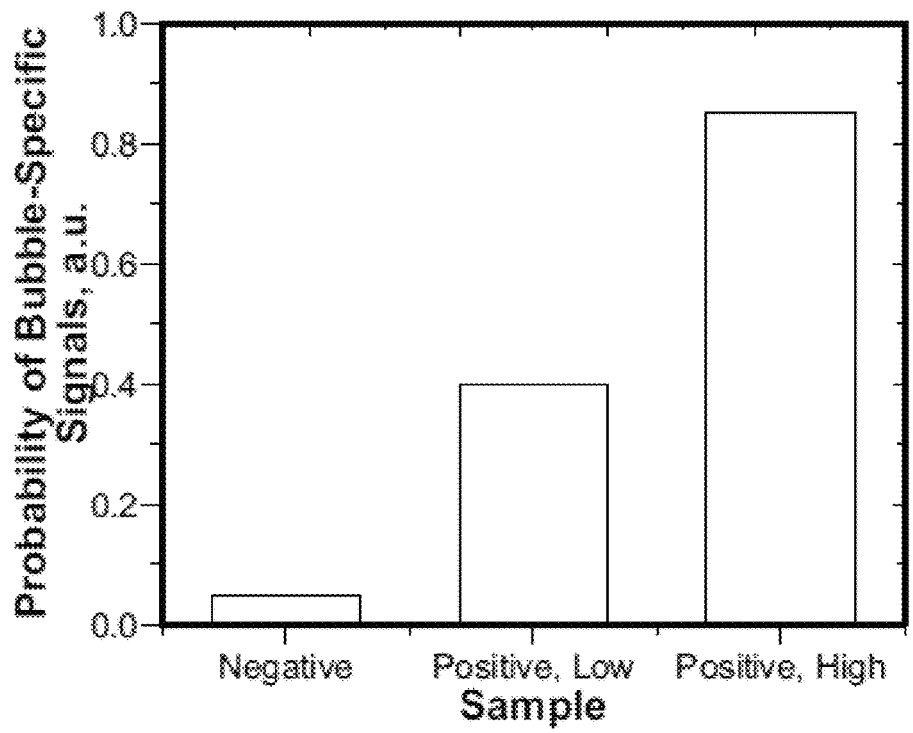
FIGS. 27A-27C illustrate example sample-averaged signal metrics for malaria-negative and malaria-positive skin samples.
Figure 27B:
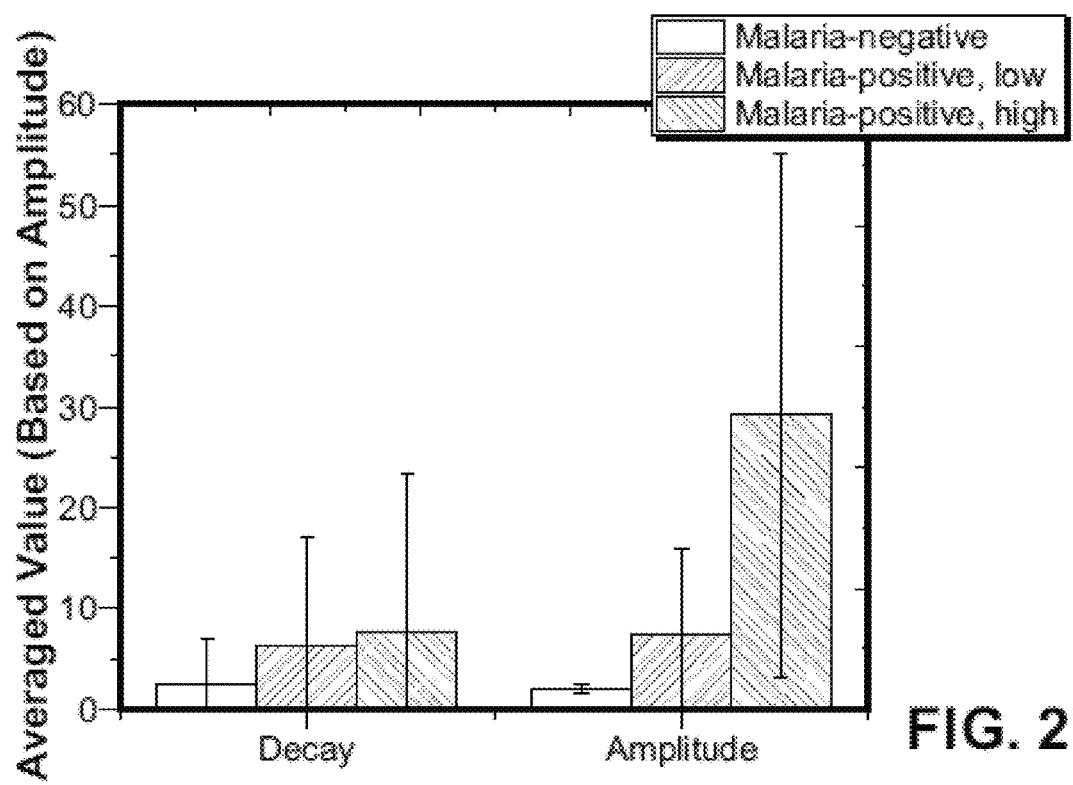
Figure 27C:
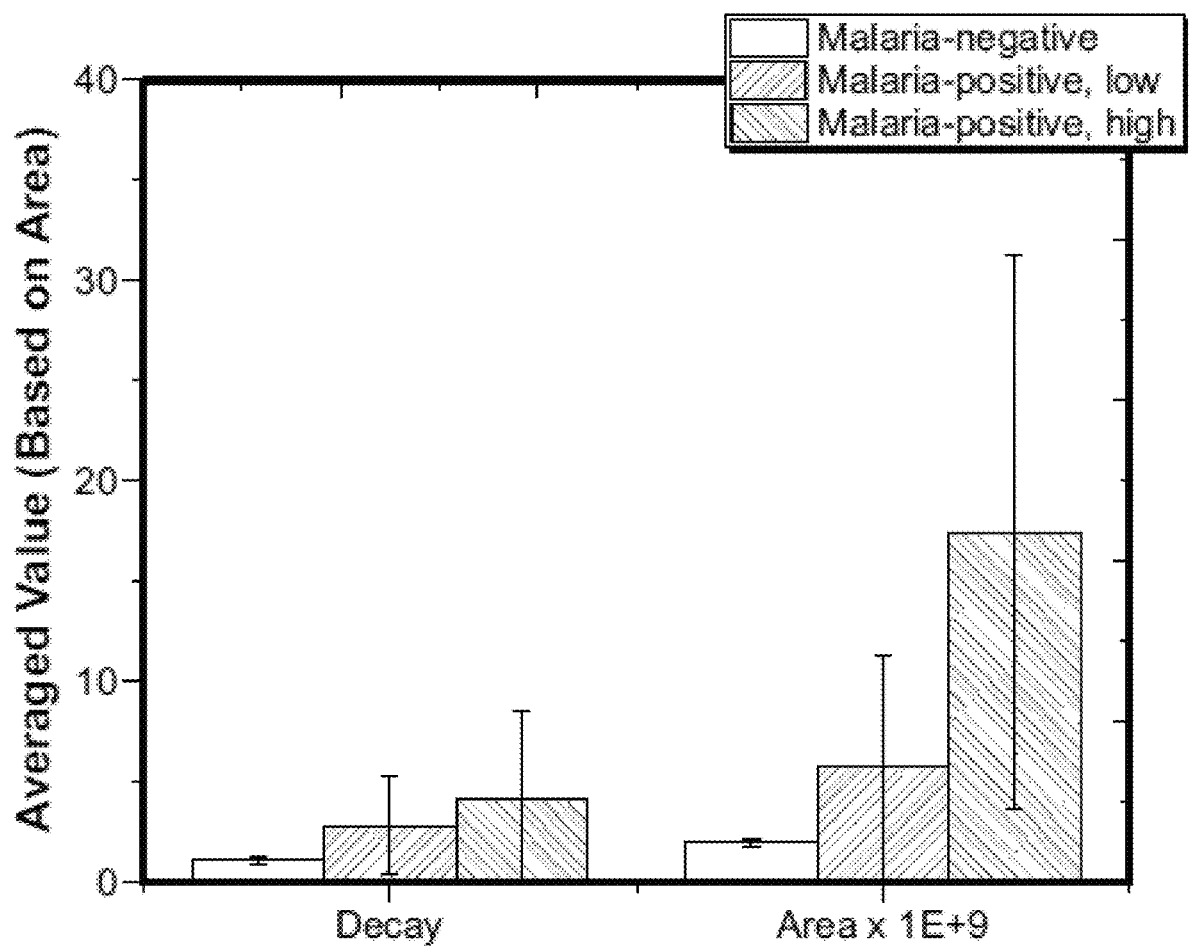

The sample-averaged metrics, including the transient vapor nanobubble probability P, the signal amplitude or area A, and the signal decay value D were also obtained and compared for the amplitude- and area-based methods, as shown in FIGS. 27A-27C. The metrics P and A require collecting only one signal per location, while the decay metrics requires collecting four pulses per location. FIG. 27A illustrates the probability P of the malaria-positive signal for the three skin samples described above (that is, malaria negative skin sample, malaria positive skin sample with low concentration of the malaria parasites, and malaria positive skin sample with higher (or normal) concentration of the malaria parasites). FIG. 27B illustrates the A-D diagram based on the nanobubble signal amplitudes. FIG. 27C illustrates the A-D diagram based on the nanobubble signal area.

As shown in FIGS. 27A-27C, the intact malaria-negative sample served as the control. The malaria-positive samples with lower and higher concentrations were the test samples. Most of the A and D metrics were statistically significantly different for three samples studied, and the differences are summarized below in Table 11. All three sample-averaged metrics, P, A, and D seem to indicate a difference, up to one order of magnitude, between malaria-negative and malaria-positive samples. Further, these metrics also showed a difference between the lower and higher concentrations of the malaria parasites in the skin samples. The test sample with a higher concentration of the malaria parasites had higher amplitude and/or area, and higher decay value, than the test sample with a lower concentration of the malaria parasites. A skilled artisan can appreciate based on the present disclosure that alternative parameters can be used in additional embodiments.

TABLE 11

| | Metric | Amplitude/Area | Decay |
|---|---|---|---|
| Amplitude | Negative/Positive high | + | − |
| | Negative/Positive low | + | − |
| | Positive high/Positive low | + | − |
| Area | Negative/Positive high | + | + |
| | Negative/Positive low | + | + |
| | Positive high/Positive low | + | − |

Figure 28A:
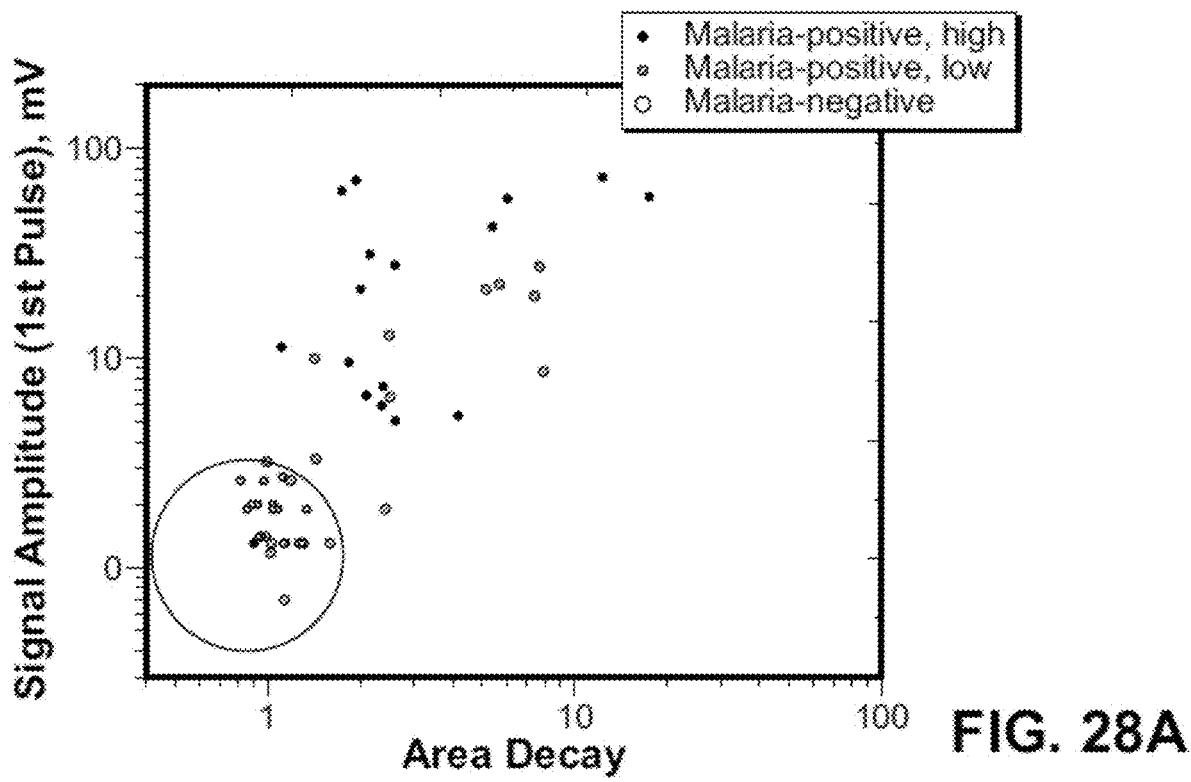
FIG. 28A illustrates the A-D diagram of FIG. 26A after background noise reduction, with a circle showing a possible diagnostic threshold for malaria-positive signals being outside of that threshold.

As shown in Table 11 and FIG. 28A, the area-based A-D diagram can be better at separating the malaria-negative and malaria-positive signals. FIG. 28A shows the area-based A-D diagram for individual locations probed in the three samples, with a circle showing a possible threshold for malaria-positive signals.

As suggested by FIGS. 27A-27C, the way the area is calculated can be further improved. This is because the calculation of the signal area in FIGS. 27A-27C and Table 11 still included the background level. The background component can be quite significant and contribute significantly to the metrics values of small signals, mainly associated with malaria-negative samples. Therefore, the presence of noise or background level can result in elevated values for the malaria-negative sample and in decreased values for the decay metric.

In some embodiments, the area calculation algorithm can use the following steps to remove the background component. The processor or controller coupled to or in communication with the photodetector can determine the baseline level by calculating the average of the part of the signal with negative time (that is, pre-trigger signal). The processor or controller can apply the baseline and the threshold (such as determined by the circle in FIG. 28A) to determine a background range with a higher end as the "baseline level plus threshold" and a lower end as "baseline level minus threshold." The processor or controller can apply the time window as the start time and the stop time, and can calculate the signal area that is inside the time window but outside the background range. As the result, the processor or controller can calculate a corrected signal area value for each raw signal.

Figure 28B:
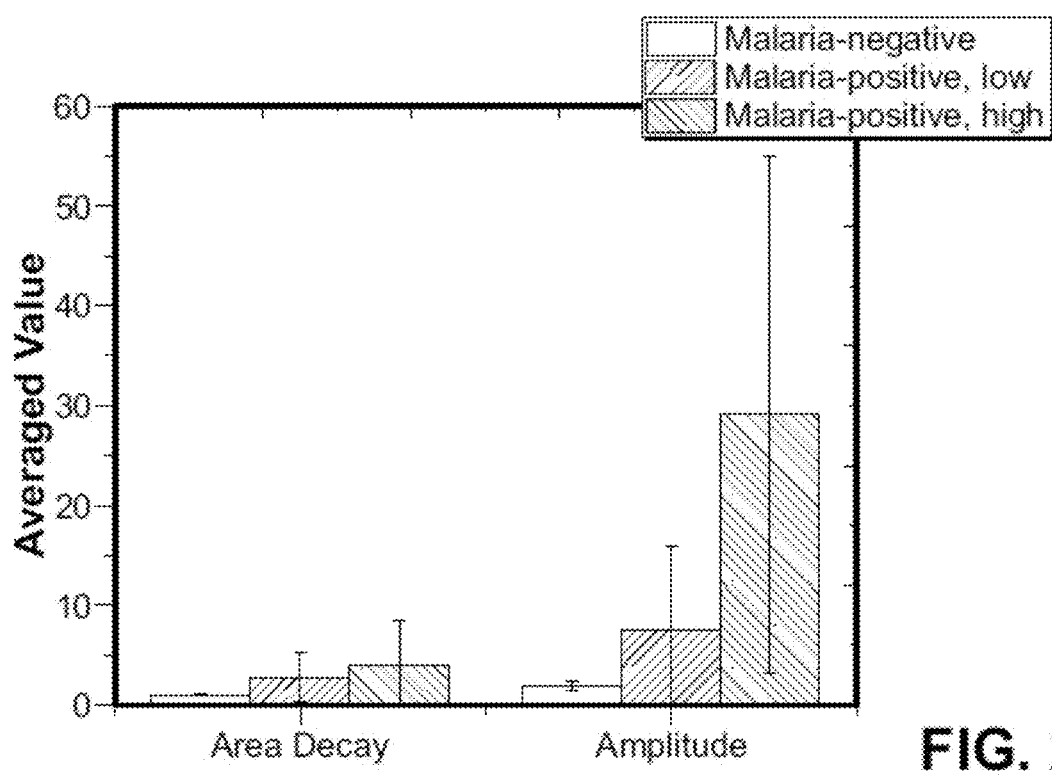
FIG. 28B illustrates example sample averaged signal metrics after background noise reduction.

FIG. 28B illustrates the sample-averaged signal metrics, the amplitude A, and the decay D after removing the noise or background component from the signal. The diagnosis can be further improved after the area is calculated without the noise or background component. As shown in FIG. 28B, removing the noise or background component can significantly decrease the area of malaria-negative signals.

In some embodiments, sample metrics, HI and N (as described in U.S. application Ser. No. 16/213,923), can be applied for the statistical description of P (as N), A amplitude, and A area, in which the metric HI can be the amplitude thresholds, and the decay can be the modified HI. The use of HI and N can result in up to about three or five (if amplitude and area both are analyzed) metrics per sample. Data for malaria-negative samples can be used to determine the diagnostic thresholds for each of these metrics.

Example Optical Detection Systems with Optical Fibers

In some embodiments, instead of a system of free-space optics, such as the lenses described above, an optical malaria detection system can include two optical fibers to deliver the probe laser beam to a transient vapor nanobubble (Hemozoin-generated transient vapor nanobubble in the case of the malaria detection), and to collect the light scattered by the nanobubble. An example system is illustrated schematically in FIG. 29A. The system can be used to detect transient vapor nanobubbles in skin and/or in liquid. All light sources and detectors and other equipment can be installed in a core unit and can be connected to the optical fibers via standard optical fiber connectors.

Figure 29A:
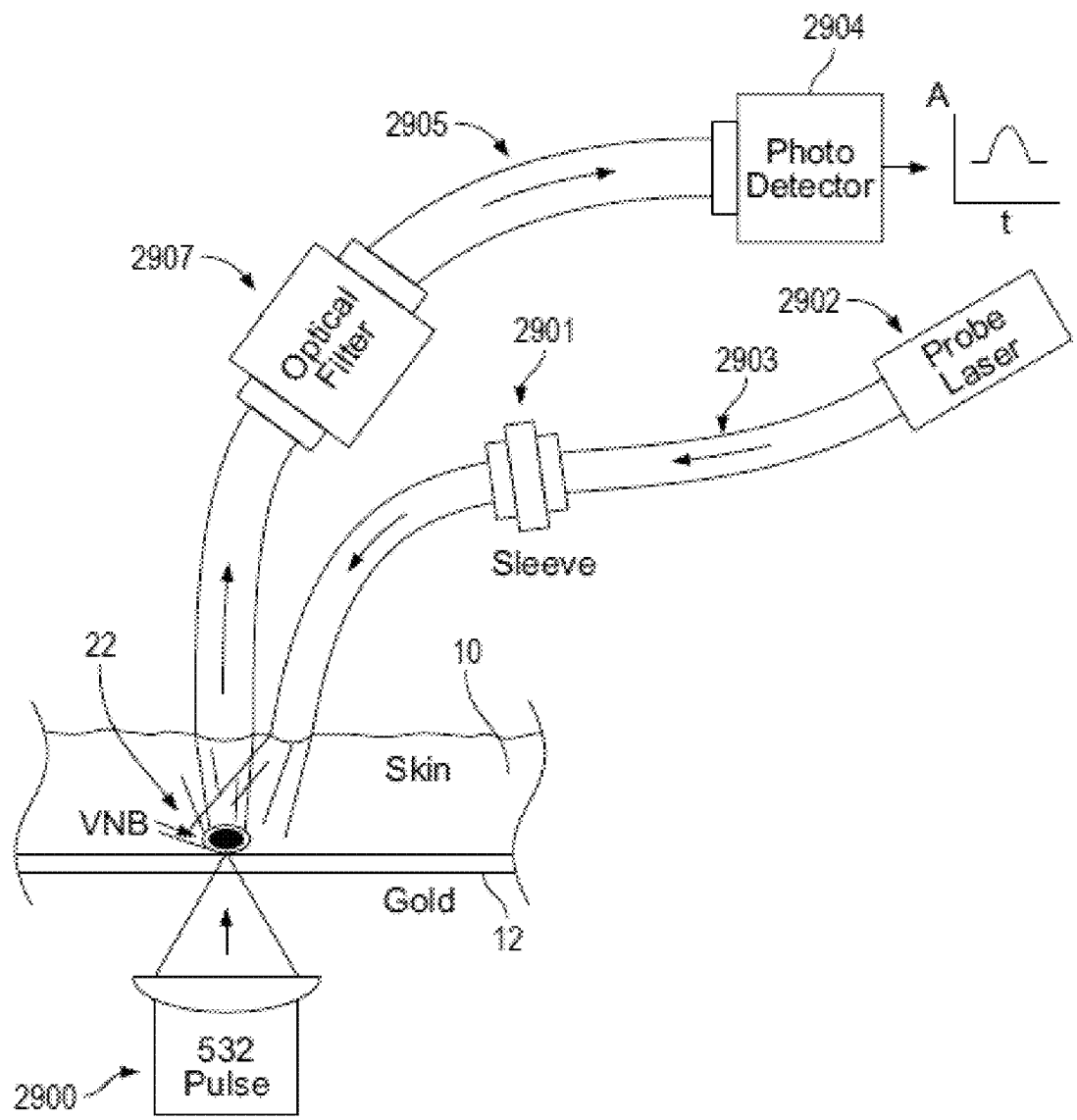
FIG. 29A illustrates schematically an optical detection experimental setup with two optical fibers.

As shown in FIG. 29A, the probe laser 2902 can be coupled to a first optical fiber (such as a single-mode fiber) 2903. The photodetector 2904 can be coupled to a second optical fiber (such as a multi-mode fiber) 2905. The second optical fiber 2905 can optionally include an optical filter 2907, similar the filter block F shown in FIG. 3A. The fiber tips of the first and second optical fibers 2903, 2905 can be directed to a surface of a skin sample 10 from above the skin sample 10 (or to a top surface of a liquid sample, for example, a liquid flowing through a micro-fluidic device or a liquid absorbed by a static filter). The skin sample can have a thickness of about 260 um.

The skin sample 10 can be placed on top of a gold nanoparticle film 12. The gold nanoparticle film 12 can be deposited on a microscope slide glass. The gold nanoparticle film 12 can be covered with the skin sample 10 as shown in FIG. 29A. The gold nanoparticle film 12 can alternatively be without the skin sample 10 or be covered with a drop of water. The pump laser pulse 2900 (such as having a wavelength of 532 nm and/or having a pulse duration of about 150 ps) can be directed to the gold nanoparticle film 12 from underneath the film 12.

The pump laser pulse 2900 can also be delivered by an optical fiber, such as a lensed optical fiber. The pump laser pulse 2900 can generate transient vapor nanobubbles 20 in gold nano-film. The skin-gold model can simulate the malaria parasites and/or Hemozoin in the skin tissue of a patient and the transient vapor nanobubble 20 can simulate the Hemozoin-generated transient vapor nanobubble. The transient vapor nanobubble 20 can scatter the probe beam delivered via the first optical fiber 2903. The scattered probe light can travel along the second optical fiber 2905 and be detected by the photodetector 2904.

Figure 29B:
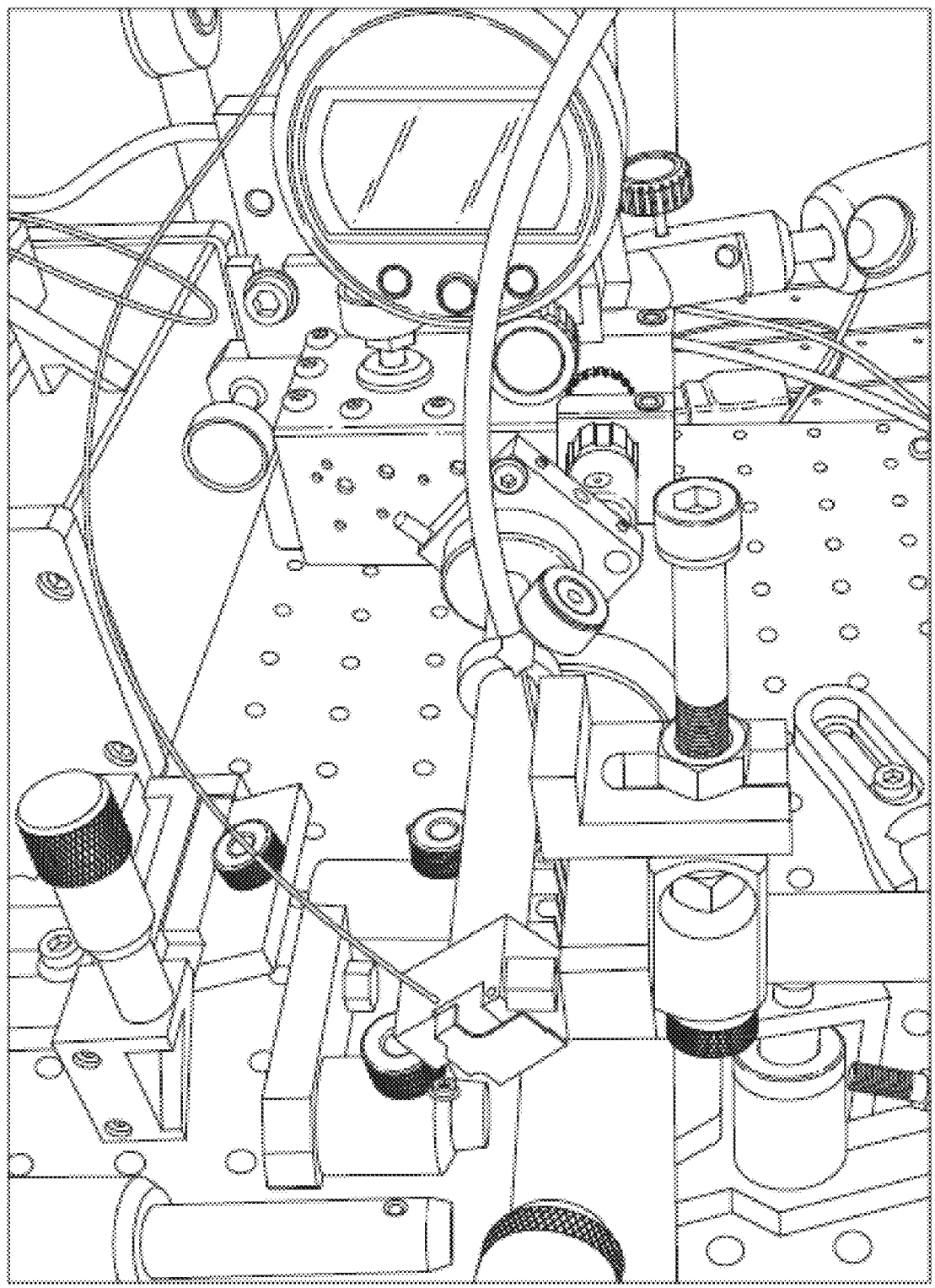
FIG. 29B illustrates an example experimental setup of FIG. 29A.

FIG. 29B illustrates an experimental prototype of the fiber optical detection system of FIG. 29A. The probe beam can include distributed feedback (DFB) laser diodes configured for continuous wave (c.w.) operation. The probe beam can have a wavelength of 785 nm. The probe beam can have a power level of 28 mW. The low-noise DFB feature can be active.

The first optical fiber, also known as the delivery fiber, can be a single-mode optical fiber. The delivery fiber can have a core diameter of about 5 um. The delivery fiber can have an outer diameter of about 125 um. The delivery fiber can have a numerical aperture of about 0.13. In some embodiments, the first optical fiber can be a pigtailed single mode fiber. In some embodiments, the delivery fiber can have a standard tip. In some embodiments, the delivery fiber can have a lensed tip. The delivery fiber can have a length of about 1 m. The delivery fiber can be coupled to the probe beam laser via a connecting sleeve (such as the sleeve 2901 shown in FIG. 29A), which can be a standard connecting sleeve or otherwise.

The delivery fiber can be secured by a fiber holder with micro-positioning screws. The screws can allow adjustment of angles and positions in the X, Y, and Z directions. A micrometer indicator can be included to indicate the height of the fiber holder.

The photodetector can be connected to the second optical fiber, which can be a multi-mode fiber. The second optical fiber is also known as the collecting fiber. The collecting fiber can include a fiber optical filter (similar to the filter 2907 in FIG. 29A). The collecting fiber can have a core diameter of about 200 um. The outer diameter of the collecting fiber can be about 220 um. The length of the collecting fiber can be about 1 m. The collecting fiber can have a numerical aperture of about 0.5. The collecting fiber can have a step index profile. The collecting fiber can also be secured by a fiber holder with micro-positioning screws. The screws can allow adjustment of angles and positions in the X, Y, and Z directions.

Figure 29D:
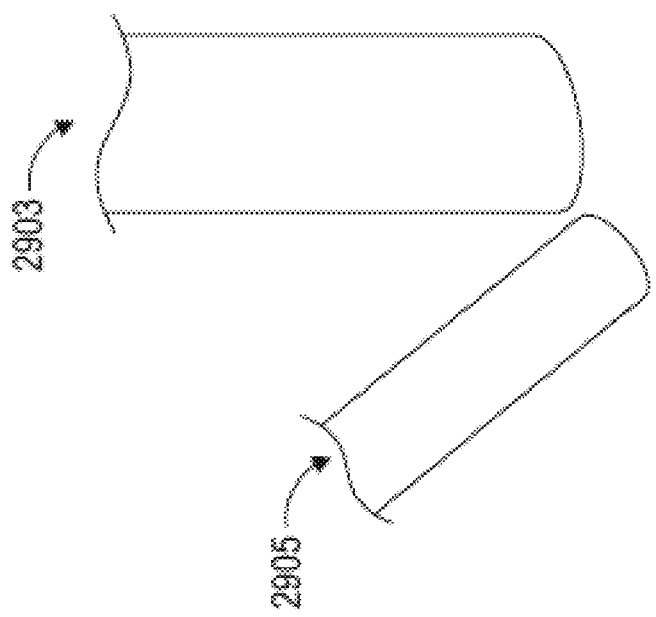
FIG. 29D illustrates an example configuration of the fiber tips of the delivery and collecting optical fibers.
Figure 29C:
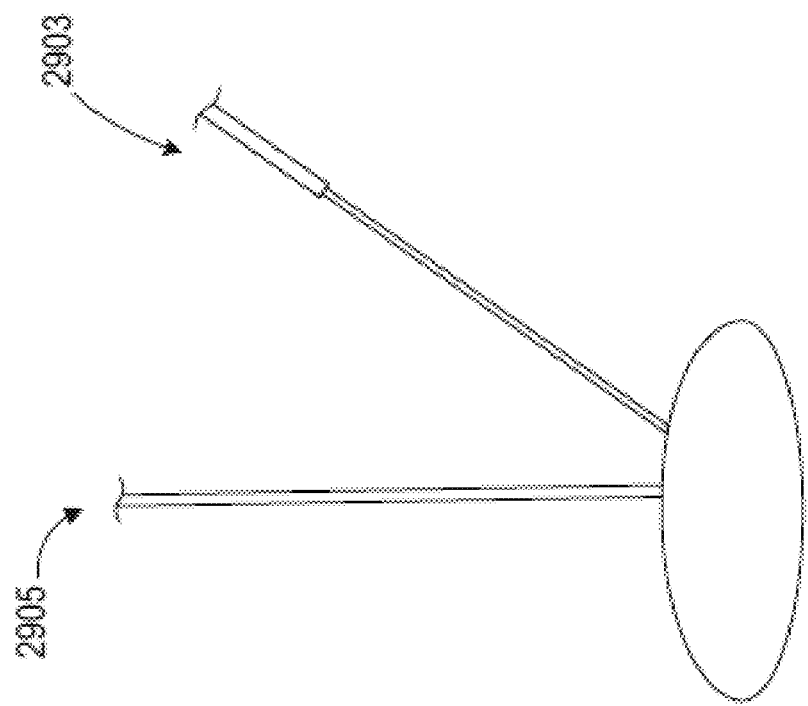
FIG. 29C illustrates an example configuration of delivery and collecting optical fibers in an optical detection system.

As shown in FIG. 29C, the probe beam is delivered via the delivery fiber 2903, which can be applied to the test sample, such as a drop of water in FIG. 29C or a skin sample, at an angle. In some embodiments, the angle can be between about 30 degree to about 45 degree, or about 38 degree. The scattered probe light can be picked up or collected by the collecting fiber 2905, which can be applied to the skin substantially vertically, that is, at the angle of about zero to a top surface of the test sample.

FIG. 29D illustrates the fiber tips of the delivery fiber 2903 and the collecting fiber 2905 in the testing sample, such as in the water or skin sample. The configuration of the fiber tips can use a predetermined mutual location of the fiber tips at a predetermined angle, which can improve the signal output amplitude. The geometrical position of the fibers showed their extrapolated intersection at the distance of about 243 nm to about 244 nm from the tip of each fiber and at the angle of about 37 degree. This location of intersection can be in line with the skin thickness of about 230 um and the signals detected could be the maximal when the delivery and collection fibers are brought close and pointed at the source of the transient vapor nanobubble.

Figure 30A:
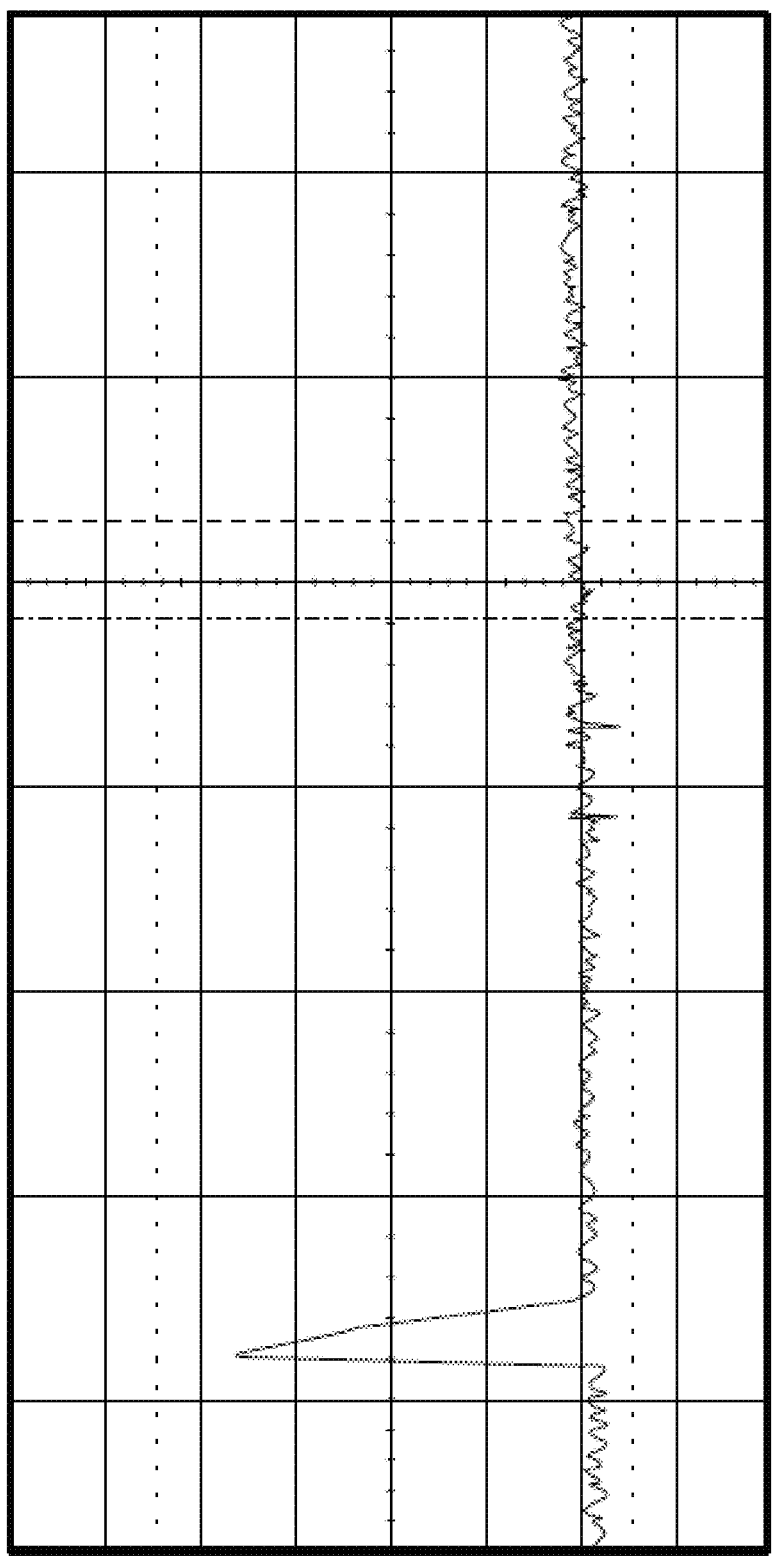
FIG. 30A illustrates an example photodetector output signal from water using the experimental setup of FIG. 29B during the generation of a 140-ns transient vapor nanobubble.
Figure 30B:
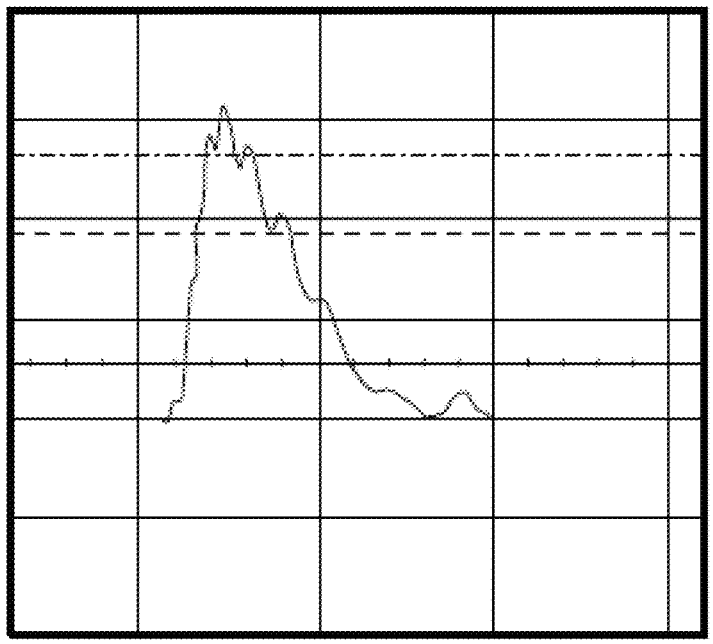
FIG. 30B illustrates an example photodetector output signal from water using the experimental setup of FIG. 29B during the generation of a 500-ns transient vapor nanobubble.
Figure 30C:
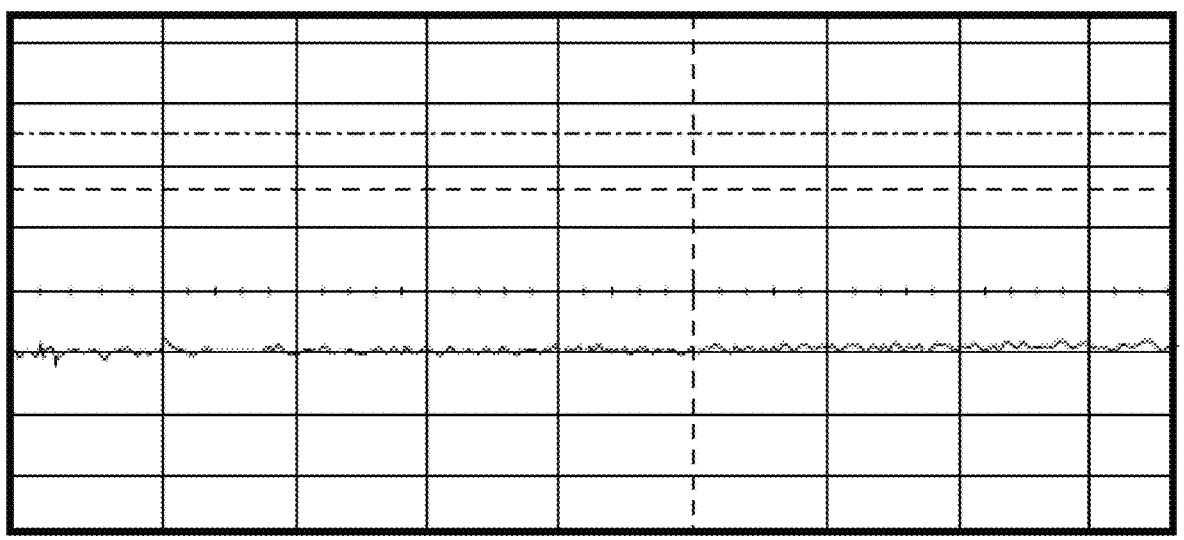
FIG. 30C illustrates an example photodetector output signal from water using the experimental setup of FIG. 29B in the absence of transient vapor nanobubbles.

FIGS. 30A-30C illustrate the signal output from the photodetector when the fiber optical detection system of FIGS. 29B-20D were used on a testing sample including a drop of water on the gold nanoparticle film. FIG. 30A illustrates a signal (1 mV/div, 500 ns/div) from a small transient vapor nanobubble with a lifetime of about 140 ns. The transient vapor nanobubble was detected at the distance of about 260 um from the surface of the test sample with a SNR greater than 10. FIG. 30B illustrates a signal (50 mV/div, 500 ns/div) from a larger transient vapor nanobubble with a lifetime of about 300 ns to about 500 ns. The amplitude of the signal was up to about 200 mV. The signal (2 mV/div, 200 ns/div) in FIG. 30C was obtained with the pump laser turned off and the probe laser turned on. As shown in FIG. 30C, the optical noise or background level in the time window of the transient vapor nanobubble signal was within about 0.4 mV.

Figure 31A:
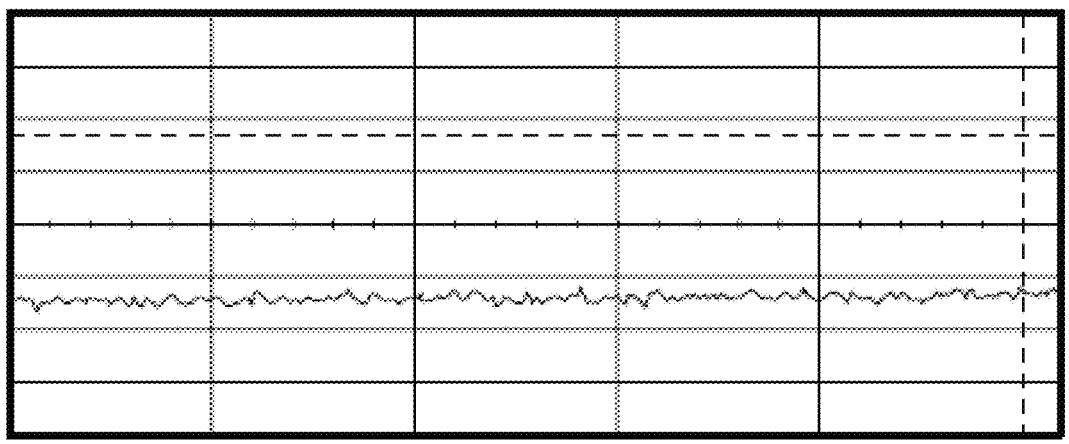
FIG. 31A illustrates an example photodetector output signal from a skin sample using the experimental setup of FIG. 29B in the absence of transient vapor nanobubbles.
Figure 31B:
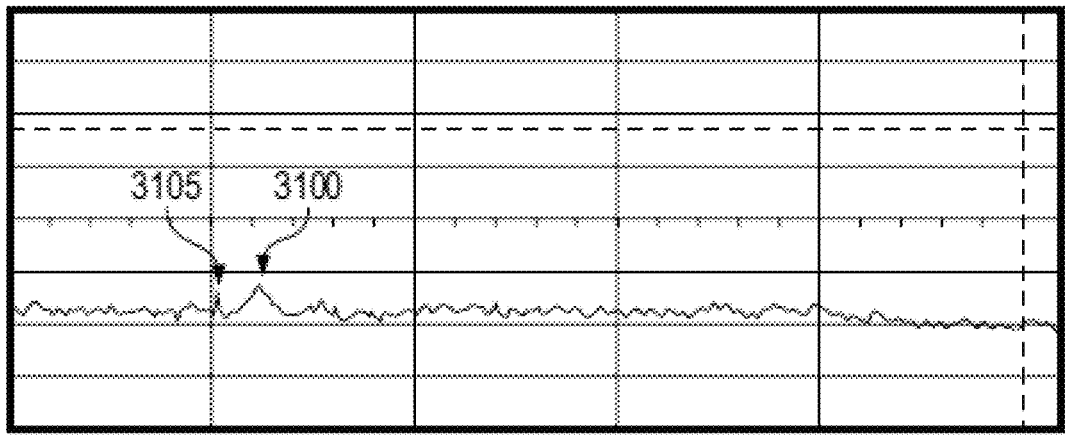
FIG. 31B illustrates an example photodetector output signal from a skin sample using the experimental setup of FIG. 29B during the generation of a 140-ns transient vapor nanobubble.
Figure 31C:
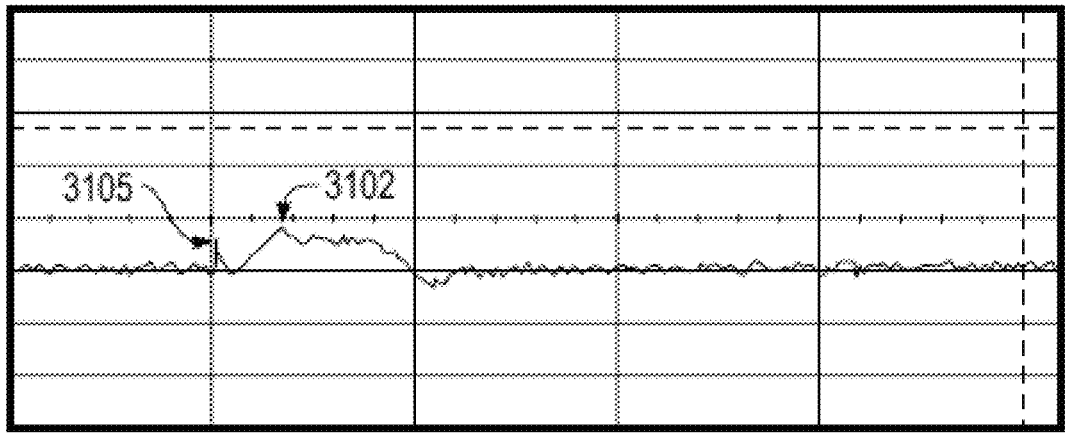
FIG. 31C illustrates an example photodetector output signal from a skin sample using the experimental setup of FIG. 29B during the generation of a 500-ns transient vapor nanobubble.

FIGS. 31A-31C illustrate the signal output from the photodetector when the fiber optical detection system of FIGS. 29B-20D were used on a testing sample including a human skin sample such as shown in FIG. 29A. The skin sample was a piece of dark human skin having a thickness of about 230 um. Gold-generated transient vapor nanobubbles were generated by the pump beam under the skin sample.

As shown in FIG. 31A, a background signal (5 mV/div, 500 ns/div) was obtained with the pump laser turned off and the probe laser turned on. Compared to the background level in water, the optical noise has increased from about 0.4 mV to about 1.5-2.0 mV Transient vapor nanobubbles (for example, having a lifetime between about 100 ns and about 500 ns) can be detected in the dark human skin sample with the optical scattering method with two standard optical fibers that deliver and collect the probe laser beam. As shown in FIGS. 31B and 31C, with the pump pulses applied to the gold nanoparticle film under the skin sample and the probe laser turned on, small (5 mV/div, 500 ns/div) 3100 and larger (5 mV/div, 500 ns/div) 3102 vapor nanobubble signals were observed with a good reproducibility. The small vapor nanobubble signal 3100 had a lifetime of about 140 ns. The larger vapor nanobubble signal 3102 had a lifetime of about 500 ns. The vapor nanobubble signals were observed at specific positions of both optical fibers relative to the skin and the source of the vapor nanobubble, that is, the gold nanoparticles. Unlike in water, the vapor nanobubble signals showed both positive and negative components depending upon the position of the fibers relative to the vapor nanobubble.

As also shown in FIGS. 31B and 31C, a short reproducible signal 3105 before the vapor nanobubble signal 3100, 3102 can be observed. The signal 3105 is indicative of the residual unfiltered pump pulse hitting the photodetector. The signal 3105 does not interfere much with the detection of a vapor nanobubble signal. In addition, the signal 3105 may also be used as an indicator of the pump pulse being applied.

Comparing the signal amplitudes in water (60 mV to 200 mV for a vapor nanobubble having a lifetime of about 300 ns to about 500 ns) and skin (2 mV to 5 mV for a vapor nanobubble having a lifetime of about 100 ns to about 300 ns) under the same energy level of the pump laser pulse, there can be a 40-60 fold decrease of the signal amplitude in the skin sample compared to the water sample. This ratio matches a similar water/skin ratio observed for similar signals described above with the free-space optical detection system.

In the experiment with the dark human skin sample, standard fibers with flat tips can be sufficient to detect a small transient vapor nanobubble (for example, having a lifetime of about 200 nm to about 500 ns) under the skin. In some embodiments, the optical detection system can be further improved to result in an increased sensitivity to the transient vapor nanobubbles. The improved optical detection system can also include bundling of the optical fibers into a single fiber bundle optimized for the delivery and collection of the probe light to and/or from the human skin.

A malaria sensor including an optical detection system may be designed as a combination of two or three bundled optical fibers to deliver the pump pulse and probe light and to collect the scattered probe light. To probe multiple locations, the malaria sensor can be designed as a matrix of multiple bundles united into a single sensor. A single bundle sensor can mechanically scan across the skin to probe multiple close locations of the skin. The pump and probe laser beams can be sequentially launched into each bundle to probe each location sequentially.

In some embodiments, the delivery and collection fibers can be united into a bundle with a common distal tip and separate proximal ends. Each of the proximal ends can be coupled to a FC/PC connector. The common distal tip can provide the delivery of the probe beam (which may have a wavelength of about 785 nm) along the axis of the collection fiber at a depth of 250 um into a test sample. For example, when the common distal tip was inserted into water, the probe beam can be delivered along the axis of the collection fiber at a depth of about 250 as measured from the tip of the bundle into the water. The point at the depth of 250 um is defined as the focal point. The common distal tip can also improve and/or maximize the optical collection of the light scattered at the focal point. The collection fiber can have a numerical aperture such as 0.5 or higher. A skilled artisan can appreciate based on the present disclosure that alternative parameters can be used in additional embodiments.

The delivery fiber of the probe beam may be a single-mode fiber. The output beam from the delivery fiber, that is, the probe beam, can have the aperture 20 um or less (which the single-mode fiber is suitable for). The surface of the tip of the fiber bundle can be angled in the way so as to direct the probe beam to the focal point. This corresponds to angles of between about 30 degree and about 50 degrees. The angle can depend upon the outer diameters of the delivery and/or collection fibers. The distal tip surface of the fiber bundle can be smooth and without any sharp parts.

FIGS. 32A-36 illustrate various examples of a fiber bundle. In some embodiments, the delivery and collection fibers can be bonded by epoxy or otherwise. The delivery fiber can be a single-mode fiber (for example, having a core diameter of about 50 um). The collection fiber can be a multi-mode fiber (for example, having a core diameter of about 200 um). The collection fiber can have an outer diameter of about 220 um.

FIGS. 32A and 32B illustrate the delivery 3203 and collection 3205 fibers being applied substantially vertically to a top surface of the test sample. The fiber bundle can have front output and front input. As shown in the distal end views of the fiber bundle, the delivery 3203 and collection 3205 fibers can run parallel to each other. The fiber bundle may be restricted by the refractive index of water to achieve a focal point at about 250 um depth. The fiber bundle in FIGS. 32A and 32B can also have a longer focal distance. As shown in FIG. 32A, the fiber bundle can have a flat distal tip. The collection fiber 3205 can have a straight-edged tip. The delivery fiber 3203 can include a straight-edged tip. The straight-edged tip of the delivery fiber 3203 can be at a slight angle to the straight-edged tip of the collection fiber 3205. As shown in FIG. 32B, the fiber bundle can also optionally include a lensed distal tip. The delivery fiber 3203 and the collection fiber 3205 can both include a convex distal tip. The curvature of the convex distal tips of the delivery 3203 and collection 3205 fibers can optionally be continuous. The lensed distal tip can have a greater numerical aperture than the flat distal tip.

Figure 33:
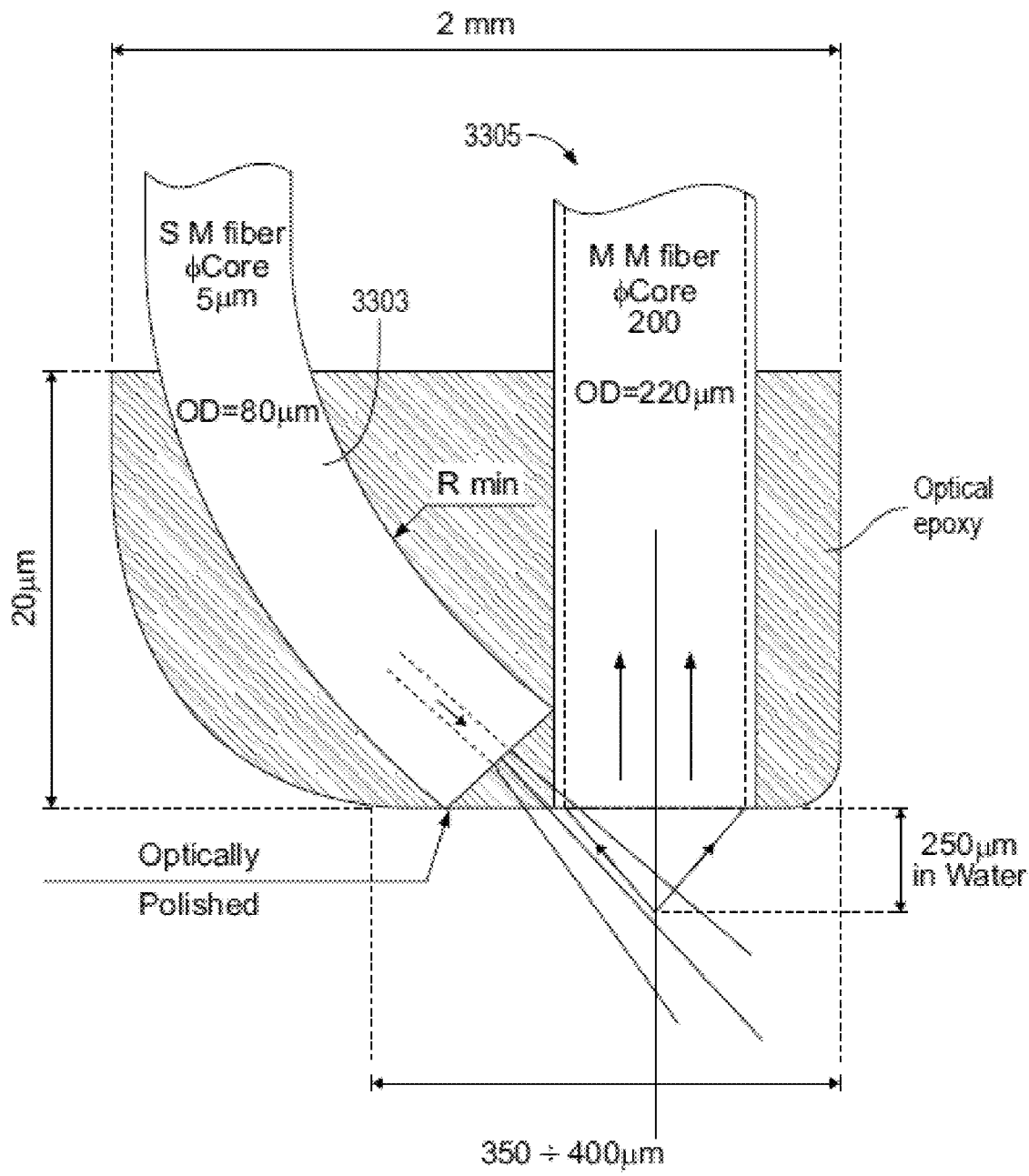

FIG. 33 illustrates a fiber bundle with the collection fiber 3305 being applied substantially vertically to a top surface of the test sample and the delivery fiber 3303 being applied at an angle to the longitudinal axis of the collection fiber 3305. The delivery fiber 3303 can generally run along the collection fiber 3305 and have a turn or a curvature near its distal end so as to form an angle with the longitudinal axis of the collection fiber 3305. In some embodiments, the curved portion of the delivery fiber 3303 has a height of about 20 mm or otherwise. Other configurations can be used for the delivery fiber 3303. The fiber bundle can have front output and front input. The fiber bundle can have a diameter of about 2 mm along a substantial portion of its length prior to the turn or the curved portion of the delivery fiber 3303. The fiber bundle can have a diameter of about 350 um to about 400 um at its distal end. The fiber bundle can have a focal point at a depth of about 250 um. The distal end of the fiber bundle can have a flushed surface. The distal surface of the fiber bundle can be optically polished.

Figure 34:
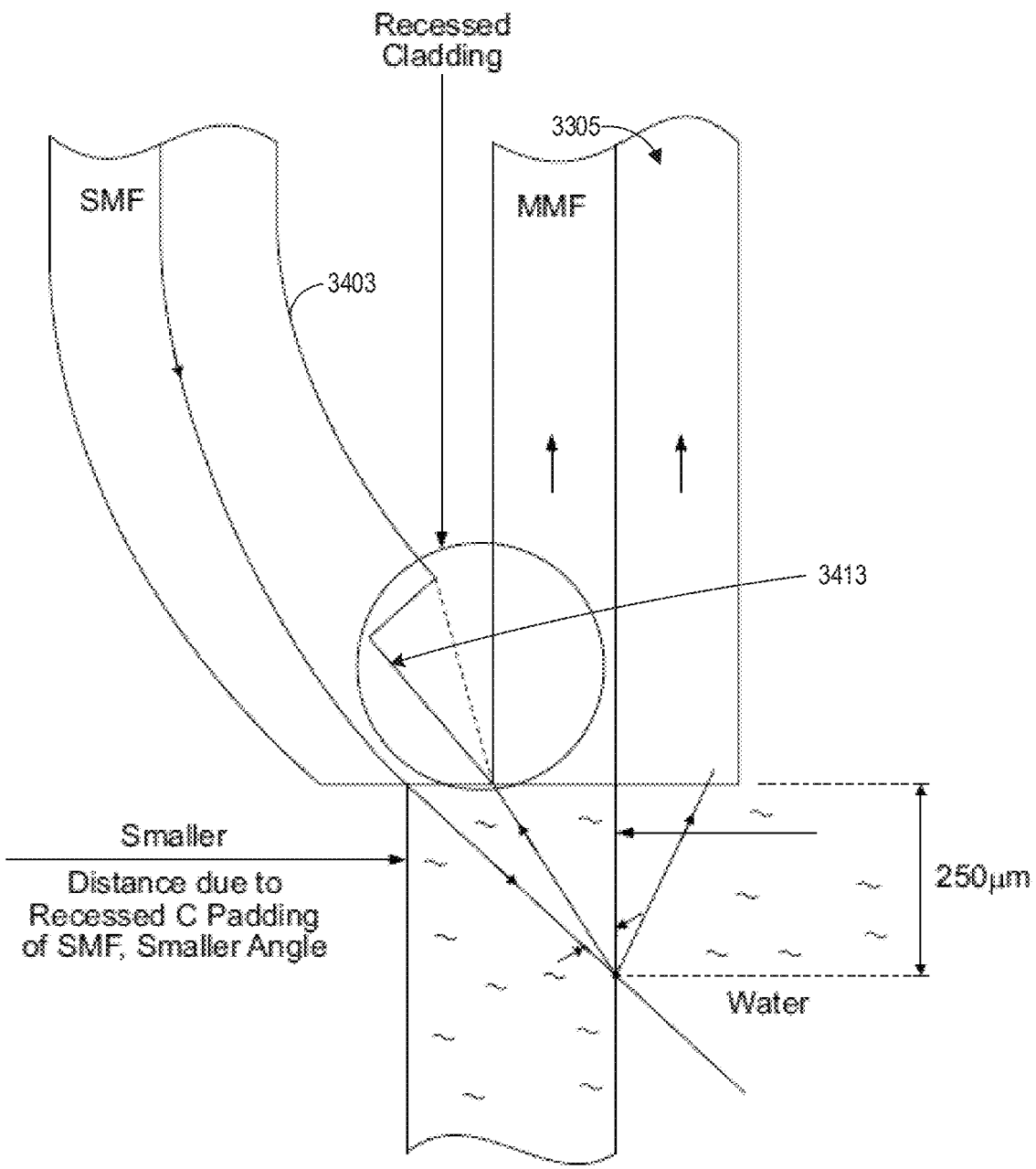

FIG. 34 illustrates a modification of the fiber bundle as shown in FIG. 33. The fiber bundle in FIG. 34 can have any of features of the fiber bundle in FIG. 33. The delivery fiber 3403 can have a distal portion with recessed cladding 3413. The recessed cladding can allow the distal portions of the delivery fiber 3403 and the collection fiber 3305 to be closer to each other. The delivery fiber 3403 can be applied to the test sample at a reduced delivery angle than the fiber bundle in FIG. 33. The smaller delivery angle can reduce the amount of disturbances or noise in the delivery of the probe beam to the test sample.

Figure 35:
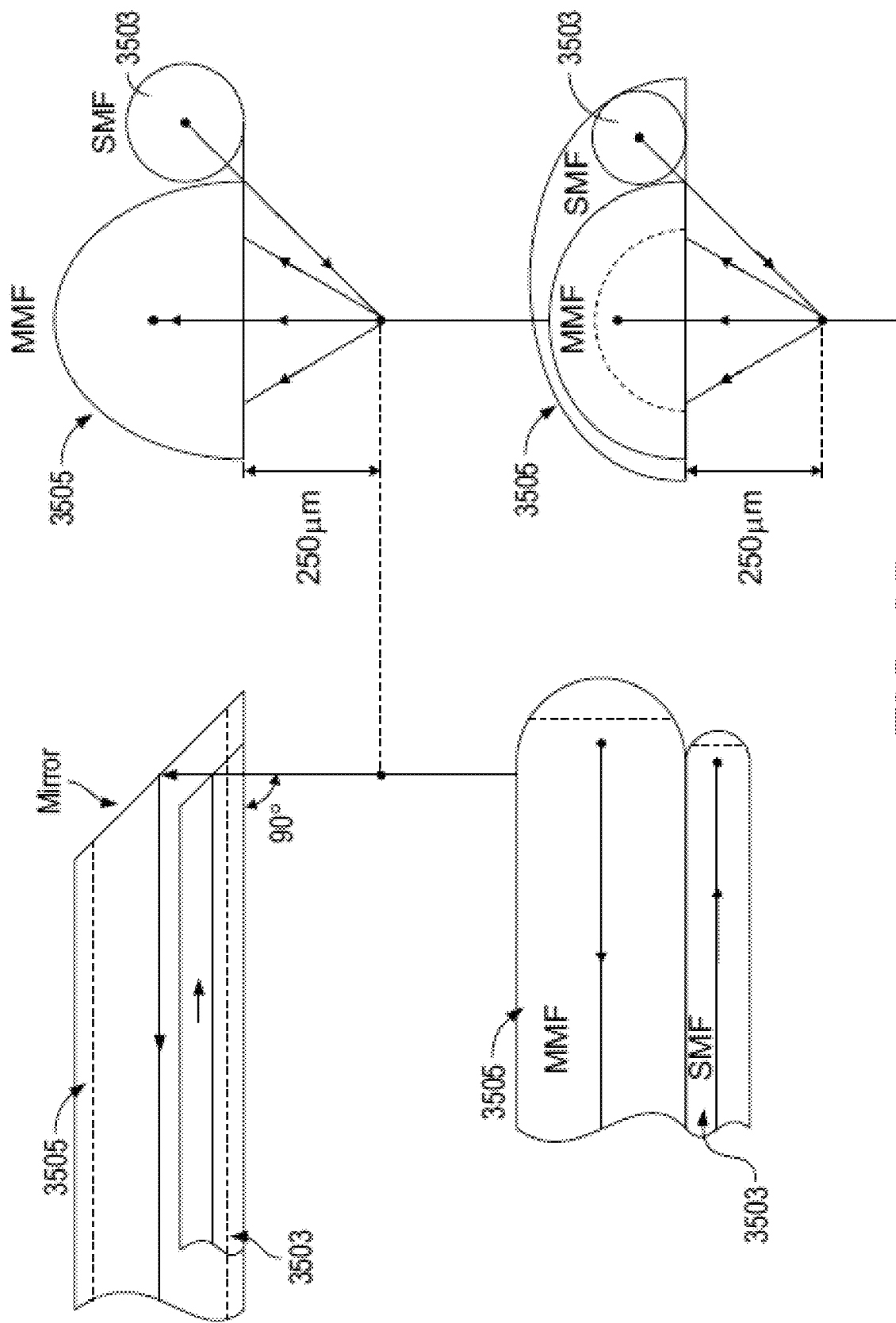
FIGS. 35 (not drawn to scale), 36A-36C, 37, and 38 illustrate schematically example optical detection systems with two horizontal optical fibers.

As shown in FIGS. 35 and 36, the fiber bundle can have side-firing fibers. The delivery fiber 3503, 3603 and the collection fiber 3505, 3605 in the fiber bundles shown in FIGS. 35 and 36 can run horizontally relative to a top surface of a test sample. The fiber bundle can have side output and side input. At the distal end, light traveling in the delivery fiber 3503, 3603 can be deflected or reflected by the distal surface (which can include a mirror) of the delivery fiber toward the test sample. Light scattered by the test sample (such as by tissue and/or transient vapor nanobubbles) can enter the collection fiber 3505, 3605 sideways and be deflected or reflected (also by a mirror) to travel along a longitudinal axis of the collection fiber 3505, 3605. The delivery fiber 3503, 3603 and the collection fiber 3505, 3605 can be aligned side by side and bundled so as to provide the focal point at a depth of about 250 um. The delivery fiber 3503, 3603 and the collection fiber 3505, 3605 can be aligned so that the delivery fiber 3503, 3603 points or reflects the light to coincide with the axis of light entering sideways into the collecting fiber 3505, 3605.

As shown in the distal end views in FIGS. 35 and 36, the bottom surface of the fiber bundle around the optical output input/output is flushed flat. The collection fiber 3505, 3605 can have a flat surface parallel to the flat surface of the bundle. The delivery fiber 3503, 3603 can have a flat surface that is at a slight angle to the flat surface of the bundle. In some embodiments, optical epoxy or other material can be used to bond the delivery and collection fibers and/or to achieve the flat surface.

The collection fiber 3505, 3605 can have a high numerical aperture (such as 0.5 or more). As shown in the top drawings of FIG. 35, the delivery fiber 3503 and/or the collection fiber 3505 can have a generally flat or straight-edged distal surface to deflect or reflect light. As shown in the bottom drawings of FIG. 35, the delivery fiber 3503 and/or the collection fiber 3505 can have a rounded, convex, or spherical distal surface to deflect or reflect light. The fibers with a convex distal surface can have a greater numerical aperture than the fibers with a generally flat distal surface.

Figure 37:
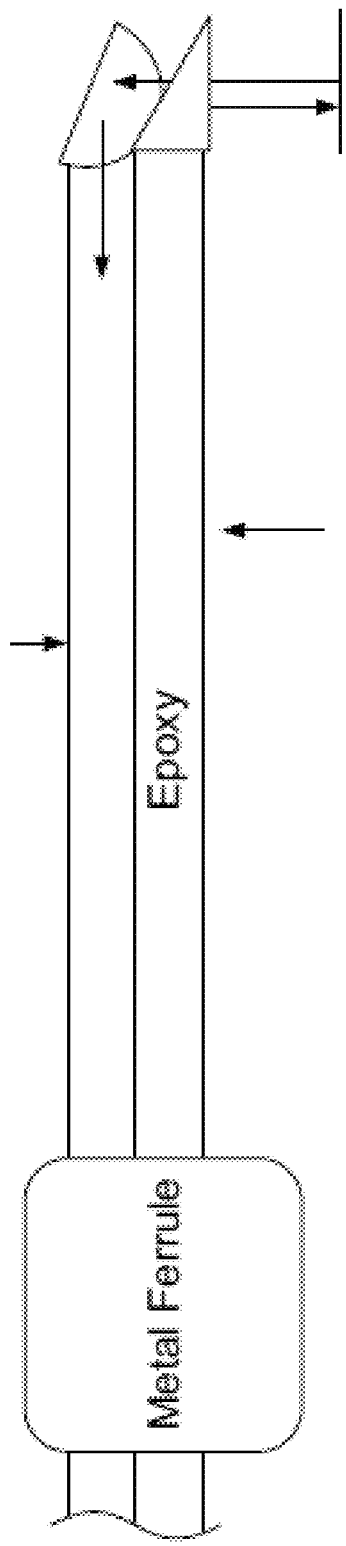
Figure 38:
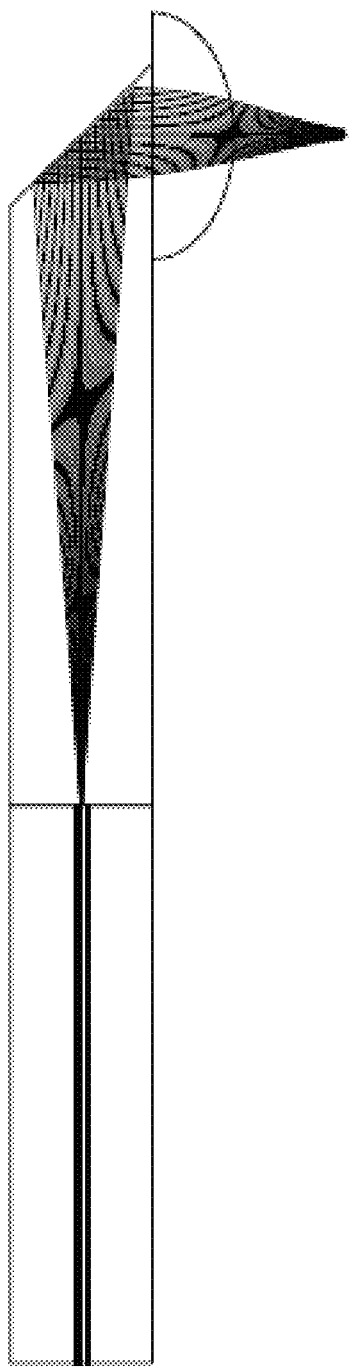

As shown in FIGS. 36A-36C, the fiber bundle can optionally have a lens 3607 at the bottom surface of the fiber bundle. The lens 3607 can span across the area of optical output/input. The lens 3607 can improve the collection of the scattered light and/or the bringing of the probe beam from the delivery fiber 3603 to the focal point. The collection 3605 and delivery 3603 fibers and the lens 3607 can be aligned and bundled so as to provide a focal point at the depth of about 250 um. The alignment can allow the delivery fiber 3603 to point the light exactly or substantially at the axis of the collection fiber 3605. FIGS. 37-38 illustrate another example fiber bundle including side-firing fibers with a lens at the distal end of the fiber bundle. The slanted end surface of the fibers can include mirror coating. The mirrors and the lenses can enhance the fiber performance in the side-firing mode.

An optical fiber sensor for detecting malaria can include the horizontal fibers described herein. The fiber sensor can be applied parallel to the human skin. The optical fiber sensor can serve at least three functions. The optical fiber sensor can deliver a pump laser pulse. The optical fiber sensor can deliver a probe beam, for example, a continuous wave beam. The optical fiber can also collect the scattered probe light.

Figure 39A:
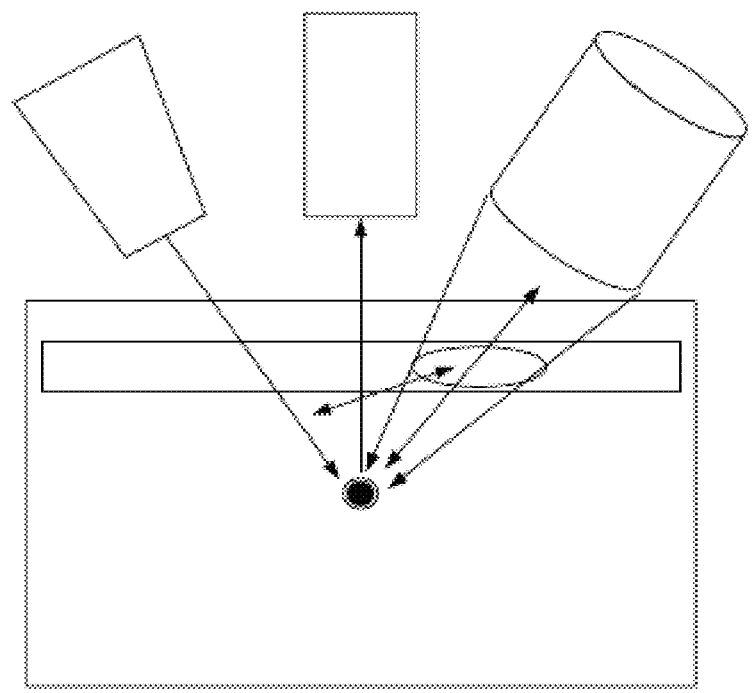
FIG. 39A illustrates schematically a three optical fiber configuration.

The sensor may optionally include three optical fibers assembled into a single bundle or a matrix of such bundles. In embodiments of the sensor having three fibers, such as shown schematically in FIG. 39A, a separate fiber can be used for delivering the pump beam, delivering the probe beam, and collecting the scattered probe light.

Figure 39B:
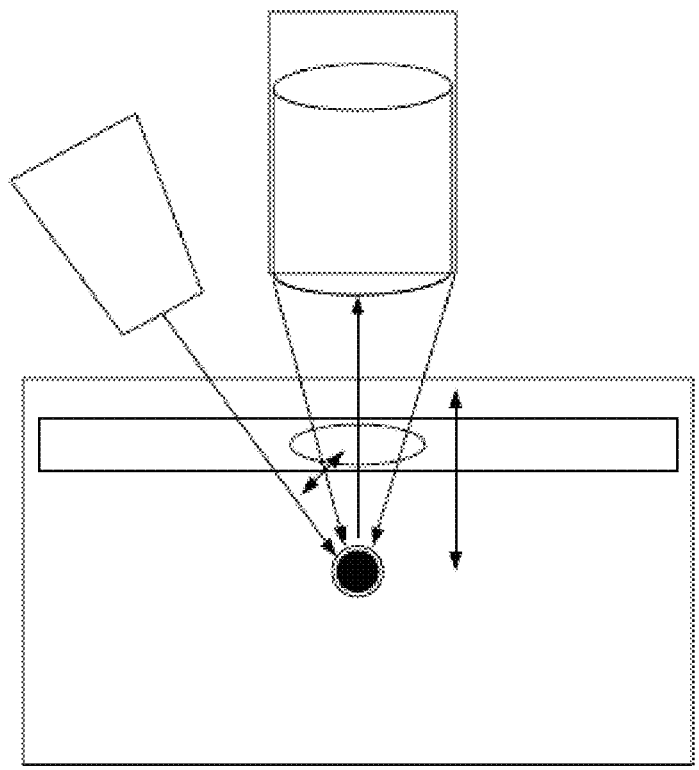
FIG. 39B illustrates schematically a two optical fiber configuration.

The sensor may include two fibers, such as shown schematically in FIG. 39B, the delivery fiber and the collection fiber as described above. In some embodiments, the same fiber (such as a multi-mode fiber) can be used to deliver the pump beam and to collect the scattered probe light and a separate fiber (such as a single-mode fiber) can be used to deliver the probe beam. Bundling the two or three optical fibers can ensure the permanent relative alignment of those fibers.

In some embodiments, the sensor may include the combination of optical fibers and ultrasound detectors, assembled to detect same HVNBs. The combination can further improve the sensitivity of detection of malaria parasites and/or Hemozoin in the patient.

The fibers in the optical fiber sensor can have flat tips. The flat tips may not be able to focus or collimate the light, and therefore may have a lower energy efficacy and/or lower detection sensitivity than fibers with lensed or convex tips. The lensed fiber or fibers with the engineered tips for delivering the pump beam and collecting the scattered probe light can better concentrate the pump fluence into the skin, and/or collect more scattered light from the skin compared to identical fibers with flat tips. Therefore, the lensed tips can increase the energy efficacy of Hemozoin-generated transient vapor nanobubble generation and/or the sensitivity of detection thereof.

In some embodiments, the fibers in an optical fiber sensor can be assembled at the relative angles to each other in order to achieve the desired angle of the delivery. The desired angle of delivery can affect the location or depth of the focal point in water or skin.

Example Detection Systems with a Fiber Mating Device

In some embodiments, an optical and/or acoustic malaria detection system disclosed herein can include a fiber mating device (rather than a standard fiber mating sleeve or just an optical fiber coupler) to further improve the malaria detection sensitivity threshold and/or consistency (that is, the diagnostic performance), for example, by reducing false positive detection in malaria-negative samples. Example methods, mechanisms, and designs for further improving the delivery of the laser pulse to the human skin through the effect of the self-collimation of the laser pulse in the optical fiber will be described below, in particular with reference to a unique way of delivering the pump laser pulse in a malaria detection system using the fiber mating device. In these embodiments, the fiber mating device can optically decouple a permanently-installed fiber (a service fiber in the sensor, which is described in more detail below) from the laser source using an additional optical fiber (a delivery fiber). The delivery fiber may be longer than the service fiber. The fiber mating device can include free space optics and mechanics with spatially disconnected fiber tips.

The self-collimation of the laser pulse in an optical fiber will now be explained. Typically the fiber numerical aperture, NA, of optical fiber determines the NA of an out-of-fiber light beam. However, the combination of the properties of a short high energy laser pulse (used for malaria detection and/or diagnostics as described herein) with specific coupling (launching) of such pulses, for example, using the fiber mating device described herein, into a multimode optical fiber can result in unique propagation of the laser pulse in the optical fiber, with the divergence (numerical aperture, NA) of the out-of-fiber laser beam being self-controlled by a laser pulse rather than by the numerical aperture of the optical fiber. This is because the NA of the laser beam at the fiber input is much smaller than that of the optical fiber. The pulsed laser beam self-collimates in the fiber, thus improving the delivery of the optical energy into the skin and hence the diagnostic performance of the optical malaria detection system described herein.

The actual NA of the out-of-fiber laser beams under different source-fiber settings were compared. Light sources with different pulse durations were used, namely 247 ps, 300 ps, and 370 ps. Optical fibers (Thorlabs Inc) according to the parameters described above were used. The optical fiber length and NA were varied, with all other parameters kept the same: for example, with a core diameter of 105 um, a step index (SI) multi-mode (MM) design, and having FC/PC standard connectors on both sides. Optical fiber tips were checked to be clean and to have no damage. Different optical fiber couplers and coupling lenses were used. Laser Source 1 and Source 2 were not coupled to a fiber mating device (which will be described in greater detail below). Laser Source 3 was coupled to the fiber mating device described above (which will be described in greater detail below), which could filter out unintended wavelengths (for example, wavelengths not according to design specification) and more optimally connect various fibers, as described above. For each coupling device and fiber, the lateral position of the fiber tip was adjusted for the maximum of the output laser energy.

For the NA measurement, the beam profile was measured with an Ophir SP928 system, which has been calibrated to measure an absolute NA of the beam, by using a fiber test optical source LE-1R-CE for multi-mode fibers (660 nm, LED non-coherent device, WWT Inc), which delivered the beam NA equal to that of the fiber (see FIG. 43A, which illustrates an example beam image for the fiber NA of 0.22). The beam diameter was measured for the full beam image. The NA of the beam was calculated as NA=0.05×[beam diameter, mm], after calibrating the beam profiler. The profiler setting were adjusted to avoid the pixel intensity saturation. The NA measurement error was 0.005. The actual NA of the out-of-fiber beams was measured under the output laser pulse energy range of 18-20 uJ for all combinations of the fiber, and the results are shown in Table 12.

TABLE 12

| Fiber NA (length, m) | | | | |
|---|---|---|---|---|
| Light source | Fiber coupler | 0.22 (2.0) | 0.22 (12.0) | 0.1 (2.0) | 0.1 (12.0) |
| Source 1 | Standa, f11 mm | 0.065 | 0.060 | 0.07 | 0.065 |
| Source 2 | Thorlabs, f15 mm | 0.065 | 0.065 | 0.07 | 0.063 |
| Source 3 | Prototype fiber mating device, f11 mm | 0.065 | 0.065 | 0.075 | 0.060 |

The NA of the laser beam out of the SI MM optical fibers was found to be significantly lower (for example, about 0.06-0.07) than the NA of the fiber (about 0.1-0.22). As a result, the beam out of the fiber was collimated much better (up to about 3-fold) than what the fiber provides.

Figure 44A:
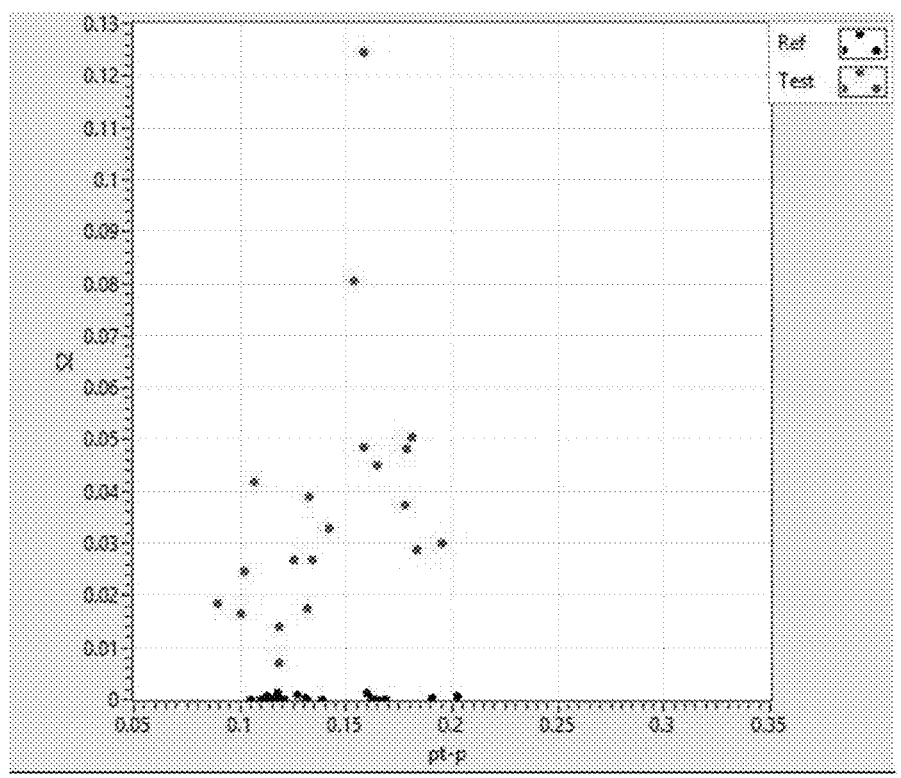
FIGS. 44A-C illustrate example Hemozoin detection signal metrics for Hemozoin-positive skin samples (Test) and Hemozoin-negative skin samples (Reference).
Figure 44B:
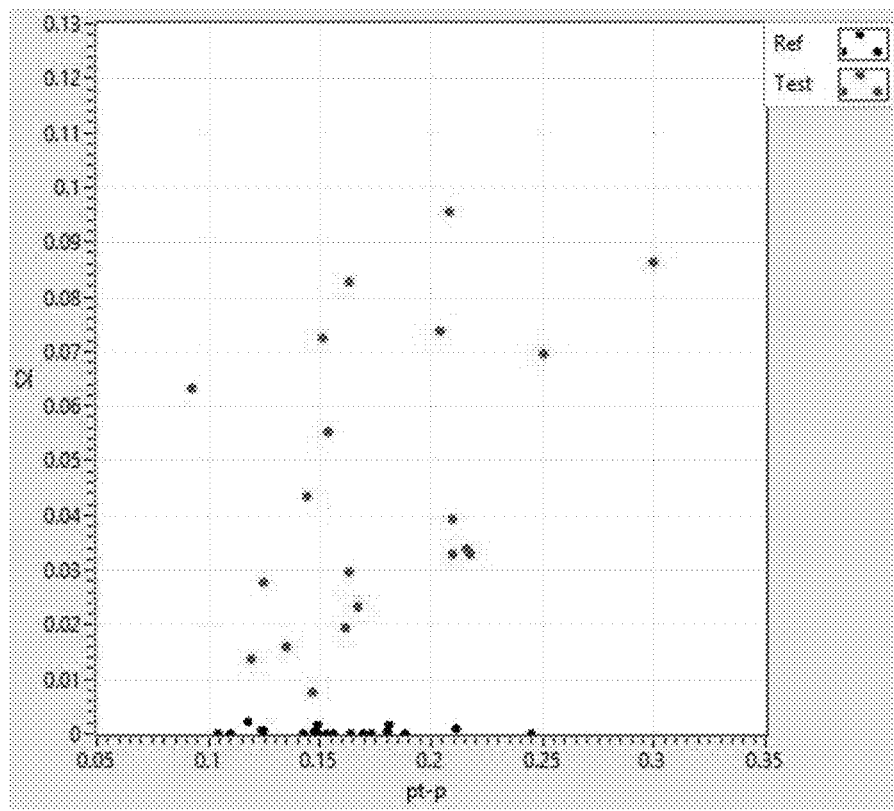

The effect of the NA of the optical fiber for malaria diagnostics through Hemozoin-generated vapor nanobubbles will now be described. The generation and detection of Hemozoin-generated vapor nanobubbles in human skin was studied in 9 independent experiments with dark human skin with or without Hemozoin nanoparticles. The pump laser beam was directed to the depth of 250 um under the human skin. The NA of the optical fiber used for the delivery of the laser pulse into the skin was varied between 0.1 and 0.22. The combination of a light Source 1 (see Table 12 above) and a 12-m standard optical fibers was used. The energy of the laser pulse was maintained at the maximal possible level in the range of 18-20 uJ (at the skin entrance). Hemozoin-generated vapor nanobubbles were detected with an ultrasound sensor (Blatek Inc, model 0919-5782). Ultrasound signals were analyzed with two metrics, one related to the skin background (peak-to-peak parameter) and another related to the Hemozoin-generated vapor nanobubble (an "S2" parameter) in the signal tail, both as a function of the Hemozoin status and the optical fiber NA. An example of two experiments is shown in FIGS. 44A-B: red dots show signals in Hemozoin-positive human skin samples and black dots show signals in Hemozoin-negative human skin samples.

Among the nine experiments performed, 5 experiments used an optical fiber with the NA 0.1 and 4 experiments used an optical fiber with the NA 0.22. Signal metrics were averaged for each of 9 experiments as presented below in the Table 13 and the S2-p-t-p diagram (FIG. 44C) for all experiments:

TABLE 13

| 0.22 NA | | | | 0.1 NA | | | |
|---|---|---|---|---|---|---|---|
| Skin | | Skin + Hz | | Skin | | Skin + Hz | |
| Peak-to-peak, mV | S2 | Peak-to-peak, mV | S2 | Peak-to-peak, mV | S2 | Peak-to-peak, mV | S2 |
| 148 | 0.0004 | 160 | 0.0275 | 154 | 0.0022 | 210 | 0.0556 |
| 140 | 0.0003 | 143 | 0.0379 | 158 | 0.0004 | 177 | 0.0460 |
| 183 | 0.0005 | 156 | 0.0493 | 186 | 0.0001 | 195 | 0.0264 |
| 171 | 0.0031 | 183 | 0.0463 | 185 | 0.0009 | 230 | 0.0356 |
| | | 154 | 0.0591 | | | | |
| Averaged for all experiments | | | | | | | |
| 160 ± 20 | 0.0011 ± 0.0014 | 159 ± 15 | 0.0440 ± 0.012 | 171 ± 17 | 0.0009 ± 0.0009 | 203 ± 23 | 0.0409 ± 0.0127 |

Figure 44C:
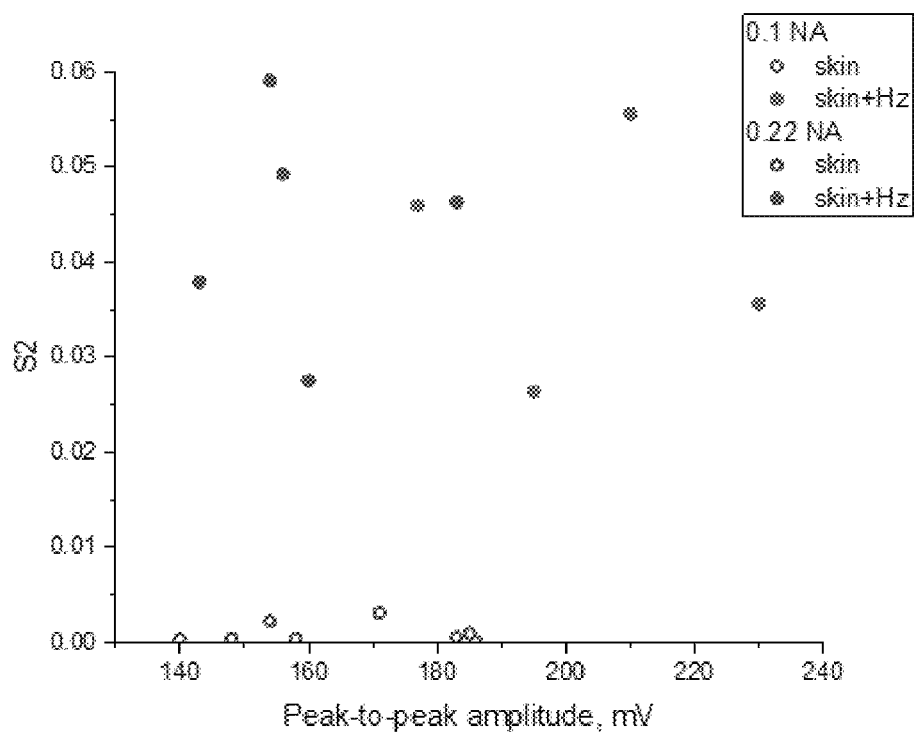

As shown in Table 13 and FIG. 44C, there was no statistically significant difference between the optical fiber NA 0.1 and 0.22, both in the skin background metrics p-t-p (for example, 160±20 v. 171±17 in Table 13) and the S2 metrics (for example, 0.0440±0.012 v. 0.0409±0.0127 in Table 13). This suggests the laser pulse fluences at the Hemozoin-generated vapor nanobubble generation depth, 250 um, were very similar for the beams delivered with optical fibers having NA 0.1 and 0.22, respectively. However, if the pump beams are assumed to propagate in accordance with the fiber NA 0.22, the laser pulse fluence should reduce almost by half (at the depth of 250 um) compared to that delivered with the fiber NA 0.1. Such NA-dependent reduction in the optical fluence would reduce the Hemozoin-generated vapor nanobubble generation efficacy and the Hemozoin-generated vapor nanobubble signal (the level of S2 metrics). However, this assumption was not confirmed by the 9 experiments. The variation between individual experiments for the NAs 0.1 and 0.22 was within the variation between the experiments using the same NA, and this variation may have been caused by using different skin samples and de-novo alignment of the fiber and sensor for each experiment. In other words, the laser beams delivered with the optical fibers with both NAs had similar actual divergence (NA) when launched into the skin. Further, the actual laser beam NA appears to be much lower than the fiber NA. This, in turn, means the laser beam propagation may not depend upon the fiber NA and may followed the mechanism of self-collimation described above.

The effect of the laser beam self-collimation has resulted in the actual laser beam divergence (NA) out of the fiber remaining in the close range of 0.06-0.075, regardless several design parameters, including but not limited to: the optical fiber NA (0.1, 0.22) and/or the length (2 m and 12 m); the laser pulse source (the three different lasers resulted in the same output NA of the beam as shown in Table 12 above); the optical fiber coupling device and its settings (three different couplers (including a fiber mating device) with the focal length of aspheric coupling lenses being in the range of 11-15 mm, resulting in the same output NA of the beam; the variation of the axial position of the lens (within 100 um) and of the lateral position of the input fiber tip (within 20 um, X and Y)); out-of-fiber energy of the laser pulse (for the energy range of 5.1-22.2 uJ, the NA of the out-of-fiber beam remained the same, within the measurement error range of 0.005, with the minimum being 0.063 and the maximum being 0.07 (measured for a 12-m long 0.22 NA fiber with the laser Source 2)).

The data obtained indicates that the effect of a self-collimation of the laser pulse in an optical fiber can be mainly determined by the properties of the laser pulse which are common for all three lasers: the wavelength, pulse duration range, and the coupling of the laser beam into the fiber. The coupling described herein can use the divergent beam after its waist, a relatively large beam diameter at the entry into the fiber core, which is slightly less than the diameter of the fiber core. The NA of the free-space laser beam in the coupler can be close to the observed NA values in Table 12.

The physical mechanisms behind the observed self-collimation of the laser beam may be explained through additional results observed. There was no additional loss of the optical transmission in the fibers (the energy transmission efficacy for the 12-m fibers was 85% and above). The pulse duration did not increase, and even slightly decreased, by about 2-3%, as was observed for the 12-m fibers versus the 2-m fibers (from 247 ns to 241 ns, as shown in test data for Source 3 in Table 12 above). The temporal structure of the laser beam changed from a single mode (at the fiber input) to a multi-mode (at the fiber output). These factors, together with the main result described herein, may indicate two mechanisms. The first mechanism involved non-linear optical effects self-induced by a laser pulse in the fiber due to high optical intensities (such as in the GW/cm$^2$ range), which could occur during the pulse propagation through the fiber core. Such non-linear effects (for example, a weak Kerr effect) may create reversible changes in the optical fiber that, in turn, could focus the laser beam and slightly shorten the pulse duration, without damaging the optical fiber. In the second mechanism, the fiber input coupling of the free space laser beam with low NA (0.05) may help to maintain a low NA for the laser beam during its propagation through a multi-mode optical fiber.

The possibility of using this effect of self-collimation for a simpler, more reproducible, and more efficient control of the delivery of the optical energy into the skin and by using standard optical fibers is illustrated below for four different optical fibers. The out-of-fiber laser beams were imaged with the beam profiler for the combination of the light Source 3, a 12-m delivery fiber, and the fiber mating device (such as describe in more detail below) as shown in Table 14. The fiber mating device functioned as an intermediate optical filter, an attenuator, and a coupler. As shown in Table 14, all four different optical fibers delivered a relatively smooth beam (that is, without hot spots) of the NAs, similar to the results as shown in Table 12 above. In the beam profiles of FIGS. 43B-43E, the white circle shows the beam diameter assuming it follows the NA of the fiber.

TABLE 14

| Fiber NA (length, m) | 0.22 (2.0) | 0.22 (12.0) | 0.1 (2.0) | 0.1 (12.0) |
|---|---|---|---|---|
| Beam NA | 0.065 | 0.065 | 0.075 | 0.060 |
| Beam profile | FIG. 43B | FIG. 43C | FIG. 43D | FIG. 43E |

In the embodiments using the fiber mating device, the fluence of the laser pulse as delivered to skin at the depth of the vapor nanobubble generation (and hence the vapor nanobubble generation efficacy and consequently the diagnostic performance) can be increased approximately 2.5-fold higher than that when using a standard sleeve for connecting the laser source and the sensor through the direct connection of two optical fibers.

As described above, with a fiber mating device disclosed herein, the malaria diagnostic performance can be further optimized. For a range of optical fiber NA from about 0.1 to 0.22, the numerical aperture (NA) of the optical fiber may not influence the efficacy of Hemozoin-generated vapor nanobubble detection in human skin when the fiber mating device is used. Furthermore, the diagnostic performance may be higher than if assuming the out-of-fiber laser beam divergence follows the fiber NA. The improved collimation of the out-of-fiber laser beam can result in higher laser fluence in skin at the depth of generation of Hemozoin-generated vapor nanobubbles. Laser pulse mode mixing in optical fibers, as used for malaria detection sensors with a high energy picosecond laser pulse, can therefore be further improved to avoid one or more of the following issues: (1) uncontrollable divergence (and hence fluence variation) of the laser pulse in skin, (2) hot spots at the skin surface, (3) damage to the receiving end of the optical fiber resulting in a loss of the sensor as the fiber is permanently imbedded into the sensor, or (4) difficulty to maintain specific pulse energy in cases where the laser source has no attenuator. Any of these factors may compromise diagnostic performance. The fiber mating device can also address additional technical problems, including but not limited to (5) a parasite laser wavelength of about 808 nm, also present out of the optical fiber in case it is unfiltered in the laser, or (6) laser damage to the fiber tips when using two optical fibers mated in a standard sleeve (such mating also may not improve the laser beam profile since it simply extends one fiber into the second one and may not allow for control of the laser energy and/or wavelength). In other words, the fiber coupling using the fiber mating device between the laser source and the malaria detection sensor can facilitate in achieving improved and more reproducible diagnostic performance than the use of a standard sleeve for connecting two optical fibers.

Figure 42A:
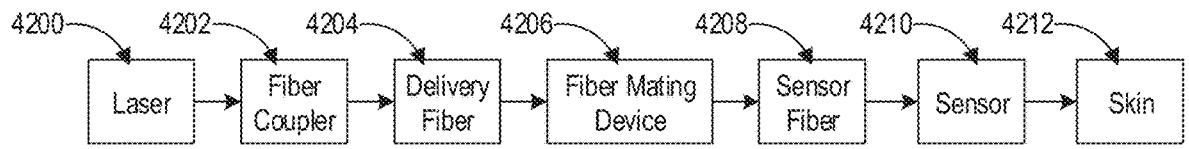
FIG. 42A illustrates schematically a block diagram of an example malaria non-invasive detection system including a fiber mating device.

In some embodiments, an optical and/or malaria detection system can perform a self-collimated delivery of the laser pulse with a standard optical fiber. The system can achieve a laser beam NA at the skin entrance in the range of about 0.05 to 0.07. FIG. 42A illustrates schematically such a system. The system can include a laser source 4200. The laser sources 4200 can be configured to generate the pulsed pump beam (and the probe beam in an optical detection system disclosed herein). The pulses laser beam can have a duration of about 100-500 ps, a wavelength of about 670-680 nm, and/or an energy of about 10-40 uJ. The pulsed pump beam can include a free-space collimated beam out of the laser source 4200.

Using a fiber coupler 4202, the laser source 4200 can be coupled into a delivery fiber 4204. The delivery fiber 4204 can be a multi-mode fiber. In some embodiments, the delivery fiber 4204 can include a standard multi-mode step index optical fiber with a core diameter of about 50-200 um (for example, about 105 um), a length of about 2-20 m length (for example, about 12 m), and/or an NA of about 0.1-0.22 (for example, about 0.22). The fiber coupler 4202 can include aspheric lens (or other type lens), which may have a focal distance of about 7-18 mm (for example, about 11 mm). The laser beam at the entrance of the delivery fiber 4204 can be divergent, with the NA of about 0.0-0.1 (for example, about 0.05). The beam diameter at the tip of the delivery fiber 4204, which can be adjustable in a lateral directions, should be about 60-80% of the core diameter of the delivery fiber 4204.

The fiber mating device 4206, couples the delivery fiber 4204 with a sensor fiber (service fiber) 4210, which ultimately couples the laser source 4200 and the malaria sensor 4210. The fiber mating device 4206 can include an adjustable fiber mating free-space unit. The unit can include an optical filter and attenuator to control the laser beam energy and/or the divergence of the beam at the skin. As shown in beam into the service fiber 4208. The mating device can be designed as one solid integrated opto-mechanical unit as well.

The service fiber 4208 can be a permanent and/or integral part of a non-invasive malaria sensor 4210 (for example, any malaria sensor examples including the photodetector as described above). For example, the service fiber 4208 can be permanently and/or integrally coupled to the sensor 4210. In some embodiments, the service fiber 4208 can include a standard multi-mode, step index optical fiber. The service fiber 4208 can have a core diameter of about 105 um (which can also be any value from about 50 um to about 200 um), a length of about 2 m (which can also be any value from about 1 m to about 10 m), and/or a NA of about 0.22 (which can also be any value from about 0.1 to about 0.4).

Additional example specifications of the components in the malaria detection system of FIG. 42A are summarized in Table 15. A skilled artisan will appreciate from the disclosure herein that these specifications are for illustrative purposes and not limiting.

TABLE 15

| Component | Optical | Mechanical | Other optional features |
|---|---|---|---|
| Laser source 4200 | FC/PC port | Secured to a base | — |
| MM SI delivery fiber 4204 | 0.22 NA, 105 um core diameter, 12 m length | Secured to the base | may be coiled on a drum to reduce movement |
| Collimator 4216 | FC/PC port, F 9.9 mm, for MM fibers, AR (anti-reflective)-coated OR F15.2 NA 0.16, beam OD 2.8 mm | Cage-rod system, secured to the base | — |
| Short-pass filter 4218 | 700 nm cut-off wavelength, >95% transmission | Cage-rod system | — |
| Variable iris aperture 4220 | Variable iris aperture | Cage-rod system | — |
| Coupling lens, aspheric 4222 | F7.5 mm, AR-coated OR F13.9 NA 0.18, CA5.1 | Cage-rod system | Z-adjustment drive, 5-um precision |
| FC/PC fiber port 4214, 4224 | — | Cage-rod system, | X-Y adjustment drive, 2-um precision, 105 (may be lowered to 80) mm from the tip of the delivery fiber |
| MM SI service fiber 4208 | 0.22 NA, 105 um core diameter, 2-3 m length, with 2.5 coils 80 mm OD, 50 mm to the receiving end | Stand-alone, the output coil can be secured to the base with a stress relief | Part of the sensor |

Figure 42B:
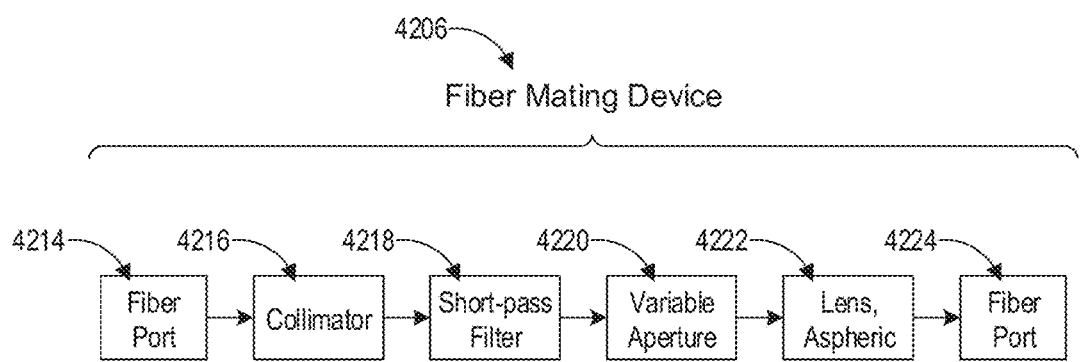
FIG. 42B illustrates schematically a block diagram of the fiber mating device of FIG. 42A.
Figure 42C:
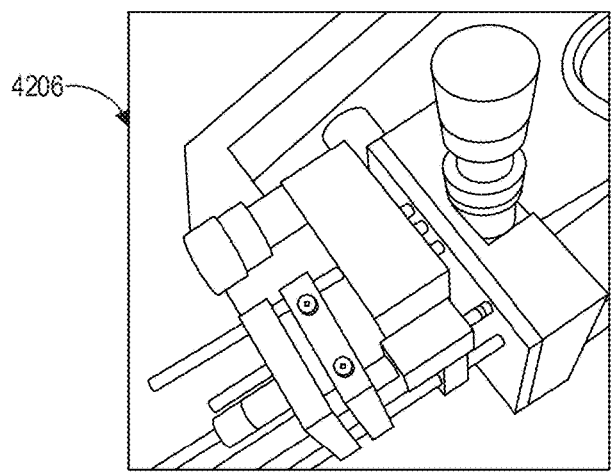
FIG. 42C illustrates an example fiber mating device.

FIG. 42B, the fiber mating device 4206 can include a short-pass optical filter 4218 and a variable aperture attenuator 4220 located between two fiber ports 4214, 4224 at two opposite ends of the mating device 4206. The fiber ports 4214, 4224 are connected to the delivery fiber 4204 and the service fiber 4208 respectively. The filter 4218 and the variable aperture attenuator 4220 can be connected next to each other. A collimator 4216 can be connected between the first fiber port 4214 and the filter 4218. An aspheric lens 4222 can be connected between the variable aperture attenuator 4220 and the second fiber port 4224. FIG. 42C illustrates an example fiber mating device 4206, which includes a cage-rod system. The mating device 4206 uses the laser beam out of the delivery fiber 4204, rather than directly from the laser source 4200 and tunes the launch of the out-of-fiber Splitting the delivery of the laser pulse into two optical fibers (delivery and service fibers), such as when connected via the fiber mating device, allows improvement of the laser beam intensity profile at the skin entrance so as to avoid or minimize hot spots in skin, among other technical problems described above when using a standard sleeve or a single optical fiber, and allows quicker replacement of the malaria sensors. In a modular design, the laser source, the fiber coupler, the delivery fiber, and the fiber mating device can be mounted as a whole and represent one unit, while a sensor with the service fiber can represent a separate unit.

The use of the fiber mating device can result in one or more of the following features: (1) improving stability of the intensity profile of the laser beam out of the malaria sensor: the spatial modulation (hot spots) could be reduced from about 80% (after an about 12-m fiber, see for example, FIG.

Figure 45A:
FIG. 45A illustrates an example pump laser beam out of an optical fiber (coupled with standard mating sleeve) showing hot spots.
Figure 45B:
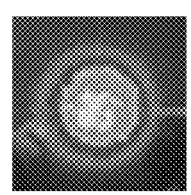
FIG. 45B illustrates an example pump laser beam out of an optical fiber (coupled to the fiber mating device disclosed herein) showing reduced hot spots compared to FIG. 45A.
Figure 45D:
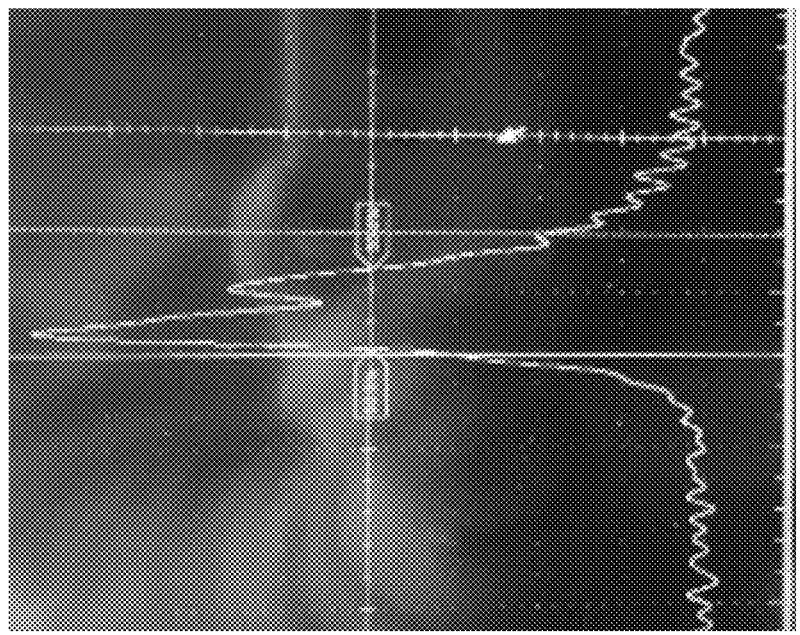
FIG. 45D illustrates an example pump laser pulse time-profile delivered by a laser device coupled to the fiber mating device disclosed herein.
Figure 45C:
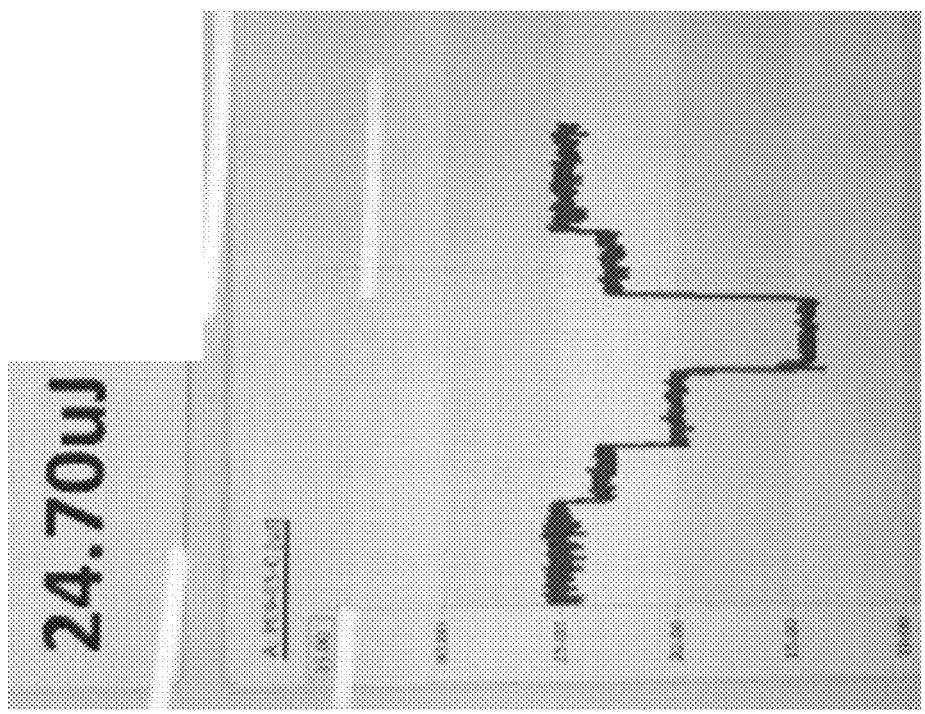
FIG. 45C illustrates an example output energy of the pump laser beam out of an optical fiber (coupled to the fiber mating device disclosed herein).

45A) to about 25-40% (see, for example, FIG. 45B), thus reducing or minimizing hot spots at the skin surface and reducing a probability of false-positive signals; (2) improving the in-skin laser fluence by about 3-5 fold by reducing the divergence (NA) of the output laser beam to below 0.1 NA, resulting in a more parallel beam (compared to the fiber with NA 0.22, which is typically used in sensors) and in the increased diagnostic sensitivity; (3) reducing damage to optical fibers (caused by the laser in incorrect coupling and/or by standard fiber mating sleeves when connecting two optical fibers): all fibers tested were damage-free (>10 fibers); (4) allowing adjustment of the output energy (see FIG. 45C) of the laser pulse in the range of about 50-100%, potentially without adding additional optical transmission losses; (5) more quickly and safely coupling different sensors to the laser than using standard fiber mating sleeves; (6) removing or reducing a parasite laser wavelength of 808 nm otherwise present at the output laser beam from an optical fiber (in the case of a sub-optimal laser source); (7) allowing use of a relatively short service fiber (imbedded into the sensor), thus eliminating the need for long fibers permanently imbedded into the sensors; (8) allowing shorter service fibers without increasing the laser pulse duration (241 ps) compared to the laser beam out of a 2-m optical fiber (247 ps), such as shown in FIG. 45D; or (9) stabilizing the output beam profile during change of the spatial position and/or orientation of the sensor (a natural situation when collecting signals from human subjects): in the experiments described above, changing the position of the distal end of the service fiber (similar to that during evaluation of a human subject) in five different spatial locations and orientations of the distal fiber tip did not change the NA of the out-of-fiber laser beam, which remained at about 0.075.

In addition, utilizing the self-collimating effect of the laser beams can allow use of an optical fiber with a standard flat tip to be used to achieve similar target depth pump laser fluence, similar to use of an optical fiber with a specialized engineered tip, which may be lensed (having a curvature) and/or include a taper.

Terminology

Terms of orientation used herein, such as "proximal," "distal," "radial," "central," "longitudinal," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "spherical" or "semi-circular" or "hemisphere" or any related or similar terms, are not required to conform strictly to the mathematical definitions of circles or spheres or other structures, but can encompass structures that are reasonably close approximations.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may permit, the term "generally parallel" can refer to something that departs from exactly parallel by less than or equal to 15 degrees.

While a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. Accordingly, it should be understood that various features and aspects of the disclosed embodiments can be combined with or substituted for one another in order to form varying modes of the disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings) may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination so disclosed.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Some embodiments have been described in connection with the accompanying drawings. The figures are not drawn to scale where appropriate, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

Although this invention has been disclosed in the context of certain embodiments and examples, the scope of this disclosure extends beyond the specifically disclosed embodiments to other alternative embodiments and/or uses of the invention and obvious modifications and equivalents thereof. Any system, method, and device described in this application can include any combination of the preceding features described in this and other paragraphs, among other features and combinations described herein, including features and combinations described in subsequent paragraphs. While several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A system for generating and detecting transient vapor nanobubbles in a fluid from a patient, the fluid comprising the patient's blood, urine, interstitial fluid or other physiological liquid, the system comprising:
    a micro-fluidic device configured to receive a flow of the fluid from the patient;
    a laser pulse source configured to provide a laser pulse to the flow of the fluid, the laser pulse entering the flow of fluid from a first side of the micro-fluidic device, the laser pulse configured to generate a transient vapor nanobubble around a nanoparticle, if present, located in the fluid;
    a probe light source configured to provide a probe light to the flow, the probe light entering the flow of the fluid from the first side of the micro-fluidic device, the probe light configured to be scattered, reflected, and/or deflected by the transient vapor nanobubble; and
    a photodetector located at a second side of the micro-fluidic device opposite the first side, the photodetector configured to detect the scattered, reflected, and/or deflected probe light and output a nanobubble signal comprising characteristics of optical scattering, reflecting, and/or deflecting by the transient vapor nanobubble,
    wherein the first side and the second side are on opposite sides along a longitudinal axis of the micro-fluidic device such that the flow of the fluid is collinear to a direction of the laser pulse entering the flow of the fluid.

2. The system of claim 1, wherein the micro-fluidic device is connected to a pump.

3. The system of claim 1, wherein the micro-fluidic device comprises a plurality of micro-cuvettes.

4. The system of claim 3, wherein the laser pulse and the probe light are directed to the flow of the fluid in the plurality of micro-cuvettes.

5. The system of claim 3, wherein each of the plurality of micro-cuvettes comprises a capillary tube.

6. The system of claim 5, wherein the capillary tube has an inner diameter of about 50 um to about 100 um.

7. The system of claim 5, wherein the capillary tube is made of glass.

8. The system of claim 1, wherein the micro-fluidic device comprises a capillary tube.

9. The system of claim 8, wherein the capillary tube comprises an optical window on each of the first side and the second side.

10. The system of claim 9, wherein the capillary tube acts as an optical guide.

11. The system of claim 8, wherein the capillary tube is the single tube of the micro-fluidic device.

12. The system of claim 8, wherein the capillary tube has an inner diameter of about 20 um to about 80 um.

13. The system of claim 8, wherein a refractive index of the capillary tube is higher than a refractive index of the fluid.

14. The system of claim 1, wherein the probe light comprises laser or an incoherent light.

15. The system of claim 1, wherein the characteristics of optical scattering, reflecting, and/or deflecting by the transient vapor nanobubble comprise:
    a dip or arch shape in the signal responsive to at least a first laser pulse;
    a decay in a signal amplitude responsive to one or more laser pulses after the first laser pulse; or
    a positive threshold calculated based in part on sample-averaged metrics of signals.

16. The system of claim 1, wherein the system has a sensitivity of being able to detect a transient vapor nanobubble of or smaller than 100 ns in lifetime.

17. The system of claim 1, further comprising a single-mode optical fiber configured to deliver the probe light.

18. The system of claim 1, further comprising a filter.

* * * * *